United States Patent
Beaudoin et al.

(10) Patent No.: US 12,264,342 B2
(45) Date of Patent: Apr. 1, 2025

(54) LACHNOSPIRACEAE BACTERIUM ND2006 CAS12A MUTANT GENES AND POLYPEPTIDES ENCODED BY SAME

(71) Applicant: INTEGRATED DNA TECHNOLOGIES, INC., Coralville, IA (US)

(72) Inventors: Sarah Franz Beaudoin, Iowa City, IA (US); Michael Allen Collingwood, North Liberty, IA (US); Christopher Anthony Vakulskas, North Liberty, IA (US)

(73) Assignee: INTEGRATED DNA TECHNOLOGIES, INC., Coralville, IA (US)

( * ) Notice: Subject to any disclaimer, the term of this patent is extended or adjusted under 35 U.S.C. 154(b) by 699 days.

(21) Appl. No.: 17/430,013

(22) PCT Filed: Feb. 21, 2020

(86) PCT No.: PCT/US2020/019168
§ 371 (c)(1),
(2) Date: Aug. 11, 2021

(87) PCT Pub. No.: WO2020/172502
PCT Pub. Date: Aug. 27, 2020

(65) Prior Publication Data
US 2023/0040148 A1 Feb. 9, 2023

Related U.S. Application Data

(60) Provisional application No. 62/808,984, filed on Feb. 22, 2019.

(51) Int. Cl.
C12N 9/22 (2006.01)
C12N 15/11 (2006.01)
(52) U.S. Cl.
CPC ............... *C12N 9/22* (2013.01); *C12N 15/11* (2013.01); *C12N 2310/20* (2017.05)
(58) Field of Classification Search
CPC ....... C12N 9/22; C12N 15/11; C12N 2310/20
See application file for complete search history.

(56) References Cited

U.S. PATENT DOCUMENTS

| | | | |
|---|---|---|---|
| 7,560,529 B2 | 7/2009 | Gabibov et al. | |
| 9,790,490 B2 | 10/2017 | Zhang et al. | |
| 9,840,702 B2 | 12/2017 | Collingwood et al. | |
| 10,266,886 B2 | 4/2019 | Abudayyeh et al. | |
| 10,717,978 B2 | 7/2020 | Vakulskas et al. | |
| 10,767,176 B2 | 9/2020 | Collingwood et al. | |
| 11,999,979 B2 | 6/2024 | Zhang et al. | |
| 12,012,433 B1 | 6/2024 | Beaudoin et al. | |
| 2016/0177304 A1 | 6/2016 | Collingwood et al. | |
| 2016/0208243 A1 | 7/2016 | Zhang et al. | |
| 2017/0044536 A1 | 2/2017 | Collingwood et al. | |
| 2018/0179523 A1 | 6/2018 | Collingwood et al. | |
| 2018/0187176 A1 | 7/2018 | Behlke et al. | |
| 2018/0273938 A1 | 9/2018 | Turk et al. | |
| 2018/0320201 A1 | 11/2018 | Vakulskas et al. | |
| 2019/0010481 A1 | 1/2019 | Joung et al. | |
| 2019/0032131 A1 | 1/2019 | Turk et al. | |
| 2020/0080096 A1 | 3/2020 | Flasinski et al. | |
| 2020/0109382 A1 | 4/2020 | Zhang et al. | |
| 2021/0348144 A1 | 11/2021 | Zhang et al. | |
| 2024/0199691 A1 | 6/2024 | Beaudoin et al. | |

FOREIGN PATENT DOCUMENTS

| | | |
|---|---|---|
| WO | 2017127807 A1 | 7/2017 |
| WO | 2017184768 A1 | 10/2017 |
| WO | 2018195545 A2 | 10/2018 |
| WO | 2019138052 A1 | 7/2019 |
| WO | 20210937752 A1 | 5/2021 |
| WO | 2021222703 A2 | 11/2021 |
| WO | 2021257716 A2 | 12/2021 |
| WO | 2023027041 A1 | 3/2023 |
| WO | 2023097316 A1 | 6/2023 |
| WO | 2023145833 A1 | 8/2023 |

OTHER PUBLICATIONS

"SEQ ID No. 3 vs SEQ ID No. 109" Downloaded from <https://blast.ncbi.nlm.nih.gov/Blast.cgi> Apr. 3, 2024. (Year: 2016).*
"SEQ ID No. 6 vs SEQ ID No. 109" Downloaded from <https://blast.ncbi.nlm.nih.gov/Blast.cgi> Apr. 3, 2024. (Year: 2016).*
Cebrian-Serrano et al., "CRISPR-Cas orthologues and variants: optimizing the repertoire, specificity and delivery of genome engineering tools", Mammalian Genome, 2017, vol. 28, No. 7, pp. 247-261.
Geneseq, "Lachnospiraceae bacterium Cpf1 gene (PL-LbCpf1-RR) encoded nuclease", Nov. 2017, EBI Accession No. GS_PROT:BEK39676, 1 pages.
Abudayyeh et al., "C2c2 is a single component programmable RNA-guided RNA-targeting CRISPR effector", Science, vol. 353(6299), 2016.
Bowie et al., "Deciphering the Message in Protein Sequences: Tolerance to Amino Acid Substitutions", Science, vol. 247, 1990, pp. 1306-1310.

(Continued)

*Primary Examiner* — Suzanne M Noakes
*Assistant Examiner* — Ciara A McKnight
(74) *Attorney, Agent, or Firm* — Michael Best & Friedrich LLP

(57) ABSTRACT

This invention pertains to mutant *Lachnospiraceae bacterium* ND2006 (Lb) Cas12a nucleic acids and proteins for use in CRISPR/Cas12a endonuclease systems, and their methods of use. In particular, the invention pertains to an isolated mutant LbCas12a protein, wherein the isolated mutant LbCas12a protein is active in a CRISPR/Cas12a endonuclease system. The invention also includes isolated nucleic acids encoding mutant LbCas12a proteins, ribonucleoprotein complexes and CRISPR/Cas12a endonuclease systems having mutant LbCas12a proteins.

8 Claims, 12 Drawing Sheets
Specification includes a Sequence Listing.

(56) References Cited

OTHER PUBLICATIONS

East-Seletsky et al., "Two distinct RNase activities of CRISPR-C2c2 enable guide-RNA processing and RNA detection", Nature, vol. 538 (7624), 2016, pp. 270-273.
Gao et al., "Engineered Cpf1 variants with altered PAM specificities increase genome targeting range", Nat Biotechnol., vol. 35, No. 8, 2017, pp. 789-792.
Gao et al., "Type V CRISPR-Cas Cas12a endonuclease employs a unique mechanism for crRNA-mediated target DNA recognition," Cell Research, vol. 26, 2016, pp. 901-913.
Gibson et al., "Enzymatic assembly of DNA molecules up to several hundred kilobases", Nature Methods, vol. 6, No. 5, 2009, pp. 343-334.
Gootenberg et al., "Nucleic acid detection with CRISPR-Cas13a/C2c2" Science, vol. 356(6336), 2017, pp. 438-442.
Hur et al., "Targeted mutagenesis in mice by electroporation of Cpf1 ribonucleoproteins," Nature Biotechnology 34(8):807-808 (2016).
International Search Report and Written Opinion for Application No. PCT/US2020/19168 dated Jul. 23, 2020 (13 pages).
Jinek et al., "A programmable dual-RNA-guided DNA endonuclease in adaptive bacterial 5 immunity", Science, vol. 337, 2012, pp. 816-821.
Kim et al., "CRISPR/Cpf1-mediated DNA-free plant genome editing," Nature Commun., vol. 8(14406), 2017, pp. 1-7.
Kim et al., "Generation of knockdown mice by Cpf1-mediated gene targeting," Nature Biotechnology, vol. 34, No. 8, 2016, pp. 808-810.
Kim et al., "In vivo high-throughput profiling of CRISPR-Cpf1 activity," Nature Methods, vol. 14, No. 2, 2017, pp. 153-159.
Kleinstiver et al., "Engineered CRISPR-Cas 12a variants with increased activities and improved targerting ranges for gene, epigenetic and base editing", Nat. Biotechnol., vol. 37, 2019, pp. 276-282.
Kleinstiver et al., "Genome-wide specificities of CRISPR-Cas Cpf1 nucleases in human cells," Nature Biotechnology, vol. 34, No. 8, 2016, pp. 869-874.
Schindele et al., "Engineering CRISPR/LbCas12a for highly efficient, temperature tolerant plant gene editing", Plant Biotechnol J., vol. 18, No. 5, 2020, pp. 1118-1120.
Wrenbeck et al., "Plasmid-based one-pot saturation mutagenesis", Nat Methods, vol. 13, 2016, pp. 928-930.
Yamano et al., "Crystal Structure of Cpf1 in Complex with Guide RNA and Target RNA," Cell vol. 65, 2016, pp. 949-962.
Zetsche et al., "Cpf1 Is a Single RNA-Guided Endonuclease of a Class 2 CRISPR-Cas System", Cell, vol. 163, 2015, pp. 759-771.
Zetsche et al., "Multiplex gene editing by CRISPR-Cpf1 using a single rRNA array," Nature Biotechnology, vol. 35, No. 1, 2017, pp. 31-34.
Yamano T., et al. "Structural basis for the canonical and non-canonical PAM recognition by CRISPR-Cpf1." Molecular cell 67.4 (2017): 633-645.
European Patent Office Extended European Search Report for Application No. 20760344.0, dated Feb. 26, 2024 (8 pages).
Canadian Patent Office Action for application 3,130,087, dated Feb. 19, 2024 (3 pages).
Japanese Patent Office Notification of Reasons for Rejection for Application No. 2021-548687, dated Aug. 4, 2023, 14 pages with translation.
Chinese Patent Office Notification of First Office Action for Application No. 202080015167.9, dated Sep. 27, 2023, 17 pages with translation.
Lu Yifan et al., LbCpf1 "Prokaryotic Expression, Purification of LbCpf1 Protein Gene and in Vitro Cleavage Activity Assay." China Biotechnology 40.8 (2020): 41-48. With English Abstract.
Zhang, Y., et al. "Highly efficient genome editing in plant protoplasts by ribonucleoprotein delivery of CRISPR-Cas12a nucleases." Frontiers in Genome Editing 4 (2022): 780238.
Australian Patent Office Examination Report No. 2 for Application No. 2020226864, dated Jun. 26, 2023 (9 pages).
Carmignotto et al., "On the expression of recombinant Cas9 protein in E. coli BL21 (DE3) and BL21 (DE3) Rosetta strains," J Biotechnol. vol. 306:62-70 (epub Sep. 20, 2019) (Year: 2019).
Evans et al., "Concentration of proteins and removal of solutes," Methods Enzymol., vol. 463:97-120 (2009), PMID: 19892169 (Year: 2009).
Francis et al., "Strategies to Optimize Protein Expression in E. coli," Current Protocols in Protein Science, 5.24.1-5.24.29 (Aug. 2010) (Year: 2010).
Hi Trap SP HP cation exchange columns Protocol, SP Sepharose™ High Performance Ion Exchange Medium Instructions 18-1060-26-AG, GE Life Sciences, 20 pages (2014) (Year: 2014).
Livingstone et al., Protein sequence alignments, CABIOS, vol. 9(6):745-756 (1993) (Year: 1993).
PET System manual (Novagen, pET System Manual 10th Edition, 68 pages, published May 2003 (Year: 2003).
Rodrigues et al, Chapter 5: One-Step Isothermal Assembly of DNA Fragments, Synthetic Biology, Methods in Molecular Biology, vol. 1073:43-47 (2013) (Year: 2013).
Spriestersbach et al., "Purification of His-Tagged Proteins," Methods Enzymol., vol. 559:1-15, PMID: 26096499 (Epub May 4, 2015) (Year: 2015).
International Search Report and Written Opinion for Application No. PCT/US2021/030089 dated May 20, 2022 (25 pages).
Studer, R.A. et al. "Residue mutations and their impact on protein structure and function: detecting beneficial and pathogenic changes." Biochemical journal 449.3 (2013): 581-594.
Australian Patent Office Examination Report No. 1 for application 2020226864, dated Jan. 19, 2023 (4 pages).
Canadian Patent Office Action for application 3,130,087, dated Nov. 24, 2022 (6 pages).
Dayhoff, Atlas of Protein Sequences and Structure, M. O. Dayhoff ed., 5 suppl. 3: 353-358 National Biomedical Research Foundation, Washington, D.C., USA, 1978, 8 pages.
Gribskov, M. et al. "Sigma factors from E. coli, B. subtilis, phage SP01, and phage T4 are homologous proteins." Nucleic Acids Research 14.16 (1986): 6745-6763.
Smith et al. Advances in Applied Mathematics 2: 4 82-489 (1981).
Zhang, L., et al. "AsCas 12a ultra nuclease facilitates the rapid generation of therapeutic cell medicines." Nature communications 12.1, 2021: 3908.
Chinese Patent Office Notification of Second Office Action for Application No. 202080015167.9, dated Apr. 19, 2024, 10 pages with translation.
International Search Report and Written Opinion for Application No. PCT/US2024/026464 dated Aug. 13, 2024 (16 pages).
Mohr, M., et al. "The CRISPR-Cas12a platform for accurate genome editing, gene disruption, and efficient transgene integration in human immune cells." ACS synthetic biology 12.2 (2023): 375-389.

* cited by examiner

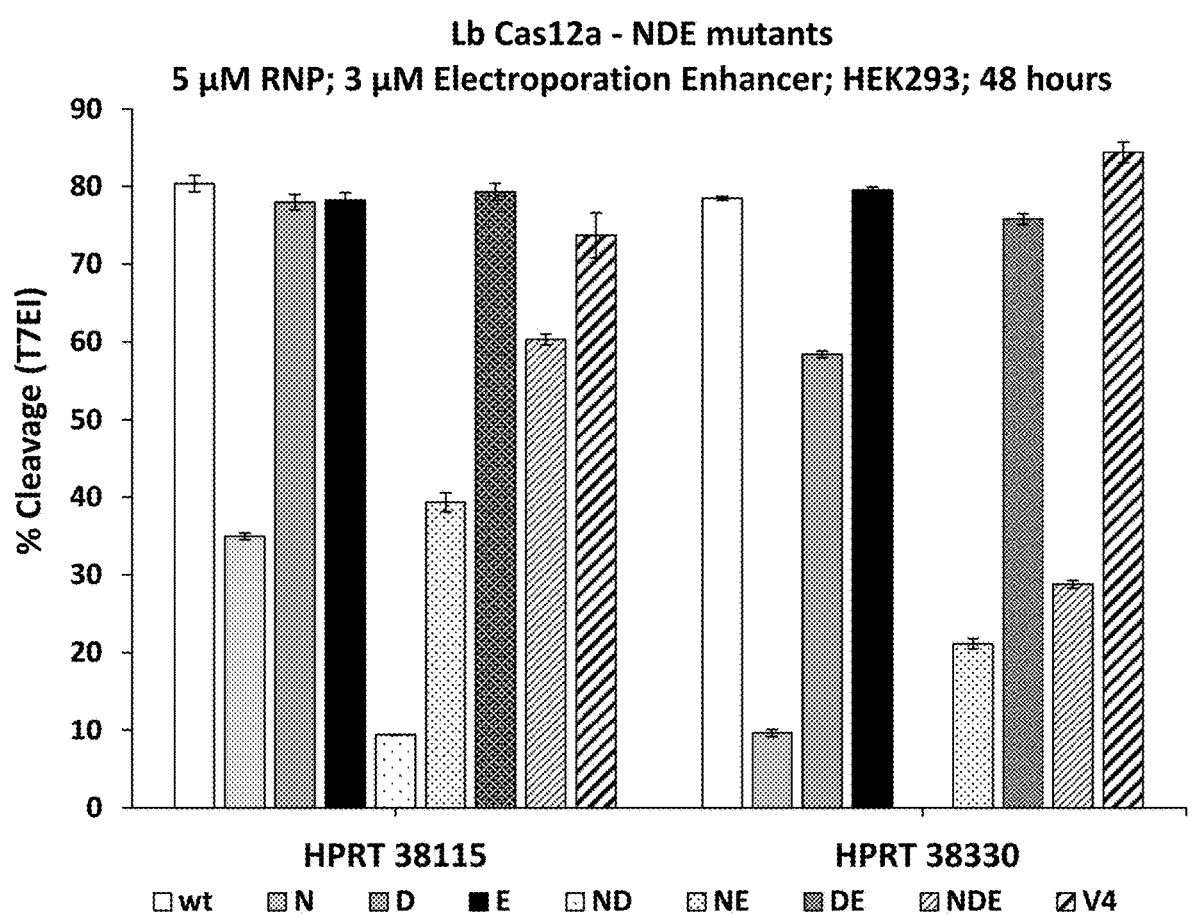

SEQUENCE LISTING

<160> NUMBER OF SEQ ID NOS: 73

<210> SEQ ID NO 1
<211> LENGTH: 3684
<212> TYPE: DNA
<213> ORGANISM: Unknown
<220> FEATURE:
<223> OTHER INFORMATION: Lachnospiraceae bacterium

<400> SEQUENCE: 1

| | | | | | |
|---|---|---|---|---|---|
| atgagcaaac | tggaaaagtt | caccaactgt | tatagcctga | gcaaaaccct | gcgttttaaa | 60 |
| gcaattccgg | ttggtaaaac | ccaagagaac | attgataata | aacgcctgct | ggtcgaagat | 120 |
| gaaaaacgcg | ctgaagatta | taaggcgtg | aaaaaactgc | tggatcgcta | ttatctgagc | 180 |
| ttcattaacg | atgtgctgca | cagcattaaa | ctgaagaacc | tgaacaacta | tatcagcctg | 240 |
| tttcgtaaaa | aaacccgcac | cgaaaaagaa | aacaaagagc | tggaaaacct | ggaaatcaat | 300 |
| ctgcgtaaag | aaatcgccaa | agcgtttaaa | ggtaacgagg | gttataaaag | cctgttcaag | 360 |
| aaagacatca | tcgaaaccat | tctgccggaa | tttctggatg | ataaagatga | aattgccctg | 420 |
| gtgaatagct | ttaatggctt | taccaccgca | tttaccggct | tttttgataa | tcgcgaaaac | 480 |
| atgttcagcg | aagaagcaaa | aagcaccagc | attgcatttc | gctgcattaa | tgaaaatctg | 540 |
| acccgctaca | ttagcaacat | ggatatcttt | gaaaaagtgg | acgcgatctt | cgataaacac | 600 |
| gaagtgcaag | agatcaaaga | gaaaatcctg | aacagcgatt | atgacgtcga | agatttttt | 660 |
| gaaggcgagt | tctttaactt | cgttctgacc | caagaaggta | tcgacgttta | taacgcaatt | 720 |
| attggtggtt | ttgttaccga | aagcggtgag | aaaatcaaag | gcctgaatga | atatatcaac | 780 |
| ctgtataacc | agaaaaccaa | acagaaactg | ccgaaattca | aaccgctgta | taaacaggtt | 840 |
| ctgagcgatc | gtgaaagcct | gagcttttat | ggtgaaggtt | ataccagtga | tgaagaggtt | 900 |
| ctggaagttt | ttcgtaacac | cctgaataaa | aacagcgaga | tctttagcag | catcaaaaag | 960 |
| cttgagaaac | tgttcaaaaa | cttttgatgag | tatagcagcg | caggcatctt | tgttaaaaat | 1020 |
| ggtccggcaa | ttagcaccat | cagcaaagat | atttttggcg | aatggaatgt | gatccgcgat | 1080 |
| aaatggaatg | ccgaatatga | tgatatccac | ctgaaaaaaa | aggccgtggt | gaccgagaaa | 1140 |
| tatgaagatg | atcgtcgtaa | aagcttcaag | aaaattggta | gctttagcct | ggaacagctg | 1200 |
| caagaatatg | cagatgcaga | tctgagcgtt | gtggaaaaac | tgaaagaaat | catcattcag | 1260 |
| aaggtggacg | agatctataa | agtttatggt | agcagcgaaa | aactgttcga | tgcagatttt | 1320 |
| gttctggaaa | aaagcctgaa | aaagaatgat | gccgttgtgg | ccattatgaa | agatctgctg | 1380 |
| gatagcgtta | agagcttcga | gaattacatc | aaagcctttt | ttggtgaggg | caaagaaacc | 1440 |
| aatcgtgatg | aaagtttcta | tggcgatttt | gtgctggcct | atgatattct | gctgaaagtg | 1500 |
| gaccatattt | atgatgccat | tcgcaattat | gttacccaga | accgtatag | caaagacaag | 1560 |
| ttcaaactgt | actttcagaa | cccgcagttt | atgggtggtt | gggataaaga | taaagaaacc | 1620 |
| gattatcgtg | ccaccatcct | gcgttatggt | agtaaatact | atctggccat | catggacaaa | 1680 |
| aaatacgcaa | aatgcctgca | gaaaatcgac | aaagatgatg | tgaatggcaa | ctatgaaaaa | 1740 |
| atcaactaca | aactgctgcc | tggtccgaat | aaaatgctgc | cgaaagtgtt | ctttagcaag | 1800 |
| aaatggatgg | cctattataa | cccgagcgag | gatattcaaa | agatctacaa | aaatggcacc | 1860 |
| tttaaaaagg | gcgacatgtt | caatctgaac | gattgccaca | aactgatcga | tttcttcaaa | 1920 |
| gattcaattt | cgcgttatcc | gaaatggtcc | aatgcctatg | attttaactt | tagcgaaacc | 1980 |
| gaaaaataca | aagacattgc | cggttttat | cgcgaagtgg | aagaacaggg | ctataaagtg | 2040 |

-continued

```
agctttgaaa gcgcaagcaa aaagaggtt gataagctgg ttgaagaggg caaactgtat      2100
atgttccaga tttacaacaa agattttagc gacaaaagcc atggcacccc gaatctgcat      2160
accatgtact ttaaactgct gttcgacgaa ataaccatg gtcagattcg tctgagcggt       2220
ggtgccgaac tgtttatgcg tcgtgcaagt ctgaaaaaag aagaactggt tgttcatccg      2280
gcaaatagcc cgattgcaaa caaaaatccg gacaatccga aaaaaccac gacactgagc       2340
tatgatgtgt ataaagacaa acgttttagc gaggatcagt atgaactgca tatcccgatt      2400
gccatcaata aatgcccgaa aaacatcttt aagatcaaca ccgaagttcg cgtgctgctg      2460
aaacatgatg ataatccgta tgtgattggc attgatcgtg gtgaacgtaa cctgctgtat      2520
attgttgttg ttgatggtaa aggcaacatc gtggaacagt atagtctgaa cgaaattatc      2580
aacaacttta acggcatccg catcaaaacc gactatcata gcctgctgga caagaaagaa      2640
aaagaacgtt ttgaagcacg tcagaactgg accagtattg aaaacatcaa gaactgaaa       2700
gccggttata ttagccaggt ggttcataaa atctgtgagc tggtagaaaa atacgatgca      2760
gttattgcac tggaagatct gaatagcggt ttcaaaaata gccgtgtgaa agtcgaaaaa      2820
caggtgtatc agaaattcga gaaatgctg atcgacaaac tgaactacat ggtcgacaaa       2880
aaaagcaatc cgtgtgcaac cggtggtgca ctgaaaggtt atcagattac caacaaattt      2940
gaaagcttta aaagcatgag cacccagaac ggctttatct tctatattcc ggcatggctg      3000
accagcaaaa ttgatccgag caccggtttt gtgaacctgc tgaaaacaaa atatacctcc      3060
attgccgaca gcaagaagtt tattagcagc tttgatcgca ttatgtatgt tccggaagag      3120
gacctgtttg aattcgcact ggattacaaa aatttcagcc gtaccgatgc cgactacatc      3180
aaaaaatgga aactgtacag ctatggtaac cgcattcgca tttttcgcaa cccgaagaaa      3240
aacaatgtgt tcgattggga agaagtttgt ctgaccagcg catataaaga acttttcaac      3300
aaatacggca tcaactatca gcagggtgat attcgtgcac tgctgtgtga acagagcgat      3360
aaagcgtttt atagcagttt tatggcactg atgagcctga tgctgcagat gcgtaatagc      3420
attaccggtc gcaccgatgt ggattttctg attagtccgg tgaaaaattc cgatggcatc      3480
ttttatgata gccgcaatta cgaagcacaa gaaaatgcaa ttctgccgaa aaacgcagat      3540
gcaaatggtg catataacat tgcacgtaaa gttctgtggg caattggcca gtttaagaaa      3600
gcagaagatg agaagctgga caaagtgaaa attgcgatca gcaataaaga gtggctggaa      3660
tacgcacaga ccagcgttaa acat                                             3684
```

<210> SEQ ID NO 2
<211> LENGTH: 1228
<212> TYPE: PRT
<213> ORGANISM: Unknown
<220> FEATURE:
<223> OTHER INFORMATION: Lachnospiraceae bacterium

<400> SEQUENCE: 2

```
Met Ser Lys Leu Glu Lys Phe Thr Asn Cys Tyr Ser Leu Ser Lys Thr
1               5                   10                  15

Leu Arg Phe Lys Ala Ile Pro Val Gly Lys Thr Gln Glu Asn Ile Asp
            20                  25                  30

Asn Lys Arg Leu Leu Val Glu Asp Glu Lys Arg Ala Glu Asp Tyr Lys
        35                  40                  45

Gly Val Lys Lys Leu Leu Asp Arg Tyr Tyr Leu Ser Phe Ile Asn Asp
    50                  55                  60
```

Val Leu His Ser Ile Lys Leu Lys Asn Leu Asn Asn Tyr Ile Ser Leu
65                  70                  75                  80

Phe Arg Lys Lys Thr Arg Thr Glu Lys Glu Asn Lys Glu Leu Glu Asn
            85                  90                  95

Leu Glu Ile Asn Leu Arg Lys Glu Ile Ala Lys Ala Phe Lys Gly Asn
            100                 105                 110

Glu Gly Tyr Lys Ser Leu Phe Lys Lys Asp Ile Ile Glu Thr Ile Leu
        115                 120                 125

Pro Glu Phe Leu Asp Asp Lys Asp Glu Ile Ala Leu Val Asn Ser Phe
    130                 135                 140

Asn Gly Phe Thr Thr Ala Phe Thr Gly Phe Phe Asp Asn Arg Glu Asn
145                 150                 155                 160

Met Phe Ser Glu Glu Ala Lys Ser Thr Ser Ile Ala Phe Arg Cys Ile
                165                 170                 175

Asn Glu Asn Leu Thr Arg Tyr Ile Ser Asn Met Asp Ile Phe Glu Lys
            180                 185                 190

Val Asp Ala Ile Phe Asp Lys His Glu Val Gln Glu Ile Lys Glu Lys
        195                 200                 205

Ile Leu Asn Ser Asp Tyr Asp Val Glu Asp Phe Phe Glu Gly Glu Phe
    210                 215                 220

Phe Asn Phe Val Leu Thr Gln Glu Gly Ile Asp Val Tyr Asn Ala Ile
225                 230                 235                 240

Ile Gly Gly Phe Val Thr Glu Ser Gly Glu Lys Ile Lys Gly Leu Asn
                245                 250                 255

Glu Tyr Ile Asn Leu Tyr Asn Gln Lys Thr Lys Gln Lys Leu Pro Lys
            260                 265                 270

Phe Lys Pro Leu Tyr Lys Gln Val Leu Ser Asp Arg Glu Ser Leu Ser
        275                 280                 285

Phe Tyr Gly Glu Gly Tyr Thr Ser Asp Glu Glu Val Leu Glu Val Phe
    290                 295                 300

Arg Asn Thr Leu Asn Lys Asn Ser Glu Ile Phe Ser Ser Ile Lys Lys
305                 310                 315                 320

Leu Glu Lys Leu Phe Lys Asn Phe Asp Glu Tyr Ser Ser Ala Gly Ile
                325                 330                 335

Phe Val Lys Asn Gly Pro Ala Ile Ser Thr Ile Ser Lys Asp Ile Phe
            340                 345                 350

Gly Glu Trp Asn Val Ile Arg Asp Lys Trp Asn Ala Glu Tyr Asp Asp
        355                 360                 365

Ile His Leu Lys Lys Lys Ala Val Val Thr Glu Lys Tyr Glu Asp Asp
    370                 375                 380

Arg Arg Lys Ser Phe Lys Lys Ile Gly Ser Phe Ser Leu Glu Gln Leu
385                 390                 395                 400

Gln Glu Tyr Ala Asp Ala Asp Leu Ser Val Val Glu Lys Leu Lys Glu
                405                 410                 415

Ile Ile Ile Gln Lys Val Asp Glu Ile Tyr Lys Val Tyr Gly Ser Ser
            420                 425                 430

Glu Lys Leu Phe Asp Ala Asp Phe Val Leu Glu Lys Ser Leu Lys Lys
        435                 440                 445

Asn Asp Ala Val Val Ala Ile Met Lys Asp Leu Leu Asp Ser Val Lys
    450                 455                 460

Ser Phe Glu Asn Tyr Ile Lys Ala Phe Phe Gly Glu Gly Lys Glu Thr
465                 470                 475                 480

Asn Arg Asp Glu Ser Phe Tyr Gly Asp Phe Val Leu Ala Tyr Asp Ile

```
                      485                 490                 495
Leu Leu Lys Val Asp His Ile Tyr Asp Ala Ile Arg Asn Tyr Val Thr
            500                 505                 510

Gln Lys Pro Tyr Ser Lys Asp Lys Phe Lys Leu Tyr Phe Gln Asn Pro
            515                 520                 525

Gln Phe Met Gly Gly Trp Asp Lys Asp Lys Glu Thr Asp Tyr Arg Ala
            530                 535                 540

Thr Ile Leu Arg Tyr Gly Ser Lys Tyr Tyr Leu Ala Ile Met Asp Lys
545                 550                 555                 560

Lys Tyr Ala Lys Cys Leu Gln Lys Ile Asp Lys Asp Val Asn Gly
                565                 570                 575

Asn Tyr Glu Lys Ile Asn Tyr Lys Leu Leu Pro Gly Pro Asn Lys Met
            580                 585                 590

Leu Pro Lys Val Phe Phe Ser Lys Lys Trp Met Ala Tyr Tyr Asn Pro
            595                 600                 605

Ser Glu Asp Ile Gln Lys Ile Tyr Lys Asn Gly Thr Phe Lys Lys Gly
            610                 615                 620

Asp Met Phe Asn Leu Asn Asp Cys His Lys Leu Ile Asp Phe Phe Lys
625                 630                 635                 640

Asp Ser Ile Ser Arg Tyr Pro Lys Trp Ser Asn Ala Tyr Asp Phe Asn
                645                 650                 655

Phe Ser Glu Thr Glu Lys Tyr Lys Asp Ile Ala Gly Phe Tyr Arg Glu
            660                 665                 670

Val Glu Glu Gln Gly Tyr Lys Val Ser Phe Glu Ser Ala Ser Lys Lys
            675                 680                 685

Glu Val Asp Lys Leu Val Glu Glu Gly Lys Leu Tyr Met Phe Gln Ile
690                 695                 700

Tyr Asn Lys Asp Phe Ser Asp Lys Ser His Gly Thr Pro Asn Leu His
705                 710                 715                 720

Thr Met Tyr Phe Lys Leu Leu Phe Asp Glu Asn Asn His Gly Gln Ile
                725                 730                 735

Arg Leu Ser Gly Gly Ala Glu Leu Phe Met Arg Arg Ala Ser Leu Lys
            740                 745                 750

Lys Glu Glu Leu Val Val His Pro Ala Asn Ser Pro Ile Ala Asn Lys
            755                 760                 765

Asn Pro Asp Asn Pro Lys Lys Thr Thr Thr Leu Ser Tyr Asp Val Tyr
            770                 775                 780

Lys Asp Lys Arg Phe Ser Glu Asp Gln Tyr Glu Leu His Ile Pro Ile
785                 790                 795                 800

Ala Ile Asn Lys Cys Pro Lys Asn Ile Phe Lys Ile Asn Thr Glu Val
                805                 810                 815

Arg Val Leu Leu Lys His Asp Asp Asn Pro Tyr Val Ile Gly Ile Asp
            820                 825                 830

Arg Gly Glu Arg Asn Leu Leu Tyr Ile Val Val Asp Gly Lys Gly
            835                 840                 845

Asn Ile Val Glu Gln Tyr Ser Leu Asn Glu Ile Ile Asn Asn Phe Asn
850                 855                 860

Gly Ile Arg Ile Lys Thr Asp Tyr His Ser Leu Leu Asp Lys Lys Glu
865                 870                 875                 880

Lys Glu Arg Phe Glu Ala Arg Gln Asn Trp Thr Ser Ile Glu Asn Ile
                885                 890                 895

Lys Glu Leu Lys Ala Gly Tyr Ile Ser Gln Val Val His Lys Ile Cys
            900                 905                 910
```

Glu Leu Val Glu Lys Tyr Asp Ala Val Ile Ala Leu Glu Asp Leu Asn
                915                 920                 925

Ser Gly Phe Lys Asn Ser Arg Val Lys Val Glu Lys Gln Val Tyr Gln
        930                 935                 940

Lys Phe Glu Lys Met Leu Ile Asp Lys Leu Asn Tyr Met Val Asp Lys
945                 950                 955                 960

Lys Ser Asn Pro Cys Ala Thr Gly Gly Ala Leu Lys Gly Tyr Gln Ile
                965                 970                 975

Thr Asn Lys Phe Glu Ser Phe Lys Ser Met Ser Thr Gln Asn Gly Phe
            980                 985                 990

Ile Phe Tyr Ile Pro Ala Trp Leu Thr Ser Lys Ile Asp Pro Ser Thr
        995                 1000                1005

Gly Phe Val Asn Leu Leu Lys Thr Lys Tyr Thr Ser Ile Ala Asp
    1010                1015                1020

Ser Lys Lys Phe Ile Ser Ser Phe Asp Arg Ile Met Tyr Val Pro
    1025                1030                1035

Glu Glu Asp Leu Phe Glu Phe Ala Leu Asp Tyr Lys Asn Phe Ser
    1040                1045                1050

Arg Thr Asp Ala Asp Tyr Ile Lys Lys Trp Lys Leu Tyr Ser Tyr
    1055                1060                1065

Gly Asn Arg Ile Arg Ile Phe Arg Asn Pro Lys Lys Asn Asn Val
    1070                1075                1080

Phe Asp Trp Glu Glu Val Cys Leu Thr Ser Ala Tyr Lys Glu Leu
    1085                1090                1095

Phe Asn Lys Tyr Gly Ile Asn Tyr Gln Gln Gly Asp Ile Arg Ala
    1100                1105                1110

Leu Leu Cys Glu Gln Ser Asp Lys Ala Phe Tyr Ser Ser Phe Met
    1115                1120                1125

Ala Leu Met Ser Leu Met Leu Gln Met Arg Asn Ser Ile Thr Gly
    1130                1135                1140

Arg Thr Asp Val Asp Phe Leu Ile Ser Pro Val Lys Asn Ser Asp
    1145                1150                1155

Gly Ile Phe Tyr Asp Ser Arg Asn Tyr Glu Ala Gln Glu Asn Ala
    1160                1165                1170

Ile Leu Pro Lys Asn Ala Asp Ala Asn Gly Ala Tyr Asn Ile Ala
    1175                1180                1185

Arg Lys Val Leu Trp Ala Ile Gly Gln Phe Lys Lys Ala Glu Asp
    1190                1195                1200

Glu Lys Leu Asp Lys Val Lys Ile Ala Ile Ser Asn Lys Glu Trp
    1205                1210                1215

Leu Glu Tyr Ala Gln Thr Ser Val Lys His
    1220                1225

<210> SEQ ID NO 3
<211> LENGTH: 1228
<212> TYPE: PRT
<213> ORGANISM: Artificial Sequence
<220> FEATURE:
<223> OTHER INFORMATION: Synthetic construct

<400> SEQUENCE: 3

Met Ser Lys Leu Glu Lys Phe Thr Asn Cys Tyr Ser Leu Ser Lys Thr
1               5                   10                  15

Leu Arg Phe Lys Ala Ile Pro Val Gly Lys Thr Gln Glu Asn Ile Asp
            20                  25                  30

```
Asn Lys Arg Leu Leu Val Glu Asp Glu Lys Arg Ala Glu Asp Tyr Lys
        35                  40                  45

Gly Val Lys Lys Leu Leu Asp Arg Tyr Tyr Leu Ser Phe Ile Asn Asp
 50                  55                  60

Val Leu His Ser Ile Lys Leu Lys Asn Leu Asn Asn Tyr Ile Ser Leu
 65                  70                  75                  80

Phe Arg Lys Lys Thr Arg Thr Glu Lys Glu Asn Lys Glu Leu Glu Asn
                85                  90                  95

Leu Glu Ile Asn Leu Arg Lys Glu Ile Ala Lys Ala Phe Lys Gly Asn
               100                 105                 110

Glu Gly Tyr Lys Ser Leu Phe Lys Lys Asp Ile Ile Glu Thr Ile Leu
               115                 120                 125

Pro Glu Phe Leu Asp Asp Lys Asp Glu Ile Ala Leu Val Asn Ser Phe
         130                 135                 140

Asn Gly Phe Thr Thr Ala Phe Thr Gly Phe Phe Asp Asn Arg Glu Asn
145                 150                 155                 160

Met Phe Ser Glu Glu Ala Lys Ser Thr Ser Ile Ala Phe Arg Cys Ile
                165                 170                 175

Asn Glu Asn Leu Thr Arg Tyr Ile Ser Asn Met Asp Ile Phe Glu Lys
              180                 185                 190

Val Asp Ala Ile Phe Asp Lys His Glu Val Gln Glu Ile Lys Glu Lys
              195                 200                 205

Ile Leu Asn Ser Asp Tyr Asp Val Glu Asp Phe Phe Glu Gly Glu Phe
      210                 215                 220

Phe Asn Phe Val Leu Thr Gln Glu Gly Ile Asp Val Tyr Asn Ala Ile
225                 230                 235                 240

Ile Gly Gly Phe Val Thr Glu Ser Gly Glu Lys Ile Lys Gly Leu Asn
                245                 250                 255

Glu Tyr Ile Asn Leu Tyr Asn Gln Lys Thr Lys Gln Lys Leu Pro Lys
              260                 265                 270

Phe Lys Pro Leu Tyr Lys Gln Val Leu Ser Asp Arg Glu Ser Leu Ser
      275                 280                 285

Phe Tyr Gly Glu Gly Tyr Thr Ser Asp Glu Glu Val Leu Glu Val Phe
290                 295                 300

Arg Asn Thr Leu Asn Lys Asn Ser Glu Ile Phe Ser Ser Ile Lys Lys
305                 310                 315                 320

Leu Glu Lys Leu Phe Lys Asn Phe Asp Glu Tyr Ser Ser Ala Gly Ile
                325                 330                 335

Phe Val Lys Asn Gly Pro Ala Ile Ser Thr Ile Ser Lys Asp Ile Phe
              340                 345                 350

Gly Glu Trp Asn Val Ile Arg Asp Lys Trp Asn Ala Glu Tyr Asp Asp
      355                 360                 365

Ile His Leu Lys Lys Lys Ala Val Val Thr Glu Lys Tyr Glu Asp Asp
370                 375                 380

Arg Arg Lys Ser Phe Lys Lys Ile Gly Ser Phe Ser Leu Glu Gln Leu
385                 390                 395                 400

Gln Glu Tyr Ala Asp Ala Asp Leu Ser Val Val Glu Lys Leu Lys Glu
                405                 410                 415

Ile Ile Ile Gln Lys Val Asp Glu Ile Tyr Lys Val Tyr Gly Ser Ser
              420                 425                 430

Glu Lys Leu Phe Asp Ala Asp Phe Val Leu Glu Lys Ser Leu Lys Lys
      435                 440                 445
```

```
Asn Asp Ala Val Val Ala Ile Met Lys Asp Leu Leu Asp Ser Val Lys
    450                 455                 460

Ser Phe Glu Asn Tyr Ile Lys Ala Phe Phe Gly Glu Gly Lys Glu Thr
465                 470                 475                 480

Asn Arg Asp Glu Ser Phe Tyr Gly Asp Phe Val Leu Ala Tyr Asp Ile
                485                 490                 495

Leu Leu Lys Val Asp His Ile Tyr Asp Ala Ile Arg Asn Tyr Val Thr
            500                 505                 510

Gln Lys Pro Tyr Ser Lys Asp Lys Phe Lys Leu Tyr Phe Gln Arg Pro
        515                 520                 525

Gln Phe Met Gly Gly Trp Asp Lys Asp Lys Glu Thr Asp Tyr Arg Ala
    530                 535                 540

Thr Ile Leu Arg Tyr Gly Ser Lys Tyr Tyr Leu Ala Ile Met Asp Lys
545                 550                 555                 560

Lys Tyr Ala Lys Cys Leu Gln Lys Ile Asp Lys Asp Val Asn Gly
                565                 570                 575

Asn Tyr Glu Lys Ile Asn Tyr Lys Leu Leu Pro Gly Pro Asn Lys Met
                580                 585                 590

Leu Pro Lys Val Phe Phe Ser Lys Lys Trp Met Ala Tyr Tyr Asn Pro
        595                 600                 605

Ser Glu Asp Ile Gln Lys Ile Tyr Lys Asn Gly Thr Phe Lys Lys Gly
    610                 615                 620

Asp Met Phe Asn Leu Asn Asp Cys His Lys Leu Ile Asp Phe Phe Lys
625                 630                 635                 640

Asp Ser Ile Ser Arg Tyr Pro Lys Trp Ser Asn Ala Tyr Asp Phe Asn
                645                 650                 655

Phe Ser Glu Thr Glu Lys Tyr Lys Asp Ile Ala Gly Phe Tyr Arg Glu
                660                 665                 670

Val Glu Glu Gln Gly Tyr Lys Val Ser Phe Glu Ser Ala Ser Lys Lys
            675                 680                 685

Glu Val Asp Lys Leu Val Glu Glu Gly Lys Leu Tyr Met Phe Gln Ile
    690                 695                 700

Tyr Asn Lys Asp Phe Ser Asp Lys Ser His Gly Thr Pro Asn Leu His
705                 710                 715                 720

Thr Met Tyr Phe Lys Leu Leu Phe Asp Glu Asn Asn His Gly Gln Ile
                725                 730                 735

Arg Leu Ser Gly Gly Ala Glu Leu Phe Met Arg Arg Ala Ser Leu Lys
            740                 745                 750

Lys Glu Glu Leu Val Val His Pro Ala Asn Ser Pro Ile Ala Asn Lys
    755                 760                 765

Asn Pro Asp Asn Pro Lys Lys Thr Thr Thr Leu Ser Tyr Asp Val Tyr
770                 775                 780

Lys Asp Lys Arg Phe Ser Glu Asp Gln Tyr Glu Leu His Ile Pro Ile
785                 790                 795                 800

Ala Ile Asn Lys Cys Pro Lys Asn Ile Phe Lys Ile Asn Thr Glu Val
                805                 810                 815

Arg Val Leu Leu Lys His Asp Asp Asn Pro Tyr Val Ile Gly Ile Asp
            820                 825                 830

Arg Gly Glu Arg Asn Leu Leu Tyr Ile Val Val Asp Gly Lys Gly
        835                 840                 845

Asn Ile Val Glu Gln Tyr Ser Leu Asn Glu Ile Asn Asn Phe Asn
    850                 855                 860

Gly Ile Arg Ile Lys Thr Asp Tyr His Ser Leu Leu Asp Lys Lys Glu
```

```
                865                 870                 875                 880
        Lys Glu Arg Phe Glu Ala Arg Gln Asn Trp Thr Ser Ile Glu Asn Ile
                        885                 890                 895

Lys Glu Leu Lys Ala Gly Tyr Ile Ser Gln Val Val His Lys Ile Cys
                    900                 905                 910

Glu Leu Val Glu Lys Tyr Asp Ala Val Ile Ala Leu Glu Asp Leu Asn
                    915                 920                 925

Ser Gly Phe Lys Asn Ser Arg Val Lys Val Lys Gln Val Tyr Gln
                930                 935                 940

Lys Phe Glu Lys Met Leu Ile Asp Lys Leu Asn Tyr Met Val Asp Lys
        945                 950                 955                 960

Lys Ser Asn Pro Cys Ala Thr Gly Gly Ala Leu Lys Gly Tyr Gln Ile
                        965                 970                 975

Thr Asn Lys Phe Glu Ser Phe Lys Ser Met Ser Thr Gln Asn Gly Phe
                        980                 985                 990

Ile Phe Tyr Ile Pro Ala Trp Leu Thr Ser Lys Ile Asp Pro Ser Thr
                    995                 1000                1005

Gly Phe Val Asn Leu Leu Lys Thr Lys Tyr Thr Ser Ile Ala Asp
            1010                1015                1020

Ser Lys Lys Phe Ile Ser Ser Phe Asp Arg Ile Met Tyr Val Pro
            1025                1030                1035

Glu Glu Asp Leu Phe Glu Phe Ala Leu Asp Tyr Lys Asn Phe Ser
            1040                1045                1050

Arg Thr Asp Ala Asp Tyr Ile Lys Lys Trp Lys Leu Tyr Ser Tyr
            1055                1060                1065

Gly Asn Arg Ile Arg Ile Phe Arg Asn Pro Lys Lys Asn Asn Val
            1070                1075                1080

Phe Asp Trp Glu Glu Val Cys Leu Thr Ser Ala Tyr Lys Glu Leu
            1085                1090                1095

Phe Asn Lys Tyr Gly Ile Asn Tyr Gln Gln Gly Asp Ile Arg Ala
            1100                1105                1110

Leu Leu Cys Glu Gln Ser Asp Lys Ala Phe Tyr Ser Ser Phe Met
            1115                1120                1125

Ala Leu Met Ser Leu Met Leu Gln Met Arg Asn Ser Ile Thr Gly
            1130                1135                1140

Arg Thr Asp Val Asp Phe Leu Ile Ser Pro Val Lys Asn Ser Asp
            1145                1150                1155

Gly Ile Phe Tyr Asp Ser Arg Asn Tyr Glu Ala Gln Glu Asn Ala
            1160                1165                1170

Ile Leu Pro Lys Asn Ala Asp Ala Asn Gly Ala Tyr Asn Ile Ala
            1175                1180                1185

Arg Lys Val Leu Trp Ala Ile Gly Gln Phe Lys Lys Ala Glu Asp
            1190                1195                1200

Glu Lys Leu Asp Lys Val Lys Ile Ala Ile Ser Asn Lys Glu Trp
            1205                1210                1215

Leu Glu Tyr Ala Gln Thr Ser Val Lys His
            1220                1225

<210> SEQ ID NO 4
<211> LENGTH: 1228
<212> TYPE: PRT
<213> ORGANISM: Artificial sequence
<220> FEATURE:
<223> OTHER INFORMATION: Synthetic construct
```

<400> SEQUENCE: 4

```
Met Ser Lys Leu Glu Lys Phe Thr Asn Cys Tyr Ser Leu Ser Lys Thr
1               5                   10                  15
Leu Arg Phe Lys Ala Ile Pro Val Gly Lys Thr Gln Glu Asn Ile Asp
            20                  25                  30
Asn Lys Arg Leu Leu Val Glu Asp Glu Lys Arg Ala Glu Asp Tyr Lys
        35                  40                  45
Gly Val Lys Lys Leu Leu Asp Arg Tyr Tyr Leu Ser Phe Ile Asn Asp
50                  55                  60
Val Leu His Ser Ile Lys Leu Lys Asn Leu Asn Asn Tyr Ile Ser Leu
65                  70                  75                  80
Phe Arg Lys Lys Thr Arg Thr Glu Lys Glu Asn Lys Glu Leu Glu Asn
                85                  90                  95
Leu Glu Ile Asn Leu Arg Lys Glu Ile Ala Lys Ala Phe Lys Gly Asn
            100                 105                 110
Glu Gly Tyr Lys Ser Leu Phe Lys Lys Asp Ile Ile Glu Thr Ile Leu
        115                 120                 125
Pro Glu Phe Leu Asp Asp Lys Asp Glu Ile Ala Leu Val Asn Ser Phe
130                 135                 140
Asn Gly Phe Thr Thr Ala Phe Thr Gly Phe Phe Asp Asn Arg Glu Asn
145                 150                 155                 160
Met Phe Ser Glu Glu Ala Lys Ser Thr Ser Ile Ala Phe Arg Cys Ile
                165                 170                 175
Asn Glu Asn Leu Thr Arg Tyr Ile Ser Asn Met Asp Ile Phe Glu Lys
            180                 185                 190
Val Asp Ala Ile Phe Asp Lys His Glu Val Gln Glu Ile Lys Glu Lys
        195                 200                 205
Ile Leu Asn Ser Asp Tyr Asp Val Glu Asp Phe Phe Glu Gly Glu Phe
210                 215                 220
Phe Asn Phe Val Leu Thr Gln Glu Gly Ile Asp Val Tyr Asn Ala Ile
225                 230                 235                 240
Ile Gly Gly Phe Val Thr Glu Ser Gly Glu Lys Ile Lys Gly Leu Asn
                245                 250                 255
Glu Tyr Ile Asn Leu Tyr Asn Gln Lys Thr Lys Gln Lys Leu Pro Lys
            260                 265                 270
Phe Lys Pro Leu Tyr Lys Gln Val Leu Ser Asp Arg Glu Ser Leu Ser
        275                 280                 285
Phe Tyr Gly Glu Gly Tyr Thr Ser Asp Glu Glu Val Leu Glu Val Phe
290                 295                 300
Arg Asn Thr Leu Asn Lys Asn Ser Glu Ile Phe Ser Ser Ile Lys Lys
305                 310                 315                 320
Leu Glu Lys Leu Phe Lys Asn Phe Asp Glu Tyr Ser Ser Ala Gly Ile
                325                 330                 335
Phe Val Lys Asn Gly Pro Ala Ile Ser Thr Ile Ser Lys Asp Ile Phe
            340                 345                 350
Gly Glu Trp Asn Val Ile Arg Asp Lys Trp Asn Ala Glu Tyr Asp Asp
        355                 360                 365
Ile His Leu Lys Lys Lys Ala Val Val Thr Glu Lys Tyr Glu Asp Asp
370                 375                 380
Arg Arg Lys Ser Phe Lys Lys Ile Gly Ser Phe Ser Leu Glu Gln Leu
385                 390                 395                 400
Gln Glu Tyr Ala Asp Ala Asp Leu Ser Val Val Glu Lys Leu Lys Glu
                405                 410                 415
```

```
Ile Ile Ile Gln Lys Val Asp Glu Ile Tyr Lys Val Tyr Gly Ser Ser
            420             425             430

Glu Lys Leu Phe Asp Ala Asp Phe Val Leu Glu Lys Ser Leu Lys Lys
            435             440             445

Asn Asp Ala Val Val Ala Ile Met Lys Asp Leu Leu Asp Ser Val Lys
            450             455             460

Ser Phe Glu Asn Tyr Ile Lys Ala Phe Phe Gly Glu Gly Lys Glu Thr
465             470             475             480

Asn Arg Asp Glu Ser Phe Tyr Gly Asp Phe Val Leu Ala Tyr Asp Ile
            485             490             495

Leu Leu Lys Val Asp His Ile Tyr Asp Ala Ile Arg Asn Tyr Val Thr
            500             505             510

Gln Lys Pro Tyr Ser Lys Asp Lys Phe Lys Leu Tyr Phe Gln Asn Pro
            515             520             525

Gln Phe Met Gly Gly Trp Asp Lys Asp Lys Glu Thr Asp Tyr Arg Ala
            530             535             540

Thr Ile Leu Arg Tyr Gly Ser Lys Tyr Tyr Leu Ala Ile Met Pro Lys
545             550             555             560

Lys Tyr Ala Lys Cys Leu Gln Lys Ile Asp Lys Asp Val Asn Gly
            565             570             575

Asn Tyr Glu Lys Ile Asn Tyr Lys Leu Leu Pro Gly Pro Asn Lys Met
            580             585             590

Leu Pro Lys Val Phe Phe Ser Lys Lys Trp Met Ala Tyr Tyr Asn Pro
            595             600             605

Ser Glu Asp Ile Gln Lys Ile Tyr Lys Asn Gly Thr Phe Lys Lys Gly
            610             615             620

Asp Met Phe Asn Leu Asn Asp Cys His Lys Leu Ile Asp Phe Phe Lys
625             630             635             640

Asp Ser Ile Ser Arg Tyr Pro Lys Trp Ser Asn Ala Tyr Asp Phe Asn
            645             650             655

Phe Ser Glu Thr Glu Lys Tyr Lys Asp Ile Ala Gly Phe Tyr Arg Glu
            660             665             670

Val Glu Glu Gln Gly Tyr Lys Val Ser Phe Glu Ser Ala Ser Lys Lys
            675             680             685

Glu Val Asp Lys Leu Val Glu Glu Gly Lys Leu Tyr Met Phe Gln Ile
            690             695             700

Tyr Asn Lys Asp Phe Ser Asp Lys Ser His Gly Thr Pro Asn Leu His
705             710             715             720

Thr Met Tyr Phe Lys Leu Leu Phe Asp Glu Asn Asn His Gly Gln Ile
            725             730             735

Arg Leu Ser Gly Gly Ala Glu Leu Phe Met Arg Arg Ala Ser Leu Lys
            740             745             750

Lys Glu Glu Leu Val Val His Pro Ala Asn Ser Pro Ile Ala Asn Lys
            755             760             765

Asn Pro Asp Asn Pro Lys Lys Thr Thr Thr Leu Ser Tyr Asp Val Tyr
            770             775             780

Lys Asp Lys Arg Phe Ser Glu Asp Gln Tyr Glu Leu His Ile Pro Ile
785             790             795             800

Ala Ile Asn Lys Cys Pro Lys Asn Ile Phe Lys Ile Asn Thr Glu Val
            805             810             815

Arg Val Leu Leu Lys His Asp Asp Asn Pro Tyr Val Ile Gly Ile Asp
            820             825             830
```

-continued

```
Arg Gly Glu Arg Asn Leu Leu Tyr Ile Val Val Asp Gly Lys Gly
            835                 840                 845

Asn Ile Val Glu Gln Tyr Ser Leu Asn Glu Ile Asn Asn Phe Asn
850                 855                 860

Gly Ile Arg Ile Lys Thr Asp Tyr His Ser Leu Leu Asp Lys Lys Glu
865                 870                 875                 880

Lys Glu Arg Phe Glu Ala Arg Gln Asn Trp Thr Ser Ile Glu Asn Ile
                885                 890                 895

Lys Glu Leu Lys Ala Gly Tyr Ile Ser Gln Val Val His Lys Ile Cys
                900                 905                 910

Glu Leu Val Glu Lys Tyr Asp Ala Val Ile Ala Leu Glu Asp Leu Asn
                915                 920                 925

Ser Gly Phe Lys Asn Ser Arg Val Lys Val Glu Lys Gln Val Tyr Gln
930                 935                 940

Lys Phe Glu Lys Met Leu Ile Asp Lys Leu Asn Tyr Met Val Asp Lys
945                 950                 955                 960

Lys Ser Asn Pro Cys Ala Thr Gly Gly Ala Leu Lys Gly Tyr Gln Ile
                965                 970                 975

Thr Asn Lys Phe Glu Ser Phe Lys Ser Met Ser Thr Gln Asn Gly Phe
                980                 985                 990

Ile Phe Tyr Ile Pro Ala Trp Leu Thr Ser Lys Ile Asp Pro Ser Thr
                995                1000                1005

Gly Phe Val Asn Leu Leu Lys Thr Lys Tyr Thr Ser Ile Ala Asp
                1010                1015                1020

Ser Lys Lys Phe Ile Ser Ser Phe Asp Arg Ile Met Tyr Val Pro
                1025                1030                1035

Glu Glu Asp Leu Phe Glu Phe Ala Leu Asp Tyr Lys Asn Phe Ser
                1040                1045                1050

Arg Thr Asp Ala Asp Tyr Ile Lys Lys Trp Lys Leu Tyr Ser Tyr
                1055                1060                1065

Gly Asn Arg Ile Arg Ile Phe Arg Asn Pro Lys Lys Asn Asn Val
                1070                1075                1080

Phe Asp Trp Glu Glu Val Cys Leu Thr Ser Ala Tyr Lys Glu Leu
                1085                1090                1095

Phe Asn Lys Tyr Gly Ile Asn Tyr Gln Gln Gly Asp Ile Arg Ala
                1100                1105                1110

Leu Leu Cys Glu Gln Ser Asp Lys Ala Phe Tyr Ser Ser Phe Met
                1115                1120                1125

Ala Leu Met Ser Leu Met Leu Gln Met Arg Asn Ser Ile Thr Gly
                1130                1135                1140

Arg Thr Asp Val Asp Phe Leu Ile Ser Pro Val Lys Asn Ser Asp
                1145                1150                1155

Gly Ile Phe Tyr Asp Ser Arg Asn Tyr Glu Ala Gln Glu Asn Ala
                1160                1165                1170

Ile Leu Pro Lys Asn Ala Asp Ala Asn Gly Ala Tyr Asn Ile Ala
                1175                1180                1185

Arg Lys Val Leu Trp Ala Ile Gly Gln Phe Lys Lys Ala Glu Asp
                1190                1195                1200

Glu Lys Leu Asp Lys Val Lys Ile Ala Ile Ser Asn Lys Glu Trp
                1205                1210                1215

Leu Glu Tyr Ala Gln Thr Ser Val Lys His
                1220                1225
```

<210> SEQ ID NO 5
<211> LENGTH: 1228
<212> TYPE: PRT
<213> ORGANISM: Artificial sequence
<220> FEATURE:
<223> OTHER INFORMATION: Synthetic construct

<400> SEQUENCE: 5

```
Met Ser Lys Leu Glu Lys Phe Thr Asn Cys Tyr Ser Leu Ser Lys Thr
1               5                   10                  15

Leu Arg Phe Lys Ala Ile Pro Val Gly Lys Thr Gln Glu Asn Ile Asp
            20                  25                  30

Asn Lys Arg Leu Leu Val Glu Asp Glu Lys Arg Ala Glu Asp Tyr Lys
        35                  40                  45

Gly Val Lys Lys Leu Leu Asp Arg Tyr Tyr Leu Ser Phe Ile Asn Asp
    50                  55                  60

Val Leu His Ser Ile Lys Leu Lys Asn Leu Asn Asn Tyr Ile Ser Leu
65                  70                  75                  80

Phe Arg Lys Lys Thr Arg Thr Glu Lys Glu Asn Lys Glu Leu Glu Asn
                85                  90                  95

Leu Glu Ile Asn Leu Arg Lys Glu Ile Ala Lys Ala Phe Lys Gly Asn
            100                 105                 110

Glu Gly Tyr Lys Ser Leu Phe Lys Lys Asp Ile Ile Glu Thr Ile Leu
        115                 120                 125

Pro Glu Phe Leu Asp Asp Lys Asp Glu Ile Ala Leu Val Asn Ser Phe
    130                 135                 140

Asn Gly Phe Thr Thr Ala Phe Thr Gly Phe Phe Asp Asn Arg Glu Asn
145                 150                 155                 160

Met Phe Ser Glu Glu Ala Lys Ser Thr Ser Ile Ala Phe Arg Cys Ile
                165                 170                 175

Asn Glu Asn Leu Thr Arg Tyr Ile Ser Asn Met Asp Ile Phe Glu Lys
            180                 185                 190

Val Asp Ala Ile Phe Asp Lys His Glu Val Gln Glu Ile Lys Glu Lys
        195                 200                 205

Ile Leu Asn Ser Asp Tyr Asp Val Glu Asp Phe Phe Glu Gly Glu Phe
    210                 215                 220

Phe Asn Phe Val Leu Thr Gln Glu Gly Ile Asp Val Tyr Asn Ala Ile
225                 230                 235                 240

Ile Gly Gly Phe Val Thr Glu Ser Gly Glu Lys Ile Lys Gly Leu Asn
                245                 250                 255

Glu Tyr Ile Asn Leu Tyr Asn Gln Lys Thr Lys Gln Lys Leu Pro Lys
            260                 265                 270

Phe Lys Pro Leu Tyr Lys Gln Val Leu Ser Asp Arg Glu Ser Leu Ser
        275                 280                 285

Phe Tyr Gly Glu Gly Tyr Thr Ser Asp Glu Val Leu Glu Val Phe
    290                 295                 300

Arg Asn Thr Leu Asn Lys Asn Ser Glu Ile Phe Ser Ser Ile Lys Lys
305                 310                 315                 320

Leu Glu Lys Leu Phe Lys Asn Phe Asp Glu Tyr Ser Ser Ala Gly Ile
                325                 330                 335

Phe Val Lys Asn Gly Pro Ala Ile Ser Thr Ile Ser Lys Asp Ile Phe
            340                 345                 350

Gly Glu Trp Asn Val Ile Arg Asp Lys Trp Asn Ala Glu Tyr Asp Asp
        355                 360                 365

Ile His Leu Lys Lys Lys Ala Val Val Thr Glu Lys Tyr Glu Asp Asp
```

-continued

```
                370                 375                 380
Arg Arg Lys Ser Phe Lys Lys Ile Gly Ser Phe Ser Leu Glu Gln Leu
385                 390                 395                 400

Gln Glu Tyr Ala Asp Ala Asp Leu Ser Val Val Glu Lys Leu Lys Glu
                405                 410                 415

Ile Ile Ile Gln Lys Val Asp Glu Ile Tyr Lys Val Tyr Gly Ser Ser
                420                 425                 430

Glu Lys Leu Phe Asp Ala Asp Phe Val Leu Glu Lys Ser Leu Lys Lys
                435                 440                 445

Asn Asp Ala Val Val Ala Ile Met Lys Asp Leu Leu Asp Ser Val Lys
450                 455                 460

Ser Phe Glu Asn Tyr Ile Lys Ala Phe Phe Gly Glu Gly Lys Glu Thr
465                 470                 475                 480

Asn Arg Asp Glu Ser Phe Tyr Gly Asp Phe Val Leu Ala Tyr Asp Ile
                485                 490                 495

Leu Leu Lys Val Asp His Ile Tyr Asp Ala Ile Arg Asn Tyr Val Thr
                500                 505                 510

Gln Lys Pro Tyr Ser Lys Asp Lys Phe Lys Leu Tyr Phe Gln Asn Pro
                515                 520                 525

Gln Phe Met Gly Gly Trp Asp Lys Asp Lys Glu Thr Asp Tyr Arg Ala
530                 535                 540

Thr Ile Leu Arg Tyr Gly Ser Lys Tyr Tyr Leu Ala Ile Met Asp Lys
545                 550                 555                 560

Lys Tyr Ala Lys Cys Leu Gln Lys Ile Asp Lys Asp Asp Val Asn Gly
                565                 570                 575

Asn Tyr Glu Lys Ile Asn Tyr Lys Leu Leu Pro Gly Pro Asn Lys Met
                580                 585                 590

Leu Pro Lys Val Phe Phe Ser Lys Trp Met Ala Tyr Tyr Asn Pro
                595                 600                 605

Ser Glu Asp Ile Gln Lys Ile Tyr Lys Asn Gly Thr Phe Lys Lys Gly
                610                 615                 620

Asp Met Phe Asn Leu Asn Asp Cys His Lys Leu Ile Asp Phe Phe Lys
625                 630                 635                 640

Asp Ser Ile Ser Arg Tyr Pro Lys Trp Ser Asn Ala Tyr Asp Phe Asn
                645                 650                 655

Phe Ser Glu Thr Glu Lys Tyr Lys Asp Ile Ala Gly Phe Tyr Arg Glu
                660                 665                 670

Val Glu Glu Gln Gly Tyr Lys Val Ser Phe Glu Ser Ala Ser Lys Lys
                675                 680                 685

Glu Val Asp Lys Leu Val Glu Glu Gly Lys Leu Tyr Met Phe Gln Ile
690                 695                 700

Tyr Asn Lys Asp Phe Ser Asp Lys Ser His Gly Thr Pro Asn Leu His
705                 710                 715                 720

Thr Met Tyr Phe Lys Leu Leu Phe Asp Glu Asn Asn His Gly Gln Ile
                725                 730                 735

Arg Leu Ser Gly Gly Ala Glu Leu Phe Met Arg Arg Ala Ser Leu Lys
                740                 745                 750

Lys Glu Glu Leu Val Val His Pro Ala Asn Ser Pro Ile Ala Asn Lys
                755                 760                 765

Asn Pro Asp Asn Pro Lys Lys Thr Thr Thr Leu Ser Tyr Asp Val Tyr
                770                 775                 780

Lys Asp Lys Arg Phe Ser Glu Asp Gln Tyr Leu Leu His Ile Pro Ile
785                 790                 795                 800
```

```
Ala Ile Asn Lys Cys Pro Lys Asn Ile Phe Lys Ile Asn Thr Glu Val
            805                 810                 815

Arg Val Leu Leu Lys His Asp Asp Asn Pro Tyr Val Ile Gly Ile Asp
            820                 825                 830

Arg Gly Glu Arg Asn Leu Leu Tyr Ile Val Val Asp Gly Lys Gly
            835                 840             845

Asn Ile Val Glu Gln Tyr Ser Leu Asn Glu Ile Ile Asn Asn Phe Asn
850                 855                 860

Gly Ile Arg Ile Lys Thr Asp Tyr His Ser Leu Leu Asp Lys Lys Glu
865                 870                 875                 880

Lys Glu Arg Phe Glu Ala Arg Gln Asn Trp Thr Ser Ile Glu Asn Ile
            885                 890                 895

Lys Glu Leu Lys Ala Gly Tyr Ile Ser Gln Val Val His Lys Ile Cys
            900                 905                 910

Glu Leu Val Glu Lys Tyr Asp Ala Val Ile Ala Leu Glu Asp Leu Asn
            915                 920                 925

Ser Gly Phe Lys Asn Ser Arg Val Lys Val Glu Lys Gln Val Tyr Gln
930                 935                 940

Lys Phe Glu Lys Met Leu Ile Asp Lys Leu Asn Tyr Met Val Asp Lys
945                 950                 955                 960

Lys Ser Asn Pro Cys Ala Thr Gly Gly Ala Leu Lys Gly Tyr Gln Ile
            965                 970                 975

Thr Asn Lys Phe Glu Ser Phe Lys Ser Met Ser Thr Gln Asn Gly Phe
            980                 985                 990

Ile Phe Tyr Ile Pro Ala Trp Leu Thr Ser Lys Ile Asp Pro Ser Thr
            995                 1000                1005

Gly Phe Val Asn Leu Leu Lys Thr Lys Tyr Thr Ser Ile Ala Asp
    1010                1015                1020

Ser Lys Lys Phe Ile Ser Ser Phe Asp Arg Ile Met Tyr Val Pro
    1025                1030                1035

Glu Glu Asp Leu Phe Glu Phe Ala Leu Asp Tyr Lys Asn Phe Ser
    1040                1045                1050

Arg Thr Asp Ala Asp Tyr Ile Lys Lys Trp Lys Leu Tyr Ser Tyr
    1055                1060                1065

Gly Asn Arg Ile Arg Ile Phe Arg Asn Pro Lys Lys Asn Asn Val
    1070                1075                1080

Phe Asp Trp Glu Glu Val Cys Leu Thr Ser Ala Tyr Lys Glu Leu
    1085                1090                1095

Phe Asn Lys Tyr Gly Ile Asn Tyr Gln Gln Gly Asp Ile Arg Ala
    1100                1105                1110

Leu Leu Cys Glu Gln Ser Asp Lys Ala Phe Tyr Ser Ser Phe Met
    1115                1120                1125

Ala Leu Met Ser Leu Met Leu Gln Met Arg Asn Ser Ile Thr Gly
    1130                1135                1140

Arg Thr Asp Val Asp Phe Leu Ile Ser Pro Val Lys Asn Ser Asp
    1145                1150                1155

Gly Ile Phe Tyr Asp Ser Arg Asn Tyr Glu Ala Gln Glu Asn Ala
    1160                1165                1170

Ile Leu Pro Lys Asn Ala Asp Ala Asn Gly Ala Tyr Asn Ile Ala
    1175                1180                1185

Arg Lys Val Leu Trp Ala Ile Gly Gln Phe Lys Lys Ala Glu Asp
    1190                1195                1200
```

-continued

```
Glu Lys Leu Asp Lys Val Lys Ile Ala Ile Ser Asn Lys Glu Trp
    1205                1210                1215

Leu Glu Tyr Ala Gln Thr Ser Val Lys His
    1220                1225

<210> SEQ ID NO 6
<211> LENGTH: 1228
<212> TYPE: PRT
<213> ORGANISM: Artificial sequence
<220> FEATURE:
<223> OTHER INFORMATION: Synthetic construct

<400> SEQUENCE: 6

Met Ser Lys Leu Glu Lys Phe Thr Asn Cys Tyr Ser Leu Ser Lys Thr
1               5                   10                  15

Leu Arg Phe Lys Ala Ile Pro Val Gly Lys Thr Gln Glu Asn Ile Asp
            20                  25                  30

Asn Lys Arg Leu Leu Val Glu Asp Glu Lys Arg Ala Glu Asp Tyr Lys
        35                  40                  45

Gly Val Lys Lys Leu Leu Asp Arg Tyr Tyr Leu Ser Phe Ile Asn Asp
    50                  55                  60

Val Leu His Ser Ile Lys Leu Lys Asn Leu Asn Asn Tyr Ile Ser Leu
65                  70                  75                  80

Phe Arg Lys Lys Thr Arg Thr Glu Lys Glu Asn Lys Glu Leu Glu Asn
                85                  90                  95

Leu Glu Ile Asn Leu Arg Lys Glu Ile Ala Lys Ala Phe Lys Gly Asn
            100                 105                 110

Glu Gly Tyr Lys Ser Leu Phe Lys Lys Asp Ile Ile Glu Thr Ile Leu
        115                 120                 125

Pro Glu Phe Leu Asp Asp Lys Asp Glu Ile Ala Leu Val Asn Ser Phe
    130                 135                 140

Asn Gly Phe Thr Thr Ala Phe Thr Gly Phe Phe Asp Asn Arg Glu Asn
145                 150                 155                 160

Met Phe Ser Glu Glu Ala Lys Ser Thr Ser Ile Ala Phe Arg Cys Ile
                165                 170                 175

Asn Glu Asn Leu Thr Arg Tyr Ile Ser Asn Met Asp Ile Phe Glu Lys
            180                 185                 190

Val Asp Ala Ile Phe Asp Lys His Glu Val Gln Glu Ile Lys Glu Lys
        195                 200                 205

Ile Leu Asn Ser Asp Tyr Asp Val Glu Asp Phe Phe Glu Gly Glu Phe
    210                 215                 220

Phe Asn Phe Val Leu Thr Gln Glu Gly Ile Asp Val Tyr Asn Ala Ile
225                 230                 235                 240

Ile Gly Gly Phe Val Thr Glu Ser Gly Glu Lys Ile Lys Gly Leu Asn
                245                 250                 255

Glu Tyr Ile Asn Leu Tyr Asn Gln Lys Thr Lys Gln Lys Leu Pro Lys
            260                 265                 270

Phe Lys Pro Leu Tyr Lys Gln Val Leu Ser Asp Arg Glu Ser Leu Ser
        275                 280                 285

Phe Tyr Gly Glu Gly Tyr Thr Ser Asp Glu Glu Val Leu Glu Val Phe
    290                 295                 300

Arg Asn Thr Leu Asn Lys Asn Ser Glu Ile Phe Ser Ser Ile Lys Lys
305                 310                 315                 320

Leu Glu Lys Leu Phe Lys Asn Phe Asp Glu Tyr Ser Ser Ala Gly Ile
                325                 330                 335
```

```
Phe Val Lys Asn Gly Pro Ala Ile Ser Thr Ile Ser Lys Asp Ile Phe
                340                 345                 350

Gly Glu Trp Asn Val Ile Arg Asp Lys Trp Asn Ala Glu Tyr Asp Asp
            355                 360                 365

Ile His Leu Lys Lys Lys Ala Val Val Thr Glu Lys Tyr Glu Asp Asp
        370                 375                 380

Arg Arg Lys Ser Phe Lys Lys Ile Gly Ser Phe Ser Leu Glu Gln Leu
385                 390                 395                 400

Gln Glu Tyr Ala Asp Ala Asp Leu Ser Val Glu Lys Leu Lys Glu
                405                 410                 415

Ile Ile Ile Gln Lys Val Asp Glu Ile Tyr Lys Val Tyr Gly Ser Ser
                420                 425                 430

Glu Lys Leu Phe Asp Ala Asp Phe Val Leu Glu Lys Ser Leu Lys Lys
            435                 440                 445

Asn Asp Ala Val Val Ala Ile Met Lys Asp Leu Leu Asp Ser Val Lys
        450                 455                 460

Ser Phe Glu Asn Tyr Ile Lys Ala Phe Phe Gly Glu Gly Lys Glu Thr
465                 470                 475                 480

Asn Arg Asp Glu Ser Phe Tyr Gly Asp Phe Val Leu Ala Tyr Asp Ile
                485                 490                 495

Leu Leu Lys Val Asp His Ile Tyr Asp Ala Ile Arg Asn Tyr Val Thr
                500                 505                 510

Gln Lys Pro Tyr Ser Lys Asp Lys Phe Lys Leu Tyr Phe Gln Arg Pro
            515                 520                 525

Gln Phe Met Gly Gly Trp Asp Lys Asp Lys Glu Thr Asp Tyr Arg Ala
        530                 535                 540

Thr Ile Leu Arg Tyr Gly Ser Lys Tyr Tyr Leu Ala Ile Met Pro Lys
545                 550                 555                 560

Lys Tyr Ala Lys Cys Leu Gln Lys Ile Asp Lys Asp Val Asn Gly
                565                 570                 575

Asn Tyr Glu Lys Ile Asn Tyr Lys Leu Leu Pro Gly Pro Asn Lys Met
            580                 585                 590

Leu Pro Lys Val Phe Phe Ser Lys Lys Trp Met Ala Tyr Tyr Asn Pro
        595                 600                 605

Ser Glu Asp Ile Gln Lys Ile Tyr Lys Asn Gly Thr Phe Lys Lys Gly
    610                 615                 620

Asp Met Phe Asn Leu Asn Asp Cys His Lys Leu Ile Asp Phe Phe Lys
625                 630                 635                 640

Asp Ser Ile Ser Arg Tyr Pro Lys Trp Ser Asn Ala Tyr Asp Phe Asn
                645                 650                 655

Phe Ser Glu Thr Glu Lys Tyr Lys Asp Ile Ala Gly Phe Tyr Arg Glu
            660                 665                 670

Val Glu Glu Gln Gly Tyr Lys Val Ser Phe Glu Ser Ala Ser Lys Lys
        675                 680                 685

Glu Val Asp Lys Leu Val Glu Glu Gly Lys Leu Tyr Met Phe Gln Ile
    690                 695                 700

Tyr Asn Lys Asp Phe Ser Asp Lys Ser His Gly Thr Pro Asn Leu His
705                 710                 715                 720

Thr Met Tyr Phe Lys Leu Leu Phe Asp Glu Asn Asn His Gly Gln Ile
                725                 730                 735

Arg Leu Ser Gly Gly Ala Glu Leu Phe Met Arg Arg Ala Ser Leu Lys
            740                 745                 750

Lys Glu Glu Leu Val Val His Pro Ala Asn Ser Pro Ile Ala Asn Lys
```

```
               755                 760                 765
Asn Pro Asp Asn Pro Lys Lys Thr Thr Thr Leu Ser Tyr Asp Val Tyr
770                 775                 780

Lys Asp Lys Arg Phe Ser Glu Asp Gln Tyr Glu Leu His Ile Pro Ile
785                 790                 795                 800

Ala Ile Asn Lys Cys Pro Lys Asn Ile Phe Lys Ile Asn Thr Glu Val
                    805                 810                 815

Arg Val Leu Leu Lys His Asp Asp Asn Pro Tyr Val Ile Gly Ile Asp
                820                 825                 830

Arg Gly Glu Arg Asn Leu Leu Tyr Ile Val Val Asp Gly Lys Gly
            835                 840                 845

Asn Ile Val Glu Gln Tyr Ser Leu Asn Glu Ile Ile Asn Asn Phe Asn
850                 855                 860

Gly Ile Arg Ile Lys Thr Asp Tyr His Ser Leu Leu Asp Lys Lys Glu
865                 870                 875                 880

Lys Glu Arg Phe Glu Ala Arg Gln Asn Trp Thr Ser Ile Glu Asn Ile
                885                 890                 895

Lys Glu Leu Lys Ala Gly Tyr Ile Ser Gln Val Val His Lys Ile Cys
            900                 905                 910

Glu Leu Val Glu Lys Tyr Asp Ala Val Ile Ala Leu Glu Asp Leu Asn
            915                 920                 925

Ser Gly Phe Lys Asn Ser Arg Val Lys Val Lys Gln Val Tyr Gln
930                 935                 940

Lys Phe Glu Lys Met Leu Ile Asp Lys Leu Asn Tyr Met Val Asp Lys
945                 950                 955                 960

Lys Ser Asn Pro Cys Ala Thr Gly Gly Ala Leu Lys Gly Tyr Gln Ile
                965                 970                 975

Thr Asn Lys Phe Glu Ser Phe Lys Ser Met Ser Thr Asn Gly Phe
            980                 985                 990

Ile Phe Tyr Ile Pro Ala Trp Leu Thr Ser Lys Ile Asp Pro Ser Thr
            995                 1000                1005

Gly Phe Val Asn Leu Leu Lys Thr Lys Tyr Thr Ser Ile Ala Asp
    1010                1015                1020

Ser Lys Lys Phe Ile Ser Ser Phe Asp Arg Ile Met Tyr Val Pro
    1025                1030                1035

Glu Glu Asp Leu Phe Glu Phe Ala Leu Asp Tyr Lys Asn Phe Ser
    1040                1045                1050

Arg Thr Asp Ala Asp Tyr Ile Lys Lys Trp Lys Leu Tyr Ser Tyr
    1055                1060                1065

Gly Asn Arg Ile Arg Ile Phe Arg Asn Pro Lys Lys Asn Asn Val
    1070                1075                1080

Phe Asp Trp Glu Glu Val Cys Leu Thr Ser Ala Tyr Lys Glu Leu
    1085                1090                1095

Phe Asn Lys Tyr Gly Ile Asn Tyr Gln Gln Gly Asp Ile Arg Ala
    1100                1105                1110

Leu Leu Cys Glu Gln Ser Asp Lys Ala Phe Tyr Ser Ser Phe Met
    1115                1120                1125

Ala Leu Met Ser Leu Met Leu Gln Met Arg Asn Ser Ile Thr Gly
    1130                1135                1140

Arg Thr Asp Val Asp Phe Leu Ile Ser Pro Val Lys Asn Ser Asp
    1145                1150                1155

Gly Ile Phe Tyr Asp Ser Arg Asn Tyr Glu Ala Gln Glu Asn Ala
    1160                1165                1170
```

```
Ile Leu Pro Lys Asn Ala Asp Ala Asn Gly Ala Tyr Asn Ile Ala
    1175                1180                1185

Arg Lys Val Leu Trp Ala Ile Gly Gln Phe Lys Ala Glu Asp
    1190                1195                1200

Glu Lys Leu Asp Lys Val Lys Ile Ala Ile Ser Asn Lys Glu Trp
    1205                1210                1215

Leu Glu Tyr Ala Gln Thr Ser Val Lys His
    1220                1225

<210> SEQ ID NO 7
<211> LENGTH: 1228
<212> TYPE: PRT
<213> ORGANISM: Artificial sequence
<220> FEATURE:
<223> OTHER INFORMATION: Synthetic construct

<400> SEQUENCE: 7

Met Ser Lys Leu Glu Lys Phe Thr Asn Cys Tyr Ser Leu Ser Lys Thr
1               5                   10                  15

Leu Arg Phe Lys Ala Ile Pro Val Gly Lys Thr Gln Glu Asn Ile Asp
            20                  25                  30

Asn Lys Arg Leu Leu Val Glu Asp Glu Lys Arg Ala Glu Asp Tyr Lys
        35                  40                  45

Gly Val Lys Lys Leu Leu Asp Arg Tyr Tyr Leu Ser Phe Ile Asn Asp
    50                  55                  60

Val Leu His Ser Ile Lys Leu Lys Asn Leu Asn Asn Tyr Ile Ser Leu
65                  70                  75                  80

Phe Arg Lys Lys Thr Arg Thr Glu Lys Glu Asn Lys Glu Leu Glu Asn
                85                  90                  95

Leu Glu Ile Asn Leu Arg Lys Glu Ile Ala Lys Ala Phe Lys Gly Asn
            100                 105                 110

Glu Gly Tyr Lys Ser Leu Phe Lys Lys Asp Ile Ile Glu Thr Ile Leu
        115                 120                 125

Pro Glu Phe Leu Asp Asp Lys Asp Glu Ile Ala Leu Val Asn Ser Phe
    130                 135                 140

Asn Gly Phe Thr Thr Ala Phe Thr Gly Phe Phe Asp Asn Arg Glu Asn
145                 150                 155                 160

Met Phe Ser Glu Glu Ala Lys Ser Thr Ser Ile Ala Phe Arg Cys Ile
                165                 170                 175

Asn Glu Asn Leu Thr Arg Tyr Ile Ser Asn Met Asp Ile Phe Glu Lys
            180                 185                 190

Val Asp Ala Ile Phe Asp Lys His Glu Val Gln Glu Ile Lys Glu Lys
        195                 200                 205

Ile Leu Asn Ser Asp Tyr Asp Val Glu Asp Phe Phe Glu Gly Glu Phe
    210                 215                 220

Phe Asn Phe Val Leu Thr Gln Glu Gly Ile Asp Val Tyr Asn Ala Ile
225                 230                 235                 240

Ile Gly Gly Phe Val Thr Glu Ser Gly Glu Lys Ile Lys Gly Leu Asn
                245                 250                 255

Glu Tyr Ile Asn Leu Tyr Asn Gln Lys Thr Lys Gln Lys Leu Pro Lys
            260                 265                 270

Phe Lys Pro Leu Tyr Lys Gln Val Leu Ser Asp Arg Glu Ser Leu Ser
        275                 280                 285

Phe Tyr Gly Glu Gly Tyr Thr Ser Asp Glu Glu Val Leu Glu Val Phe
    290                 295                 300
```

```
Arg Asn Thr Leu Asn Lys Asn Ser Glu Ile Phe Ser Ile Lys Lys
305                 310                 315                 320

Leu Glu Lys Leu Phe Lys Asn Phe Asp Glu Tyr Ser Ser Ala Gly Ile
                325                 330                 335

Phe Val Lys Asn Gly Pro Ala Ile Ser Thr Ile Ser Lys Asp Ile Phe
            340                 345                 350

Gly Glu Trp Asn Val Ile Arg Asp Lys Trp Asn Ala Glu Tyr Asp Asp
        355                 360                 365

Ile His Leu Lys Lys Lys Ala Val Val Thr Glu Lys Tyr Glu Asp Asp
    370                 375                 380

Arg Arg Lys Ser Phe Lys Lys Ile Gly Ser Phe Ser Leu Glu Gln Leu
385                 390                 395                 400

Gln Glu Tyr Ala Asp Ala Asp Leu Ser Val Val Glu Lys Leu Lys Glu
                405                 410                 415

Ile Ile Ile Gln Lys Val Asp Glu Ile Tyr Lys Val Tyr Gly Ser Ser
            420                 425                 430

Glu Lys Leu Phe Asp Ala Asp Phe Val Leu Glu Lys Ser Leu Lys Lys
        435                 440                 445

Asn Asp Ala Val Val Ala Ile Met Lys Asp Leu Leu Asp Ser Val Lys
    450                 455                 460

Ser Phe Glu Asn Tyr Ile Lys Ala Phe Phe Gly Glu Gly Lys Glu Thr
465                 470                 475                 480

Asn Arg Asp Glu Ser Phe Tyr Gly Asp Phe Val Leu Ala Tyr Asp Ile
                485                 490                 495

Leu Leu Lys Val Asp His Ile Tyr Asp Ala Ile Arg Asn Tyr Val Thr
            500                 505                 510

Gln Lys Pro Tyr Ser Lys Asp Lys Phe Lys Leu Tyr Phe Gln Arg Pro
        515                 520                 525

Gln Phe Met Gly Gly Trp Asp Lys Asp Lys Glu Thr Asp Tyr Arg Ala
    530                 535                 540

Thr Ile Leu Arg Tyr Gly Ser Lys Tyr Tyr Leu Ala Ile Met Asp Lys
545                 550                 555                 560

Lys Tyr Ala Lys Cys Leu Gln Lys Ile Asp Lys Asp Asp Val Asn Gly
                565                 570                 575

Asn Tyr Glu Lys Ile Asn Tyr Lys Leu Leu Pro Gly Pro Asn Lys Met
            580                 585                 590

Leu Pro Lys Val Phe Phe Ser Lys Lys Trp Met Ala Tyr Tyr Asn Pro
        595                 600                 605

Ser Glu Asp Ile Gln Lys Ile Tyr Lys Asn Gly Thr Phe Lys Lys Gly
    610                 615                 620

Asp Met Phe Asn Leu Asn Asp Cys His Lys Leu Ile Asp Phe Phe Lys
625                 630                 635                 640

Asp Ser Ile Ser Arg Tyr Pro Lys Trp Ser Asn Ala Tyr Asp Phe Asn
                645                 650                 655

Phe Ser Glu Thr Glu Lys Tyr Lys Asp Ile Ala Gly Phe Tyr Arg Glu
            660                 665                 670

Val Glu Glu Gln Gly Tyr Lys Val Ser Phe Glu Ser Ala Ser Lys Lys
        675                 680                 685

Glu Val Asp Lys Leu Val Glu Gly Lys Leu Tyr Met Phe Gln Ile
    690                 695                 700

Tyr Asn Lys Asp Phe Ser Asp Lys Ser His Gly Thr Pro Asn Leu His
705                 710                 715                 720
```

-continued

```
Thr Met Tyr Phe Lys Leu Leu Phe Asp Glu Asn Asn His Gly Gln Ile
            725                 730                 735
Arg Leu Ser Gly Gly Ala Glu Leu Phe Met Arg Arg Ala Ser Leu Lys
        740                 745                 750
Lys Glu Glu Leu Val Val His Pro Ala Asn Ser Pro Ile Ala Asn Lys
    755                 760                 765
Asn Pro Asp Asn Pro Lys Lys Thr Thr Thr Leu Ser Tyr Asp Val Tyr
770                 775                 780
Lys Asp Lys Arg Phe Ser Glu Asp Gln Tyr Leu His Ile Pro Ile
785                 790                 795                 800
Ala Ile Asn Lys Cys Pro Lys Asn Ile Phe Lys Ile Asn Thr Glu Val
                805                 810                 815
Arg Val Leu Leu Lys His Asp Asp Asn Pro Tyr Val Ile Gly Ile Asp
            820                 825                 830
Arg Gly Glu Arg Asn Leu Leu Tyr Ile Val Val Asp Gly Lys Gly
        835                 840                 845
Asn Ile Val Glu Gln Tyr Ser Leu Asn Glu Ile Ile Asn Asn Phe Asn
    850                 855                 860
Gly Ile Arg Ile Lys Thr Asp Tyr His Ser Leu Leu Asp Lys Lys Glu
865                 870                 875                 880
Lys Glu Arg Phe Glu Ala Arg Gln Asn Trp Thr Ser Ile Glu Asn Ile
                885                 890                 895
Lys Glu Leu Lys Ala Gly Tyr Ile Ser Gln Val Val His Lys Ile Cys
            900                 905                 910
Glu Leu Val Glu Lys Tyr Asp Ala Val Ile Ala Leu Glu Asp Leu Asn
        915                 920                 925
Ser Gly Phe Lys Asn Ser Arg Val Lys Val Glu Lys Gln Val Tyr Gln
    930                 935                 940
Lys Phe Glu Lys Met Leu Ile Asp Lys Leu Asn Tyr Met Val Asp Lys
945                 950                 955                 960
Lys Ser Asn Pro Cys Ala Thr Gly Gly Ala Leu Lys Gly Tyr Gln Ile
                965                 970                 975
Thr Asn Lys Phe Glu Ser Phe Lys Ser Met Ser Thr Gln Asn Gly Phe
            980                 985                 990
Ile Phe Tyr Ile Pro Ala Trp Leu Thr Ser Lys Ile Asp Pro Ser Thr
        995                 1000                1005
Gly Phe Val Asn Leu Leu Lys Thr Lys Tyr Thr Ser Ile Ala Asp
    1010                1015                1020
Ser Lys Lys Phe Ile Ser Ser Phe Asp Arg Ile Met Tyr Val Pro
    1025                1030                1035
Glu Glu Asp Leu Phe Glu Phe Ala Leu Asp Tyr Lys Asn Phe Ser
    1040                1045                1050
Arg Thr Asp Ala Asp Tyr Ile Lys Lys Trp Lys Leu Tyr Ser Tyr
    1055                1060                1065
Gly Asn Arg Ile Arg Ile Phe Arg Asn Pro Lys Lys Asn Asn Val
    1070                1075                1080
Phe Asp Trp Glu Glu Val Cys Leu Thr Ser Ala Tyr Lys Glu Leu
    1085                1090                1095
Phe Asn Lys Tyr Gly Ile Asn Tyr Gln Gln Gly Asp Ile Arg Ala
    1100                1105                1110
Leu Leu Cys Glu Gln Ser Asp Lys Ala Phe Tyr Ser Ser Phe Met
    1115                1120                1125
Ala Leu Met Ser Leu Met Leu Gln Met Arg Asn Ser Ile Thr Gly
```

```
                    1130                1135                1140

Arg Thr Asp Val Asp Phe Leu Ile Ser Pro Val Lys Asn Ser Asp
            1145                1150                1155

Gly Ile Phe Tyr Asp Ser Arg Asn Tyr Glu Ala Gln Glu Asn Ala
            1160                1165                1170

Ile Leu Pro Lys Asn Ala Asp Ala Asn Gly Ala Tyr Asn Ile Ala
            1175                1180                1185

Arg Lys Val Leu Trp Ala Ile Gly Gln Phe Lys Lys Ala Glu Asp
            1190                1195                1200

Glu Lys Leu Asp Lys Val Lys Ile Ala Ile Ser Asn Lys Glu Trp
            1205                1210                1215

Leu Glu Tyr Ala Gln Thr Ser Val Lys His
            1220                1225

<210> SEQ ID NO 8
<211> LENGTH: 1228
<212> TYPE: PRT
<213> ORGANISM: Artificial sequence
<220> FEATURE:
<223> OTHER INFORMATION: Synthetic construct

<400> SEQUENCE: 8

Met Ser Lys Leu Glu Lys Phe Thr Asn Cys Tyr Ser Leu Ser Lys Thr
1               5                   10                  15

Leu Arg Phe Lys Ala Ile Pro Val Gly Lys Thr Gln Glu Asn Ile Asp
                20                  25                  30

Asn Lys Arg Leu Leu Val Glu Asp Glu Lys Arg Ala Glu Asp Tyr Lys
            35                  40                  45

Gly Val Lys Lys Leu Leu Asp Arg Tyr Tyr Leu Ser Phe Ile Asn Asp
        50                  55                  60

Val Leu His Ser Ile Lys Leu Lys Asn Leu Asn Asn Tyr Ile Ser Leu
65                  70                  75                  80

Phe Arg Lys Lys Thr Arg Thr Glu Lys Glu Asn Lys Glu Leu Glu Asn
                85                  90                  95

Leu Glu Ile Asn Leu Arg Lys Glu Ile Ala Lys Ala Phe Lys Gly Asn
                100                 105                 110

Glu Gly Tyr Lys Ser Leu Phe Lys Lys Asp Ile Ile Glu Thr Ile Leu
            115                 120                 125

Pro Glu Phe Leu Asp Asp Lys Asp Glu Ile Ala Leu Val Asn Ser Phe
        130                 135                 140

Asn Gly Phe Thr Thr Ala Phe Thr Gly Phe Phe Asp Asn Arg Glu Asn
145                 150                 155                 160

Met Phe Ser Glu Glu Ala Lys Ser Thr Ser Ile Ala Phe Arg Cys Ile
                165                 170                 175

Asn Glu Asn Leu Thr Arg Tyr Ile Ser Asn Met Asp Ile Phe Glu Lys
                180                 185                 190

Val Asp Ala Ile Phe Asp Lys His Glu Val Gln Glu Ile Lys Glu Lys
            195                 200                 205

Ile Leu Asn Ser Asp Tyr Asp Val Glu Asp Phe Phe Glu Gly Glu Phe
        210                 215                 220

Phe Asn Phe Val Leu Thr Gln Glu Gly Ile Asp Val Tyr Asn Ala Ile
225                 230                 235                 240

Ile Gly Gly Phe Val Thr Glu Ser Gly Glu Lys Ile Lys Gly Leu Asn
                245                 250                 255

Glu Tyr Ile Asn Leu Tyr Asn Gln Lys Thr Lys Gln Lys Leu Pro Lys
```

```
                260                 265                 270
Phe Lys Pro Leu Tyr Lys Gln Val Leu Ser Asp Arg Glu Ser Leu Ser
            275                 280                 285
Phe Tyr Gly Glu Gly Tyr Thr Ser Asp Glu Val Leu Glu Val Phe
        290                 295                 300
Arg Asn Thr Leu Asn Lys Asn Ser Glu Ile Phe Ser Ser Ile Lys Lys
305                 310                 315                 320
Leu Glu Lys Leu Phe Lys Asn Phe Asp Glu Tyr Ser Ser Ala Gly Ile
                325                 330                 335
Phe Val Lys Asn Gly Pro Ala Ile Ser Thr Ile Ser Lys Asp Ile Phe
            340                 345                 350
Gly Glu Trp Asn Val Ile Arg Asp Lys Trp Asn Ala Glu Tyr Asp Asp
        355                 360                 365
Ile His Leu Lys Lys Lys Ala Val Val Thr Glu Lys Tyr Glu Asp Asp
        370                 375                 380
Arg Arg Lys Ser Phe Lys Lys Ile Gly Ser Phe Ser Leu Glu Gln Leu
385                 390                 395                 400
Gln Glu Tyr Ala Asp Ala Asp Leu Ser Val Val Glu Lys Leu Lys Glu
                405                 410                 415
Ile Ile Ile Gln Lys Val Asp Glu Ile Tyr Lys Val Tyr Gly Ser Ser
                420                 425                 430
Glu Lys Leu Phe Asp Ala Asp Phe Val Leu Glu Lys Ser Leu Lys Lys
            435                 440                 445
Asn Asp Ala Val Val Ala Ile Met Lys Asp Leu Leu Asp Ser Val Lys
        450                 455                 460
Ser Phe Glu Asn Tyr Ile Lys Ala Phe Phe Gly Glu Gly Lys Glu Thr
465                 470                 475                 480
Asn Arg Asp Glu Ser Phe Tyr Gly Asp Phe Val Leu Ala Tyr Asp Ile
                485                 490                 495
Leu Leu Lys Val Asp His Ile Tyr Asp Ala Ile Arg Asn Tyr Val Thr
            500                 505                 510
Gln Lys Pro Tyr Ser Lys Asp Lys Phe Lys Leu Tyr Phe Gln Asn Pro
        515                 520                 525
Gln Phe Met Gly Gly Trp Asp Lys Asp Lys Glu Thr Asp Tyr Arg Ala
        530                 535                 540
Thr Ile Leu Arg Tyr Gly Ser Lys Tyr Tyr Leu Ala Ile Met Pro Lys
545                 550                 555                 560
Lys Tyr Ala Lys Cys Leu Gln Lys Ile Asp Lys Asp Val Asn Gly
                565                 570                 575
Asn Tyr Glu Lys Ile Asn Tyr Lys Leu Leu Pro Gly Pro Asn Lys Met
            580                 585                 590
Leu Pro Lys Val Phe Phe Ser Lys Trp Met Ala Tyr Tyr Asn Pro
        595                 600                 605
Ser Glu Asp Ile Gln Lys Ile Tyr Lys Asn Gly Thr Phe Lys Lys Gly
        610                 615                 620
Asp Met Phe Asn Leu Asn Asp Cys His Lys Leu Ile Asp Phe Phe Lys
625                 630                 635                 640
Asp Ser Ile Ser Arg Tyr Pro Lys Trp Ser Asn Ala Tyr Asp Phe Asn
                645                 650                 655
Phe Ser Glu Thr Glu Lys Tyr Lys Asp Ile Ala Gly Phe Tyr Arg Glu
            660                 665                 670
Val Glu Glu Gln Gly Tyr Lys Val Ser Phe Glu Ser Ala Ser Lys Lys
        675                 680                 685
```

```
Glu Val Asp Lys Leu Val Glu Gly Lys Leu Tyr Met Phe Gln Ile
    690             695             700
Tyr Asn Lys Asp Phe Ser Asp Lys Ser His Gly Thr Pro Asn Leu His
705             710             715                         720
Thr Met Tyr Phe Lys Leu Leu Phe Asp Glu Asn Asn His Gly Gln Ile
                725             730                 735
Arg Leu Ser Gly Gly Ala Glu Leu Phe Met Arg Arg Ala Ser Leu Lys
            740             745             750
Lys Glu Glu Leu Val Val His Pro Ala Asn Ser Pro Ile Ala Asn Lys
        755             760             765
Asn Pro Asp Asn Pro Lys Lys Thr Thr Thr Leu Ser Tyr Asp Val Tyr
770             775             780
Lys Asp Lys Arg Phe Ser Glu Asp Gln Tyr Leu Leu His Ile Pro Ile
785             790             795                         800
Ala Ile Asn Lys Cys Pro Lys Asn Ile Phe Lys Ile Asn Thr Glu Val
                805             810             815
Arg Val Leu Leu Lys His Asp Asp Asn Pro Tyr Val Ile Gly Ile Asp
            820             825             830
Arg Gly Glu Arg Asn Leu Leu Tyr Ile Val Val Val Asp Gly Lys Gly
        835             840             845
Asn Ile Val Glu Gln Tyr Ser Leu Asn Glu Ile Ile Asn Asn Phe Asn
850             855             860
Gly Ile Arg Ile Lys Thr Asp Tyr His Ser Leu Leu Asp Lys Lys Glu
865             870             875                         880
Lys Glu Arg Phe Glu Ala Arg Gln Asn Trp Thr Ser Ile Glu Asn Ile
                885             890             895
Lys Glu Leu Lys Ala Gly Tyr Ile Ser Gln Val Val His Lys Ile Cys
            900             905             910
Glu Leu Val Glu Lys Tyr Asp Ala Val Ile Ala Leu Glu Asp Leu Asn
        915             920             925
Ser Gly Phe Lys Asn Ser Arg Val Lys Val Glu Lys Gln Val Tyr Gln
930             935             940
Lys Phe Glu Lys Met Leu Ile Asp Lys Leu Asn Tyr Met Val Asp Lys
945             950             955             960
Lys Ser Asn Pro Cys Ala Thr Gly Gly Ala Leu Lys Gly Tyr Gln Ile
                965             970             975
Thr Asn Lys Phe Glu Ser Phe Lys Ser Met Ser Thr Gln Asn Gly Phe
            980             985             990
Ile Phe Tyr Ile Pro Ala Trp Leu Thr Ser Lys Ile Asp Pro Ser Thr
        995             1000            1005
Gly Phe Val Asn Leu Leu Lys Thr Lys Tyr Thr Ser Ile Ala Asp
    1010            1015            1020
Ser Lys Lys Phe Ile Ser Ser Phe Asp Arg Ile Met Tyr Val Pro
    1025            1030            1035
Glu Glu Asp Leu Phe Glu Phe Ala Leu Asp Tyr Lys Asn Phe Ser
    1040            1045            1050
Arg Thr Asp Ala Asp Tyr Ile Lys Lys Trp Lys Leu Tyr Ser Tyr
    1055            1060            1065
Gly Asn Arg Ile Arg Ile Phe Arg Asn Pro Lys Lys Asn Asn Val
    1070            1075            1080
Phe Asp Trp Glu Glu Val Cys Leu Thr Ser Ala Tyr Lys Glu Leu
    1085            1090            1095
```

```
Phe Asn Lys Tyr Gly Ile Asn Tyr Gln Gln Gly Asp Ile Arg Ala
    1100                1105                1110

Leu Leu Cys Glu Gln Ser Asp Lys Ala Phe Tyr Ser Ser Phe Met
    1115                1120                1125

Ala Leu Met Ser Leu Met Leu Gln Met Arg Asn Ser Ile Thr Gly
    1130                1135                1140

Arg Thr Asp Val Asp Phe Leu Ile Ser Pro Val Lys Asn Ser Asp
    1145                1150                1155

Gly Ile Phe Tyr Asp Ser Arg Asn Tyr Glu Ala Gln Glu Asn Ala
    1160                1165                1170

Ile Leu Pro Lys Asn Ala Asp Ala Asn Gly Ala Tyr Asn Ile Ala
    1175                1180                1185

Arg Lys Val Leu Trp Ala Ile Gly Gln Phe Lys Lys Ala Glu Asp
    1190                1195                1200

Glu Lys Leu Asp Lys Val Lys Ile Ala Ile Ser Asn Lys Glu Trp
    1205                1210                1215

Leu Glu Tyr Ala Gln Thr Ser Val Lys His
    1220                1225
```

<210> SEQ ID NO 9
<211> LENGTH: 1228
<212> TYPE: PRT
<213> ORGANISM: Artificial sequence
<220> FEATURE:
<223> OTHER INFORMATION: Synthetic construct

<400> SEQUENCE: 9

```
Met Ser Lys Leu Glu Lys Phe Thr Asn Cys Tyr Ser Leu Ser Lys Thr
1               5                   10                  15

Leu Arg Phe Lys Ala Ile Pro Val Gly Lys Thr Gln Glu Asn Ile Asp
                20                  25                  30

Asn Lys Arg Leu Leu Val Glu Asp Glu Lys Arg Ala Glu Asp Tyr Lys
            35                  40                  45

Gly Val Lys Lys Leu Leu Asp Arg Tyr Tyr Leu Ser Phe Ile Asn Asp
        50                  55                  60

Val Leu His Ser Ile Lys Leu Lys Asn Leu Asn Asn Tyr Ile Ser Leu
65                  70                  75                  80

Phe Arg Lys Lys Thr Arg Thr Glu Lys Glu Asn Lys Glu Leu Glu Asn
                85                  90                  95

Leu Glu Ile Asn Leu Arg Lys Glu Ile Ala Lys Ala Phe Lys Gly Asn
                100                 105                 110

Glu Gly Tyr Lys Ser Leu Phe Lys Lys Asp Ile Ile Glu Thr Ile Leu
            115                 120                 125

Pro Glu Phe Leu Asp Asp Lys Asp Glu Ile Ala Leu Val Asn Ser Phe
        130                 135                 140

Asn Gly Phe Thr Thr Ala Phe Thr Gly Phe Phe Asp Asn Arg Glu Asn
145                 150                 155                 160

Met Phe Ser Glu Glu Ala Lys Ser Thr Ser Ile Ala Phe Arg Cys Ile
                165                 170                 175

Asn Glu Asn Leu Thr Arg Tyr Ile Ser Asn Met Asp Ile Phe Glu Lys
            180                 185                 190

Val Asp Ala Ile Phe Asp Lys His Glu Val Gln Glu Ile Lys Glu Lys
        195                 200                 205

Ile Leu Asn Ser Asp Tyr Asp Val Glu Asp Phe Phe Glu Gly Glu Phe
        210                 215                 220
```

```
Phe Asn Phe Val Leu Thr Gln Glu Gly Ile Asp Val Tyr Asn Ala Ile
225                 230                 235                 240

Ile Gly Gly Phe Val Thr Glu Ser Gly Glu Lys Ile Lys Gly Leu Asn
                245                 250                 255

Glu Tyr Ile Asn Leu Tyr Asn Gln Lys Thr Lys Gln Lys Leu Pro Lys
            260                 265                 270

Phe Lys Pro Leu Tyr Lys Gln Val Leu Ser Asp Arg Glu Ser Leu Ser
        275                 280                 285

Phe Tyr Gly Glu Gly Tyr Thr Ser Asp Glu Glu Val Leu Glu Val Phe
    290                 295                 300

Arg Asn Thr Leu Asn Lys Asn Ser Glu Ile Phe Ser Ser Ile Lys Lys
305                 310                 315                 320

Leu Glu Lys Leu Phe Lys Asn Phe Asp Glu Tyr Ser Ser Ala Gly Ile
                325                 330                 335

Phe Val Lys Asn Gly Pro Ala Ile Ser Thr Ile Ser Lys Asp Ile Phe
            340                 345                 350

Gly Glu Trp Asn Val Ile Arg Asp Lys Trp Asn Ala Glu Tyr Asp Asp
        355                 360                 365

Ile His Leu Lys Lys Lys Ala Val Val Thr Glu Lys Tyr Glu Asp Asp
    370                 375                 380

Arg Arg Lys Ser Phe Lys Lys Ile Gly Ser Phe Ser Leu Glu Gln Leu
385                 390                 395                 400

Gln Glu Tyr Ala Asp Ala Asp Leu Ser Val Val Glu Lys Leu Lys Glu
                405                 410                 415

Ile Ile Ile Gln Lys Val Asp Glu Ile Tyr Lys Val Tyr Gly Ser Ser
            420                 425                 430

Glu Lys Leu Phe Asp Ala Asp Phe Val Leu Glu Lys Ser Leu Lys Lys
        435                 440                 445

Asn Asp Ala Val Val Ala Ile Met Lys Asp Leu Leu Asp Ser Val Lys
    450                 455                 460

Ser Phe Glu Asn Tyr Ile Lys Ala Phe Phe Gly Glu Gly Lys Glu Thr
465                 470                 475                 480

Asn Arg Asp Glu Ser Phe Tyr Gly Asp Phe Val Leu Ala Tyr Asp Ile
                485                 490                 495

Leu Leu Lys Val Asp His Ile Tyr Asp Ala Ile Arg Asn Tyr Val Thr
            500                 505                 510

Gln Lys Pro Tyr Ser Lys Asp Lys Phe Lys Leu Tyr Phe Gln Arg Pro
        515                 520                 525

Gln Phe Met Gly Gly Trp Asp Lys Asp Lys Glu Thr Asp Tyr Arg Ala
    530                 535                 540

Thr Ile Leu Arg Tyr Gly Ser Lys Tyr Tyr Leu Ala Ile Met Pro Lys
545                 550                 555                 560

Lys Tyr Ala Lys Cys Leu Gln Lys Ile Asp Lys Asp Val Asn Gly
                565                 570                 575

Asn Tyr Glu Lys Ile Asn Tyr Lys Leu Leu Pro Gly Pro Asn Lys Met
            580                 585                 590

Leu Pro Lys Val Phe Phe Ser Lys Lys Trp Met Ala Tyr Tyr Asn Pro
        595                 600                 605

Ser Glu Asp Ile Gln Lys Ile Tyr Lys Asn Gly Thr Phe Lys Lys Gly
    610                 615                 620

Asp Met Phe Asn Leu Asn Asp Cys His Lys Leu Ile Asp Phe Phe Lys
625                 630                 635                 640

Asp Ser Ile Ser Arg Tyr Pro Lys Trp Ser Asn Ala Tyr Asp Phe Asn
```

-continued

```
                645                 650                 655
Phe Ser Glu Thr Glu Lys Tyr Lys Asp Ile Ala Gly Phe Tyr Arg Glu
                660                 665                 670

Val Glu Glu Gln Gly Tyr Lys Val Ser Phe Glu Ser Ala Ser Lys Lys
                675                 680                 685

Glu Val Asp Lys Leu Val Glu Gly Lys Leu Tyr Met Phe Gln Ile
    690                 695                 700

Tyr Asn Lys Asp Phe Ser Asp Lys Ser His Gly Thr Pro Asn Leu His
705                 710                 715                 720

Thr Met Tyr Phe Lys Leu Leu Phe Asp Glu Asn Asn His Gly Gln Ile
                725                 730                 735

Arg Leu Ser Gly Gly Ala Glu Leu Phe Met Arg Arg Ala Ser Leu Lys
                740                 745                 750

Lys Glu Glu Leu Val Val His Pro Ala Asn Ser Pro Ile Ala Asn Lys
                755                 760                 765

Asn Pro Asp Asn Pro Lys Lys Thr Thr Thr Leu Ser Tyr Asp Val Tyr
    770                 775                 780

Lys Asp Lys Arg Phe Ser Glu Asp Gln Tyr Leu Leu His Ile Pro Ile
785                 790                 795                 800

Ala Ile Asn Lys Cys Pro Lys Asn Ile Phe Lys Ile Asn Thr Glu Val
                805                 810                 815

Arg Val Leu Leu Lys His Asp Asp Asn Pro Tyr Val Ile Gly Ile Asp
                820                 825                 830

Arg Gly Glu Arg Asn Leu Leu Tyr Ile Val Val Asp Gly Lys Gly
                835                 840                 845

Asn Ile Val Glu Gln Tyr Ser Leu Asn Glu Ile Ile Asn Asn Phe Asn
850                 855                 860

Gly Ile Arg Ile Lys Thr Asp Tyr His Ser Leu Leu Asp Lys Lys Glu
865                 870                 875                 880

Lys Glu Arg Phe Glu Ala Arg Gln Asn Trp Thr Ser Ile Glu Asn Ile
                885                 890                 895

Lys Glu Leu Lys Ala Gly Tyr Ile Ser Gln Val Val His Lys Ile Cys
                900                 905                 910

Glu Leu Val Glu Lys Tyr Asp Ala Val Ile Ala Leu Glu Asp Leu Asn
                915                 920                 925

Ser Gly Phe Lys Asn Ser Arg Val Lys Val Glu Lys Gln Val Tyr Gln
                930                 935                 940

Lys Phe Glu Lys Met Leu Ile Asp Lys Leu Asn Tyr Met Val Asp Lys
945                 950                 955                 960

Lys Ser Asn Pro Cys Ala Thr Gly Gly Ala Leu Lys Gly Tyr Gln Ile
                965                 970                 975

Thr Asn Lys Phe Glu Ser Phe Lys Ser Met Ser Thr Gln Asn Gly Phe
                980                 985                 990

Ile Phe Tyr Ile Pro Ala Trp Leu Thr Ser Lys Ile Asp Pro Ser Thr
                995                1000                1005

Gly Phe Val Asn Leu Leu Lys Thr Lys Tyr Thr Ser Ile Ala Asp
    1010                1015                1020

Ser Lys Lys Phe Ile Ser Ser Phe Asp Arg Ile Met Tyr Val Pro
    1025                1030                1035

Glu Glu Asp Leu Phe Glu Phe Ala Leu Asp Tyr Lys Asn Phe Ser
    1040                1045                1050

Arg Thr Asp Ala Asp Tyr Ile Lys Lys Trp Lys Leu Tyr Ser Tyr
    1055                1060                1065
```

| | | | | | | | | | | |
|---|---|---|---|---|---|---|---|---|---|---|
|Gly|Asn|Arg|Ile|Arg|Ile|Phe|Arg|Asn|Pro|Lys|Lys|Asn|Asn|Val|
| |1070| | | |1075| | | | |1080| | | | |

Gly Asn Arg Ile Arg Ile Phe Arg Asn Pro Lys Lys Asn Asn Val
       1070            1075                 1080

Phe Asp Trp Glu Glu Val Cys Leu Thr Ser Ala Tyr Lys Glu Leu
       1085            1090                 1095

Phe Asn Lys Tyr Gly Ile Asn Tyr Gln Gln Gly Asp Ile Arg Ala
       1100            1105                 1110

Leu Leu Cys Glu Gln Ser Asp Lys Ala Phe Tyr Ser Ser Phe Met
       1115            1120                 1125

Ala Leu Met Ser Leu Met Leu Gln Met Arg Asn Ser Ile Thr Gly
       1130            1135                 1140

Arg Thr Asp Val Asp Phe Leu Ile Ser Pro Val Lys Asn Ser Asp
       1145            1150                 1155

Gly Ile Phe Tyr Asp Ser Arg Asn Tyr Glu Ala Gln Glu Asn Ala
       1160            1165                 1170

Ile Leu Pro Lys Asn Ala Asp Ala Asn Gly Ala Tyr Asn Ile Ala
       1175            1180                 1185

Arg Lys Val Leu Trp Ala Ile Gly Gln Phe Lys Lys Ala Glu Asp
       1190            1195                 1200

Glu Lys Leu Asp Lys Val Lys Ile Ala Ile Ser Asn Lys Glu Trp
       1205            1210                 1215

Leu Glu Tyr Ala Gln Thr Ser Val Lys His
       1220            1225

<210> SEQ ID NO 10
<211> LENGTH: 3684
<212> TYPE: DNA
<213> ORGANISM: Artificial sequence
<220> FEATURE:
<223> OTHER INFORMATION: Synthetic construct

<400> SEQUENCE: 10

```
atgagcaaac tggaaaagtt caccaactgt tatagcctga gcaaaaccct gcgttttaaa      60
gcaattccgg ttggtaaaac ccaagagaac attgataata aacgcctgct ggtcgaagat     120
gaaaaacgcg ctgaagatta taaggcgtg aaaaaactgc tggatcgcta ttatctgagc      180
ttcattaacg atgtgctgca cagcattaaa ctgaagaacc tgaacaacta tatcagcctg     240
tttcgtaaaa aaccccgcac cgaaaaagaa aacaaagagc tggaaaaccct ggaaatcaat    300
ctgcgtaaag aaatcgccaa agcgtttaaa ggtaacgagg ttataaaag cctgttcaag      360
aaagacatca tcgaaaccat tctgccggaa tttctggatg ataaagatga attgccctg      420
gtgaatagct ttaatggctt taccaccgca tttaccggct tttttgataa tcgcgaaaac     480
atgttcagcg aagaagcaaa aagcaccagc attgcatttc gctgcattaa tgaaaatctg    540
acccgctaca ttagcaacat ggatatcttt gaaaaagtgg acgcgatctt cgataaacac    600
gaagtgcaag agatcaaaga gaaaatcctg aacagcgatt atgacgtcga agattttttt    660
gaaggcgagt tctttaactt cgttctgacc caagaaggta tcgacgttta taacgcaatt    720
attggtggtt ttgttaccga aagcggtgag aaaatcaaag gcctgaatga atatatcaac    780
ctgtataacc agaaaaccaa acagaaactg ccgaaattca aaccgctgta taaacaggtt    840
ctgagcgatc gtgaaagcct gagctttat ggtgaaggtt ataccagtga tgaagaggtt     900
ctggaagttt ttcgtaacac cctgaataaa aacagcgaga tctttagcag catcaaaaag    960
cttgagaaac tgttcaaaaa cttttgatgag tatagcagcg caggcatctt tgttaaaaat   1020
ggtccggcaa ttagcaccat cagcaaagat attttttggcg aatggaatgt gatccgcgat   1080
```

```
aaatggaatg ccgaatatga tgatatccac ctgaaaaaaa aggccgtggt gaccgagaaa    1140
tatgaagatg atcgtcgtaa aagcttcaag aaaattggta gctttagcct ggaacagctg    1200
caagaatatg cagatgcaga tctgagcgtt gtggaaaaac tgaaagaaat catcattcag    1260
aaggtggacg agatctataa agtttatggt agcagcgaaa aactgttcga tgcagatttt    1320
gttctggaaa aaagcctgaa aaagaatgat gccgttgtgg ccattatgaa agatctgctg    1380
gatagcgtta gagcttcga gaattacatc aaagcctttt ttggtgaggg caaagaaacc    1440
aatcgtgatg aaagtttcta tggcgatttt gtgctggcct atgatattct gctgaaagtg    1500
gaccatattt atgatgccat tcgcaattat gttacccaga aaccgtatag caaagacaag    1560
ttcaaactgt actttcagcg tccgcagttt atgggtggtt gggataaaga taaagaaacc    1620
gattatcgtg ccaccatcct gcgttatggt agtaaatact atctggccat catggacaaa    1680
aaatacgcaa aatgcctgca gaaaatcgac aaagatgatg tgaatggcaa ctatgaaaaa    1740
atcaactaca aactgctgcc tggtccgaat aaaatgctgc cgaaagtgtt ctttagcaag    1800
aaatggatgg cctattataa cccgagcgag gatattcaaa agatctacaa aaatggcacc    1860
tttaaaaagg gcgacatgtt caatctgaac gattgccaca aactgatcga tttcttcaaa    1920
gattcaattt cgcgttatcc gaaatggtcc aatgcctatg attttaactt tagcgaaacc    1980
gaaaaataca aagacattgc cggtttttat cgcgaagtgg aagaacaggg ctataaagtg    2040
agctttgaaa gcgcaagcaa aaaagaggtt gataagctgg ttgaagaggg caaactgtat    2100
atgttccaga tttacaacaa agattttagc gacaaaagcc atggcacccc gaatctgcat    2160
accatgtact ttaaactgct gttcgacgaa ataaccatg tcagattcg tctgagcggt    2220 ggtgccgaac tgtttatgcg tcgtgcaagt ctgaaaaaag aagaactggt tgttcatccg    2280
gcaaatagcc cgattgcaaa caaaaatccg gacaatccga aaaaaaccac gacactgagc    2340
tatgatgtgt ataaagacaa acgttttagc gaggatcagt atgaactgca tatcccgatt    2400
gccatcaata aatgcccgaa aaacatcttt aagatcaaca ccgaagttcg cgtgctgctg    2460
aaacatgatg ataatccgta tgtgattggc attgatcgtg gtgaacgtaa cctgctgtat    2520
attgttgttg ttgatggtaa aggcaacatc gtggaacagt atagtctgaa cgaaattatc    2580
aacaacttta acggcatccg catcaaaacc gactatcata gcctgctgga caagaaagaa    2640
aaagaacgtt ttgaagcacg tcagaactgg accagtattg aaaacatcaa agaactgaaa    2700
gccggttata ttagccaggt ggttcataaa atctgtgagc tggtagaaaa atacgatgca    2760
gttattgcac tggaagatct gaatagcggt ttcaaaaata gccgtgtgaa agtcgaaaaa    2820
caggtgtatc agaaattcga gaaaatgctg atcgacaaac tgaactacat ggtcgacaaa    2880
aaaagcaatc cgtgtgcaac cggtggtgca ctgaaaggtt atcagattac caacaaattt    2940
gaaagcttta aaagcatgag cacccagaac ggctttatct tctatattcc ggcatggctg    3000
accagcaaaa ttgatccgag caccggtttt gtgaacctgc tgaaaacaaa atatacctcc    3060
attgccgaca gcaagaagtt tattagcagc tttgatcgca ttatgtatgt tccggaagag    3120
gacctgtttg aattcgcact ggattacaaa aatttcagcc gtaccgatgc cgactacatc    3180
aaaaaatgga aactgtacag ctatggtaac cgcattcgca ttttcgcaa cccgaagaaa    3240 aacaatgtgt cgattggga agaagtttgt ctgaccagcg catataaaga acttttcaac    3300
aaatacggca tcaactatca gcagggtgat attcgtgcac tgctgtgtga acagagcgat    3360
aaagcgtttt atagcagttt tatggcactg atgagcctga tgctgcagat gcgtaatagc    3420
```

| attaccggtc gcaccgatgt ggattttctg attagtccgg tgaaaaattc cgatggcatc | 3480 |
| tttatgata gccgcaatta cgaagcacaa gaaaatgcaa ttctgccgaa aaacgcagat | 3540 |
| gcaaatggtg catataacat tgcacgtaaa gttctgtggg caattggcca gtttaagaaa | 3600 |
| gcagaagata gaagctgga caaagtgaaa attgcgatca gcaataaaga gtggctggaa | 3660 |
| tacgcacaga ccagcgttaa acat | 3684 |

<210> SEQ ID NO 11
<211> LENGTH: 3684
<212> TYPE: DNA
<213> ORGANISM: Artificial sequence
<220> FEATURE:
<223> OTHER INFORMATION: Synthetic construct

<400> SEQUENCE: 11

| atgagcaaac tggaaaagtt caccaactgt tatagcctga gcaaaaccct gcgttttaaa | 60 |
| gcaattccgg ttggtaaaac ccaagagaac attgataata aacgcctgct ggtcgaagat | 120 |
| gaaaaacgcg ctgaagatta taaggcgtg aaaaaactgc tggatcgcta ttatctgagc | 180 |
| ttcattaacg atgtgctgca cagcattaaa ctgaagaacc tgaacaacta tatcagcctg | 240 |
| tttcgtaaaa aacccgcac cgaaaagaa acaaagagc tggaaaaccct ggaaatcaat | 300 |
| ctgcgtaaag aaatcgccaa agcgtttaaa ggtaacgagg ttataaaag cctgttcaag | 360 |
| aaagacatca tcgaaaccat tctgccggaa tttctggatg ataaagatga aattgccctg | 420 |
| gtgaatagct ttaatggctt taccaccgca tttaccggct ttttgataa tcgcgaaaac | 480 |
| atgttcagcg aagaagcaaa aagcaccagc attgcatttc gctgcattaa tgaaaatctg | 540 |
| acccgctaca ttagcaacat ggatatcttt gaaaagtgg acgcgatctt cgataaacac | 600 |
| gaagtgcaag atcaaagaa aaatcctg aacagcgatt atgacgtcga agatttttt | 660 |
| gaaggcgagt tctttaactt cgttctgacc caagaaggta tcgacgttta acgcaatt | 720 |
| attggtggtt ttgttaccga agcggtgag aaaatcaaag gcctgaatga atatatcaac | 780 |
| ctgtataacc agaaaaccaa acagaaactg ccgaaattca aaccgctgta taaacaggtt | 840 |
| ctgagcgatc gtgaaagcct gagctttat ggtgaaggtt ataccagtga tgaagaggtt | 900 |
| ctggaagttt ttcgtaacac cctgaataaa aacagcgaga tctttagcag catcaaaaag | 960 |
| cttgagaaac tgttcaaaaa ctttgatgag tatagcagcg caggcatctt tgttaaaaat | 1020 |
| ggtccggcaa ttagcaccat cagcaaagat atttttggcg aatggaatgt gatccgcgat | 1080 |
| aaatggaatg ccgaatatga tgatatccac ctgaaaaaaa aggccgtggt gaccgagaaa | 1140 |
| tatgaagatg atcgtcgtaa aagcttcaag aaaattggta gctttagcct ggaacagctg | 1200 |
| caagaatatg cagatgcaga tctgagcgtt gtggaaaaac tgaaagaaat catcattcag | 1260 |
| aaggtggacg agatctataa agtttatggt agcagcgaaa aactgttcga tgcagatttt | 1320 |
| gttctggaaa aaagcctgaa aaagaatgat gccgttgtgg ccattatgaa agatctgctg | 1380 |
| gatagcgtta gagcttcga gaattacatc aaagcctttt ttggtgaggg caaagaaacc | 1440 |
| aatcgtgatg aaagtttcta tggcgatttt gtgctggcct atgatattct gctgaaagtg | 1500 |
| gaccatattt atgatgccat tcgcaattat gttacccaga accgtatag caaagacaag | 1560 |
| ttcaaactgt actttcagaa cccgcagttt atgggtggtt gggataaaga taagaaaacc | 1620 |
| gattatcgtg ccaccatcct gcgttatggt agtaaatact atctggccat catgccgaaa | 1680 |
| aaatacgcaa aatgcctgca gaaaatcgac aaagatgatg tgaatggcaa ctatgaaaaa | 1740 |
| atcaactaca aactgctgcc tggtccgaat aaaatgctgc cgaaagtgtt ctttagcaag | 1800 |

```
aaatggatgg cctattataa cccgagcgag gatattcaaa agatctacaa aaatggcacc    1860
tttaaaaagg gcgacatgtt caatctgaac gattgccaca aactgatcga tttcttcaaa    1920
gattcaattt cgcgttatcc gaaatggtcc aatgcctatg attttaactt tagcgaaacc    1980
gaaaaataca aagacattgc cggtttttat cgcgaagtgg aagaacaggg ctataaagtg    2040
agctttgaaa gcgcaagcaa aaagaggtt gataagctgg ttgaagaggg caaactgtat    2100
atgttccaga tttacaacaa agattttagc gacaaaagcc atggcacccc gaatctgcat    2160
accatgtact ttaaactgct gttcgacgaa ataaccatg gtcagattcg tctgagcggt    2220
ggtgccgaac tgtttatgcg tcgtgcaagt ctgaaaaaag aagaactggt tgttcatccg    2280
gcaaatagcc cgattgcaaa caaaaatccg gacaatccga aaaaaccac gacactgagc    2340 tatgatgtgt ataagacaa acgttttagc gaggatcagt atgaactgca tatcccgatt    2400
gccatcaata aatgcccgaa aaacatcttt aagatcaaca ccgaagttcg cgtgctgctg    2460
aaacatgatg ataatccgta tgtgattggc attgatcgtg gtgaacgtaa cctgctgtat    2520
attgttgttg ttgatggtaa aggcaacatc gtggaacagt atagtctgaa cgaaattatc    2580
aacaacttta cggcatccg catcaaaacc gactatcata gcctgctgga caagaaagaa    2640
aaagaacgtt ttgaagcacg tcagaactgg accagtattg aaaacatcaa agaactgaaa    2700
gccggttata ttagccaggt ggttcataaa atctgtgagc tggtagaaaa atacgatgca    2760
gttattgcac tggaagatct gaatagcggt ttcaaaaata gccgtgtgaa agtcgaaaaa    2820
caggtgtatc agaaattcga gaaaatgctg atcgacaaac tgaactacat ggtcgacaaa    2880
aaaagcaatc cgtgtgcaac cggtggtgca ctgaaaggtt atcagattac caacaaattt    2940
gaaagcttta aaagcatgag cacccagaac ggctttatct tctatattcc ggcatggctg    3000
accagcaaaa ttgatccgag caccggtttt gtgaacctgc tgaaaacaaa atatacctcc    3060
attgccgaca gcaagaagtt tattagcagc tttgatcgca ttatgtatgt tccggaagag    3120
gacctgtttg aattcgcact ggattacaaa aatttcagcc gtaccgatgc cgactacatc    3180
aaaaaatgga aactgtacag ctatggtaac cgcattcgca ttttcgcaa cccgaagaaa    3240 aacaatgtgt tcgattggga agaagtttgt ctgaccagcg catataaaga acttttcaac    3300
aaatacggca tcaactatca gcagggtgat attcgtgcac tgctgtgtga acagagcgat    3360
aaagcgtttt atagcagttt tatggcactg atgagcctga tgctgcagat gcgtaatagc    3420
attaccggtc gcaccgatgt ggattttctg attagtccgg tgaaaaattc cgatggcatc    3480
ttttatgata gccgcaatta cgaagcacaa gaaaatgcaa ttctgccgaa aaacgcagat    3540
gcaaatggtg catataacat tgcacgtaaa gttctgtggg caattggcca gtttaagaaa    3600
gcagaagatg agaagctgga caaagtgaaa attgcgatca gcaataaaga gtggctggaa    3660
tacgcacaga ccagcgttaa acat                                          3684
```

<210> SEQ ID NO 12
<211> LENGTH: 3684
<212> TYPE: DNA
<213> ORGANISM: Artificial sequence
<220> FEATURE:
<223> OTHER INFORMATION: Synthetic construct

<400> SEQUENCE: 12

```
atgagcaaac tggaaaagtt caccaactgt tatagcctga gcaaaaccct gcgttttaaa      60
gcaattccgg ttggtaaaac ccaagagaac attgataata aacgcctgct ggtcgaagat     120
```

-continued

```
gaaaaacgcg ctgaagatta taaaggcgtg aaaaaactgc tggatcgcta ttatctgagc      180
ttcattaacg atgtgctgca cagcattaaa ctgaagaacc tgaacaacta tatcagcctg      240
tttcgtaaaa aaacccgcac cgaaaaagaa acaaagagc tggaaaacct ggaaatcaat       300
ctgcgtaaaa aaatcgccaa agcgtttaaa ggtaacgagg gttataaaag cctgttcaag      360
aaagacatca tcgaaaccat tctgccggaa tttctggatg ataaagatga aattgccctg      420
gtgaatagct ttaatggctt taccaccgca tttaccggct tttttgataa tcgcgaaaac      480
atgttcagcg aagaagcaaa aagcaccagc attgcatttc gctgcattaa tgaaaatctg      540
acccgctaca ttagcaacat ggatatcttt gaaaagtgg acgcgatctt cgataaacac       600
gaagtgcaag agatcaaaga gaaaatcctg aacagcgatt atgacgtcga agatttttt      660 gaaggcgagt tctttaactt cgttctgacc caagaaggta tcgacgttta taacgcaatt      720
attggtggtt ttgttaccga aagcggtgag aaaatcaaag gcctgaatga atatatcaac     780
ctgtataacc agaaaaccaa acagaaactg ccgaaattca aaccgctgta taaacaggtt     840
ctgagcgatc gtgaaagcct gagcttttat ggtgaaggtt ataccagtga tgagaggtt     900 ctggaagttt tcgtaacac cctgaataaa aacagcgaga tctttagcag catcaaaaag      960
cttgagaaac tgttcaaaaa ctttgatgag tatagcagcg caggcatctt tgttaaaaat     1020
ggtccggcaa ttagcaccat cagcaaagat attttggcg aatggaatgt gatccgcgat      1080
aaatggaatg ccgaatatga tgatatccac ctgaaaaaaa aggccgtggt gaccgagaaa     1140
tatgaagatg atcgtcgtaa aagcttcaag aaaattggta gctttagcct ggaacagctg     1200
caagaatatg cagatgcaga tctgagcgtt gtggaaaaac tgaaagaaat catcattcag     1260
aaggtggacg agatctataa agtttatggt agcagcgaaa aactgttcga tgcagatttt     1320
gttctggaaa aaagcctgaa aaagaatgat gccgttgtgg ccattatgaa agatctgctg     1380
gatagcgtta agagcttcga gaattacatc aaagccttt ttggtgaggg caaagaaacc      1440
aatcgtgatg aaagtttcta tggcgatttt gtgctggcct atgatattct gctgaaagtg     1500
gaccatattt atgatgccat tcgcaattat gttacccaga accgtatag caaagacaag      1560 ttcaaactgt actttcagaa cccgcagttt atgggtggtt gggataaaga taagaaaacc     1620
gattatcgtg ccaccatcct gcgttatggt agtaaatact atctggccat catggacaaa     1680
aaatacgcaa aatgcctgca gaaaatcgac aaagatgatg tgaatggcaa ctatgaaaaa    1740
atcaactaca aactgctgcc tggtccgaat aaaatgctgc cgaaagtgtt ctttagcaag     1800
aaatggatgg cctattataa cccgagcgag gatattcaaa agatctacaa aaatggcacc     1860
tttaaaaagg gcgacatgtt caatctgaac gattgccaca aactgatcga tttcttcaaa     1920
gattcaattt cgcgttatcc gaaatggtcc aatgcctatg attttaactt tagcgaaacc     1980
gaaaaataca aagacattgc cggttttat cgcgaagtgg aagaacaggg ctataaagtg      2040
agctttgaaa gcgcaagcaa aaagaggtt gataagctgg ttgaagaggg caaactgtat      2100
atgttccaga tttacaacaa agatttagc gacaaaagcc atggcacccc gaatctgcat      2160
accatgtact ttaaactgct gttcgacgaa ataaccatg gtcagattcg tctgagcggt       2220
ggtgccgaac tgtttatgcg tcgtgcaagt ctgaaaaaag aagaactggt tgttcatccg     2280
gcaaatagcc cgattgcaaa caaaaatccg gacaatccga aaaaaccac gacactgagc      2340 tatgatgtgt ataaagacaa acgttttagc gaggatcagt atctgctgca tatcccgatt     2400
gccatcaata aatgcccgaa aaacatcttt aagatcaaca ccgaagttcg cgtgctgctg     2460
aaacatgatg ataatccgta tgtgattggc attgatcgtg gtgaacgtaa cctgctgtat     2520
```

| | |
|---|---|
| attgttgttg ttgatggtaa aggcaacatc gtggaacagt atagtctgaa cgaaattatc | 2580 |
| aacaacttta acggcatccg catcaaaacc gactatcata gcctgctgga caagaaagaa | 2640 |
| aaagaacgtt ttgaagcacg tcagaactgg accagtattg aaaacatcaa agaactgaaa | 2700 |
| gccggttata ttagccaggt ggttcataaa atctgtgagc tggtagaaaa atacgatgca | 2760 |
| gttattgcac tggaagatct gaatagcggt ttcaaaaata gccgtgtgaa agtcgaaaaa | 2820 |
| caggtgtatc agaaattcga gaaaatgctg atcgacaaac tgaactacat ggtcgacaaa | 2880 |
| aaaagcaatc cgtgtgcaac cggtggtgca ctgaaaggtt atcagattac caacaaattt | 2940 |
| gaaagcttta aaagcatgag cacccagaac ggctttatct tctatattcc ggcatggctg | 3000 |
| accagcaaaa ttgatccgag caccggtttt gtgaacctgc tgaaaacaaa atatacctcc | 3060 |
| attgccgaca gcaagaagtt tattagcagc tttgatcgca ttatgtatgt tccggaagag | 3120 |
| gacctgtttg aattcgcact ggattacaaa aatttcagcc gtaccgatgc cgactacatc | 3180 |
| aaaaaatgga actgtacag ctatggtaac cgcattcgca tttttcgcaa cccgaagaaa | 3240 |
| aacaatgtgt tcgattggga agaagtttgt ctgaccagcg catataaaga acttttcaac | 3300 |
| aaatacggca tcaactatca gcagggtgat attcgtgcac tgctgtgtga acagagcgat | 3360 |
| aaagcgtttt atagcagttt tatggcactg atgagcctga tgctgcagat gcgtaatagc | 3420 |
| attaccggtc gcaccgatgt ggattttctg attagtccgg tgaaaaattc cgatggcatc | 3480 |
| ttttatgata gccgcaatta cgaagcacaa gaaaatgcaa ttctgccgaa aaacgcagat | 3540 |
| gcaaatggtg catataacat tgcacgtaaa gttctgtggg caattggcca gtttaagaaa | 3600 |
| gcagaagatg agaagctgga caaagtgaaa attgcgatca gcaataaaga gtggctggaa | 3660 |
| tacgcacaga ccagcgttaa acat | 3684 |

<210> SEQ ID NO 13
<211> LENGTH: 3684
<212> TYPE: DNA
<213> ORGANISM: Artificial sequence
<220> FEATURE:
<223> OTHER INFORMATION: Synthetic construct

<400> SEQUENCE: 13

| | |
|---|---|
| atgagcaaac tggaaaaagtt caccaactgt tatagcctga gcaaaaccct gcgttttaaa | 60 |
| gcaattccgg ttggtaaaac ccaagagaac attgataata aacgcctgct ggtcgaagat | 120 |
| gaaaaacgcg ctgaagatta taaggcgtg aaaaaactgc tggatcgcta ttatctgagc | 180 |
| ttcattaacg atgtgctgca cagcattaaa ctgaagaacc tgaacaacta tatcagcctg | 240 |
| tttcgtaaaa aaacccgcac cgaaaaagaa aacaaagagc tggaaaaccct ggaaatcaat | 300 |
| ctgcgtaaag aaatcgccaa agcgtttaaa ggtaacgagg ttataaaag cctgttcaag | 360 |
| aaagacatca tcgaaaccat tctgccggaa tttctggatg ataaagatga aattgccctg | 420 |
| gtgaatagct ttaatggctt taccaccgca tttaccggct ttttgataa tcgcgaaaac | 480 |
| atgttcagcg aagaagcaaa aagcaccagc attgcatttc gctgcattaa tgaaaatctg | 540 |
| acccgctaca ttagcaacat ggatatcttt gaaaaagtgg acgcgatctt cgataaacac | 600 |
| gaagtgcaag agatcaaaga gaaatcctg aacagcgatt atgacgtcga agatttttt | 660 |
| gaaggcgagt tctttaactt cgttctgacc caagaaggta tcgacgttta acgcaatt | 720 |
| attggtggtt tgttaccga aagcggtgag aaaatcaaag cctgaatga atatatcaac | 780 |
| ctgtataacc agaaaaccaa acagaaactg ccgaaattca accgctgta taaacaggtt | 840 |

```
ctgagcgatc gtgaaagcct gagcttttat ggtgaaggtt ataccagtga tgaagaggtt    900
ctggaagttt ttcgtaacac cctgaataaa aacagcgaga tctttagcag catcaaaaag    960
cttgagaaac tgttcaaaaa ctttgatgag tatagcagcg caggcatctt tgttaaaaat   1020
ggtccggcaa ttagcaccat cagcaaagat attttttggcg aatggaatgt gatccgcgat   1080
aaatggaatg ccgaatatga tgatatccac ctgaaaaaaa aggccgtggt gaccgagaaa   1140
tatgaagatg atcgtcgtaa aagcttcaag aaaattggta gctttagcct ggaacagctg   1200
caagaatatg cagatgcaga tctgagcgtt gtggaaaaac tgaaagaaat catcattcag   1260
aaggtggacg agatctataa agtttatggt agcagcgaaa aactgttcga tgcagatttt   1320
gttctggaaa aaagcctgaa aaagaatgat gccgttgtgg ccattatgaa agatctgctg   1380
gatagcgtta agagcttcga gaattacatc aaagcctttt ttggtgaggg caaagaaacc   1440
aatcgtgatg aaagtttcta tggcgatttt gtgctggcct atgatattct gctgaaagtg   1500
gaccatattt atgatgccat cgcaattat gttacccaga accgtatag caaagacaag   1560
ttcaaactgt actttcagcg tccgcagttt atgggtggtt gggataaaga taagaaaacc   1620
gattatcgtg ccaccatcct gcgttatggt agtaaatact atctggccat catgccgaaa   1680
aaatacgcaa aatgcctgca gaaaatcgac aaagatgatg tgaatggcaa ctatgaaaaa   1740
atcaactaca aactgctgcc tggtccgaat aaaatgctgc cgaaagtgtt ctttagcaag   1800
aaatggatgg cctattataa cccgagcgag gatattcaaa agatctacaa aaatggcacc   1860
tttaaaaagg gcgacatgtt caatctgaac gattgccaca aactgatcga tttcttcaaa   1920
gattcaattt cgcgttatcc gaaatggtcc aatgcctatg attttaactt tagcgaaacc   1980
gaaaaataca agacattgc cggttttat cgcgaagtgg aagaacaggg ctataaagtg   2040
agctttgaaa gcgcaagcaa aaaagaggtt gataagctgg ttgaagaggg caaactgtat   2100
atgttccaga tttacaacaa agattttagc gacaaaagcc atggcacccc gaatctgcat   2160
accatgtact ttaaaactgct gttcgacgaa ataaccatg gtcagattcg tctgagcggt   2220
ggtgccgaac tgtttatgcg tcgtgcaagt ctgaaaaaag aagaactggt tgttcatccg   2280
gcaaatagcc cgattgcaaa caaaaatccg gacaatccga aaaaaaccac gacactgagc   2340
tatgatgtgt ataaagacaa acgttttagc gaggatcagt atgaactgca tatcccgatt   2400
gccatcaata aatgcccgaa aaacatcttt aagatcaaca ccgaagttcg cgtgctgctg   2460
aaacatgatg ataatccgta tgtgattggc attgatcgtg gtgaacgtaa cctgctgtat   2520
attgttgttg ttgatggtaa aggcaacatc gtggaacagt atagtctgaa cgaaattatc   2580
aacaacttta acggcatccg catcaaaacc gactatcata gcctgctgga caagaaagaa   2640
aaagaacgtt ttgaagcacg tcagaactgg accagtattg aaaacatcaa agaactgaaa   2700
gccggttata ttagccaggt ggttcataaa atctgtgagc tggtagaaaa atacgatgca   2760
gttattgcac tggaagatct gaatagcggt tcaaaaaata gccgtgtgaa agtcgaaaaa   2820
caggtgtatc agaaattcga gaaaatgctg atcgacaaac tgaactacat ggtcgacaaa   2880
aaaagcaatc cgtgtgcaac cggtggtgca ctgaaaggtt atcagattac caacaaattt   2940
gaaagcttta aaagcatgag cacccagaac ggctttatct tctatattcc ggcatggctg   3000
accagcaaaa ttgatccgag caccggtttt gtgaacctgc tgaaaacaaa atatacctcc   3060
attgccgaca gcaagaagtt tattagcagc tttgatcgca ttatgtatgt tccggaagag   3120
gacctgtttg aattcgcact ggattacaaa aatttcagcc gtaccgatgc cgactacatc   3180
aaaaaatgga aactgtacag ctatggtaac cgcattcgca tttttcgcaa cccgaagaaa   3240
```

| aacaatgtgt tcgattggga agaagtttgt ctgaccagcg catataaaga acttttcaac | 3300 |
| aaatacggca tcaactatca gcagggtgat attcgtgcac tgctgtgtga acagagcgat | 3360 |
| aaagcgtttt atagcagttt tatggcactg atgagcctga tgctgcagat gcgtaatagc | 3420 |
| attaccggtc gcaccgatgt ggattttctg attagtccgg tgaaaaattc cgatggcatc | 3480 |
| ttttatgata gccgcaatta cgaagcacaa gaaaatgcaa ttctgccgaa aaacgcagat | 3540 |
| gcaaatggtg catataacat tgcacgtaaa gttctgtggg caattggcca gtttaagaaa | 3600 |
| gcagaagatg agaagctgga caaagtgaaa attgcgatca gcaataaaga gtggctggaa | 3660 |
| tacgcacaga ccagcgttaa acat | 3684 |

<210> SEQ ID NO 14
<211> LENGTH: 3684
<212> TYPE: DNA
<213> ORGANISM: Artificial sequence
<220> FEATURE:
<223> OTHER INFORMATION: Synthetic construct

<400> SEQUENCE: 14

| atgagcaaac tggaaaagtt caccaactgt tatagcctga gcaaaaccct gcgttttaaa | 60 |
| gcaattccgg ttggtaaaac ccaagagaac attgataata aacgcctgct ggtcgaagat | 120 |
| gaaaaacgcg ctgaagatta taaggcgtg aaaaaactgc tggatcgcta ttatctgagc | 180 |
| ttcattaacg atgtgctgca cagcattaaa ctgaagaacc tgaacaacta tatcagcctg | 240 |
| tttcgtaaaa aaacccgcac cgaaaaagaa aacaaagagc tggaaaacct ggaaatcaat | 300 |
| ctgcgtaaag aaatcgccaa agcgtttaaa ggtaacgagg ttataaaag cctgttcaag | 360 |
| aaagacatca tcgaaaccat tctgccggaa tttctggatg ataaagatga aattgccctg | 420 |
| gtgaatagct ttaatggctt taccaccgca tttaccggct ttttttgataa tcgcgaaaac | 480 |
| atgttcagcg aagaagcaaa aagcaccagc attgcatttc gctgcattaa tgaaaatctg | 540 |
| acccgctaca ttagcaacat ggatatcttt gaaaaagtgg acgcgatctt cgataaacac | 600 |
| gaagtgcaag atcaaaaga gaaaatcctg aacagcgatt atgacgtcga agatttttt | 660 |
| gaaggcgagt tctttaactt cgttctgacc caagaaggta tcgacgttta taacgcaatt | 720 |
| attggtggtt ttgttaccga aagcggtgag aaaatcaaag gcctgaatga atatatcaac | 780 |
| ctgtataacc agaaaaccaa acagaaactg ccgaaattca aaccgctgta taaacaggtt | 840 |
| ctgagcgatc gtgaaagcct gagcttttat ggtgaaggtt ataccagtga tgaagaggtt | 900 |
| ctggaagttt tcgtaacac cctgaataaa acagcgaga tctttagcag catcaaaaag | 960 |
| cttgagaaac tgttcaaaaa ctttgatgag tatagcagcg caggcatctt tgttaaaaat | 1020 |
| ggtccggcaa ttagcaccat cagcaaagat attttttggcg aatggaatgt gatccgcgat | 1080 |
| aaatggaatg ccgaatatga tgatatccac ctgaaaaaaa aggccgtggt gaccgagaaa | 1140 |
| tatgaagatg atcgtcgtaa aagcttcaag aaaattggta gctttagcct ggaacagctg | 1200 |
| caagaatatg cagatgcaga tctgagcgtt gtggaaaaac tgaaagaaat catcattcag | 1260 |
| aaggtggacg agatctataa agtttatggt agcagcgaaa aactgttcga tgcagatttt | 1320 |
| gttctggaaa aagcctgaa aaagaatgat gccgttgtgg ccattatgaa agatctgctg | 1380 |
| gatagcgtta agagcttcga gaattacatc aaagcctttt ttggtgaggg caaagaaacc | 1440 |
| aatcgtgatg aaagtttcta tggcgatttt gtgctggcct atgatattct gctgaaagtg | 1500 |
| gaccatattt atgatgccat tcgcaattat gttacccaga aaccgtatag caaagacaag | 1560 |

```
ttcaaactgt actttcagcg tccgcagttt atgggtggtt gggataaaga taaagaaacc    1620
gattatcgtg ccaccatcct gcgttatggt agtaaatact atctggccat catggacaaa    1680
aaatacgcaa aatgcctgca gaaaatcgac aaagatgatg tgaatggcaa ctatgaaaaa    1740
atcaactaca aactgctgcc tggtccgaat aaaatgctgc cgaaagtgtt ctttagcaag    1800
aaatggatgg cctattataa cccgagcgag gatattcaaa agatctacaa aaatggcacc    1860
tttaaaaagg gcgacatgtt caatctgaac gattgccaca aactgatcga tttcttcaaa    1920
gattcaattt cgcgttatcc gaaatggtcc aatgcctatg attttaactt tagcgaaacc    1980
gaaaaataca aagacattgc cggttttat cgcgaagtgg aagaacaggg ctataaagtg     2040
agctttgaaa gcgcaagcaa aaaagaggtt gataagctgg ttgaagaggg caaactgtat    2100
atgttccaga tttacaacaa agattttagc gacaaaagcc atggcacccc gaatctgcat    2160
accatgtact ttaaactgct gttcgacgaa ataaccatg gtcagattcg tctgagcggt     2220
ggtgccgaac tgtttatgcg tcgtgcaagt ctgaaaaaag aagaactggt tgttcatccg    2280
gcaaatagcc cgattgcaaa caaaaatccg gacaatccga aaaaaccac gacactgagc     2340 tatgatgtgt ataaagacaa acgttttagc gaggatcagt atctgctgca tatcccgatt    2400
gccatcaata aatgcccgaa aaacatcttt aagatcaaca ccgaagttcg cgtgctgctg    2460
aaacatgatg ataatccgta tgtgattggc attgatcgtg gtgaacgtaa cctgctgtat    2520
attgttgttg ttgatggtaa aggcaacatc gtggaacagt atagtctgaa cgaaattatc    2580
aacaacttta cggcatccg catcaaaacc gactatcata gcctgctgga caagaaagaa     2640
aaagaacgtt ttgaagcacg tcagaactgg accagtattg aaaacatcaa agaactgaaa    2700
gccggttata ttagccaggt ggttcataaa atctgtgagc tggtagaaaa atacgatgca    2760
gttattgcac tggaagatct gaatagcggt ttcaaaaata gccgtgtgaa agtcgaaaaa    2820
caggtgtatc agaaattcga gaaaatgctg atcgacaaac tgaactacat ggtcgacaaa    2880
aaaagcaatc cgtgtgcaac cggtggtgca ctgaaaggtt atcagattac caacaaattt    2940
gaaagcttta aaagcatgag cacccagaac ggctttatct tctatattcc ggcatggctg    3000
accagcaaaa ttgatccgag caccggtttt gtgaacctgc tgaaaacaaa atatacctcc    3060
attgccgaca gcaagaagtt tattagcagc tttgatcgca ttatgtatgt tccggaagag    3120
gacctgtttg aattcgcact ggattacaaa aatttcagcc gtaccgatgc cgactacatc    3180
aaaaaatgga aactgtacag ctatggtaac cgcattcgca ttttcgcaa cccgaagaaa     3240 aacaatgtgt tcgattggga agaagtttgt ctgaccagcg catataaaga acttttcaac    3300
aaatacggca tcaactatca gcagggtgat attcgtgcac tgctgtgtga acagagcgat    3360
aaaagcgttt atagcagttt tatggcactg atgagcctga tgctgcagat gcgtaatagc    3420
attaccggtc gcaccgatgt ggattttctg attagtccgg tgaaaaattc cgatggcatc    3480
ttttatgata gccgcaatta cgaagcacaa gaaaatgcaa ttctgccgaa aaacgcagat    3540
gcaaatggtg catataacat tgcacgtaaa gttctgtggg caattggcca gtttaagaaa    3600
gcagaagatg agaagctgga caaagtgaaa attgcgatca gcaataaaga gtggctggaa    3660
tacgcacaga ccagcgttaa acat                                           3684

<210> SEQ ID NO 15
<211> LENGTH: 3684
<212> TYPE: DNA
<213> ORGANISM: Artificial sequence
<220> FEATURE:
<223> OTHER INFORMATION: Synthetic construct
```

<400> SEQUENCE: 15

| | | | | | |
|---|---|---|---|---|---|
| atgagcaaac | tggaaaagtt | caccaactgt | tatagcctga | gcaaaccct | gcgttttaaa | 60
| gcaattccgg | ttggtaaaac | ccaagagaac | attgataata | aacgcctgct | ggtcgaagat | 120
| gaaaaacgcg | ctgaagatta | taaggcgtg | aaaaaactgc | tggatcgcta | ttatctgagc | 180
| ttcattaacg | atgtgctgca | cagcattaaa | ctgaagaacc | tgaacaacta | tatcagcctg | 240
| tttcgtaaaa | aacccgcac | cgaaaaagaa | aacaaagagc | tggaaaacct | ggaaatcaat | 300
| ctgcgtaaag | aaatcgccaa | agcgtttaaa | ggtaacgagg | gttataaaag | cctgttcaag | 360
| aaagacatca | tcgaaaccat | tctgccggaa | tttctggatg | ataaagatga | aattgccctg | 420
| gtgaatagct | ttaatggctt | taccaccgca | tttaccggct | tttttgataa | tcgcgaaaac | 480
| atgttcagcg | aagaagcaaa | aagcaccagc | attgcatttc | gctgcattaa | tgaaaatctg | 540
| acccgctaca | ttagcaacat | ggatatcttt | gaaaagtgg | acgcgatctt | cgataaacac | 600
| gaagtgcaag | agatcaaaga | gaaaatcctg | aacagcgatt | atgacgtcga | agatttttt | 660
| gaaggcgagt | tctttaactt | cgttctgacc | caagaaggta | tcgacgttta | taacgcaatt | 720
| attggtggtt | ttgttaccga | aagcggtgag | aaaatcaaag | gcctgaatga | atatatcaac | 780
| ctgtataacc | agaaaaccaa | acagaaactg | ccgaaattca | aaccgctgta | taaacaggtt | 840
| ctgagcgatc | gtgaaagcct | gagcttttat | ggtgaaggtt | ataccagtga | tgaagaggtt | 900
| ctggaagttt | ttcgtaacac | cctgaataaa | aacagcgaga | tctttagcag | catcaaaaag | 960
| cttgagaaac | tgttcaaaaa | ctttgatgag | tatagcagcg | caggcatctt | tgttaaaaat | 1020
| ggtccggcaa | ttagcaccat | cagcaaagat | atttttggcg | aatggaatgt | gatccgcgat | 1080
| aaatggaatg | ccgaatatga | tgatatccac | ctgaaaaaaa | aggccgtggt | gaccgagaaa | 1140
| tatgaagatg | atcgtcgtaa | aagcttcaag | aaaattggta | gctttagcct | ggaacagctg | 1200
| caagaatatg | cagatgcaga | tctgagcgtt | gtggaaaaac | tgaaagaaat | catcattcag | 1260
| aaggtggacg | agatctataa | agtttatggt | agcagcgaaa | aactgttcga | tgcagatttt | 1320
| gttctggaaa | aaagcctgaa | aaagaatgat | gccgttgtgg | ccattatgaa | agatctgctg | 1380
| gatagcgtta | agagcttcga | gaattacatc | aaagccttt | ttggtgaggg | caaagaaacc | 1440
| aatcgtgatg | aaagtttcta | tggcgatttt | gtgctggcct | atgatattct | gctgaaagtg | 1500
| gaccatattt | atgatgccat | cgcaattat | gttacccaga | aaccgtatag | caaagacaag | 1560
| ttcaaactgt | actttcagaa | cccgcagttt | atgggtggtt | gggataaaga | taagaaaacc | 1620
| gattatcgtg | ccaccatcct | gcgttatggt | agtaaatact | atctggccat | catgccgaaa | 1680
| aaatacgcaa | aatgcctgca | gaaaatcgac | aaagatgatg | tgaatggcaa | ctatgaaaaa | 1740
| atcaactaca | aactgctgcc | tggtccgaat | aaaatgctgc | cgaaagtgtt | ctttagcaag | 1800
| aaatggatgg | cctattataa | cccgagcgag | gatattcaaa | agatctacaa | aaatggcacc | 1860
| tttaaaaagg | cgacatgtt | caatctgaac | gattgccaca | aactgatcga | tttcttcaaa | 1920
| gattcaattt | cgcgttatcc | gaaatggtcc | aatgcctatg | attttaactt | tagcgaaacc | 1980
| gaaaaataca | aagacattgc | cggtttttat | cgcgaagtgg | aagaacaggg | ctataaagtg | 2040
| agctttgaaa | gcgcaagcaa | aaaagaggtt | gataagctgg | ttgaagaggg | caaactgtat | 2100
| atgttccaga | tttacaacaa | agattttagc | gacaaaagcc | atggcacccc | gaatctgcat | 2160
| accatgtact | ttaaactgct | gttcgacgaa | aataaccatg | gtcagattcg | tctgagcggt | 2220
| ggtgccgaac | tgtttatgcg | tcgtgcaagt | ctgaaaaag | aagaactggt | tgttcatccg | 2280

| | |
|---|---:|
| gcaaatagcc cgattgcaaa caaaaatccg gacaatccga aaaaaccac gacactgagc | 2340 |
| tatgatgtgt ataaagacaa acgttttagc gaggatcagt atctgctgca tatcccgatt | 2400 |
| gccatcaata aatgcccgaa aacatctttt aagatcaaca ccgaagttcg cgtgctgctg | 2460 |
| aaacatgatg ataatccgta tgtgattggc attgatcgtg gtgaacgtaa cctgctgtat | 2520 |
| attgttgttg ttgatggtaa aggcaacatc gtggaacagt atagtctgaa cgaaattatc | 2580 |
| aacaacttta acggcatccg catcaaaacc gactatcata gcctgctgga caagaaagaa | 2640 |
| aaagaacgtt ttgaagcacg tcagaactgg accagtattg aaaacatcaa agaactgaaa | 2700 |
| gccggttata ttagccaggt ggttcataaa atctgtgagc tggtagaaaa atacgatgca | 2760 |
| gttattgcac tggaagatct gaatagcggt ttcaaaaata gccgtgtgaa agtcgaaaaa | 2820 |
| caggtgtatc agaaattcga gaaaatgctg atcgacaaac tgaactacat ggtcgacaaa | 2880 |
| aaaagcaatc cgtgtgcaac cggtggtgca ctgaaaggtt atcagattac caacaaattt | 2940 |
| gaaagcttta aaagcatgag cacccagaac ggctttatct tctatattcc ggcatggctg | 3000 |
| accagcaaaa ttgatccgag caccggtttt gtgaacctgc tgaaaacaaa atatacctcc | 3060 |
| attgccgaca gcaagaagtt tattagcagc tttgatcgca ttatgtatgt tccggaagag | 3120 |
| gacctgtttg aattcgcact ggattacaaa aatttcagcc gtaccgatgc cgactacatc | 3180 |
| aaaaaatgga actgtacag ctatggtaac cgcattcgca tttttcgcaa cccgaagaaa | 3240 |
| aacaatgtgt tcgattggga agaagtttgt ctgaccagcg catataaaga acttttcaac | 3300 |
| aaatacggca tcaactatca gcagggtgat attcgtgcac tgctgtgtga acagagcgat | 3360 |
| aaaagcgtttt atagcagttt tatggcactg atgagcctga tgctgcagat gcgtaatagc | 3420 |
| attaccggtc gcaccgatgt ggattttctg attagtccgg tgaaaaattc cgatggcatc | 3480 |
| ttttatgata gccgcaatta cgaagcacaa gaaaatgcaa ttctgccgaa aaacgcagat | 3540 |
| gcaaatggtg catataacat tgcacgtaaa gttctgtggg caattggcca gtttaagaaa | 3600 |
| gcagaagatg agaagctgga caaagtgaaa attgcgatca gcaataaaga gtggctggaa | 3660 |
| tacgcacaga ccagcgttaa acat | 3684 |

<210> SEQ ID NO 16
<211> LENGTH: 3684
<212> TYPE: DNA
<213> ORGANISM: Artificial sequence
<220> FEATURE:
<223> OTHER INFORMATION: Synthetic construct

<400> SEQUENCE: 16

| | |
|---|---:|
| atgagcaaac tggaaaagtt caccaactgt tatagcctga gcaaaaccct gcgttttaaa | 60 |
| gcaattccgg ttggtaaaac ccaagagaac attgataata aacgcctgct ggtcgaagat | 120 |
| gaaaaacgcg ctgaagatta taaaggcgtg aaaaaactgc tggatcgcta ttatctgagc | 180 |
| ttcattaacg atgtgctgca cagcattaaa ctgaagaacc tgaacaacta tatcagcctg | 240 |
| tttcgtaaaa aaacccgcac cgaaaaagaa acaaagagc tggaaaacct ggaaatcaat | 300 |
| ctgcgtaaag aaatcgccaa agcgtttaaa ggtaacgagg ttataaaag cctgttcaag | 360 |
| aaagacatca tcgaaaccat tctgccggaa tttctggatg ataagatga attgccctg | 420 |
| gtgaatagct ttaatggctt taccaccgca tttaccggct tttttgataa tcgcgaaaac | 480 |
| atgttcagcg aagaagcaaa aagcaccagc attgcatttc gctgcattaa tgaaaatctg | 540 |
| acccgctaca ttagcaacat ggatatcttt gaaaagtgg acgcgatctt cgataaacac | 600 |
| gaagtgcaag agatcaaaga gaaaatcctg aacagcgatt atgacgtcga agattttttt | 660 |

-continued

```
gaaggcgagt tctttaactt cgttctgacc caagaaggta tcgacgttta taacgcaatt      720
attggtggtt ttgttaccga aagcggtgag aaaatcaaag gcctgaatga atatatcaac      780
ctgtataacc agaaaaccaa acagaaactg ccgaaattca aaccgctgta taaacaggtt      840
ctgagcgatc gtgaaagcct gagctttat  ggtgaaggtt ataccagtga tgaagaggtt      900
ctggaagttt ttcgtaacac cctgaataaa aacagcgaga tctttagcag catcaaaaag      960
cttgagaaac tgttcaaaaa ctttgatgag tatagcagcg caggcatctt tgttaaaaat     1020
ggtccggcaa ttagcaccat cagcaaagat atttttggcg aatggaatgt gatccgcgat     1080
aaatggaatc cgaatatga  tgatatccac ctgaaaaaaa aggccgtggt gaccgagaaa     1140
tatgaagatg atcgtcgtaa aagcttcaag aaaattggta gctttagcct ggaacagctg     1200
caagaatatg cagatgcaga tctgagcgtt gtggaaaaac tgaaagaaat catcattcag     1260
aaggtggacg agatctataa agtttatggt agcagcgaaa aactgttcga tgcagatttt     1320
gttctggaaa aaagcctgaa aaagaatgat gccgttgtgg ccattatgaa agatctgctg     1380
gatagcgtta agagcttcga gaattacatc aaagcctttt ttggtgaggg caaagaaacc     1440
aatcgtgatg aaagtttcta tggcgatttt gtgctggcct atgatattct gctgaaagtg     1500
gaccatattt atgatgccat tcgcaattat gttacccaga aaccgtatag caaagacaag     1560
ttcaaactgt actttcagcg tccgcagttt atgggtggtt gggataaaga taagaaaacc     1620
gattatcgtg ccaccatcct gcgttatggt agtaaatact atctggccat catgccgaaa     1680
aaatacgcaa aatgcctgca gaaaatcgac aaagatgatg tgaatggcaa ctatgaaaaa     1740
atcaactaca aactgctgcc tggtccgaat aaaatgctgc cgaaagtgtt ctttagcaag     1800
aaatggatgg cctattataa cccgagcgag gatattcaaa agatctacaa aaatggcacc     1860
tttaaaaagg gcgacatgtt caatctgaac gattgccaca aactgatcga tttcttcaaa     1920
gattcaattt cgcgttatcc gaaatggtcc aatgcctatg attttaactt tagcgaaacc     1980
gaaaaataca agacattgc  cggttttat  cgcgaagtgg aagaacaggg ctataaagtg     2040
agctttgaaa gcgcaagcaa aaagagggtt gataagctgg ttgaagaggg caaactgtat     2100
atgttccaga tttacaacaa agattttagc gacaaaagcc atggcacccc gaatctgcat     2160
accatgtact ttaaactgct gttcgacgaa ataaccatg  gtcagattcg tctgagcgtt     2220
ggtgccgaac tgtttatgcg tcgtgcaagt ctgaaaaaag aagaactggt tgttcatccg     2280
gcaaatagcc cgattgcaaa caaaaatccg gacaatccga aaaaaccac  gacactgagc     2340 tatgatgtgt ataaagacaa acgttttagc gaggatcagt atctgctgca tcccgatt      2400 gccatcaata aatgcccgaa aaacatcttt aagatcaaca ccgaagttcg cgtgctgctg     2460
aaacatgatg ataatccgta tgtgattggc attgatcgtg gtgaacgtaa cctgctgtat     2520
attgttgttg ttgatggtaa aggcaacatc gtggaacagt atagtctgaa cgaaattatc     2580
aacaacttta cggcatccg  catcaaaacc gactatcata gcctgctgga caagaaagaa     2640
aaagaacgtt ttgaagcacg tcagaactgg accagtattg aaaacatcaa agaactgaaa     2700
gccggttata ttagccaggt ggttcataaa atctgtgagc tggtagaaaa atacgatgca     2760
gttattgcac tggaagatct gaatagcggt ttcaaaaata gccgtgtgaa agtcgaaaaa     2820
caggtgtatc agaaattcga gaaaatgctg atcgacaaac tgaactacat ggtcgacaaa     2880
aaaagcaatc cgtgtgcaac cggtggtgca ctgaaaggtt atcagattac caacaaattt     2940
gaaagcttta aaagcatgag cacccagaac ggctttatct tctatattcc ggcatggctg     3000
```

| | |
|---|---|
| accagcaaaa ttgatccgag caccggtttt gtgaacctgc tgaaaacaaa atatacctcc | 3060 |
| attgccgaca gcaagaagtt tattagcagc tttgatcgca ttatgtatgt tccggaagag | 3120 |
| gacctgtttg aattcgcact ggattacaaa aatttcagcc gtaccgatgc cgactacatc | 3180 |
| aaaaaatgga aactgtacag ctatggtaac cgcattcgca tttttcgcaa cccgaagaaa | 3240 |
| aacaatgtgt tcgattggga agaagtttgt ctgaccagcg catataaaga acttttcaac | 3300 |
| aaatacggca tcaactatca gcagggtgat attcgtgcac tgctgtgtga acagagcgat | 3360 |
| aaagcgtttt atagcagttt tatggcactg atgagcctga tgctgcagat gcgtaatagc | 3420 |
| attaccggtc gcaccgatgt ggattttctg attagtccgg tgaaaaattc cgatggcatc | 3480 |
| tttatgata gccgcaatta cgaagcacaa gaaaatgcaa ttctgccgaa aaacgcagat | 3540 |
| gcaaatggtg catataacat tgcacgtaaa gttctgtggg caattggcca gtttaagaaa | 3600 |
| gcagaagatg agaagctgga caaagtgaaa attgcgatca gcaataaaga gtggctggaa | 3660 |
| tacgcacaga ccagcgttaa acat | 3684 |

<210> SEQ ID NO 17
<211> LENGTH: 3921
<212> TYPE: DNA
<213> ORGANISM: Unknown
<220> FEATURE:
<223> OTHER INFORMATION: Acidaminococcus sp.

<400> SEQUENCE: 17

| | |
|---|---|
| atgacccagt ttgaaggttt caccaatctg tatcaggtta gcaaaaccct gcgttttgaa | 60 |
| ctgattccgc agggtaaaac cctgaaacat attcaagaac agggcttcat cgaagaggat | 120 |
| aaagcacgta acgatcacta caagaactg aaaccgatta tcgaccgcat ctataaaacc | 180 |
| tatgcagatc agtgtctgca gctggttcag ctggattggg aaaatctgag cgcagcaatt | 240 |
| gatagttatc gcaaagaaaa aaccgaagaa acccgtaatg cactgattga agaacaggca | 300 |
| acctatcgta tgccatcca tgattatttc attggtcgta ccgataatct gaccgatgca | 360 |
| attaacaaac gtcacgccga atctataaa ggcctgttta aagccgaact gtttaatggc | 420 |
| aaagttctga acagctggg caccgttacc accaccgaac atgaaaatgc actgctgcgt | 480 |
| agctttgata aattcaccac ctatttcagc ggcttttatg agaatcgcaa aaacgtgttt | 540 |
| agcgcagaag atattagcac cgcaattccg catcgtattg tgcaggataa tttcccgaaa | 600 |
| ttcaaagaga actgccacat ttttacccgt ctgattaccg cagttccgag cctgcgtgaa | 660 |
| cattttgaaa acgttaaaaa agccatcggc atctttgtta gcaccagcat tgaagaagtt | 720 |
| tttagcttcc cgttttacaa tcagctgctg acccagaccc agattgatct gtataaccaa | 780 |
| ctgctgggtg gtattagccg tgaagcaggc accgaaaaaa tcaaaggtct gaatgaagtg | 840 |
| ctgaatctgg ccattcagaa aaatgatgaa accgcacata ttattgcaag cctgccgcat | 900 |
| cgttttattc cgctgttcaa acaaattctg agcgatcgta taccctgag ctttattctg | 960 |
| gaagaattca atccgatga gaggtgatt cagagctttt gcaaatacaa aacgctgctg | 1020 |
| cgcaatgaaa atgttctgga aactgccgaa gcactgttta cgaactgaa tagcattgat | 1080 |
| ctgacccaca tctttatcag ccacaaaaaa ctggaaacca tttcaagcgc actgtgtgat | 1140 |
| cattgggata ccctgcgtaa tgccctgtat aacgtcgta ttagcgaact gaccggtaaa | 1200 |
| attaccaaaa gcgcgaaaga aaagttcag cgcagtctga acatgagga tattaatctg | 1260 |
| caagagatta ttagcgcagc cggtaaagaa ctgtcagaag catttaaaca gaaaaccagc | 1320 |
| gaaattctgt cacatgcaca tgcagcactg gatcagccgc tgccgaccac cctgaaaaaa | 1380 |

```
caagaagaaa aagaaatcct gaaaagccag ctggatagcc tgctgggtct gtatcatctg   1440
ctggactggt ttgcagttga tgaaagcaat gaagttgatc cggaatttag cgcacgtctg   1500
accggcatta aactggaaat ggaaccgagc ctgagctttt ataacaaagc ccgtaattat   1560
gccaccaaaa aaccgtatag cgtcgaaaaa ttcaaactga actttcagat gccgaccctg   1620
gcaagcggtt gggatgttaa taaagaaaaa acaacggtg ccatcctgtt cgtgaaaaat    1680
ggcctgtatt atctgggtat tatgccgaaa cagaaaggtc gttataaagc gctgagcttt   1740
gaaccgacgg aaaaaaccag tgaaggtttt gataaaatgt actacgacta ttttccggat   1800
gcagccaaaa tgattccgaa atgtagcacc cagctgaaag cagttaccgc acattttcag   1860
acccatacca ccccgattct gctgagcaat aactttattg aaccgctgga aatcaccaaa   1920
gagatctacg atctgaataa cccggaaaaa gagccgaaaa aattccagac cgcatatgca   1980
aaaaaaaccg gtgatcagaa aggttatcgt gaagcgctgt gtaaatggat tgatttcacc   2040
cgtgattttc tgagcaaata caccaaaacc accagtatcg atctgagcag cctgcgtccg   2100
agcagccagt ataaagatct gggcgaatat tatgcagaaa ctgaatccgct gctgtatcat   2160 attagctttc agcgtattgc cgagaaagaa atcatggacg cagttgaaac cggtaaactg   2220
tacctgttcc agatctacaa taaagatttt gccaaaggcc atcatggcaa accgaatctg   2280 catccctgt attggaccgg tctgtttagc cctgaaaatc tggcaaaaac ctcgattaaa    2340
ctgaatggtc aggcggaact gttttatcgt ccgaaaagcc gtatgaaacg tatggcacat   2400
cgtctgggtg aaaaaatgct gaacaaaaaa ctgaaagacc agaaaacccc gatcccggat   2460
acactgtatc aagaactgta tgattatgtg aaccatcgtc tgagccatga tctgagtgat   2520
gaagcacgtg ccctgctgcc gaatgttatt accaagaag ttagccacga gatcattaaa    2580
gatcgtcgtt ttaccagcga caaattcttt tttcatgtgc cgattaccct gaattatcag   2640
gcagcaaata gcccgagcaa atttaaccag cgtgttaatg catatctgaa agaacatcca   2700
gaaacgccga ttattggtat tgatcgtggt gaacgtaacc tgatttatat caccgttatt   2760
gatagcaccg gcaaaatcct ggaacagcgt agcctgaata ccattcagca gtttgattac   2820
cagaaaaaac tggataatcg cgagaaagaa cgtgttgcag cacgtcaggc atggtcagtt   2880
gttggtacaa ttaaagacct gaaacagggt tatctgagcc aggttattca tgaaattgtg   2940
gatctgatga ttcactatca ggccgttgtt gtgctgaaa acctgaattt tggctttaaa    3000
agcaaacgta ccggcattgc agaaaaagca gtttatcagc agttcgagaa aatgctgatt   3060
gacaaactga attgcctggt gctgaaagat tatccggctg aaaaagttgg tggtgttctg   3120
aatccgtatc agctgaccga tcagtttacc agctttgcaa aaatgggcac cagagcgga    3180 tttctgtttt atgttccggc accgtatacg agcaaaattg atccgctgac cggttttgtt   3240
gatccgtttg tttggaaaac catcaaaaac catgaaagcc gcaaacattt tctggaaggt   3300
ttcgattttc tgcattacga cgttaaaacg ggtgatttca tcctgcactt taaaatgaat   3360
cgcaatctga gttttcagcg tggcctgcct ggttttatgc ctgcatggga tattgtgttt   3420
gagaaaaacg aaaacagtt cgatgcaaaa ggcaccccgt ttattgcagg taaacgtatt    3480
gttccggtga ttgaaaatca tcgtttcacc ggtcgttatc gcgatctgta tccggcaaat   3540
gaactgatcg cactgctgga agagaaaggt attgtttttc gtgatggctc aaacattctg   3600
ccgaaactgc tggaaaatga tgatagccat gcaattgata ccatggttgc actgattcgt   3660
agcgttctgc agatgcgtaa tagcaatgca gcaaccggtg aagattacat taatagtccg   3720
```

-continued

```
gttcgtgatc tgaatggtgt ttgttttgat agccgttttc agaatccgga atggccgatg    3780
gatgcagatg caaatggtgc atatcatatt gcactgaaag acagctgct gctgaaccac     3840 ctgaaagaaa gcaaagatct gaaactgcaa acggcatta gcaatcagga ttggctggca    3900
tatatccaag aactgcgtaa c                                                3921
```

```
<210> SEQ ID NO 18
<211> LENGTH: 1307
<212> TYPE: PRT
<213> ORGANISM: Unknown
<220> FEATURE:
<223> OTHER INFORMATION: Acidaminococcus sp.

<400> SEQUENCE: 18
```

| | | | | | | | | | | | | | | | |
|---|---|---|---|---|---|---|---|---|---|---|---|---|---|---|---|
| Met | Thr | Gln | Phe | Glu | Gly | Phe | Thr | Asn | Leu | Tyr | Gln | Val | Ser | Lys | Thr |
| 1 | | | | 5 | | | | | 10 | | | | | 15 | |
| Leu | Arg | Phe | Glu | Leu | Ile | Pro | Gln | Gly | Lys | Thr | Leu | Lys | His | Ile | Gln |
| | | | 20 | | | | | 25 | | | | | 30 | | |
| Glu | Gln | Gly | Phe | Ile | Glu | Asp | Lys | Ala | Arg | Asn | Asp | His | Tyr | Lys | |
| | | 35 | | | | | 40 | | | | | 45 | | | |
| Glu | Leu | Lys | Pro | Ile | Ile | Asp | Arg | Ile | Tyr | Lys | Thr | Tyr | Ala | Asp | Gln |
| 50 | | | | | 55 | | | | | 60 | | | | | |
| Cys | Leu | Gln | Leu | Val | Gln | Leu | Asp | Trp | Glu | Asn | Leu | Ser | Ala | Ala | Ile |
| 65 | | | | 70 | | | | | 75 | | | | | 80 | |
| Asp | Ser | Tyr | Arg | Lys | Glu | Lys | Thr | Glu | Glu | Thr | Arg | Asn | Ala | Leu | Ile |
| | | | | 85 | | | | | 90 | | | | | 95 | |
| Glu | Glu | Gln | Ala | Thr | Tyr | Arg | Asn | Ala | Ile | His | Asp | Tyr | Phe | Ile | Gly |
| | | | 100 | | | | | 105 | | | | | 110 | | |
| Arg | Thr | Asp | Asn | Leu | Thr | Asp | Ala | Ile | Asn | Lys | Arg | His | Ala | Glu | Ile |
| | | 115 | | | | | 120 | | | | | 125 | | | |
| Tyr | Lys | Gly | Leu | Phe | Lys | Ala | Glu | Leu | Phe | Asn | Gly | Lys | Val | Leu | Lys |
| 130 | | | | | 135 | | | | | 140 | | | | | |
| Gln | Leu | Gly | Thr | Val | Thr | Thr | Thr | Glu | His | Glu | Asn | Ala | Leu | Leu | Arg |
| 145 | | | | 150 | | | | | 155 | | | | | 160 | |
| Ser | Phe | Asp | Lys | Phe | Thr | Thr | Tyr | Phe | Ser | Gly | Phe | Tyr | Glu | Asn | Arg |
| | | | | 165 | | | | | 170 | | | | | 175 | |
| Lys | Asn | Val | Phe | Ser | Ala | Glu | Asp | Ile | Ser | Thr | Ala | Ile | Pro | His | Arg |
| | | | 180 | | | | | 185 | | | | | 190 | | |
| Ile | Val | Gln | Asp | Asn | Phe | Pro | Lys | Phe | Lys | Glu | Asn | Cys | His | Ile | Phe |
| | | 195 | | | | | 200 | | | | | 205 | | | |
| Thr | Arg | Leu | Ile | Thr | Ala | Val | Pro | Ser | Leu | Arg | Glu | His | Phe | Glu | Asn |
| | 210 | | | | | 215 | | | | | 220 | | | | |
| Val | Lys | Lys | Ala | Ile | Gly | Ile | Phe | Val | Ser | Thr | Ser | Ile | Glu | Val | |
| 225 | | | | | 230 | | | | | 235 | | | | | 240 |
| Phe | Ser | Phe | Pro | Phe | Tyr | Asn | Gln | Leu | Leu | Thr | Gln | Thr | Gln | Ile | Asp |
| | | | | 245 | | | | | 250 | | | | | 255 | |
| Leu | Tyr | Asn | Gln | Leu | Leu | Gly | Gly | Ile | Ser | Arg | Glu | Ala | Gly | Thr | Glu |
| | | | 260 | | | | | 265 | | | | | 270 | | |
| Lys | Ile | Lys | Gly | Leu | Asn | Glu | Val | Leu | Asn | Leu | Ala | Ile | Gln | Lys | Asn |
| | | 275 | | | | | 280 | | | | | 285 | | | |
| Asp | Glu | Thr | Ala | His | Ile | Ile | Ala | Ser | Leu | Pro | His | Arg | Phe | Ile | Pro |
| | 290 | | | | | 295 | | | | | 300 | | | | |
| Leu | Phe | Lys | Gln | Ile | Leu | Ser | Asp | Arg | Asn | Thr | Leu | Ser | Phe | Ile | Leu |
| 305 | | | | | 310 | | | | | 315 | | | | | 320 |
| Glu | Glu | Phe | Lys | Ser | Asp | Glu | Glu | Val | Ile | Gln | Ser | Phe | Cys | Lys | Tyr |

```
                    325                 330                 335
Lys Thr Leu Leu Arg Asn Glu Asn Val Leu Glu Thr Ala Glu Ala Leu
                340                 345                 350

Phe Asn Glu Leu Asn Ser Ile Asp Leu Thr His Ile Phe Ile Ser His
                355                 360                 365

Lys Lys Leu Glu Thr Ile Ser Ser Ala Leu Cys Asp His Trp Asp Thr
                370                 375                 380

Leu Arg Asn Ala Leu Tyr Glu Arg Arg Ile Ser Glu Leu Thr Gly Lys
385                 390                 395                 400

Ile Thr Lys Ser Ala Lys Glu Lys Val Gln Arg Ser Leu Lys His Glu
                405                 410                 415

Asp Ile Asn Leu Gln Glu Ile Ile Ser Ala Ala Gly Lys Glu Leu Ser
                420                 425                 430

Glu Ala Phe Lys Gln Lys Thr Ser Glu Ile Leu Ser His Ala His Ala
                435                 440                 445

Ala Leu Asp Gln Pro Leu Pro Thr Thr Leu Lys Lys Gln Glu Glu Lys
                450                 455                 460

Glu Ile Leu Lys Ser Gln Leu Asp Ser Leu Leu Gly Leu Tyr His Leu
465                 470                 475                 480

Leu Asp Trp Phe Ala Val Asp Glu Ser Asn Glu Val Asp Pro Glu Phe
                485                 490                 495

Ser Ala Arg Leu Thr Gly Ile Lys Leu Glu Met Glu Pro Ser Leu Ser
                500                 505                 510

Phe Tyr Asn Lys Ala Arg Asn Tyr Ala Thr Lys Lys Pro Tyr Ser Val
                515                 520                 525

Glu Lys Phe Lys Leu Asn Phe Gln Met Pro Thr Leu Ala Ser Gly Trp
                530                 535                 540

Asp Val Asn Lys Glu Lys Asn Asn Gly Ala Ile Leu Phe Val Lys Asn
545                 550                 555                 560

Gly Leu Tyr Tyr Leu Gly Ile Met Pro Lys Gln Lys Gly Arg Tyr Lys
                565                 570                 575

Ala Leu Ser Phe Glu Pro Thr Glu Lys Thr Ser Glu Gly Phe Asp Lys
                580                 585                 590

Met Tyr Tyr Asp Tyr Phe Pro Asp Ala Ala Lys Met Ile Pro Lys Cys
                595                 600                 605

Ser Thr Gln Leu Lys Ala Val Thr Ala His Phe Gln Thr His Thr Thr
                610                 615                 620

Pro Ile Leu Leu Ser Asn Asn Phe Ile Glu Pro Leu Glu Ile Thr Lys
625                 630                 635                 640

Glu Ile Tyr Asp Leu Asn Asn Pro Glu Lys Glu Pro Lys Lys Phe Gln
                645                 650                 655

Thr Ala Tyr Ala Lys Lys Thr Gly Asp Gln Lys Gly Tyr Arg Glu Ala
                660                 665                 670

Leu Cys Lys Trp Ile Asp Phe Thr Arg Asp Phe Leu Ser Lys Tyr Thr
                675                 680                 685

Lys Thr Thr Ser Ile Asp Leu Ser Ser Leu Arg Pro Ser Ser Gln Tyr
                690                 695                 700

Lys Asp Leu Gly Glu Tyr Tyr Ala Glu Leu Asn Pro Leu Leu Tyr His
705                 710                 715                 720

Ile Ser Phe Gln Arg Ile Ala Glu Lys Glu Ile Met Asp Ala Val Glu
                725                 730                 735

Thr Gly Lys Leu Tyr Leu Phe Gln Ile Tyr Asn Lys Asp Phe Ala Lys
                740                 745                 750
```

-continued

Gly His His Gly Lys Pro Asn Leu His Thr Leu Tyr Trp Thr Gly Leu
          755                 760                 765

Phe Ser Pro Glu Asn Leu Ala Lys Thr Ser Ile Lys Leu Asn Gly Gln
    770                 775                 780

Ala Glu Leu Phe Tyr Arg Pro Lys Ser Arg Met Lys Arg Met Ala His
785                 790                 795                 800

Arg Leu Gly Glu Lys Met Leu Asn Lys Leu Lys Asp Gln Lys Thr
              805                 810                 815

Pro Ile Pro Asp Thr Leu Tyr Gln Glu Leu Tyr Asp Tyr Val Asn His
              820                 825                 830

Arg Leu Ser His Asp Leu Ser Asp Glu Ala Arg Ala Leu Leu Pro Asn
              835                 840                 845

Val Ile Thr Lys Glu Val Ser His Glu Ile Ile Lys Asp Arg Arg Phe
    850                 855                 860

Thr Ser Asp Lys Phe Phe Phe His Val Pro Ile Thr Leu Asn Tyr Gln
865                 870                 875                 880

Ala Ala Asn Ser Pro Ser Lys Phe Asn Gln Arg Val Asn Ala Tyr Leu
                  885                 890                 895

Lys Glu His Pro Glu Thr Pro Ile Ile Gly Ile Asp Arg Gly Glu Arg
              900                 905                 910

Asn Leu Ile Tyr Ile Thr Val Ile Asp Ser Thr Gly Lys Ile Leu Glu
              915                 920                 925

Gln Arg Ser Leu Asn Thr Ile Gln Gln Phe Asp Tyr Gln Lys Lys Leu
              930                 935                 940

Asp Asn Arg Glu Lys Glu Arg Val Ala Ala Arg Gln Ala Trp Ser Val
945                 950                 955                 960

Val Gly Thr Ile Lys Asp Leu Lys Gln Gly Tyr Leu Ser Gln Val Ile
              965                 970                 975

His Glu Ile Val Asp Leu Met Ile His Tyr Gln Ala Val Val Val Leu
              980                 985                 990

Glu Asn Leu Asn Phe Gly Phe Lys Ser Lys Arg Thr Gly Ile Ala Glu
              995                 1000                1005

Lys Ala Val Tyr Gln Gln Phe Glu Lys Met Leu Ile Asp Lys Leu
    1010                1015                1020

Asn Cys Leu Val Leu Lys Asp Tyr Pro Ala Glu Lys Val Gly Gly
    1025                1030                1035

Val Leu Asn Pro Tyr Gln Leu Thr Asp Gln Phe Thr Ser Phe Ala
    1040                1045                1050

Lys Met Gly Thr Gln Ser Gly Phe Leu Phe Tyr Val Pro Ala Pro
    1055                1060                1065

Tyr Thr Ser Lys Ile Asp Pro Leu Thr Gly Phe Val Asp Pro Phe
    1070                1075                1080

Val Trp Lys Thr Ile Lys Asn His Glu Ser Arg Lys His Phe Leu
    1085                1090                1095

Glu Gly Phe Asp Phe Leu His Tyr Asp Val Lys Thr Gly Asp Phe
    1100                1105                1110

Ile Leu His Phe Lys Met Asn Arg Asn Leu Ser Phe Gln Arg Gly
    1115                1120                1125

Leu Pro Gly Phe Met Pro Ala Trp Asp Ile Val Phe Glu Lys Asn
    1130                1135                1140

Glu Thr Gln Phe Asp Ala Lys Gly Thr Pro Phe Ile Ala Gly Lys
    1145                1150                1155

| Arg | Ile | Val | Pro | Val | Ile | Glu | Asn | His | Arg | Phe | Thr | Gly | Arg | Tyr |
|-----|-----|-----|-----|-----|-----|-----|-----|-----|-----|-----|-----|-----|-----|-----|
| 1160 | | | | | 1165 | | | | | 1170 | | | | |

Arg Asp Leu Tyr Pro Ala Asn Glu Leu Ile Ala Leu Leu Glu Glu
1175              1180              1185

Lys Gly Ile Val Phe Arg Asp Gly Ser Asn Ile Leu Pro Lys Leu
1190              1195              1200

Leu Glu Asn Asp Asp Ser His Ala Ile Asp Thr Met Val Ala Leu
1205              1210              1215

Ile Arg Ser Val Leu Gln Met Arg Asn Ser Asn Ala Ala Thr Gly
1220              1225              1230

Glu Asp Tyr Ile Asn Ser Pro Val Arg Asp Leu Asn Gly Val Cys
1235              1240              1245

Phe Asp Ser Arg Phe Gln Asn Pro Glu Trp Pro Met Asp Ala Asp
1250              1255              1260

Ala Asn Gly Ala Tyr His Ile Ala Leu Lys Gly Gln Leu Leu Leu
1265              1270              1275

Asn His Leu Lys Glu Ser Lys Asp Leu Lys Leu Gln Asn Gly Ile
1280              1285              1290

Ser Asn Gln Asp Trp Leu Ala Tyr Ile Gln Glu Leu Arg Asn
1295              1300              1305

<210> SEQ ID NO 19
<211> LENGTH: 3921
<212> TYPE: DNA
<213> ORGANISM: Artificial sequence
<220> FEATURE:
<223> OTHER INFORMATION: Synthetic construct

<400> SEQUENCE: 19

```
atgacccagt tgaaggtttt caccaatctg tatcaggtta gcaaaaccct gcgttttgaa      60
ctgattccgc agggtaaaac cctgaaacat attcaagaac agggcttcat cgaagaggat     120
aaagcacgta acgatcacta caaagaactg aaaccgatta tcgaccgcat ctataaaacc     180
tatgcagatc agtgtctgca gctggttcag ctggattggg aaaatctgag cgcagcaatt     240
gatagttatc gcaaagaaaa aaccgaagaa acccgtaatg cactgattga agaacaggca     300
acctatcgta atgccatcca tgattatttc attggtcgta ccgataatct gaccgatgca     360
attaacaaac gtcacgccga aatctataaa ggcctgttta agccgaaact gtttaatggc     420
aaagttctga acagctggg caccgttacc accaccgaac atgaaaatgc actgctgcgt     480
agctttgata aattcaccac ctatttcagc ggcttttatg agaatcgcaa aaacgtgttt     540
agcgcagaag atattagcac cgcaattccg catcgtattg tgcaggataa tttcccgaaa     600
ttcaaagaga actgccacat ttttacccgt ctgattaccg cagttccgag cctgcgtgaa     660
cattttgaaa acgttaaaaa agccatcggc atctttgtta gcaccagcat tgaagaagtt     720
tttagcttcc cgttttacaa tcagctgctg acccagaccc agattgatct gtataaccaa     780
ctgctgggtg gtattagccg tgaagcaggc accgaaaaaa tcaaaggtct gaatgaagtg     840
ctgaatctgg ccattcagaa aaatgatgaa accgcacata ttattgcaag cctgccgcat     900
cgttttattc gcctgttcaa acaaattctg agcgatcgta tacccctgag ctttattctg     960
gaagaattca atccgatga agaggtgatt cagagctttt gcaaatacaa aacgctgctg    1020
cgcaatgaaa atgttctgga aactgccgaa gcactgttta cgaactgaa tagcattgat    1080
ctgacccaca tctttatcag ccacaaaaaa ctggaaacca tttcaagcgc actgtgtgat    1140
cattgggata ccctgcgtaa tgccctgtat gaacgtcgta ttagcgaact gaccggtaaa    1200
```

```
attaccaaaa gcgcgaaaga aaaagttcag cgcagtctga aacatgagga tattaatctg    1260
caagagatta ttagcgcagc cggtaaagaa ctgtcagaag catttaaaca gaaaaccagc    1320
gaaattctgt cacatgcaca tgcagcactg gatcagccgc tgccgaccac cctgaaaaaa    1380
caagaagaaa aagaaatcct gaaaagccag ctggatagcc tgctgggtct gtatcatctg    1440
ctggactggt ttgcagttga tgaaagcaat gaagttgatc cggaatttag cgcacgtctg    1500
accggcatta aactggaaat ggaaccgagc ctgagctttt ataacaaagc ccgtaattat    1560
gccaccaaaa aaccgtatag cgtcgaaaaa ttcaaactga actttcagcg tccgaccctg    1620
gcaagcggtt gggatgttaa taagaaaaaa acaacggtg ccatcctgtt cgtgaaaaat    1680
ggcctgtatt atctgggtat tatgccgaaa cagaaaggtc gttataaagc gctgagcttt    1740
gaaccgacgg aaaaaaccag tgaaggtttt gataaaatgt actacgacta ttttccggat    1800
gcagccaaaa tgattccgaa atgtagcacc cagctgaaag cagttaccgc acattttcag    1860
acccatacca ccccgattct gctgagcaat aactttattg aaccgctgga atcaccaaaa    1920
gagatctacg atctgaataa cccggaaaaa gagccgaaaa aattccagac cgcatatgca    1980
aaaaaaaccg gtgatcagaa aggttatcgt gaagcgctgt gtaaatggat tgatttcacc    2040
cgtgattttc tgagcaaata caccaaaaacc accagtatcg atctgagcag cctgcgtccg    2100
agcagccagt ataagatct gggcgaatat tatgcagaac tgaatccgct gctgtatcat    2160
attagctttc agcgtattgc cgagaaagaa atcatggacg cagttgaaac cggtaaactg    2220
tacctgttcc agatctacaa taagattttt gccaaaggcc atcatggcaa accgaatctg    2280
cataccctgt attggaccgg tctgtttagc cctgaaaatc tggcaaaaac ctcgattaaa    2340
ctgaatggtc aggcggaact gttttatcgt ccgaaaagcc gtatgaaacg tatggcacat    2400
cgtctgggtg aaaaaatgct gaacaaaaaa ctgaaagacc agaaaacccc gatcccggat    2460
acactgtatc aagaactgta tgattatgtg aaccatcgtc tgagccatga tctgagtgat    2520
gaagcacgtg ccctgctgcc gaatgttatt accaaagaag ttagccacga gatcattaaa    2580
gatcgtcgtt ttaccagcga caaattcctg tttcatgtgc cgattaccct gaattatcag    2640
gcagcaaata gcccgagcaa atttaaccag cgtgttaatg catatctgaa agaacatcca    2700
gaaacgccga ttattggtat tgatcgtggt gaacgtaacc tgatttatat caccgttatt    2760
gatagcaccg gcaaaatcct ggaacagcgt agcctgaata ccattcagca gtttgattac    2820
cagaaaaaac tggataatcg cgagaaagaa cgtgttgcag cacgtcaggc atggtcagtt    2880
gttggtacaa ttaaagacct gaaacagggt tatctgagcc aggttattca tgaaattgtg    2940
gatctgatga ttcactatca ggccgttgtt gtgctggaaa acctgaattt tggctttaaa    3000
agcaaacgta ccggcattgc agaaaaagca gtttatcagc agttcgagaa aatgctgatt    3060
gacaaactga attgcctggt gctgaaagat tatccggctg aaaaagttgg tggtgttctg    3120
aatccgtatc agctgaccga tcagtttacc agctttgcaa aaatgggcac ccagagcgga    3180
tttctgtttt atgttccggc accgtatacg agcaaaattg atccgctgac cggttttgtt    3240
gatccgtttg tttggaaaac catcaaaaac catgaaagcc gcaaacattt tctggaaggt    3300
ttcgattttc tgcattacga cgttaaaacg ggtgatttca tcctgcactt taaaatgaat    3360
cgcaatctga gttttcagcg tggcctgcct ggttttatgc ctgcatggga tattgtgttt    3420
gagaaaaacg aaacacagtt cgatgcaaaa ggcacccgt ttattgcagg taaacgtatt    3480
gttccggtga ttgaaaatca tcgtttcacc ggtcgttatc gcgatctgta tccggcaaat    3540
```

```
gaactgatcg cactgctgga agagaaaggt attgttttc  gtgatggctc aaacattctg   3600
ccgaaactgc tggaaaatga tgatagccat gcaattgata ccatggttgc actgattcgt   3660
agcgttctgc agatgcgtaa tagcaatgca gcaaccggtg aagattacat taatagtccg   3720
gttcgtgatc tgaatggtgt ttgttttgat agccgttttc agaatccgga atggccgatg   3780
gatgcagatg caaatggtgc atatcatatt gcactgaaag acagctgct  gctgaaccac   3840 ctgaaagaaa gcaaagatct gaaactgcaa aacggcatta gcaatcagga ttggctggca   3900
tatatccaag aactgcgtaa c                                            3921
```

<210> SEQ ID NO 20
<211> LENGTH: 1307
<212> TYPE: PRT
<213> ORGANISM: Artificial sequence
<220> FEATURE:
<223> OTHER INFORMATION: Synthetic construct

<400> SEQUENCE: 20

```
Met Thr Gln Phe Glu Gly Phe Thr Asn Leu Tyr Gln Val Ser Lys Thr
1               5                   10                  15

Leu Arg Phe Glu Leu Ile Pro Gln Gly Lys Thr Leu Lys His Ile Gln
            20                  25                  30

Glu Gln Gly Phe Ile Glu Glu Asp Lys Ala Arg Asn Asp His Tyr Lys
        35                  40                  45

Glu Leu Lys Pro Ile Ile Asp Arg Ile Tyr Lys Thr Tyr Ala Asp Gln
    50                  55                  60

Cys Leu Gln Leu Val Gln Leu Asp Trp Glu Asn Leu Ser Ala Ala Ile
65                  70                  75                  80

Asp Ser Tyr Arg Lys Glu Lys Thr Glu Thr Arg Asn Ala Leu Ile
            85                  90                  95

Glu Glu Gln Ala Thr Tyr Arg Asn Ala Ile His Asp Tyr Phe Ile Gly
            100                 105                 110

Arg Thr Asp Asn Leu Thr Asp Ala Ile Asn Lys Arg His Ala Glu Ile
            115                 120                 125

Tyr Lys Gly Leu Phe Lys Ala Glu Leu Phe Asn Gly Lys Val Leu Lys
        130                 135                 140

Gln Leu Gly Thr Val Thr Thr Thr Glu His Glu Asn Ala Leu Leu Arg
145                 150                 155                 160

Ser Phe Asp Lys Phe Thr Thr Tyr Phe Ser Gly Phe Tyr Glu Asn Arg
            165                 170                 175

Lys Asn Val Phe Ser Ala Glu Asp Ile Ser Thr Ala Ile Pro His Arg
            180                 185                 190

Ile Val Gln Asp Asn Phe Pro Lys Phe Lys Glu Asn Cys His Ile Phe
        195                 200                 205

Thr Arg Leu Ile Thr Ala Val Pro Ser Leu Arg Glu His Phe Glu Asn
    210                 215                 220

Val Lys Lys Ala Ile Gly Ile Phe Val Ser Thr Ser Ile Glu Glu Val
225                 230                 235                 240

Phe Ser Phe Pro Phe Tyr Asn Gln Leu Leu Thr Gln Thr Gln Ile Asp
            245                 250                 255

Leu Tyr Asn Gln Leu Leu Gly Gly Ile Ser Arg Glu Ala Gly Thr Glu
            260                 265                 270

Lys Ile Lys Gly Leu Asn Glu Val Leu Asn Leu Ala Ile Gln Lys Asn
        275                 280                 285

Asp Glu Thr Ala His Ile Ile Ala Ser Leu Pro His Arg Phe Ile Pro
```

```
                    290                 295                 300
Leu Phe Lys Gln Ile Leu Ser Asp Arg Asn Thr Leu Ser Phe Ile Leu
305                 310                 315                 320
Glu Glu Phe Lys Ser Asp Glu Val Ile Gln Ser Phe Cys Lys Tyr
                325                 330                 335
Lys Thr Leu Leu Arg Asn Glu Asn Val Leu Glu Thr Ala Glu Ala Leu
                340                 345                 350
Phe Asn Glu Leu Asn Ser Ile Asp Leu Thr His Ile Phe Ile Ser His
                355                 360                 365
Lys Lys Leu Glu Thr Ile Ser Ser Ala Leu Cys Asp His Trp Asp Thr
370                 375                 380
Leu Arg Asn Ala Leu Tyr Glu Arg Arg Ile Ser Glu Leu Thr Gly Lys
385                 390                 395                 400
Ile Thr Lys Ser Ala Lys Glu Lys Val Gln Arg Ser Leu Lys His Glu
                405                 410                 415
Asp Ile Asn Leu Gln Glu Ile Ile Ser Ala Ala Gly Lys Glu Leu Ser
                420                 425                 430
Glu Ala Phe Lys Gln Lys Thr Ser Glu Ile Leu Ser His Ala His Ala
                435                 440                 445
Ala Leu Asp Gln Pro Leu Pro Thr Thr Leu Lys Lys Gln Glu Glu Lys
450                 455                 460
Glu Ile Leu Lys Ser Gln Leu Asp Ser Leu Leu Gly Leu Tyr His Leu
465                 470                 475                 480
Leu Asp Trp Phe Ala Val Asp Glu Ser Asn Glu Val Asp Pro Glu Phe
                485                 490                 495
Ser Ala Arg Leu Thr Gly Ile Lys Leu Glu Met Glu Pro Ser Leu Ser
                500                 505                 510
Phe Tyr Asn Lys Ala Arg Asn Tyr Ala Thr Lys Lys Pro Tyr Ser Val
                515                 520                 525
Glu Lys Phe Lys Leu Asn Phe Gln Arg Pro Thr Leu Ala Ser Gly Trp
                530                 535                 540
Asp Val Asn Lys Glu Lys Asn Asn Gly Ala Ile Leu Phe Val Lys Asn
545                 550                 555                 560
Gly Leu Tyr Tyr Leu Gly Ile Met Pro Lys Gln Lys Gly Arg Tyr Lys
                565                 570                 575
Ala Leu Ser Phe Glu Pro Thr Glu Lys Thr Ser Glu Gly Phe Asp Lys
                580                 585                 590
Met Tyr Tyr Asp Tyr Phe Pro Asp Ala Ala Lys Met Ile Pro Lys Cys
                595                 600                 605
Ser Thr Gln Leu Lys Ala Val Thr Ala His Phe Gln Thr His Thr Thr
610                 615                 620
Pro Ile Leu Leu Ser Asn Phe Ile Glu Pro Leu Glu Ile Thr Lys
625                 630                 635                 640
Glu Ile Tyr Asp Leu Asn Asn Pro Glu Lys Glu Pro Lys Lys Phe Gln
                645                 650                 655
Thr Ala Tyr Ala Lys Lys Thr Gly Asp Gln Lys Gly Tyr Arg Glu Ala
                660                 665                 670
Leu Cys Lys Trp Ile Asp Phe Thr Arg Asp Phe Leu Ser Lys Tyr Thr
                675                 680                 685
Lys Thr Thr Ser Ile Asp Leu Ser Ser Leu Arg Pro Ser Ser Gln Tyr
                690                 695                 700
Lys Asp Leu Gly Glu Tyr Tyr Ala Glu Leu Asn Pro Leu Leu Tyr His
705                 710                 715                 720
```

-continued

Ile Ser Phe Gln Arg Ile Ala Glu Lys Glu Ile Met Asp Ala Val Glu
                725                 730                 735

Thr Gly Lys Leu Tyr Leu Phe Gln Ile Tyr Asn Lys Asp Phe Ala Lys
                740                 745                 750

Gly His His Gly Lys Pro Asn Leu His Thr Leu Tyr Trp Thr Gly Leu
            755                 760                 765

Phe Ser Pro Glu Asn Leu Ala Lys Thr Ser Ile Lys Leu Asn Gly Gln
770                 775                 780

Ala Glu Leu Phe Tyr Arg Pro Lys Ser Arg Met Lys Arg Met Ala His
785                 790                 795                 800

Arg Leu Gly Glu Lys Met Leu Asn Lys Lys Leu Lys Asp Gln Lys Thr
                805                 810                 815

Pro Ile Pro Asp Thr Leu Tyr Gln Glu Leu Tyr Asp Tyr Val Asn His
                820                 825                 830

Arg Leu Ser His Asp Leu Ser Asp Glu Ala Arg Ala Leu Leu Pro Asn
                835                 840                 845

Val Ile Thr Lys Glu Val Ser His Glu Ile Ile Lys Asp Arg Arg Phe
            850                 855                 860

Thr Ser Asp Lys Phe Leu Phe His Val Pro Ile Thr Leu Asn Tyr Gln
865                 870                 875                 880

Ala Ala Asn Ser Pro Ser Lys Phe Asn Gln Arg Val Asn Ala Tyr Leu
                885                 890                 895

Lys Glu His Pro Glu Thr Pro Ile Ile Gly Ile Asp Arg Gly Glu Arg
                900                 905                 910

Asn Leu Ile Tyr Ile Thr Val Ile Asp Ser Thr Gly Lys Ile Leu Glu
            915                 920                 925

Gln Arg Ser Leu Asn Thr Ile Gln Gln Phe Asp Tyr Gln Lys Lys Leu
            930                 935                 940

Asp Asn Arg Glu Lys Glu Arg Val Ala Ala Arg Gln Ala Trp Ser Val
945                 950                 955                 960

Val Gly Thr Ile Lys Asp Leu Lys Gln Gly Tyr Leu Ser Gln Val Ile
                965                 970                 975

His Glu Ile Val Asp Leu Met Ile His Tyr Gln Ala Val Val Val Leu
                980                 985                 990

Glu Asn Leu Asn Phe Gly Phe Lys Ser Lys Arg Thr Gly Ile Ala Glu
            995                 1000                1005

Lys Ala Val Tyr Gln Gln Phe Glu Lys Met Leu Ile Asp Lys Leu
    1010                1015                1020

Asn Cys Leu Val Leu Lys Asp Tyr Pro Ala Glu Lys Val Gly Gly
    1025                1030                1035

Val Leu Asn Pro Tyr Gln Leu Thr Asp Gln Phe Thr Ser Phe Ala
    1040                1045                1050

Lys Met Gly Thr Gln Ser Gly Phe Leu Phe Tyr Val Pro Ala Pro
    1055                1060                1065

Tyr Thr Ser Lys Ile Asp Pro Leu Thr Gly Phe Val Asp Pro Phe
    1070                1075                1080

Val Trp Lys Thr Ile Lys Asn His Glu Ser Arg Lys His Phe Leu
    1085                1090                1095

Glu Gly Phe Asp Phe Leu His Tyr Asp Val Lys Thr Gly Asp Phe
    1100                1105                1110

Ile Leu His Phe Lys Met Asn Arg Asn Leu Ser Phe Gln Arg Gly
    1115                1120                1125

```
Leu Pro Gly Phe Met Pro Ala Trp Asp Ile Val Phe Glu Lys Asn
    1130            1135                1140

Glu Thr Gln Phe Asp Ala Lys Gly Thr Pro Phe Ile Ala Gly Lys
    1145            1150                1155

Arg Ile Val Pro Val Ile Glu Asn His Arg Phe Thr Gly Arg Tyr
    1160            1165                1170

Arg Asp Leu Tyr Pro Ala Asn Glu Leu Ile Ala Leu Leu Glu Glu
    1175            1180                1185

Lys Gly Ile Val Phe Arg Asp Gly Ser Asn Ile Leu Pro Lys Leu
    1190            1195                1200

Leu Glu Asn Asp Asp Ser His Ala Ile Asp Thr Met Val Ala Leu
    1205            1210                1215

Ile Arg Ser Val Leu Gln Met Arg Asn Ser Asn Ala Ala Thr Gly
    1220            1225                1230

Glu Asp Tyr Ile Asn Ser Pro Val Arg Asp Leu Asn Gly Val Cys
    1235            1240                1245

Phe Asp Ser Arg Phe Gln Asn Pro Glu Trp Pro Met Asp Ala Asp
    1250            1255                1260

Ala Asn Gly Ala Tyr His Ile Ala Leu Lys Gly Gln Leu Leu Leu
    1265            1270                1275

Asn His Leu Lys Glu Ser Lys Asp Leu Lys Leu Gln Asn Gly Ile
    1280            1285                1290

Ser Asn Gln Asp Trp Leu Ala Tyr Ile Gln Glu Leu Arg Asn
    1295            1300                1305

<210> SEQ ID NO 21
<211> LENGTH: 53
<212> TYPE: DNA
<213> ORGANISM: Artificial sequence
<220> FEATURE:
<223> OTHER INFORMATION: Synthetic construct

<400> SEQUENCE: 21
gcaaagacaa gttcaaactg tactttcagc gtccgcagtt tatgggtggt tgg        53

<210> SEQ ID NO 22
<211> LENGTH: 53
<212> TYPE: DNA
<213> ORGANISM: Artificial sequence
<220> FEATURE:
<223> OTHER INFORMATION: Synthetic construct

<400> SEQUENCE: 22
ccaaccaccc ataaactgcg gacgctgaaa gtacagtttg aacttgtctt tgc        53

<210> SEQ ID NO 23
<211> LENGTH: 58
<212> TYPE: DNA
<213> ORGANISM: Artificial sequence
<220> FEATURE:
<223> OTHER INFORMATION: Synthetic construct

<400> SEQUENCE: 23
tatggtagta atactatct ggccatcatg ccgaaaaaat acgcaaaatg cctgcaga    58

<210> SEQ ID NO 24
<211> LENGTH: 58
<212> TYPE: DNA
<213> ORGANISM: Artificial sequence
<220> FEATURE:
<223> OTHER INFORMATION: Synthetic construct
```

-continued

<400> SEQUENCE: 24
tctgcaggca ttttgcgtat tttttcggca tgatggccag atagtattta ctaccata    58

<210> SEQ ID NO 25
<211> LENGTH: 51
<212> TYPE: DNA
<213> ORGANISM: Artificial sequence
<220> FEATURE:
<223> OTHER INFORMATION: Synthetic construct

<400> SEQUENCE: 25
acaaacgttt tagcgaggat cagtatctgc tgcatatccc gattgccatc a    51

<210> SEQ ID NO 26
<211> LENGTH: 51
<212> TYPE: DNA
<213> ORGANISM: Artificial sequence
<220> FEATURE:
<223> OTHER INFORMATION: Synthetic construct

<400> SEQUENCE: 26
tgatggcaat cgggatatgc agcagatact gatcctcgct aaaacgtttg t    51

<210> SEQ ID NO 27
<211> LENGTH: 44
<212> TYPE: RNA
<213> ORGANISM: Artificial sequence
<220> FEATURE:
<223> OTHER INFORMATION: Synthetic construct

<400> SEQUENCE: 27
uaauuucuac uaaguguaga uauagucuuu ccuugggucu guua    44

<210> SEQ ID NO 28
<211> LENGTH: 44
<212> TYPE: RNA
<213> ORGANISM: Artificial sequence
<220> FEATURE:
<223> OTHER INFORMATION: Synthetic construct

<400> SEQUENCE: 28
uaauuucuac uaaguguaga ucuugggugu guuaaaagug acca    44

<210> SEQ ID NO 29
<211> LENGTH: 44
<212> TYPE: RNA
<213> ORGANISM: Artificial sequence
<220> FEATURE:
<223> OTHER INFORMATION: Synthetic construct

<400> SEQUENCE: 29
uaauuucuac uaaguguaga uacacaccca aggaaagacu auga    44

<210> SEQ ID NO 30
<211> LENGTH: 44
<212> TYPE: RNA
<213> ORGANISM: Artificial sequence
<220> FEATURE:
<223> OTHER INFORMATION: Synthetic construct

<400> SEQUENCE: 30
uaauuucuac uaaguguaga uauccgugcu gaguguacca ugca    44

<210> SEQ ID NO 31

```
<211> LENGTH: 44
<212> TYPE: RNA
<213> ORGANISM: Artificial sequence
<220> FEATURE:
<223> OTHER INFORMATION: Synthetic construct

<400> SEQUENCE: 31
uaauuucuac uaaguguaga uuaaacacug uuucauuuca uccg        44

<210> SEQ ID NO 32
<211> LENGTH: 44
<212> TYPE: RNA
<213> ORGANISM: Artificial sequence
<220> FEATURE:
<223> OTHER INFORMATION: Synthetic construct

<400> SEQUENCE: 32
uaauuucuac uaaguguaga ugaaacguca gucuucucuu uugu        44

<210> SEQ ID NO 33
<211> LENGTH: 44
<212> TYPE: RNA
<213> ORGANISM: Artificial sequence
<220> FEATURE:
<223> OTHER INFORMATION: Synthetic construct

<400> SEQUENCE: 33
uaauuucuac uaaguguaga uuaaugcccu guagucucuc ugua        44

<210> SEQ ID NO 34
<211> LENGTH: 44
<212> TYPE: RNA
<213> ORGANISM: Artificial sequence
<220> FEATURE:
<223> OTHER INFORMATION: Synthetic construct

<400> SEQUENCE: 34
uaauuucuac uaaguguaga uuaauuaaca gcuugcuggu gaaa        44

<210> SEQ ID NO 35
<211> LENGTH: 44
<212> TYPE: RNA
<213> ORGANISM: Artificial sequence
<220> FEATURE:
<223> OTHER INFORMATION: Synthetic construct

<400> SEQUENCE: 35
uaauuucuac uaaguguaga ugguuaaaga ugguuaaaug auug        44

<210> SEQ ID NO 36
<211> LENGTH: 44
<212> TYPE: RNA
<213> ORGANISM: Artificial sequence
<220> FEATURE:
<223> OTHER INFORMATION: Synthetic construct

<400> SEQUENCE: 36
uaauuucuac uaaguguaga uugugaaaug gcuuauaauu gcuu        44

<210> SEQ ID NO 37
<211> LENGTH: 44
<212> TYPE: RNA
<213> ORGANISM: Artificial sequence
<220> FEATURE:
<223> OTHER INFORMATION: Synthetic construct

<400> SEQUENCE: 37
```
uaauuucuac uaaguguaga uguuguugga uuugaaauuc caga        44

<210> SEQ ID NO 38
<211> LENGTH: 44
<212> TYPE: RNA
<213> ORGANISM: Artificial sequence
<220> FEATURE:
<223> OTHER INFORMATION: Synthetic construct

<400> SEQUENCE: 38
uaauuucuac uaaguguaga uuuguaggau augcccuuga cuau        44

<210> SEQ ID NO 39
<211> LENGTH: 41
<212> TYPE: RNA
<213> ORGANISM: Artificial sequence
<220> FEATURE:
<223> OTHER INFORMATION: Synthetic construct

<400> SEQUENCE: 39
uaauuucuac ucuuguagau auagucuuuc cuugggugug u        41

<210> SEQ ID NO 40
<211> LENGTH: 41
<212> TYPE: RNA
<213> ORGANISM: Artificial sequence
<220> FEATURE:
<223> OTHER INFORMATION: Synthetic construct

<400> SEQUENCE: 40
uaauuucuac ucuuguagau cuugggugug uuaaaaguga c        41

<210> SEQ ID NO 41
<211> LENGTH: 41
<212> TYPE: RNA
<213> ORGANISM: Artificial sequence
<220> FEATURE:
<223> OTHER INFORMATION: Synthetic construct

<400> SEQUENCE: 41
uaauuucuac ucuuguagau acacacccaa ggaaagacua u        41

<210> SEQ ID NO 42
<211> LENGTH: 41
<212> TYPE: RNA
<213> ORGANISM: Artificial sequence
<220> FEATURE:
<223> OTHER INFORMATION: Synthetic construct

<400> SEQUENCE: 42
uaauuucuac ucuuguagau auccgugcug aguguaccau g        41

<210> SEQ ID NO 43
<211> LENGTH: 41
<212> TYPE: RNA
<213> ORGANISM: Artificial sequence
<220> FEATURE:
<223> OTHER INFORMATION: Synthetic construct

<400> SEQUENCE: 43
uaauuucuac ucuuguagau uaaacacugu uucauuucau c        41

<210> SEQ ID NO 44
<211> LENGTH: 41
<212> TYPE: RNA

```
<213> ORGANISM: Artificial sequence
<220> FEATURE:
<223> OTHER INFORMATION: Synthetic construct

<400> SEQUENCE: 44
uaauuucuac ucuuguagau gaaacgucag ucuucucuuu u                    41

<210> SEQ ID NO 45
<211> LENGTH: 41
<212> TYPE: RNA
<213> ORGANISM: Artificial sequence
<220> FEATURE:
<223> OTHER INFORMATION: Synthetic construct

<400> SEQUENCE: 45
uaauuucuac ucuuguagau uaaugcccug uagucucucu g                    41

<210> SEQ ID NO 46
<211> LENGTH: 41
<212> TYPE: RNA
<213> ORGANISM: Artificial sequence
<220> FEATURE:
<223> OTHER INFORMATION: Synthetic construct

<400> SEQUENCE: 46
uaauuucuac ucuuguagau uaauuaacag cuugcuggug a                    41

<210> SEQ ID NO 47
<211> LENGTH: 41
<212> TYPE: RNA
<213> ORGANISM: Artificial sequence
<220> FEATURE:
<223> OTHER INFORMATION: Synthetic construct

<400> SEQUENCE: 47
uaauuucuac ucuuguagau gguuaaagau gguuaaauga u                    41

<210> SEQ ID NO 48
<211> LENGTH: 41
<212> TYPE: RNA
<213> ORGANISM: Artificial sequence
<220> FEATURE:
<223> OTHER INFORMATION: Synthetic construct

<400> SEQUENCE: 48
uaauuucuac ucuuguagau ugugaaaugg cuuauaauug c                    41

<210> SEQ ID NO 49
<211> LENGTH: 41
<212> TYPE: RNA
<213> ORGANISM: Artificial sequence
<220> FEATURE:
<223> OTHER INFORMATION: Synthetic construct

<400> SEQUENCE: 49
uaauuucuac ucuuguagau guuguuggau uugaaauucc a                    41

<210> SEQ ID NO 50
<211> LENGTH: 41
<212> TYPE: RNA
<213> ORGANISM: Artificial sequence
<220> FEATURE:
<223> OTHER INFORMATION: Synthetic construct

<400> SEQUENCE: 50
uaauuucuac ucuuguagau uuguaggaua ugcccuugac u                    41
```

<210> SEQ ID NO 51
<211> LENGTH: 26
<212> TYPE: DNA
<213> ORGANISM: Artificial sequence
<220> FEATURE:
<223> OTHER INFORMATION: Synthetic construct

<400> SEQUENCE: 51
aagaagttgt gataaaaggt gatgct                                          26

<210> SEQ ID NO 52
<211> LENGTH: 24
<212> TYPE: DNA
<213> ORGANISM: Artificial sequence
<220> FEATURE:
<223> OTHER INFORMATION: Synthetic construct

<400> SEQUENCE: 52
acacatccat gggacttctg cctc                                            24

<210> SEQ ID NO 53
<211> LENGTH: 15
<212> TYPE: PRT
<213> ORGANISM: Artificial sequence
<220> FEATURE:
<223> OTHER INFORMATION: Synthetic construct

<400> SEQUENCE: 53

Gly Leu Asn Asp Ile Phe Glu Ala Gln Lys Ile Glu Trp His Glu
1               5                   10                  15

<210> SEQ ID NO 54
<211> LENGTH: 26
<212> TYPE: PRT
<213> ORGANISM: Artificial sequence
<220> FEATURE:
<223> OTHER INFORMATION: Synthetic construct

<400> SEQUENCE: 54

Lys Arg Arg Trp Lys Lys Asn Phe Ile Ala Val Ser Ala Ala Asn Arg
1               5                   10                  15

Phe Lys Lys Ile Ser Ser Ser Gly Ala Leu
            20                  25

<210> SEQ ID NO 55
<211> LENGTH: 6
<212> TYPE: PRT
<213> ORGANISM: Artificial sequence
<220> FEATURE:
<223> OTHER INFORMATION: Synthetic construct

<400> SEQUENCE: 55

Glu Glu Glu Glu Glu Glu
1               5

<210> SEQ ID NO 56
<211> LENGTH: 13
<212> TYPE: PRT
<213> ORGANISM: Artificial sequence
<220> FEATURE:
<223> OTHER INFORMATION: Synthetic construct

<400> SEQUENCE: 56

Gly Ala Pro Val Pro Tyr Pro Asp Pro Leu Glu Pro Arg
1               5                   10

<210> SEQ ID NO 57
<211> LENGTH: 8
<212> TYPE: PRT
<213> ORGANISM: Artificial sequence
<220> FEATURE:
<223> OTHER INFORMATION: Synthetic construct

<400> SEQUENCE: 57

Asp Tyr Lys Asp Asp Asp Asp Lys
1               5

<210> SEQ ID NO 58
<211> LENGTH: 9
<212> TYPE: PRT
<213> ORGANISM: Artificial sequence
<220> FEATURE:
<223> OTHER INFORMATION: Synthetic construct

<400> SEQUENCE: 58

Tyr Pro Tyr Asp Val Pro Asp Tyr Ala
1               5

<210> SEQ ID NO 59
<211> LENGTH: 6
<212> TYPE: PRT
<213> ORGANISM: Artificial sequence
<220> FEATURE:
<223> OTHER INFORMATION: Synthetic construct

<400> SEQUENCE: 59

His His His His His His
1               5

<210> SEQ ID NO 60
<211> LENGTH: 10
<212> TYPE: PRT
<213> ORGANISM: Artificial sequence
<220> FEATURE:
<223> OTHER INFORMATION: Synthetic construct

<400> SEQUENCE: 60

Glu Gln Lys Leu Ile Ser Glu Glu Asp Leu
1               5                   10

<210> SEQ ID NO 61
<211> LENGTH: 18
<212> TYPE: PRT
<213> ORGANISM: Artificial sequence
<220> FEATURE:
<223> OTHER INFORMATION: Synthetic construct

<400> SEQUENCE: 61

Thr Lys Glu Asn Pro Arg Ser Asn Gln Glu Glu Ser Tyr Asp Asp Asn
1               5                   10                  15

Glu Ser

<210> SEQ ID NO 62
<211> LENGTH: 15
<212> TYPE: PRT
<213> ORGANISM: Artificial sequence
<220> FEATURE:
<223> OTHER INFORMATION: Synthetic construct

<400> SEQUENCE: 62

Lys Glu Thr Ala Ala Ala Lys Phe Glu Arg Gln His Met Asp Ser

<210> SEQ ID NO 63
<211> LENGTH: 38
<212> TYPE: PRT
<213> ORGANISM: Artificial sequence
<220> FEATURE:
<223> OTHER INFORMATION: Synthetic construct

<400> SEQUENCE: 63

Met Asp Glu Lys Thr Thr Gly Trp Arg Gly Gly His Val Val Glu Gly
1               5                   10                  15

Leu Ala Gly Glu Leu Glu Gln Leu Arg Ala Arg Leu Glu His His Pro
            20                  25                  30

Gln Gly Gln Arg Glu Pro
        35

<210> SEQ ID NO 64
<211> LENGTH: 13
<212> TYPE: PRT
<213> ORGANISM: Artificial sequence
<220> FEATURE:
<223> OTHER INFORMATION: Synthetic construct

<400> SEQUENCE: 64

Ser Leu Ala Glu Leu Leu Asn Ala Gly Leu Gly Gly Ser
1               5                   10

<210> SEQ ID NO 65
<211> LENGTH: 8
<212> TYPE: PRT
<213> ORGANISM: Artificial sequence
<220> FEATURE:
<223> OTHER INFORMATION: Synthetic construct

<400> SEQUENCE: 65

Thr Gln Asp Pro Ser Arg Val Gly
1               5

<210> SEQ ID NO 66
<211> LENGTH: 8
<212> TYPE: PRT
<213> ORGANISM: Artificial sequence
<220> FEATURE:
<223> OTHER INFORMATION: Synthetic construct

<400> SEQUENCE: 66

Trp Ser His Pro Gln Phe Glu Lys
1               5

<210> SEQ ID NO 67
<211> LENGTH: 6
<212> TYPE: PRT
<213> ORGANISM: Artificial sequence
<220> FEATURE:
<223> OTHER INFORMATION: Synthetic construct

<400> SEQUENCE: 67

Cys Cys Pro Gly Cys Cys
1               5

<210> SEQ ID NO 68
<211> LENGTH: 14
<212> TYPE: PRT
<213> ORGANISM: Artificial sequence
<220> FEATURE:

<223> OTHER INFORMATION: Synthetic construct

<400> SEQUENCE: 68

Gly Lys Pro Ile Pro Asn Pro Leu Leu Gly Leu Asp Ser Thr
1               5                   10

<210> SEQ ID NO 69
<211> LENGTH: 11
<212> TYPE: PRT
<213> ORGANISM: Artificial sequence
<220> FEATURE:
<223> OTHER INFORMATION: Synthetic construct

<400> SEQUENCE: 69

Tyr Thr Asp Ile Glu Met Asn Arg Leu Gly Lys
1               5                   10

<210> SEQ ID NO 70
<211> LENGTH: 8
<212> TYPE: PRT
<213> ORGANISM: Artificial sequence
<220> FEATURE:
<223> OTHER INFORMATION: Synthetic construct

<400> SEQUENCE: 70

Asp Leu Tyr Asp Asp Asp Asp Lys
1               5

<210> SEQ ID NO 71
<211> LENGTH: 16
<212> TYPE: PRT
<213> ORGANISM: Artificial sequence
<220> FEATURE:
<223> OTHER INFORMATION: Synthetic construct

<400> SEQUENCE: 71

Thr Asp Lys Asp Met Thr Ile Thr Phe Thr Asn Lys Lys Asp Ala Glu
1               5                   10                  15

<210> SEQ ID NO 72
<211> LENGTH: 13
<212> TYPE: PRT
<213> ORGANISM: Artificial sequence
<220> FEATURE:
<223> OTHER INFORMATION: Synthetic construct

<400> SEQUENCE: 72

Ala His Ile Val Met Val Asp Ala Tyr Lys Pro Thr Lys
1               5                   10

<210> SEQ ID NO 73
<211> LENGTH: 12
<212> TYPE: PRT
<213> ORGANISM: Artificial sequence
<220> FEATURE:
<223> OTHER INFORMATION: Synthetic construct

<400> SEQUENCE: 73

Lys Leu Gly Asp Ile Glu Phe Ile Lys Val Asn Lys
1               5                   10

LACHNOSPIRACEAE BACTERIUM ND2006 CAS12A MUTANT GENES AND POLYPEPTIDES ENCODED BY SAME

CROSS-REFERENCE TO RELATED APPLICATIONS

This application is a U.S. national stage entry of International Patent Application No. PCT/US2020/019168, filed on Feb. 21, 2020, which claims the benefit to U.S. Provisional Patent Application No. 62/808,984, filed on Feb. 22, 2019, the disclosure of which is hereby incorporated by reference in its entirety.

FIELD OF THE INVENTION

This invention pertains to *Lachnospiraceae bacterium* Cas12a based CRISPR genes, polypeptides encoded by the same, mammalian cell lines that stably express Cas12, crRNAs and the use of these materials in compositions of CRISPR-Cas12a systems and methods.

REFERENCE TO SEQUENCE LISTING

This application is filed with a Computer Readable Form of a Sequence Listing in accord with 37 C.F.R. § 1.821(c). The text file submitted in the USPTO Patent Center, "013670-9059-US02_sequence_listing_17-10-2024_ST25.txt," was created on Oct. 17, 2024, contains 73 sequences, has a file size of 168 kilobytes (172,032 bytes), and is hereby incorporated by reference in its entirety.

BACKGROUND OF THE INVENTION

Cas12a (previously named Cpf1) is a class 2/type V CRISPR RNA-guided endonuclease. (Zetsche, B et al., (2015) Cas12a is a single RNA-guided endonuclease of a class 2 CRISPR-Cas system. *Cell* 163:1-13). Cas12a is an effective nuclease used for genome editing and is an alternative to the Cas9 enzyme. Cas12a is a ~1300 amino acid protein and is slightly smaller than Cas9 from *S. pyogenes*. The Cas12 system does not utilize a separate tracrRNA, and only requires a single short crRNA of 40-45 nucleotides in length that both specifies target DNA sequence and directs binding of the RNA to the Cas12a nuclease. (Hur, J. K., et al. (2016) Targeted mutagenesis in mice by electroporation of Cas12a ribonucleoproteins. *Nature Biotechnology*, 34:807-808). The PAM recognition sequence of Cas12a is TTTV which allows for expanded coverage in adenine and thymidine rich areas of the genome that Cas9 cannot access.

Cleavage by Cas12a results in a staggered double-stranded break in the DNA with 4-5 nucleotide overhangs, which leaves staggered ends distal to the PAM site (Gao, P. et al., (2016) Type V CRISPR-Cas Cas12a endonuclease employs a unique mechanism for crRNA-mediated target DNA recognition. *Cell Research* 26:901-913. These double stranded breaks can then be repaired via non-homologous end joining (NHEJ) which often leads to mutations or insertions/deletions at the cut site or site or homology directed repair (HDR) which can generate precise editing events. Furthermore, when Cas12a cleaves, it does so further away from PAM than Cas9, which is also further away from the target site. As a result, the protospacer, and especially the seed sequence of the protospacer, are less likely to be edited, thereby leaving open the potential for a second round of cleavage if the desired repair event doesn't occur the first time.

LbCas12a is an RNA guided endonuclease from the Clustered Regularly Interspaced Short Palindromic Repeat (CRISPR) adaptive immune system from *Lachnospiraceae bacterium* ND2006 (Lb) species. Cas12a nucleases are classified as a class 2 type V CRISPR system that provide a staggered DNA double-stranded break with a 5-nucleotide 5'-overhang when complexed with a CRISPR RNA (crRNA) [1]. The LbCas12a:crRNA complex is referred to as a CRISPR ribonucleoprotein (RNP) complex.

LbCas12a, along with AsCas12a (*Acidaminococcus* sp. BV3L6), was first characterized in 2015 [1] and since have successfully been used for genome editing in eukaryotic cells [1-8]. The two Cas12a variants, As and Lb, share a 34% sequence identity and have both been crystallized by the Nureki group [9-10]. The RuvC and Nuc domains of both variants of Cas12a are structurally similar and cleave the target DNA by similar mechanisms [9-10]. Both variants recognize the TTTV as the canonical PAM and have been shown to tolerate CTTV, TCTV and TTCV as non-canonical PAMs [6, 10].

Engineered Cas12a proteins have been reported by Zhang and coworkers that show altered PAM specificities [11]. Their primary objective was to perform a structure guided mutagenesis screen on AsCas12a, followed by mirror mutations in LbCas12a. This resulted in two mutant variants, AsCas12a-S542R/K607R and AsCas12a-S542R/K548V/N552R, which recognized the PAMs TYCV and TATV, respectively. These mutants retained the high specificity of these CRISPR proteins and introducing these mutations into LbCas12a (G532R/K595R and G532R/K538V/T542R, respectively) resulted in similar PAM-altering specificity [11].

BRIEF SUMMARY OF THE INVENTION

This invention pertains to Cas12a CRISPR genes and mutants, polypeptides encoded by the same, mammalian cell lines that stably express Cas12a and their use in compositions of CIRSPR-Cas12a systems and methods. Examples are shown employing the Cpf1 systems from *Lachnospiraceae bacterium* ND2006 (Lb) however this is not intended to limit scope, which extends to Cas12a homologs or orthologs isolated from other species.

Additionally, the present invention pertains to the ability to cleave double-stranded DNA of living organisms at precise locations with the CRISPR/LbCas12a nuclease system. Additionally, the present invention describes the single amino acid substitution of LbCas12a that enhances genome editing efficiency as compared to wild type Cas12a variants, LbCas12a and AsCas12a, and is claimed as LbCas12a-E795L. This invention also includes six other mutants of LbCas12a, N527R, D559P, N527R/D559P, N527R/E795L, D559P/E795L and N527R/D559P/E795L, that showed similar genome editing as wild type LbCas12a.

In a first embodiment an isolated mutant Cas12a protein is provided. The isolated mutant Cas12a protein is active in Clustered Regularly Interspaced Short Palindromic Repeats (CRISPR)/CRISPR-associated protein endonuclease system ("CRISPR/Cas12a endonuclease system"). The CRISPR/Cas12a endonuclease system maintained on-target editing activity relative to a wild-type CRISPR/Cas12a endonuclease system. In another aspect the Cas12a protein is isolated from *Lachnospiraceae bacterium* ND2006 (Lb).

In a second embodiment, an isolated ribonucleoprotein (RNP) complex is provided. The RNP complex includes a mutant Cas12a protein and a crRNA. The isolated ribonucleoprotein complex is active as a CRISPR/Cas12a endonuclease system, wherein the resultant CRISPR/Cas12a endonuclease system displays maintained on-target editing activity relative to a wild-type CRISPR/Cas12a endonuclease system.

In a third embodiment, an isolated nucleic acid encoding a mutant Cas12a protein is provided. The mutant Cas12a protein is active in a CRISPR/Cas12a endonuclease system, wherein the CRISPR/Cas12a endonuclease system displays maintained on-target editing activity relative to wild-type CRISPR/Cas12a endonuclease system.

In a fourth embodiment, a CRISPR/Cas12a endonuclease system is provided. The CRISPR/Cas12a endonuclease system includes a mutant Cas12a protein and a crRNA. The CRISPR/Cas12a endonuclease system displays maintained on-target editing activity relative to wild-type CRISPR/Cas12a endonuclease system.

In a fifth embodiment, a method of performing gene editing having maintained on-target editing activity is provided. The method includes the step of contacting a candidate editing DNA target site locus with an active CRISPR/Cas12a endonuclease system having a mutant Cas12 a protein complexed with an appropriate crRNA. Said interaction can occur an any context, for example, in a live animal, in live cells, or an isolated DNA in vitro.

In another embodiment the CRISPR/Cas12a endonuclease system of the present invention displays maintained on-target editing activity relative to a wild type CRISPR/Cas endonuclease system and may display reduced off-target editing activity when compared to wild type CRISPR/Cas endonuclease systems. In another aspect the CRISPR/Cas12a endonuclease system of the present invention displays maintained on-target editing activity relative to a wild type CRISPR/Cas12a endonuclease system and may display reduced off-target editing activity when compared to wild type CRISPR/Cas12a endonuclease system.

In another embodiment the CRISPR/Cas12a endonuclease system of the present invention displays maintained on-target editing activity relative to a wild type CRISPR/Cas endonuclease system and may display reduced off-target editing activity when compared to wild type CRISPR/Cas endonuclease systems. In another aspect the CRISPR/Cas12a endonuclease system of the present invention displays maintained on-target editing activity relative to a wild type CRISPR/Cas12a endonuclease system and may display reduced off-target editing activity when compared to wild type CRISPR/Cas12a endonuclease system.

BRIEF DESCRIPTION OF THE DRAWINGS

Figure 1B:
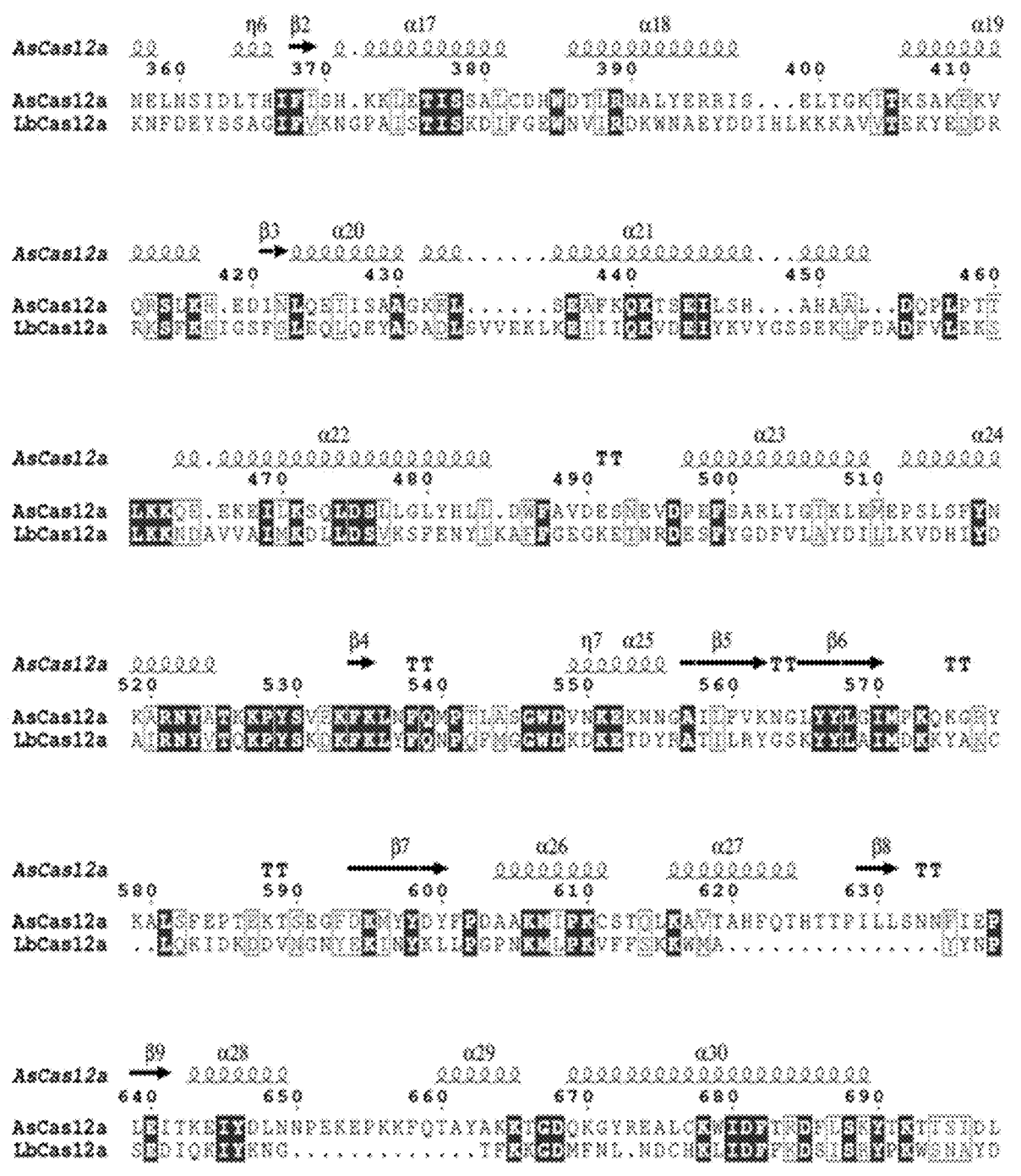
Figure 1C:
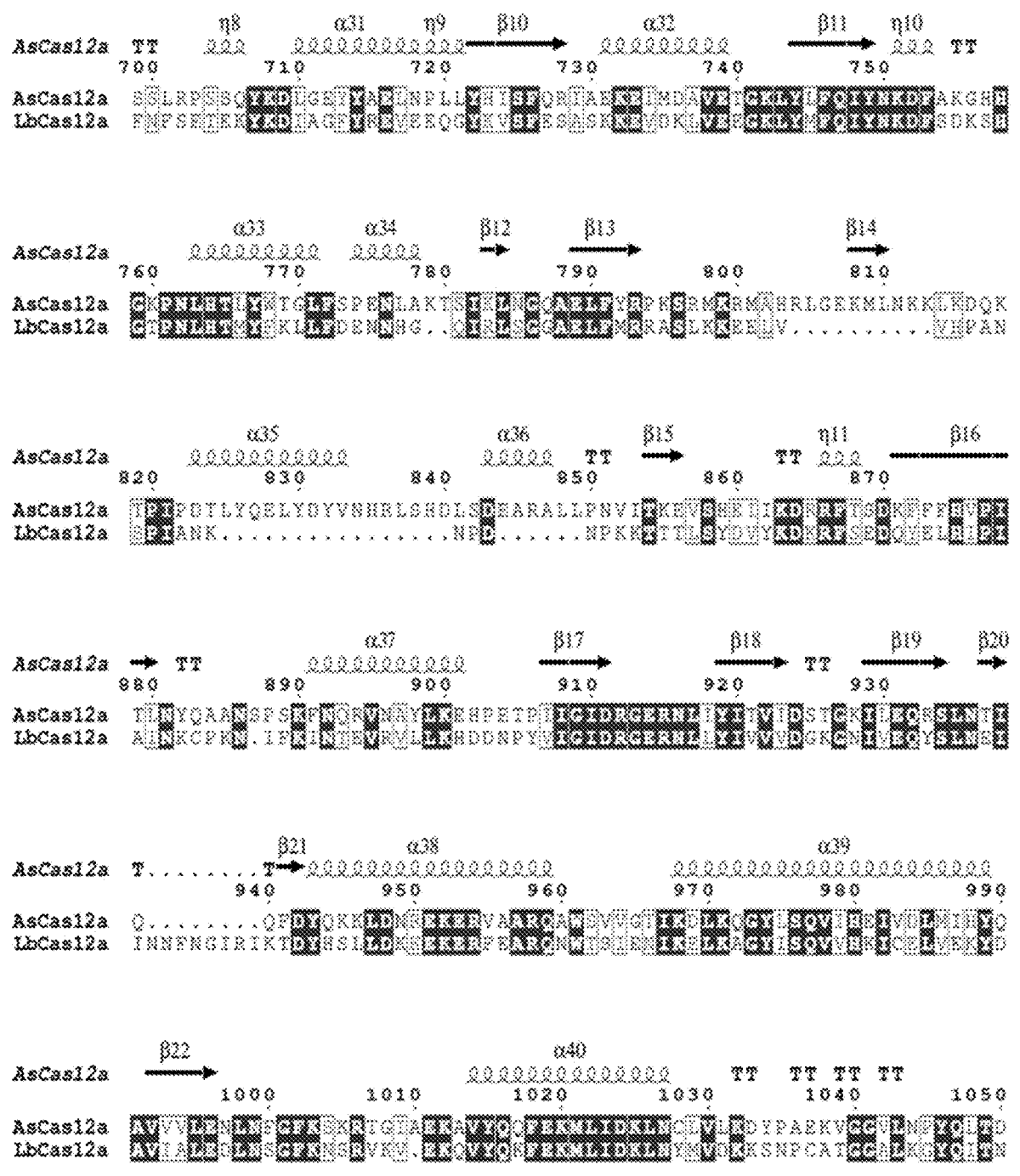
Figure 1D:
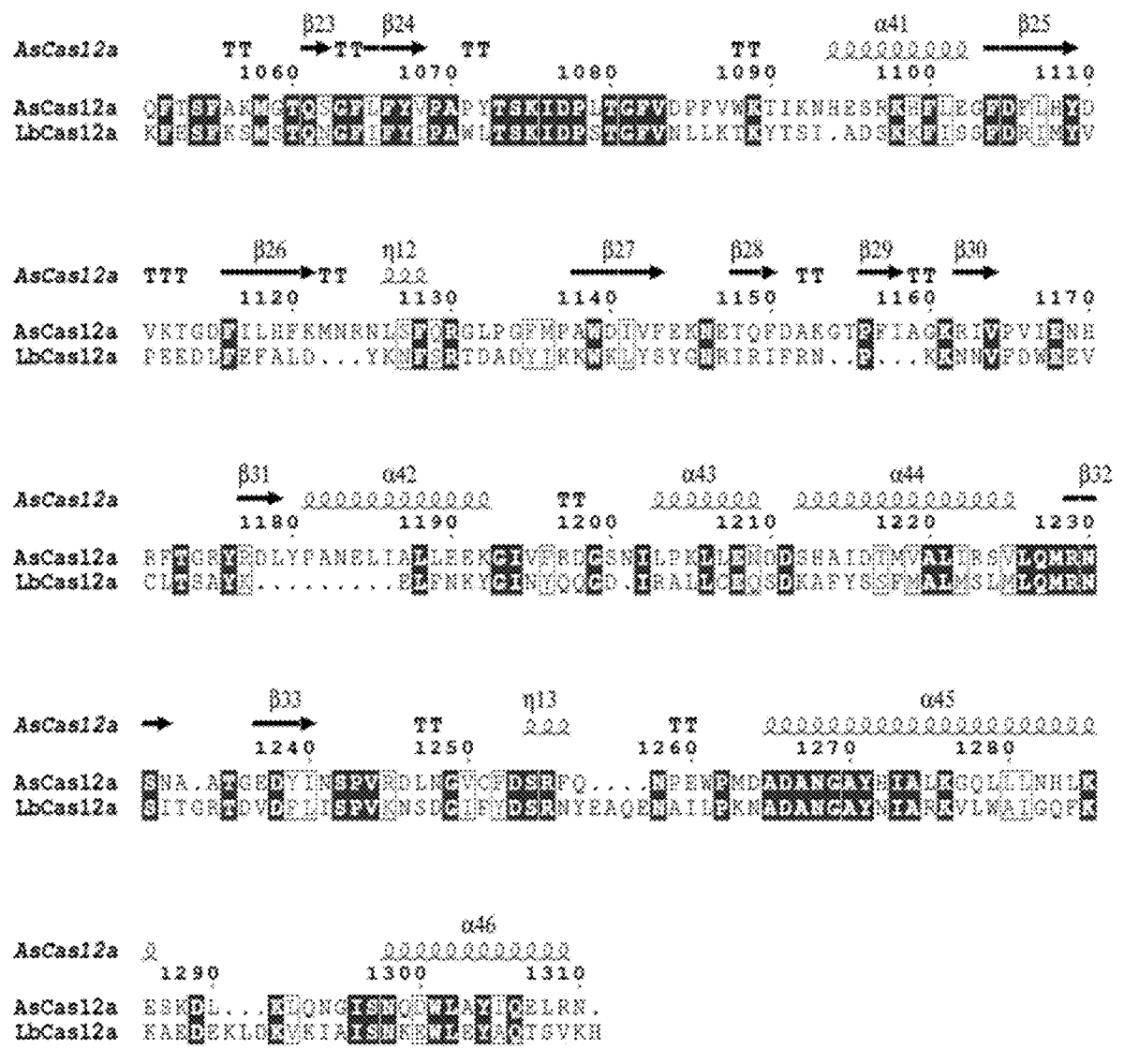

FIGS. 1A to 1D show the primary and secondary structure alignment of AsCas12a (top) (SEQ ID NO: 18) and LbCas12a (bottom) (SEQ ID NO: 2). A-Helices are represented with squiggles, β-strands with arrows and turns with 'TT'. Identical residues are boxed with solid red and similar residues are boxed with a blue outline.

FIG. 2 shows the editing efficiency of the LbCas12a mutants as compared to wild-type LbCas12a and AsCas12a-M537R/F870L mutant after 48 hours in HEK 293 human cells.

DETAILED DESCRIPTION OF THE INVENTION

Figure 1A:
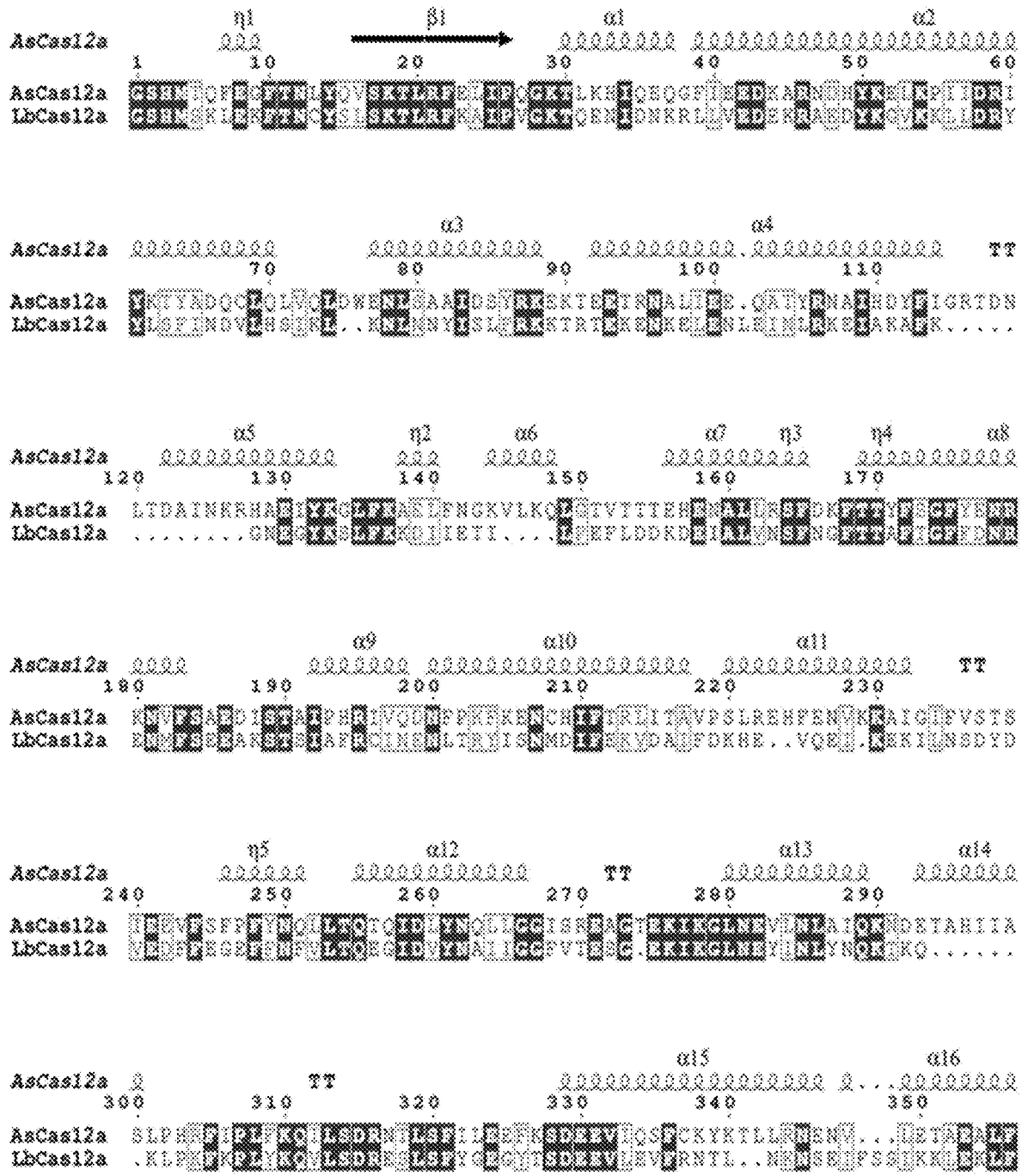

The methods and compositions of the invention described herein provide mutant LbCas12a nucleic acids and polypeptides for use in a CRISPR/Cas12a system. The present invention describes novel Cas12a mutants that reduce off-target editing activity to low levels while maintaining high on-target editing activity relative to the wild-type protein even when delivered as an RNP complex. These and other advantages of the invention, as well as additional inventive features, will be apparent from the description of the invention provided herein.

Cas12a provides a useful complement to Cas9 by expanding the range of PAM sequences that can be targeted from GC-Rich areas (Cas9) to AT-rich areas of the genome (Cas12a), thereby expanding the range of sequences that can be modified using CRISPR genome engineering methods. In addition to having a T-rich PAM site, another advantage of the Cas12a system as compared with Cas9 is the use of a single short RNA molecule.

In a first embodiment an isolated mutant Cas12a protein is provided. The isolated mutant Cas12a protein is active in Clustered Regularly Interspaced Short Palindromic Repeats (CRISPR)/CRISPR-associated protein endonuclease system ("CRISPR/Cas12a endonuclease system"). The CRISPR/Cas12a endonuclease system displays maintained on-target editing activity relative to a wild-type CRISPR/Cas endonuclease system. In another aspect the Cas12a protein is isolated from *Lachnospiraceae bacterium* ND2006 (Lb). Preferred single mutant Cas12a proteins include substitution mutations into the WT-LbCas12a introduced at the following positions: N527, D559, and E795.

Exemplarily single mutant Cas12a proteins include the following specific mutations introduced into the WT-LbCas12a: N527R, D559P, and E795L. Exemplary single mutant Cas12a proteins include at least one-member selected form the group consisting of SEQ ID NO: 3-9. Additional substitution mutations can be included in the amino acid backgrounds of the single mutant Cas12a protein amino acid sequences, provided that the resultant Cas12a protein is active as a CRISPR/Cas12a endonuclease system, wherein the resultant CRISPR/Cas12a endonuclease system displays maintained on-target editing activity relative to a wild-type CRISPR/Cas12a endonuclease system.

Preferred multi-substitution mutant Cas12a proteins include mutations in the WT-LbCas12a introduced to at least two of the following positions: N527/D559, D559/E795, N527/E795, and N527/D559/E795. Exemplary multi-substitution mutant Cas12a proteins include mutations in the WT-LbCas12a selected from the following amino acid mutations: N527R/D559P, D559P/E795L, N527R/E795L and N527R/D559P/E795L.

Exemplary multi substitution mutant Cas12a proteins include at least one member selected from the group consisting of SEQ ID NO: 3-9. Additional substitution mutations can be included in the amino acid backgrounds of the single mutant Cas12a protein amino acid sequences, provided that the resultant Cas12a protein is active as a CRISPR/Cas12a endonuclease system, wherein the resultant CRISPR/Cas12a endonuclease system displays maintained on-target editing activity relative to a wild-type CRISPR/Cas12a endonuclease system.

In second embodiment, an isolated ribonucleoprotein complex is provided. The RNP includes mutant Cas12a protein and a crRNA complex. In one respect the crRNA includes an Alt-R® crRNA (Integrated DNA Technologies, Inc. (Coralville, IA, (US)) directed against a specific editing target site for a given locus. Preferred mutant Cas9 proteins include those as described above.

In another embodiment, an isolated nucleic acid encoding a mutant LbCas12a protein is provided. Preferred isolated nucleic acids encode mutant LbCas12a proteins as described above. Exemplary isolated nucleic acids encoding mutant LbCas12a proteins can be readily generated from a nucleic acid encoding the wild-type LbCas12a protein using recombinant DNA procedures or chemical synthesis methods. Preferred nucleic acids for this purpose include those optimized for expression of the LbCas12a proteins in bacteria, (e.g., *E. coli*) or mammalian (e.g., human) cells. Exemplary codon-optimized nucleic acids for expressing WT-LbCas12a in *E. coli* and human cells includes SEQ ID NO: 1. Moreover, the present invention contemplates fusion proteins of WT-Cas12a and mutant LbCas12a, wherein the coding sequences of WT-Cas12a and mutant LbCas12a are fused to amino acid sequences encoding for nuclear localization ("NLS") of the fusion protein in eukaryotic cells or amino acid sequences to facilitate purification of the proteins.

In a further embodiment, the isolated nucleic acid includes mRNA encoding one of the aforementioned mutant LbCas12a proteins. In a second respect, the isolated nucleic acid includes DNA encoding a gene for one of the aforementioned mutant LbCas12a proteins. A preferred DNA includes a vector that encodes a gene encoding for a mutant LbCas12a protein. Such delivery methods include plasmid and various viral delivery vectors as are well known to those with skill in the art. The mutant LbCas12a protein can also be stably transformed into cells using suitable expression vectors to produce a cell line that constitutively or inducibly expresses the mutant LbCas12a. The aforementioned methods can also be applied to embryos to product progeny animals that constitutively or inducibly expresses the mutant LbCas12a.

In another embodiment a CRISPR/Cas12a endonuclease systems is provided.

The CRISPR/Cas12a endonuclease system includes a mutant LbCas12a protein. Preferred mutant LbCas12a proteins include those describe above. In one aspect, the CRISPR/Cas12a endonuclease system is encoded by a DNA expression vector. In one embodiment, the DNA expression vector is selected from a bacterial expression vector or a eukaryotic expression vector. In another aspect the CRISPR/Cas12a endonuclease system comprises a ribonucleoprotein complex comprising a mutant LbCas12a protein and a crRNA.

In a further embodiment, a method of performing gene editing having increased on-target editing activity is provided. The method includes the step of contacting a candidate editing target site locus with an active CRISPR/Cas12a endonuclease system having a mutant LbCas12a protein. In one aspect, the method includes a single mutant LbCas12a protein having mutations in the WT-LbCas12a introduced at one of the following positions: N527, D559, and E795. Exemplary single mutant LbCas12a proteins include the following specific mutations introduced into the WT-LbCas12a: N527R, D559P, and E795L. Exemplary single mutant LbCas12a proteins include at least one member selected form the group consisting of SEQ ID NO: 3-9. Additional substitution mutations can be included in the amino acid backgrounds of the single mutant LbCas12a protein amino acid sequences, provided that the resultant LbCas12a protein is active as a CRISPR/Cas12a endonuclease system, wherein the resultant CRISPR/Cas12a endonuclease system displays maintained on-target editing activity relative to a wild-type CRISPR/Cas12a endonuclease system.

In another embodiment, the method includes a multi-substitution mutant LbCas12a proteins include mutations in the WT-LbCas12a introduced to at least two of the following positions: N527/D559, D559/E795, N527/E795, and N527/D559/E795. Exemplary multi-substitution mutant Cas12a proteins include mutations in the WT-LbCas12a selected from the following amino acid mutations: N527R/D559P, D559P/E795L, N527R/E795L and N527R/D559P/E795L. Exemplary multi substitution mutant LbCas12a proteins include at least one member selected from the group consisting of SEQ ID NO: 3-9. Additional substitution mutations can be included in the amino acid backgrounds of the single mutant LbCas12a protein amino acid sequences, provided that the resultant LbCas12a protein is active as a CRISPR/Cas12a endonuclease system, wherein the resultant CRISPR/Cas12a endonuclease system displays maintained on-target editing activity relative to a wild-type CRISPR/Cas12a endonuclease system.

The applications of Cas12a and LbCas12a based tools are many and varied. The applications include, but are not limited to: plant gene editing, yeast gene editing, mammalian gene editing, editing of cells in the organs of live animals, editing of embryos, rapid generation of knockout/knock-in animal lines, generating an animal model of disease state, correcting a disease state, inserting a reporter gene, and whole genome functional screening.

EXAMPLE 1

DNA and Amino Acid Sequences of Wild Type and Mutant LbCas12a Proteins and AsCas12a Proteins.

The list below shows different wild type (WT) and mutant Cas12a nucleases described in present invention. It will be appreciated by one with skill in the art that many different DNA sequences can encode/express the same amino acid (AA) sequence since in many cases more than one codon can encode the same amino acid. The DNA sequences shown below only serve as example and other DNA sequences that encode the same protein (e.g., same amino acid sequence) are contemplated. It is further appreciated that additional features, elements or tags may be added to said sequences, such as NLS domains and the like. Examples are shown for WT LbCas12a (Cpf1), WT AsCas12a, and mutant N527R LbCas12a, mutant D559P LbCas12a, mutant E759L LbCas12a, double mutant N527R/D559P LbCas12a, double mutant N527R/E795L LbCas12a, double mutant D559P/E795L LbCas12a, triple mutant N527R/D559P/E795L LbCas12a, and double mutant M537R/F870L AsCas12a. For LbCas12a and AsCas12a mutants only the amino acid and DNA sequences are provided, but it is contemplated that NLS domains and His-tag domains may be added to facilitate use in producing recombinant proteins for use in mammalian cells.

```
SEQ ID NO: 1
WT Lachnospiraceae bacterium ND2006 (Lb) Cas12a DNA sequence
ATGAGCAAACTGGAAAAGTTCACCAACTGTTATAGCCTGAGCAAAACCCTGCGTTTTAAAGCAATTCCGGTTGGTA
AAACCCAAGAGAACATTGATAATAAACGCCTGCTGGTCGAAGATGAAAAACGCGCTGAAGATTATAAAGGCGTGAA
AAAACTGCTGGATCGCTATTATCTGAGCTTCATTAACGATGTGCTGCACAGCATTAAACTGAAGAACCTGAACAAC
TATATCAGCCTGTTTCGTAAAAAAACCCGCACCGAAAAAGAAAACAAAGAGCTGGAAAACCTGGAAATCAATCTGC
GTAAAGAAATCGCCAAAGCGTTTAAAGGTAACGAGGGTTATAAAAGCCTGTTCAAGAAAGACATCATCGAAACCAT
TCTGCCGGAATTTCTGGATGATAAAGATGAAATTGCCCTGGTGAATAGCTTTAATGGCTTTACCACCGCATTTACC
GGCTTTTTTGATAATCGCGAAAACATGTTCAGCGAAGAAGCAAAAAGCACCAGCATTGCATTTCGCTGCATTAATG
AAAATCTGACCCGCTACATTAGCAACATGGATATCTTTGAAAAAGTGGACGCGATCTTCGATAAACACGAAGTGCA
AGAGATCAAAGAGAAAATCCTGAACAGCGATTATGACGTCGAAGATTTTTTTGAAGGCGAGTTCTTTAACTTCGTT
CTGACCCAAGAAGGTATCGACGTTTATAACGCAATTATTGGTGGTTTTGTTACCGAAAGCGGTGAGAAAATCAAAG
GCCTGAATGAATATATCAACCTGTATAACCAGAAAACCAAACAGAAACTGCCGAAATTCAAACCGCTGTATAAACA
GGTTCTGAGCGATCGTGAAAGCCTGAGCTTTTATGGTGAAGGTTATACCAGTGATGAAGAGGTTCTGGAAGTTTTT
CGTAACACCCTGAATAAAACAGCGAGATCTTTAGCAGCATCAAAAAGCTTGAGAAACTGTTCAAAAACTTTGATG
AGTATAGCAGCGCAGGCATCTTTGTTAAAAATGGTCCGGCAATTAGCACCATCAGCAAAGATATTTTTGGCGAATG
GAATGTGATCCGCGATAAATGGAATGCCGAATATGATGAATCCACCTGAAAAAAAAGGCCGTGGTGACCGAGAAA
TATGAAGATGATCGTCGTAAAAGCTTCAAGAAAATTGGTAGCTTTAGCCTGGAACAGCTGCAAGAATATGCAGATG
CAGATCTGAGCGTTGTGGAAAAACTGAAAGAAATCATCATTCAGAAGGTGGACGAGATCTATAAAGTTTATGGTAG
CAGCGAAAAACTGTTCGATGCAGATTTTGTTCTGGAAAAAAAGCCTGAAAAAGAATGATGCCGTTGTGGCCATTATG
AAAGATCTGCTGGATAGCGTTAAGAGCTTCGAGAATTACATCAAAGCCTTTTTTGGTGAGGGCAAAGAAACCAATC
GTGATGAAAGTTTCTATGGCGATTTTGTGCTGGCCTATGATATTCTGCTGAAAGTGGACCATATTTATGATGCCAT
TCGCAATTATGTTACCCAGAAACCGTATAGCAAAGACAAGTTCAAACTGTACTTTCAGAACCCGCAGTTTATGGGT
GGTTGGGATAAAGATAAAGAAACCGATTATCGTGCCACCATCCTGCGTTATGGTAGTAAATACTATCTGGCCATCA
TGGACAAAAAATACGCAAAATGCCTGCAGAAAATCGACAAAGATGATGTGAATGGCAACTATGAAAAAATCAACTA
CAAACTGCTGCCTGGTCCGAATAAAATGCTGCCGAAAGTGTTCTTTAGCAAGAAATGGATGGCTATTATAACCCG
AGCGAGGATATTCAAAAGATCTACAAAATGGCACCTTTAAAAAGGGCGACATGTTCAATCTGAACGATTGCCACA
AACTGATCGATTTCTTCAAAGATTCAATTTCGCGTTATCCGAAATGGTCCAATGCCTATGATTTTAACTTTAGCGA
AACCGAAAAATACAAAGACATTGCCGGTTTTTATCGCGAAGTGGAAGAACAGGGCTATAAAGTGAGCTTTGAAAGC
GCAAGCAAAAAAGAGGTTGATAAGCTGGTTGAAGAGGGCAAACTGTATATGTTCCAGATTTACAACAAAGATTTTA
GCGACAAAAGCCATGGCACCCCGAATCTGCATACCATGTACTTTAAACTGCTGTTCGACGAAAATAACCATGGTCA
GATTCGTCTGAGCGGTGGTGCCGAACTGTTTATGCGTCGTCAAGTCTGAAAAAAGAAGAACTGGTTGTTCATCCG
GCAAATAGCCCGATTGCAAACAAAAATCCGGACAATCCGAAAAAAACCACGACACTGAGCTATGATGTGTATAAAG
ACAAAGTTTTAGCGAGGATCAGTATGAACTGCATATCCCGATTGCCATCAATAAATGCCCGAAAAACATCTTTAA
GATCAACACCGAAGTTCGCGTGCTGCTGAAACATGATGATAATCCGTATGTGATTGGCATTGATCGTGGTGAACGT
AACCTGCTGTATATTGTTGTTGATGGTAAAGGCAACATCGTGGAACAGTATAGTCTGAACGAAATTATCAACA
ACTTTAACGGCATCCGCATCAAAACCGACTATCATAGCCTGCTGGACAAGAAAGAAAAAGAACGTTTTGAAGCACG
TCAGAACTGGACCAGTATTGAAAACATCAAAGAACTGAAAGCCGGTTATATTAGCCAGGTGGTTCATAAAATCTGT
GAGCTGGTAGAAAAATACGATGCAGTTATTGCACTGGAAGATCTGAATAGCGGTTTCAAAAATAGCCGTGTGAAAG
TCGAAAACAGGTGTATCAGAAATTCGAGAAAATGCTGATCGACAAACTGAACTACATGGTCGACAAAAAAAGCAA
TCCGTGTGCAACCGGTGGTGCACTGAAAGGTTATCAGATTACCAACAAATTTGAAAGCTTTAAAAGCATGAGCACC
CAGAACGGCTTTATCTTCTATATTCCGGCATGGCTGACCAGCAAAATTGATCCGAGCACCGGTTTTGTGAACCTGC
TGAAAACAAAATATACCTCCATTGCCGACAGCAAGAAGTTTATTAGCAGCTTTGATCGCATTATGTATGTTCCGGA
AGAGGACCTGTTTGAATTCGCACTGGATTACAAAAATTTCAGCCGTACCGATGCCGACTACATCAAAAAATGGAAA
CTGTACAGCTATGGTAACCGCATTCGCATTTTTCGCAACCCGAAGAAAAACAATGTGTTCGATTGGGAAGAAGTTT
GTCTGACCAGCGCATATAAAGAACTTTTCAACAAATACGGCATCAACTATCAGCAGGGTGATATTCGTGCACTGCT
GTGTGAACAGAGCGATAAAGCGTTTTATAGCAGTTTTATGGCACTGATGAGCCTGATGCTGCAGATGCGTAATAGC
ATTACCGGTCGCACCGATGTGGATTTTCTGATTAGTCCGGTGAAAAATTCCGATGGCATCTTTTATGATAGCCGCA
ATTACGAAGCACAAGAAAATGCAATTCTGCCGAAAAACGCAGATGCAAATGGTGCATATAACATTGCACGTAAAGT
TCTGTGGGCAATTGGCCAGTTTAAGAAAGCAGAAGATGAGAAGCTGGACAAAGTGAAAATTGCGATCAGCAATAAA
GAGTGGCTGGAATACGCACAGACCAGCGTTAAACAT SEQ ID NO: 2
WT LbCas12 amino acid sequence
MSKLEKFTNCYSLSKTLRFKAIPVGKTQENIDNKRLLVEDEKRAEDYKGVKKLLDRYYLSFINDVLHSIKLKNLNN
YISLFRKKTRTEKENKELENLEINLRKEIAKAFKGNEGYKSLFKKDIIETILPEFLDDKDEIALVNSFNGFTTAFT
GFFDNRENMFSEEAKSTSIAFRCINENLTRYISNMDIFEKVDAIFDKHEVQEIKEKILNSDYDVEDFFEGEFFNFV
LTQEGIDVYNAIIGGFVTESGEKIKGLNEYINLYNQKTKQLPKFKPLYKQVLSDRESLSFYGEGYTSDEEVLEVF
RNTLNKNSEIFSSIKKLEKLFKNFDEYSSAGIFVKNGPAISTISKDIFGEWNVIRDKWNAEYDDIHLKKKAVVTEK
YEDDRRKSFKKIGSFSLEQLQEYADADLSVVEKLKEIIIQKVDEIYKVYGSSEKLFDADFVLEKSLKKNDAVVAIM
KDLLDSVKSFENYIKAFFGEGKETNRDESFYGDFVLAYDILLKVDHIYDAIRNYVTQKPYSKDKFKLYFQNPQFMG
GWDKDKETDYRATILRYGSKYYLAIMDKKYAKCLQKIDKDDVNGNYEKINYKLLPGPNKMLPKVFFSKKWMAYYNP
SEDIQKIYKNGTFKKGDMFNLNDCHKLIDFFKDSISRYPKWSNAYDFNFSETEKYKDIAGFYREVEEQGYKVSFES
ASKKEVDKLVEEGKLYMFQIYNKDFSDKSHGTPNLHTMYFKLLFDENNHGQIRLSGGAELFMRRASLKKEELVVHP
ANSPIANKNPDNPKKTTTLSYDVYKDKRFSEDQYELHIPIAINKCPKNIFKINTEVRVLLKHDDNPYVIGIDRGER
NLLYIVVVDGKGNIVEQYSLNEIINNFNGIRIKTDYHSLLDKKEKERFEARQNWTSIENIKELKAGYISQVVHKIC
ELVEKYDAVIALEDLNSGFKNSRVKVEKQVYQKFEKMLIDKLNYMVDKKSNPCATGGALKGYQITNKFESFKSMST
QNGFIFYIPAWLTSKIDPSTGFVNLLKTKYTSIADSKKFISSFDRIMYVPEEDLFEFALDYKNFSRTDADYIKKWK
LYSYGNRIRIFRNPKKNNVFDWEEVCLTSAYKELFNKYGINYQQGDIRALLCEQSDKAFYSSFMALMSLMLQMRNS
ITGRTDVDFLISPVKNSDGIFYDSRNYEAQENAILPKNADANGAYNIARKVLWAIGQFKKAEDEKLDKVKIAISNK
EWLEYAQTSVKH
```

```
SEQ ID NO: 3
Mutant N527R LbCas12a amino acid sequence
MSKLEKFTNCYSLSKTLRFKAIPVGKTQENIDNKRLLVEDEKRAEDYKGVKKLLDRYYLSFINDVLHSIKLKNLNN
YISLFRKKTRTEKENKELENLEINLRKEIAKAFKGNEGYKSLFKKDIIETILPEFLDDKDEIALVNSFNGFTTAFT
GFFDNRENMFSEEAKSTSIAFRCINENLTRYISNMDIFEKVDAIFDKHEVQEIKEKILNSDYDVEDFFEGEFFNFV
LTQEGIDVYNAIIGGFVTESGEKIKGLNEYINLYNQKTKQLPKFKPLYKQVLSDRESLSFYGEGYTSDEEVLEVF
RNTLNKNSEIFSSIKKLEKLFKNFDEYSSAGIFVKNGPAISTISKDIFGEWNVIRDKWNAEYDDIHLKKKAVVTEK
YEDDRRKSFKKIGSFSLEQLQEYADADLSVVEKLKEIIQKVDEIYKVYGSSEKLFDADFVLEKSLKKNDAVVAIM
KDLLDSVKSFENYIKAFFGEGKETNRDESFYGDFVLAYDILLKVDHIYDAIRNYVTQKPYSKDKFKLYFQRPQFMG
GWDKDKETDYRATILRYGSKYYLAIMDKKYAKCLQKIDKDDVNGNYEKINYKLLPGPNKMLPKVFFSKKWMAYYNP
SEDIQKIYKNGTFKKGDMFNLNDCHKLIDFFKDSISRYPKWSNAYDFNFSETEKYKDIAGFYREVEEQGYKVSFES
ASKKEVDKLVEEGKLYMFQIYNKDFSDKSHGTPNLHTMYFKLLFDENNHGQIRLSGGAELFMRRASLKKEELVVHP
ANSPIANKNPDNPKKTTTLSYDVYKDKRFSEDQYELHIPIAINKCPKNIFKINTEVRVLLKHDDNPYVIGIDRGER
NLLYIVVVDGKGNIVEQYSLNEIINNFNGIRIKTDYHSLLDKKEKERFEARQNWTSIENIKELKAGYISQVVHKIC
ELVEKYDAVIALEDLNSGFKNSRVKVEKQVYQKFEKMLIDKLNYMVDKKSNPCATGGALKGYQITNKFESFKSMST
QNGFIFYIPAWLTSKIDPSTGFVNLLKTKYTSIADSKKFISSFDRIMYVPEEDLFEFALDYKNFSRTDADYIKKWK
LYSYGNRIRIFRNPKKNNVFDWEEVCLTSAYKELFNKYGINYQQGDIRALLCEQSDKAFYSSFMALMSLMLQMRNS
ITGRTDVDFLISPVKNSDGIFYDSRNYEAQENAILPKNADANGAYNIARKVLWAIGQFKKAEDEKLDKVKIAISNK
EWLEYAQTSVKH SEQ ID NO: 4
Mutant D559P LbCas12a amino acid sequence
MSKLEKFTNCYSLSKTLRFKAIPVGKTQENIDNKRLLVEDEKRAEDYKGVKKLLDRYYLSFINDVLHSIKLKNLNN
YISLFRKKTRTEKENKELENLEINLRKEIAKAFKGNEGYKSLFKKDIIETILPEFLDDKDEIALVNSFNGFTTAFT
GFFDNRENMFSEEAKSTSIAFRCINENLTRYISNMDIFEKVDAIFDKHEVQEIKEKILNSDYDVEDFFEGEFFNFV
LTQEGIDVYNAIIGGFVTESGEKIKGLNEYINLYNQKTKQLPKFKPLYKQVLSDRESLSFYGEGYTSDEEVLEVF
RNTLNKNSEIFSSIKKLEKLFKNFDEYSSAGIFVKNGPAISTISKDIFGEWNVIRDKWNAEYDDIHLKKKAVVTEK
YEDDRRKSFKKIGSFSLEQLQEYADADLSVVEKLKEIIQKVDEIYKVYGSSEKLFDADFVLEKSLKKNDAVVAIM
KDLLDSVKSFENYIKAFFGEGKETNRDESFYGDFVLAYDILLKVDHIYDAIRNYVTQKPYSKDKFKLYFQNPQFMG
GWDKDKETDYRATILRYGSKYYLAIMPKKYAKCLQKIDKDDVNGNYEKINYKLLPGPNKMLPKVFFSKKWMAYYNP
SEDIQKIYKNGTFKKGDMFNLNDCHKLIDFFKDSISRYPKWSNAYDFNFSETEKYKDIAGFYREVEEQGYKVSFES
ASKKEVDKLVEEGKLYMFQIYNKDFSDKSHGTPNLHTMYFKLLFDENNHGQIRLSGGAELFMRRASLKKEELVVHP
ANSPIANKNPDNPKKTTTLSYDVYKDKRFSEDQYELHIPIAINKCPKNIFKINTEVRVLLKHDDNPYVIGIDRGER
NLLYIVVVDGKGNIVEQYSLNEIINNFNGIRIKTDYHSLLDKKEKERFEARQNWTSIENIKELKAGYISQVVHKIC
ELVEKYDAVIALEDLNSGFKNSRVKVEKQVYQKFEKMLIDKLNYMVDKKSNPCATGGALKGYQITNKFESFKSMST
QNGFIFYIPAWLTSKIDPSTGFVNLLKTKYTSIADSKKFISSFDRIMYVPEEDLFEFALDYKNFSRTDADYIKKWK
LYSYGNRIRIFRNPKKNNVFDWEEVCLTSAYKELFNKYGINYQQGDIRALLCEQSDKAFYSSFMALMSLMLQMRNS
ITGRTDVDFLISPVKNSDGIFYDSRNYEAQENAILPKNADANGAYNIARKVLWAIGQFKKAEDEKLDKVKIAISNK
EWLEYAQTSVKH SEQ ID NO: 5
Mutant E795L LbCas12a amino acid sequence
MSKLEKFTNCYSLSKTLRFKAIPVGKTQENIDNKRLLVEDEKRAEDYKGVKKLLDRYYLSFINDVLHSIKLKNLNN
YISLFRKKTRTEKENKELENLEINLRKEIAKAFKGNEGYKSLFKKDIIETILPEFLDDKDEIALVNSFNGFTTAFT
GFFDNRENMFSEEAKSTSIAFRCINENLTRYISNMDIFEKVDAIFDKHEVQEIKEKILNSDYDVEDFFEGEFFNFV
LTQEGIDVYNAIIGGFVTESGEKIKGLNEYINLYNQKTKQLPKFKPLYKQVLSDRESLSFYGEGYTSDEEVLEVF
RNTLNKNSEIFSSIKKLEKLFKNFDEYSSAGIFVKNGPAISTISKDIFGEWNVIRDKWNAEYDDIHLKKKAVVTEK
YEDDRRKSFKKIGSFSLEQLQEYADADLSVVEKLKEIIQKVDEIYKVYGSSEKLFDADFVLEKSLKKNDAVVAIM
KDLLDSVKSFENYIKAFFGEGKETNRDESFYGDFVLAYDILLKVDHIYDAIRNYVTQKPYSKDKFKLYFQNPQFMG
GWDKDKETDYRATILRYGSKYYLAIMDKKYAKCLQKIDKDDVNGNYEKINYKLLPGPNKMLPKVFFSKKWMAYYNP
SEDIQKIYKNGTFKKGDMFNLNDCHKLIDFFKDSISRYPKWSNAYDFNFSETEKYKDIAGFYREVEEQGYKVSFES
ASKKEVDKLVEEGKLYMFQIYNKDFSDKSHGTPNLHTMYFKLLFDENNHGQIRLSGGAELFMRRASLKKEELVVHP
ANSPIANKNPDNPKKTTTLSYDVYKDKRFSEDQYLLHIPIAINKCPKNIFKINTEVRVLLKHDDNPYVIGIDRGER
NLLYIVVVDGKGNIVEQYSLNEIINNFNGIRIKTDYHSLLDKKEKERFEARQNWTSIENIKELKAGYISQVVHKIC
ELVEKYDAVIALEDLNSGFKNSRVKVEKQVYQKFEKMLIDKLNYMVDKKSNPCATGGALKGYQITNKFESFKSMST
QNGFIFYIPAWLTSKIDPSTGFVNLLKTKYTSIADSKKFISSFDRIMYVPEEDLFEFALDYKNFSRTDADYIKKWK
LYSYGNRIRIFRNPKKNNVFDWEEVCLTSAYKELFNKYGINYQQGDIRALLCEQSDKAFYSSFMALMSLMLQMRNS
ITGRTDVDFLISPVKNSDGIFYDSRNYEAQENAILPKNADANGAYNIARKVLWAIGQFKKAEDEKLDKVKIAISNK
EWLEYAQTSVKH SEQ ID NO: 6
Mutant N527R/D559P LbCas12a amino acid sequence
MSKLEKFTNCYSLSKTLRFKAIPVGKTQENIDNKRLLVEDEKRAEDYKGVKKLLDRYYLSFINDVLHSIKLKNLNNYISLF
RKKTRTEKENKELENLEINLRKEIAKAFKGNEGYKSLFKKDIIETILPEFLDDKDEIALVNSFNGFTTAFTGFFDN
RENMFSEEAKSTSIAFRCINENLTRYISNMDIFEKVDAIFDKHEVQEIKEKILNSDYDVEDFFEGEFFNFVLTQEG
IDVYNAIIGGFVTESGEKIKGLNEYINLYNQKTKQLPKFKPLYKQVLSDRESLSFYGEGYTSDEEVLEVFRNTLN
KNSEIFSSIKKLEKLFKNFDEYSSAGIFVKNGPAISTISKDIFGEWNVIRDKWNAEYDDIHLKKKAVVTEKYEDDR
RKSFKKIGSFSLEQLQEYADADLSVVEKLKEIIQKVDEIYKVYGSSEKLFDADFVLEKSLKKNDAVVAIMKDLLD
SVKSFENYIKAFFGEGKETNRDESFYGDFVLAYDILLKVDHIYDAIRNYVTQKPYSKDKFKLYFQRPQFMGGWDKD
KETDYRATILRYGSKYYLAIMPKKYAKCLQKIDKDDVNGNYEKINYKLLPGPNKMLPKVFFSKKWMAYYNPSEDIQ
KIYKNGTFKKGDMFNLNDCHKLIDFFKDSISRYPKWSNAYDFNFSETEKYKDIAGFYREVEEQGYKVSFESASKKE
VDKLVEEGKLYMFQIYNKDFSDKSHGTPNLHTMYFKLLFDENNHGQIRLSGGAELFMRRASLKKEELVVHPANSPI
ANKNPDNPKKTTTLSYDVYKDKRFSEDQYELHIPIAINKCPKNIFKINTEVRVLLKHDDNPYVIGIDRGERNLLYI
VVVDGKGNIVEQYSLNEIINNFNGIRIKTDYHSLLDKKEKERFEARQNWTSIENIKELKAGYISQVVHKICELVEK
YDAVIALEDLNSGFKNSRVKVEKQVYQKFEKMLIDKLNYMVDKKSNPCATGGALKGYQITNKFESFKSMSTQNGFI
FYIPAWLTSKIDPSTGFVNLLKTKYTSIADSKKFISSFDRIMYVPEEDLFEFALDYKNFSRTDADYIKKWKLYSYG
NRIRIFRNPKKNNVFDWEEVCLTSAYKELFNKYGINYQQGDIRALLCEQSDKAFYSSFMALMSLMLQMRNSITGRT
DVDFLISPVKNSDGIFYDSRNYEAQENAILPKNADANGAYNIARKVLWAIGQFKKAEDEKLDKVKIAISNKEWLEY
AQTSVKH
```

SEQ ID NO: 7
Mutant 527R/E795L LbCas12a amino acid sequence
MSKLEKFTNCYSLSKTLRFKAIPVGKTQENIDNKRLLVEDEKRAEDYKGVKKLLDRYYLSFINDVLHSIKLKNLNN
YISLFRKKTRTEKENKELENLEINLRKEIAKAFKGNEGYKSLFKKDIIETILPEFLDDKDEIALVNSFNGFTTAFT
GFFDNRENMFSEEAKSTSIAFRCINENLTRYISNMDIFEKVDAIFDKHEVQEIKEKILNSDYDVEDFFEGEFFNFV
LTQEGIDVYNAIIGGFVTESGEKIKGLNEYINLYNQKTKQLPKFKPLYKQVLSDRESLSFYGEGYTSDEEVLEVF
RNTLNKNSEIFSSIKKLEKLFKNFDEYSSAGIFVKNGPAISTISKDIFGEWNVIRDKWNAEYDDIHLKKKAVVTEK
YEDDRRKSFKKIGSFSLEQLQEYADADLSVVEKLKEIIIQKVDEIYKVYGSSEKLFDADFVLEKSLKKNDAVVAIM
KDLLDSVKSFENYIKAFFGEGKETNRDESFYGDFVLAYDILLKVDHIYDAIRNYVTQKPYSKDKFKLYFQRPQFMG
GWDKDKETDYRATILRYGSKYYLAIMDKKYAKCLQKIDKDDVNGNYEKINYKLLPGPNKMLPKVFFSKKWMAYYNP
SEDIQKIYKNGTFKKGDMFNLNDCHKLIDFFKDSISRYPKWSNAYDFNFSETEKYKDIAGFYREVEEQGYKVSFES
ASKKEVDKLVEEGKLYMFQIYNKDFSDKSHGTPNLHTMYFKLLFDENNHGQIRLSGGAELFMRRASLKKEELVVHP
ANSPIANKNPDNPKKTTTLSYDVYKDKRFSEDQYLLHIPIAINKCPKNIFKINTEVRVLLKHDDNPYVIGIDRGER
NLLYIVVVDGKGNIVEQYSLNEIINNFNGIRIKTDYHSLLDKKEKERFEARQNWTSIENIKELKAGYISQVVHKIC
ELVEKYDAVIALEDLNSGFKNSRVKVEKQVYQKFEKMLIDKLNYMVDKKSNPCATGGALKGYQITNKFESFKSMST
QNGFIFYIPAWLTSKIDPSTGFVNLLKTKYTSIADSKKFISSFDRIMYVPEEDLFEFALDYKNFSRTDADYIKKWK
LYSYGNRIRIFRNPKKNNVFDWEEVCLTSAYKELFNKYGINYQQGDIRALLCEQSDKAFYSSFMALMSLMLQMRNS
ITGRTDVDFLISPVKNSDGIFYDSRNYEAQENAILPKNADANGAYNIARKVLWAIGQFKKAEDEKLDKVKIAISNK
EWLEYAQTSVKH SEQ ID NO: 8
Mutant D559P/E795L LbCas12a amino acid sequence
MSKLEKFTNCYSLSKTLRFKAIPVGKTQENIDNKRLLVEDEKRAEDYKGVKKLLDRYYLSFINDVLHSIKLKNLNN
YISLFRKKTRTEKENKELENLEINLRKEIAKAFKGNEGYKSLFKKDIIETILPEFLDDKDEIALVNSFNGFTTAFT
GFFDNRENMFSEEAKSTSIAFRCINENLTRYISNMDIFEKVDAIFDKHEVQEIKEKILNSDYDVEDFFEGEFFNFV
LTQEGIDVYNAIIGGFVTESGEKIKGLNEYINLYNQKTKQLPKFKPLYKQVLSDRESLSFYGEGYTSDEEVLEVF
RNTLNKNSEIFSSIKKLEKLFKNFDEYSSAGIFVKNGPAISTISKDIFGEWNVIRDKWNAEYDDIHLKKKAVVTEK
YEDDRRKSFKKIGSFSLEQLQEYADADLSVVEKLKEIIIQKVDEIYKVYGSSEKLFDADFVLEKSLKKNDAVVAIM
KDLLDSVKSFENYIKAFFGEGKETNRDESFYGDFVLAYDILLKVDHIYDAIRNYVTQKPYSKDKFKLYFQRPQFMG
GWDKDKETDYRATILRYGSKYYLAIMPKKYAKCLQKIDKDDVNGNYEKINYKLLPGPNKMLPKVFFSKKWMAYYNP
SEDIQKIYKNGTFKKGDMFNLNDCHKLIDFFKDSISRYPKWSNAYDFNFSETEKYKDIAGFYREVEEQGYKVSFES
ASKKEVDKLVEEGKLYMFQIYNKDFSDKSHGTPNLHTMYFKLLFDENNHGQIRLSGGAELFMRRASLKKEELVVHP
ANSPIANKNPDNPKKTTTLSYDVYKDKRFSEDQYLLHIPIAINKCPKNIFKINTEVRVLLKHDDNPYVIGIDRGER
NLLYIVVVDGKGNIVEQYSLNEIINNFNGIRIKTDYHSLLDKKEKERFEARQNWTSIENIKELKAGYISQVVHKIC
ELVEKYDAVIALEDLNSGFKNSRVKVEKQVYQKFEKMLIDKLNYMVDKKSNPCATGGALKGYQITNKFESFKSMST
QNGFIFYIPAWLTSKIDPSTGFVNLLKTKYTSIADSKKFISSFDRIMYVPEEDLFEFALDYKNFSRTDADYIKKWK
LYSYGNRIRIFRNPKKNNVFDWEEVCLTSAYKELFNKYGINYQQGDIRALLCEQSDKAFYSSFMALMSLMLQMRNS
ITGRTDVDFLISPVKNSDGIFYDSRNYEAQENAILPKNADANGAYNIARKVLWAIGQFKKAEDEKLDKVKIAISNK
EWLEYAQTSVKH SEQ ID NO: 9
Mutant N527R/D559P/E795L LbCas12a amino acid sequence
MSKLEKFTNCYSLSKTLRFKAIPVGKTQENIDNKRLLVEDEKRAEDYKGVKKLLDRYYLSFINDVLHSIKLKNLNN
YISLFRKKTRTEKENKELENLEINLRKEIAKAFKGNEGYKSLFKKDIIETILPEFLDDKDEIALVNSFNGFTTAFT
GFFDNRENMFSEEAKSTSIAFRCINENLTRYISNMDIFEKVDAIFDKHEVQEIKEKILNSDYDVEDFFEGEFFNFV
LTQEGIDVYNAIIGGFVTESGEKIKGLNEYINLYNQKTKQLPKFKPLYKQVLSDRESLSFYGEGYTSDEEVLEVF
RNTLNKNSEIFSSIKKLEKLFKNFDEYSSAGIFVKNGPAISTISKDIFGEWNVIRDKWNAEYDDIHLKKKAVVTEK
YEDDRRKSFKKIGSFSLEQLQEYADADLSVVEKLKEIIIQKVDEIYKVYGSSEKLFDADFVLEKSLKKNDAVVAIM
KDLLDSVKSFENYIKAFFGEGKETNRDESFYGDFVLAYDILLKVDHIYDAIRNYVTQKPYSKDKFKLYFQRPQFMG
GWDKDKETDYRATILRYGSKYYLAIMPKKYAKCLQKIDKDDVNGNYEKINYKLLPGPNKMLPKVFFSKKWMAYYNP
SEDIQKIYKNGTFKKGDMFNLNDCHKLIDFFKDSISRYPKWSNAYDFNFSETEKYKDIAGFYREVEEQGYKVSFES
ASKKEVDKLVEEGKLYMFQIYNKDFSDKSHGTPNLHTMYFKLLFDENNHGQIRLSGGAELFMRRASLKKEELVVHP
ANSPIANKNPDNPKKTTTLSYDVYKDKRFSEDQYLLHIPIAINKCPKNIFKINTEVRVLLKHDDNPYVIGIDRGER
NLLYIVVVDGKGNIVEQYSLNEIINNFNGIRIKTDYHSLLDKKEKERFEARQNWTSIENIKELKAGYISQVVHKIC
ELVEKYDAVIALEDLNSGFKNSRVKVEKQVYQKFEKMLIDKLNYMVDKKSNPCATGGALKGYQITNKFESFKSMST
QNGFIFYIPAWLTSKIDPSTGFVNLLKTKYTSIADSKKFISSFDRIMYVPEEDLFEFALDYKNFSRTDADYIKKWK
LYSYGNRIRIFRNPKKNNVFDWEEVCLTSAYKELFNKYGINYQQGDIRALLCEQSDKAFYSSFMALMSLMLQMRNS
ITGRTDVDFLISPVKNSDGIFYDSRNYEAQENAILPKNADANGAYNIARKVLWAIGQFKKAEDEKLDKVKIAISNK
EWLEYAQTSVKH SEQ ID NO: 10
Mutant N527R LbCas12a DNA sequence
ATGAGCAAACTGGAAAAGTTCACCAACTGTTATAGCCTGAGCAAAACCCTGCGTTTTAAAGCAATTCCGGTTGGTA
AAACCCAAGAGAACATTGATAATAAAGCGCTGCTGGTCGAAGATGAAAAACGCGCTGAAGATTATAAAGGCGTGAA
AAAACTGCTGGATCGCTATTATCTGAGCTTCATTAACGATGTGCTGCACAGCATTAAACTGAAGAACCTGAACAAC
TATATCAGCCTGTTTCGTAAAAAAACCCGCACCGAAAAGAAAACAAAGAGCTGGAAAACCTGGAAATCAATCTGC
GTAAAGAAATCGCCAAGCGTTTAAAGGTAACGAGGGTTATAAAAGCCTGTTCAAGAAAGACATCATCGAAACCAT
TCTGCCGGAATTTCTGGATGATAAAGATGAAATTGCCCTGGTGAATAGCTTTAATGGCTTTACCACCGCATTTACC
GGCTTTTTTGATAATCGCGAAAACATGTTCAGCGAAGAAGCAAAAAGCACCAGCATTGCATTTCGCTGCATTAATG
AAAATCTGACCCGCTACATTAGCAACATGGATATCTTTGAAAAGTGGACGCGATCTTCGATAAACACGAAGTGCA
AGAGATCAAAGAGAAAATCCTGAACAGCGATTATGACGTCGAAGATTTTTTTGAAGGCGAGTTCTTTAACTTCGTT
CTGACCCAAGAAGGTATCGACGTTTATAACGCAATTATTGGTGGTTTTGTTACCGAAAGCGGTGAGAAAATCAAAG
GCCTGAATGAATATATCAACCTGTATAACCAGAAAACCAAACAGAAACTGCCGAAATTCAAACCGCTGTATAAACA
GGTTCTGAGCGATCGTGAAAGCCTGAGCTTTTATGGTGAAGGTTATACCAGTGATGAAGAGGTTCTGGAAGTTTTT
CGTAACACCCTGAATAAAAACAGCGAGATCTTTAGCAGCATCAAAAAGCTTGAGAAACTGTTCAAAAACTTTGATG
AGTATAGCAGCGCAGGCATCTTTGTTAAAAATGGTCCGGCAATTAGCACCATCAGCAAAGATATTTTTGGCGAATG
GAATGTGATCCGCGATAAATGGAATGCCGAATATGATGATATCCACCTGAAAAAAAGGCCGTGGTGACCGAGAAA
TATGAAGATGATCGTCGTAAAAGCTTCAAGAAAATTGGTAGCTTTAGCCTGGAACAGCTGCAAGAATATGCAGATG

```
CAGATCTGAGCGTTGTGGAAAAACTGAAAGAAATCATCATTCAGAAGGTGGACGAGATCTATAAAGTTTATGGTAG
CAGCGAAAAACTGTTCGATGCAGATTTTGTTCTGGAAAAAAGCCTGAAAAAGAATGATGCCGTTGTGGCCATTATG
AAAGATCTGCTGGATAGCGTTAAGAGCTTCGAGAATTACATCAAAGCCTTTTTTGGTGAGGGCAAAGAAACCAATC
GTGATGAAAGTTTCTATGGCGATTTTGTGCTGGCCTATGATATTCTGCTGAAAGTGGACCATATTTATGATGCCAT
TCGCAATTATGTTACCCAGAAACCGTATAGCAAAGACAAGTTCAAACTGTACTTTCAGCGTCCGCAGTTTATGGGT
GGTTGGGATAAAGATAAAGAAACCGATTATCGTGCCACCATCCTGCGTTATGGTAGTAAATACTATCTGGCCATCA
TGGACAAAAAATACGCAAATGCCTGCAGAAAATCGACAAAGATGATGTGAATGGCAACTATGAAAAATCAACTA
CAAACTGCTGCCTGGTCCGAATAAAATGCTGCCGAAAGTGTTCTTTAGCAAGAAATGGATGGCCTATTATAACCCG
AGCGAGGATATTCAAAAGATCTACAAAAATGGCACCTTTAAAAAGGGCGACATGTTCAATCTGAACGATTGCCACA
AACTGATCGATTTCTTCAAAGATTCAATTTCGCGTTATCCGAAATGGTCCAATGCCTATGATTTTAACTTTAGCGA
AACCGAAAAATACAAAGACATTGCCGGTTTTTATCGCGAAGTGGAAGAACAGGGCTATAAAGTGAGCTTTGAAAGC
GCAAGCAAAAAGAGGTTGATAAGCTGGTTGAAGAGGGCAAACTGTATATGTTCCAGATTTACAACAAAGATTTTA
GCGACAAAAGCCATGGCACCCCGAATCTGCATACCATGTACTTTAAACTGCTGTTCGACGAAAATAACCATGGTCA
GATTCGTCTGAGCGGTGGTGCCGAACTGTTTATGCGTCGTGCAAGTCTGAAAAAAGAAGAACTGGTTGTTCATCCG
GCAAATAGCCCGATTGCAAACAAAAATCCGGACAATCCGAAAAAAACCACGACACTGAGCTATGATGTGTATAAAG
ACAAACGTTTTAGCGAGGATCAGTATGAACTGCATATCCCGATTGCCATCAATAAATGCCCGAAAAACATCTTTAA
GATCAACACCGAAGTTCGCGTGCTGCTGAAACATGATGATAATCCGTATGTGATTGGCATTGATCGTGGTGAACGT
AACCTGCTGTATATTGTTGTTGTTGATGGTAAAGGCAACATCGTGGAACAGTATAGTCTGAACGAAATTATCAACA
ACTTTAACGGCATCCGCATCAAAACCGACTATCATAGCCTGCTGGACAAGAAAGAAAAAGAACGTTTTGAAGCACG
TCAGAACTGGACCAGTATTGAAAACATCAAAGAACTGAAAGCCGGTTATATTAGCCAGGTGGTTCATAAAATCTGT
GAGCTGGTAGAAAAATACGATGCAGTTATTGCACTGGAAGATCTGAATAGCGGTTTCAAAAATAGCCGTGTGAAAG
TCGAAAAACAGGTGTATCAGAAATTCGAGAAAATGCTGATCGACAAACTGAACTACATGGTCGACAAAAAAAGCAA
TCCGTGTGCAACCGGTGGTGCACTGAAAGGTTATCAGATTACCAACAAATTTGAAAGCTTTAAAAGCATGAGCACC
CAGAACGGCTTTATCTTCTATATTCCGGCATGGCTGACCAGCAAAATTGATCCGAGCACCGGTTTTGTGAACCTGC
TGAAAACAAAATATACCTCCATTGCCGACAGCAAGAAGTTTATTAGCAGCTTTGATCGCATTATGTATGTTCCGGA
AGAGGACCTGTTTGAATTCGCACTGGATTACAAAAATTTCAGCCGTACCGATGCCGACTACATCAAAAAATGGAAA
CTGTACAGCTATGGTAACCGCATTCGCATTTTTCGCAACCCGAAGAAAAACAATGTGTTCGATTGGGAAGAAGTTT
GTCTGACCAGCGCATATAAAGAACTTTTCAACAAATACGGCATCAACTATCAGCAGGGTGATATTCGTGCACTGCT
GTGTGAACAGAGCGATAAAGCGTTTTATAGCAGTTTTATGGCACTGATGAGCCTGATGCTGCAGATGCGTAATAGC
ATTACCGGTCGCACCGATGTGGATTTTCTGATTAGTCCGGTGAAAAATTCCGATGGCATCTTTTTATGATAGCCGCA
ATTACGAAGCACAAGAAAATGCAATTCTGCCGAAAAACCAGATGCAAATGGTGCATATAACATTGCACGTAAAGT
TCTGTGGGCAATTGGCCAGTTTAAGAAAGCAGAAGATGAGAAGCTGGACAAAGTGAAAATTGCGATCAGCAATAAA
GAGTGGCTGGAATACGCACAGACCAGCGTTAAACAT
```

SEQ ID NO: 11
Mutant D559P LbCas12a DNA sequence
```
ATGAGCAAACTGGAAAAAGTTCACCAACTGTTATAGCCTGAGCAAAACCCTGCGTTTTAAAGCAATTCCGGTTGGTA
AAACCCAAGAGAACATTGATAATAAACGCCTGCTGGTCGAAGATGAAAACGCGCTGAAGATTATAAAGGCGTGAA
AAAACTGCTGGATCGCTATTATCTGAGCTTCATTAACGATGTGCTGCACAGCATTAAACTGAAGAACCTGAACAAC
TATATCAGCCTGTTTCGTAAAAAAACCCGCACCGAAAAAGAAACAAAGAGCTGGAAAACCTGGAAATCAATCTGC
GTAAAGAAATCGCCAAAGCGTTTAAAGGTAACGAGGGTTATAAAAGCCTGTTCAAGAAAGACATCATCGAAACCAT
TCTGCCGGAATTTCTGGATGATAAAGATGAAATTGCCCTGGTGAATAGCTTTAATGGCTTTACCACCGCATTTACC
GGCTTTTTTGATAATCGCAAAAATGTTCAGCGAAGAAGCAAAAAGCACCAGCATTGCATTTCGCTGCATTATG
AAAATCTGACCCGCTACATTAGCAACATGGATATCTTTGAAAAAGTGGACGCGATCTTCGATAAACACGAAGTGCA
AGAGATCAAAGAGAAAATCCTGAACAGCGATTATGACGTCGAAGATTTTTTTGAAGGCGAGTTCTTTAACTTCGTT
CTGACCCAAGAAGGTATCGACGTTTATAACGCAATTATTGGTGGTTTTGTTACCGAAAGCGGTGAGAAAATCAAAG
GCCTGAATGAATATATCAACCTGTATAACCAGAAACGCAAACAGAAACTGCCCGAAATTCAAACCGCGTGTATAAACA
GGTTCTGAGCGATCGTGAAAGCCTGAGCTTTTATGGTGAAGGTTATACCAGTGATGAAGAGGTTCTGGAAGTTTT
CGTAACACCCTGAATAAAAACAGCGAGATCTTTAGCAGCATCAAAAGCTTGAGAAACTGTTCAAAACTTTGATG
AGTATAGCAGCGCAGGCATCTTTGTTAAAAATGGTCCGGCAATTAGCACCATCAGCAAAGATATTTTTGGCGAATG
GAATGTGATCCGCGATAAATGAATGCCGAATATGATGATATCCACCTGAAAAAAAAGGCCGTGACCGAGAAA
TATGAAGATGATCGTCGTAAAGCTTCAAGAAATTGGTAGCTTTAGCCTGGAACAGCTGCAAGAATATGCAGATG
CAGATCTGAGCGTTGTGGAAAAACTGAAAGAAATCATCATTCAGAAGGTGGACGAGATCTATAAAGTTTATGGTAG
CAGCGAAAAACTGTTCGATGCAGATTTTGTTCTGGAAAAAAGCCTGAAAAAGAATGATGCCGTTGTGGCCATTATG
AAAGATCTGCTGGATAGCGTTAAGAGCTTCGAGAATTACATCAAAGCCTTTTTTGGTGAGGGCAAAGAAACCAATC
GTGATGAAAGTTTCTATGGCGATTTTGTGCTGGCCTATGATATTCTGCTGAAAGTGGACCATATTTATGATGCCAT
TCGCAATTATGTTACCCAGAAACCGTATAGCAAAGACAAGTTCAAACTGTACTTTCAGAACCCGCAGTTATGGGT
GGTTGGGATAAAGATAAAGAAACCGATTATCGTGCCACCATCCTGCGTTATGGTAGTAAATACTATCTGGCCATCA
TGCCGAAAAAATACGCAAATGCCTGCAGAAAATCGACAAAGATGATGTGAATGGCAACTATGAAAAATCAACTA
CAAACTGCTGCCTGGTCCGAATAAAATGCTGCCGAAAGTGTTCTTTAGCAAGAAATGGATGGCCTATTATAACCCG
AGCGAGGATATTCAAAAGATCTACAAAAATGGCACCTTTAAAAAGGGCGACATGTTCAATCTGAACGATTGCCACA
AACTGATCGATTTCTTCAAAGATTCAATTTCGCGTTATCCGAAATGGTCCAATGCCTATGATTTTAACTTTAGCGA
AACCGAAAAATACAAAGACATTGCCGGTTTTTATCGCGAAGTGGAAGAACAGGGCTATAAAGTGAGCTTTGAAAGC
GCAAGCAAAAAGAGGTTGATAAGCTGGTTGAAGAGGGCAAACTGTATATGTTCCAGATTTACAACAAAGATTTTA
GCGACAAAAGCCATGGCACCCCGAATCTGCATACCATGTACTTTAAACTGCTGTTCGACGAAAATAACCATGGTCA
GATTCGTCTGAGCGGTGGTGCCGAACTGTTTATGCGTCGTGCAAGTCTGAAAAAAGAAGAACTGGTTGTTCATCCG
GCAAATAGCCCGATTGCAAACAAAAATCCGGACAATCCGAAAAAAACCACGACACTGAGCTATGATGTGTATAAAG
ACAAACGTTTTAGCGAGGATCAGTATGAACTGCATATCCCGATTGCCATCAATAAATGCCCGAAAAACATCTTTAA
GATCAACACCGAAGTTCGCGTGCTGCTGAAACATGATGATAATCCGTATGTGATTGGCATTGATCGTGGTGAACGT
AACCTGCTGTATATTGTTGTTGTTGATGGTAAAGGCAACATCGTGGAACAGTATAGTCTGAACGAAATTATCAACA
ACTTTAACGGCATCCGCATCAAAACCGACTATCATAGCCTGCTGGACAAGAAAGAAAAAGAACGTTTTGAAGCACG
TCAGAACTGGACCAGTATTGAAAACATCAAAGAACTGAAAGCCGGTTATATTAGCCAGGTGGTTCATAAAATCTGT
GAGCTGGTAGAAAAATACGATGCAGTTATTGCACTGGAAGATCTGAATAGCGGTTTCAAAAATAGCCGTGTGAAAG
TCGAAAAACAGGTGTATCAGAAATTCGAGAAAATGCTGATCGACAAACTGAACTACATGGTCGACAAAAAAAGCAA
TCCGTGTGCAACCGGTGGTGCACTGAAAGGTTATCAGATTACCAACAAATTTGAAAGCTTTAAAAGCATGAGCACC
CAGAACGGCTTTATCTTCTATATTCCGGCATGGCTGACCAGCAAAATTGATCCGAGCACCGGTTTTGTGAACCTGC
TGAAAACAAAATATACCTCCATTGCCGACAGCAAGAAGTTTATTAGCAGCTTTGATCGCATTATGTATGTTCCGGA
AGAGGACCTGTTTGAATTCGCACTGGATTACAAAAATTTCAGCCGTACCGATGCCGACTACATCAAAAAATGGAAA
CTGTACAGCTATGGTAACCGCATTCGCATTTTTCGCAACCCGAAGAAAAACAATGTGTTCGATTGGGAAGAAGTTT
```

-continued

```
GTCTGACCAGCGCATATAAAGAACTTTTCAACAAATACGGCATCAACTATCAGCAGGGTGATATTCGTGCACTGCT
GTGTGAACAGAGCGATAAAGCGTTTTATAGCAGTTTTATGGCACTGATGAGCCTGATGCTGCAGATGCGTAATAGC
ATTACCGGTCGCACCGATGTGGATTTTCTGATTAGTCCGGTGAAAAATTCCGATGGCATCTTTTATGATAGCCGCA
ATTACGAAGCACAAGAAAATGCAATTCTGCCGAAAAACGCAGATGCAAATGGTGCATATAACATTGCACGTAAAGT
TCTGTGGGCAATTGGCCAGTTTAAGAAAGCAGAAGATGAGAAGCTGGACAAAGTGAAAATTGCGATCAGCAATAAA
GAGTGGCTGGAATACGCACAGACCAGCGTTAAACAT
```

SEQ ID NO: 12.
Mutant E795L LbCas12a DNA sequence
```
ATGAGCAAACTGGAAAAGTTCACCAACTGTTATAGCCTGAGCAAAACCCTGCGTTTTAAAGCAATTCCGGTTGGTA
AAACCCAAGAGAACATTGATAATAAACGCCTGCTGGTCGAAGATGAAAAACGCGCTGAAGATTATAAAGGCGTGAA
AAAACTGCTGGATCGCTATTATCTGAGCTTCATTAACGATGTGCTGCACAGCATTAAACTGAAGAACCTGAACAAC
TATATCAGCCTGTTTCGTAAAAAAACCCGCACCGAAAAAGAAAACAAAGAGCTGGAAAACCTGGAAATCAATCTGC
GTAAAGAAATCGCCAAAGCGTTTAAAGGTAACGAGGGTTATAAAAGCCTGTTCAAGAAAGACATCATCGAAACCAT
TCTGCCGGAATTTCTGGATGATAAAGATGAAATTGCCCTGGTGAATAGCTTTAATGGCTTTACCACCGCATTTACC
GGCTTTTTTGATAATCGCGAAAACATGTTCAGCGAAGAAGCAAAAAGCACCAGCATTGCATTTCGCTGCATTAATG
AAAATCTGACCCGCTACATTAGCAACATGGATATCTTTGAAAAAGTGGACGCGATCTTCGATAAACACGAAGTGCA
AGAGATCAAAGAGAAAATCCTGAACAGCGATTATGACGTTGAAGATTTTTTTGAAGGCGAGTTCTTTAACTTCGTT
CTGACCCAAGAAGGTATCGACGTTTATAACGCAATTATTGGTGGTTTTGTTACCGAAAGCGGTGAGAAAATCAAAG
GCCTGAATGAATATATCAACCTGTATAACCAGAAAACCAAACAGAAACTGCCGAAATTCAAACCGCTGTATAAACA
GGTTCTGAGCGATCGTGAAAGCCTGAGCTTTTATGGTGAAGGTTATACCAGTGATGAAGAGGTTCTGGAAGTTTTT
CGTAACACCCTGAATAAAAACAGCGAGATCTTTAGCAGCATCAAAAAGCTTGAGAAACTGTTCAAAAACTTTGATG
AGTATATCAGCAGCGCAGGCATCTTTGTTAAAAATGGTCCGGCAATTAGCACCATCAGCAAAGATATTTTTGGCGAATG
GAATGTGATCCGCGATAAATGGAATGCCGAATATGATGATATCCACCTGAAAAAAAGGCCGTGGTGACCGAGAAA
TATGAAGATGATCGTCGTAAAAGCTTCAAGAAAATTGGTAGCTTTAGCCTGGAACAGCTGCAAGAATATGCAGATG
CAGATCTGAGCGTTGTGGAAAAACTGAAAGAAATCATCATTCAGAAGGTGGACGAGATCTATAAAGTTTATGGTAG
CAGCGAAAAACTGTTCGATGCAGATTTTGTTCTGGAAAAAAGCCTGAAAAAGAATGATGCCGTTGTGGCCATTATG
AAAGATCTGCTGGATAGCGTTAAGAGCTTCGAGAATTACATCAAAGCCTTTTTGGTGAGGGCAAAGAAACCAATC
GTGATGAAAGTTTCTATGGCGATTTTGTGCTGGCCTATGATATTCTGCTGAAAGTGGACCATATTTATGATGCCAT
TCGCAATTATGTTACCCAGAAACCGTATAGCAAAGACAAGTTCAAACTGTACTTTCAGACAACCCGCAGCGAAAATAACCATGGGT
GGTTGGGATAAAGATAAAGAAACCGATTATCGTGCCACCATCCTGCGTTATGGTAGTAAATACTATCTGGCCATCA
TGGACAAAAAATACGCAAATGCCTGCAGAAAATCGACAAAGATGATGTGAATGGCAACTATGAAAAATCAACTA
CAAACTGCTGCCTGGTCCGAATAAAATGCTGCCGAAAGTGTTCTTTAGCAAGAAATGGATGGCCTATTATAACCCG
AGCGAGGATATTCAAAAGATCTACAAAAATGCACCTTTAAAAAGGGCACATGTTCAATCTGAACGATTGCACA
AACTGATCGATTTCTTCAAAGATTCAATTTCGCGTTATCCGAAATGGTCCAATGCCTATGATTTTAACTTTAGCGA
AACCGAAAAATACAAAGACATTGCCGGTTTTTATCGCAAGTGGAAGAACAGGGCTATAAAGTGAGCTTTGAAAGC
GCAAGCAAAAAGAGGTTGATAAGCTGGTTGAAGAGGGCAAACTGTATATGTTCCAGATTTACAACAAAGATTTTA
GCGACAAAAGCCATGGCACCCCGAATCTGCATACCATGTACTTTAAACTGCTGTTCGACGAAAATAACCATGGTCA
GATTCGTCTGAGCGGTGGTGCCGAACTGTTTATGCGTCGTGCAAGTCTGAAAAAAGAAGAACTGGTTGTTCATCCG
GCAAATAGCCCGATTGCAAACAAAAATCCGGACAATCCGAAAAAAACCACGACACTGAGCTATGATGTGTATAAAG
ACAAACGTTTTAGCGAGGATCAGTATCTGCTGCATATCCCGATTGCCATCAATAAATGCCCGAAAAACATCTTTAA
GATCAACACCGAAGTTCGCGTGCTGCTGAAACATGATGATAATCCGTATGTGATTGGCATTGATCGTGGTGAACGT
AACCTGCTGTATATTGTTGTTGTTGATGGTAAAGGCAACATCGTGGAACAGTATAGTCTGAACGAAATTATCAACA
ACTTTAACGGCATCCGCATCAAAACCGACTATCATAGCCTGCTGGACAAGAAAGAAAAAGAACGTTTTGAAGCACG
TCAGAACTGGACCAGTATTGAAAACATCAAGAACTGAAAGCCGGTTATATTAGCCAGGTGGTTCATAAAATCTGT
GAGCTGGTAGAAAAATACGATGCAGTTATTGCACTGGAAGATCTGAATAGCGGTTTCAAAAATAGCCGTGTGAAAG
TCGAAAAACAGGTGTATCAGAAATTCGAGAAAATGCTGATCGACAAACTGAACTACATGGTCGACAAAAAAGCAA
TCCGTGTGCAACCGGTGGTGCACTGAAAGGTTATCAGATTACCAACAAATTTGAAAGCTTTAAAAGCATGAGCACC
CAGAACGGCTTTATCTTCTATATTCCGGCATGGCTGACCAGCAAAATTGATCCGAGCACCGGTTTTGTGAACCTGC
TGAAAACAAAATATACCTCCATTGCCGACAGCAAGAAGTTTATTAGCAGCTTTGATCGCATTATGTATGTTCCGGA
AGAGGACCTGTTTGAATTCGCACTGGATTACAAAAATTTCAGCCGTACCATCCGACTACATCAAAAATGGCAA
CTGTACAGCTATGGTAACCGCATTCGCATTTTTCGCAACCCGAAGAAAACAATGTGTTCGATTGGGAAGAAGTTT
GTCTGACCAGCGCATATAAAGAACTTTTCAACAAATACGGCATCAACTATCAGCAGGGTGATATTCGTGCACTGCT
GTGTGAACAGAGCGATAAAGCGTTTTATAGCAGTTTTATGGCACTGATGAGCCTGATGCTGCAGATGCGTAATAGC
ATTACCGGTCGCACCGATGTGGATTTTCTGATTAGTCCGGTGAAAAATTCCGATGGCATCTTTTATGATAGCCGCA
ATTACGAAGCACAAGAAAATGCAATTCTGCCGAAAAACGCAGATGCAAATGGTGCATATAACATTGCACGTAAAGT
TCTGTGGGCAATTGGCCAGTTTAAGAAAGCAGAAGATGAGAAGCTGGACAAAGTGAAAATTGCGATCAGCAATAAA
GAGTGGCTGGAATACGCACAGACCAGCGTTAAACAT
```

SEQ ID NO: 13
Mutant N527R/D559P LbCas12a DNA sequence
```
ATGAGCAAACTGGAAAAGTTCACCAACTGTTATAGCCTGAGCAAAACCCTGCGTTTTAAAGCAATTCCGGTTGGTA
AAACCCAAGAGAACATTGATAATAAACGCCTGCTGGTCGAAGATGAAAAACGCGCTGAAGATTATAAAGGCGTGAA
AAAACTGCTGGATCGCTATTATCTGAGCTTCATTAACGATGTGCTGCACAGCATTAAACTGAAGAACCTGAACAAC
TATATCAGCCTGTTTCGTAAAAAAACCCGCACCGAAAAAGAAAACAAAGAGCTGGAAAACCTGGAAATCAATCTGC
GTAAAGAAATCGCCAAAGCGTTTAAAGGTAACGAGGGTTATAAAAGCCTGTTCAAGAAAGACATCATCGAAACCAT
TCTGCCGGAATTTCTGGATGATAAAGATGAAATTGCCCTGGTGAATAGCTTTAATGGCTTTACCACCGCATTTACC
GGCTTTTTTGATAATCGCGAAAACATGTTCAGCGAAGAAGCAAAAAGCACCAGCATTGCATTTCGCTGCATTAATG
AAAATCTGACCCGCTACATTAGCAACATGGATATCTTTGAAAAGTGGACGCGATCTTCGATAAACACGAAGTGCA
AGAGATCAAAGAGAAAATCCTGAACAGCGATTATGACGTCGAAGATTTTTTTGAAGGCGAGTTCTTTAACTTCGTT
CTGACCCAAGAAGGTATCGACGTTTATAACGCAATTATTGGTGGTTTTGTTACCGAAAGCGGTGAGAAAATCAAAG
GCCTGAATGAATATATCAACCTGTATAACCAGAAAACCAAACAGAAACTGCCGAAATTCAAACCGCTGTATAAACA
GGTTCTGAGCGATCGTGAAAGCCTGAGCTTTTATGGTGAAGGTTATACCAGTGATGAAGAGGTTCTGGAAGTTTTT
CGTAACACCCTGAATAAAAACAGCGAGATCTTTAGCAGCATCAAAAAGCTTGAGAAACTGTTCAAAAACTTTGATG
AGTATATCAGCAGCGCAGGCATCTTTGTTAAAAATGGTCCGGCAATTAGCACCATCAGCAAAGATATTTTTGGCGAATG
GAATGTGATCCGCGATAAATGGAATGCCGAATATGATGATATCCACCTGAAAAAAAGGCCGTGGTGACCGAGAAA
TATGAAGATGATCGTCGTAAAAGCTTCAAGAAAATTGGTAGCTTTAGCCTGGAACAGCTGCAAGAATATGCAGATG
CAGATCTGAGCGTTGTGGAAAAACTGAAAGAAATCATCATTCAGAAGGTGGACGAGATCTATAAAGTTTATGGTAG
CAGCGAAAAACTGTTCGATGCAGATTTTGTTCTGGAAAAAAGCCTGAAAAAGAATGATGCCGTTGTGGCCATTATG
```

```
AAAGATCTGCTGGATAGCGTTAAGAGCTTCGAGAATTACATCAAAGCCTTTTTTGGTGAGGGCAAAGAAACCAATC
GTGATGAAAGTTTCTATGGCGATTTTGTGCTGGCCTATGATATTCTGCTGAAAGTGGACCATATTTATGATGCCAT
TCGCAATTATGTTACCCAGAAACCGTATAGCAAAGACAAGTTCAAACTGTACTTTCAGCGTCCGCAGTTTATGGGT
GGTTGGGATAAAGATAAAGAAACCGATTATCGTGCCACCATCCTGCGTTATGGTAGTAAATACTATCTGGCCATCA
TGCCGAAAAAATACGCAAATGCCTGCAGAAAATCGACAAAGATGATGTGAATGGCAACTATGAAAAATCAACTA
CAAACTGCTGCCTGGTCCGAATAAAATGCTGCCGAAAGTGTTCTTTAGCAAGAAATGGATGGCCTATTATAACCCG
AGCGAGGATATTCAAAGATCTACAAAAATGGCACCTTTAAAAGGGCGACATGTTCAATCTGAACGATTGCCACA
AACTGATCGATTTCTTCAAAGATTCAATTTCGCGTTATCCGAAATGGTCCAATGCCTATGATTTTAACTTTAGCGA
AACCGAAAAATACAAAGACATTGCCGGTTTTTATCGCGAAGTGGAAGAACAGGGCTATAAAGTGAGCTTTGAAAGC
GCAAGCAAAAAGAGGTTGATAAGCTGGTTGAAGAGGGCAAACTGTATATGTTCCAGATTTACAACAAAGATTTTA
GCGACAAAAGCCATGGCACCCCGAATCTGCATACCATGTACTTTAAACTGCTGTTCGACGAAAATAACCATGGTCA
GATTCGTCTGAGCGGTGGTGCCGAACTGTTTATGCGTCGTGCAAGTCTGAAAAAAGAAGAACTGGTTGTTCATCCG
GCAAATAGCCCGATTGCAAACAAAAATCCGGACAATCCGAAAAAAACCACGACACTGAGCTATGATGTGTATAAAG
ACAAACGTTTTAGCGAGGATCAGTATGAACTGCATATCCCGATTGCCATCAATAAATGCCCGAAAAACATCTTTAA
GATCAACACCGAAGTTCGCGTGCTGCTGAAACATGATGATAATCCGTATGTGATTGGCATTGATCGTGGTGAACGT
AACCTGCTGTATATTGTTGTTGTTGATGGTAAAGGCAACATCGTGGAACAGTATAGTCTGAACGAAATTATCAACA
ACTTTAACGGCATCCGCATCAAAACCGACTATCATAGCCTGCTGGACAAGAAAGAAAAAGAACGTTTTGAAGCACG
TCAGAACTGGACCAGTATTGAAAACATCAAAGAACTGAAAGCCGGTTATATTAGCCAGGTGGTTCATAAAATCTGT
GAGCTGGTAGAAAAATACGATGCAGTTATTGCACTGGAAGATCTGAATAGCGGTTTCAAAAATAGCCGTGTGAAAG
TCGAAAAACAGGTGTATCAGAAATTCGAGAAAATGCTGATCGACAAACTGAACTACATGGTCGACAAAAAAAGCAA
TCCGTGTGCAACCGGTGGTGCACTGAAAGGTTATCAGATTACCAACAAATTTGAAAGCTTTAAAAGCATGAGCACC
CAGAACGGCTTTATCTTCTATATTCCGGCATGGCTGACCAGCAAATTGATCCGAGCACCGGTTTTGTGAACCTGC
TGAAAACAAAATATACCTCCATTGCCGACAGCAAGAAGTTTATTAGCAGCTTTGATCGCATTATGTATGTTCCGGA
AGAGGACCTGTTTGAATTCGCACTGGATTACAAAAATTTCAGCCGTACCGATGCCGACTACATCAAAAAATGGAAA
CTGTACAGCTATGGTAACCGCATTCGCATTTTTCGCAACCCGAAGAAAAACAATGTGTTCGATTGGGAAGAAGTTT
GTCTGACCAGCGCATATAAAGAACTTTTCAACAAATACGGCATCAACTATCAGCAGGGTGATATTCGTCACTGCT
GTGTGAACAGAGCGATAAAGCGTTTTATAGCAGTTTTATGGCACTGATGAGCCTGATGCTGCAGATGCGTAATAGC
ATTACCGGTCGCACCGATGTGGATTTTCTGATTAGTCCGGTGAAAAATTCCGATGGCATCTTTTATGATAGCCGCA
ATTACGAAGCACAAGAAATGCAATTCTGCCGAAAAACGCAGATGCAAATGGTGCATATAACATTGCACGTAAAGT
TCTGTGGGCAATTGGCCAGTTTAAGAAAGCAGAAGATGAGAAGCTGGACAAAGTGAAAATTGCGATCAGCAATAAA
GAGTGGCTGGAATACGCACAGACCAGCGTTAAACAT
```

SEQ ID NO: 14
Mutant N527R/E795L LbCas12a DNA sequence
```
ATGAGCAAACTGGAAAAGTTCACCAACTGTTATAGCCTGAGCAAAACCCTGCGTTTTAAAGCAATTCCGGTTGGTA
AAACCCAAGAGAACATTGATAATAAACGCCTGCTGGTCGAAGATGAAAAACGCGCTGAAGATTATAAAGGCGTGAA
AAAACTGCTGGATCGCTATTATCTGAGCTTCATTAACGATGTGCTGCACAGCATTAAACTGAAGAACCTGAACAAC
TATATCAGCCTGTTTCGTAAAAAAACCCGCACCGAAAAAGAAAACAAAGAGCTGGAAAACCTGGAAATCAATCTGC
GTAAAGAAATCGCCAAAGCGTTTAAAGGTAACGAGGGTTATAAAAGCCTGTTCAAGAAAGACATCATCGAAACCAT
TCTGCCGGAATTTCTGGATGATAAAGATGAAATTGCCCTGGTGAATAGCTTTAATGGCTTTACCACCGCATTTACC
GGCTTTTTTGATAATCGCGAAAACATGTTCAGCGAAGAAGCAAAAAGCACCAGCATTGCATTTCGCTGCATTAATG
AAAATCTGACCCGCTACATTAGCAACATGGATATCTTTGAAAAAGTGGACGCGATCTTCGATAAACACGAAGTGCA
AGAGATCAAAGAGAAATCCTGAACGATGACGTCGAAGATTTTTTTGAAGGCGAGTTCTTTAACTTCGTT
CTGACCCAAGAAGGTATCGACGTTTATAACGCAATTATTGGTGGTTTTGTTACCGAAAGCGGTGAGAAAATCAAAG
GCCTGAATGAATATATCAACCTGTATAACCAGAAAACCAAACAGAAACTGCCGAAATTCAAACCGCTGTATAAACA
GGTTCTGAGCGATCGTGAAAGCCTGAGCTTTTATGGTGAAGGTTATACCAGTGATGAAGAGGTTCTGGAAGTTTTT
CGTAACACCCTGAATAAAAACAGCGAGATCTTTAGCAGCATCAAAAAACTGTTCAAAAACTTTGATG
AGTATAGCAGCGCAGGCATCTTTGTTAAAAATGGCTCGGCAATTAGCACCATCAGCAAAGATATTTTTGGCGAATG
GAATGTGATCCGCGATAAATGGAATGCCGAATATGATGATATCCACCTGAAAAAAAAGGCCGTGGTGACCGAGAAA
TATGAAGATGATCGTCGTAAAAGCTTCAAGAAAATTGGTAGCTTTAGCCTGGAACAGCTGCAAGAATATGCAGATG
CAGATCTGAGCGTTGTGGAAAAACTGAAAGAAATCATCATTCAGAAGGTGGACGAGATCTATAAAGTTTATGGTAG
CAGCGAAAAACTGTTCGATGCAGATTTTGTTCTGGAAAAAAGCCTGAAAAAGAATGATGCCGTTGTGGCCATTATG
AAAGATCTGCTGGATAGCGTTAAGAGCTTCGAGAATTACATCAAAGCCTTTTTTGGTGAGGGCAAAGAAACCAATC
GTGATGAAAGTTTCTATGGCGATTTTGTGCTGGCCTATGATATTCTGCTGAAAGTGGACCATATTTATGATGCCAT
TCGCAATTATGTTACCCAGAAACCGTATAGCAAAGACAAGTTCAAACTGTACTTTCAGCGTCCGCAGTTTATGGGT
GGTTGGGATAAAGATAAAGAAACCGATTATCGTGCCACCATCCTGCGTTATGGTAGTAAATACTATCTGGCCATCA
TGGACAAAAAATACGCAAATGCCTGCAGAAAATCGACAAAGATGATGTGAATGGCAACTATGAAAAATCAACTA
CAAACTGCTGCCTGGTCCGAATAAAATGCTGCCGAAAGTGTTCTTTAGCAAGAAATGGATGGCCTATTATAACCCG
AGCGAGGATATTCAAAGATCTACAAAAATGGCACCTTTAAAAGGGCGACATGTTCAATCTGAACGATTGCCACA
AACTGATCGATTTCTTCAAAGATTCAATTTCGCGTTATCCGAAATGGTCCAATGCCTATGATTTTAACTTTAGCGA
AACCGAAAAATACAAAGACATTGCCGGTTTTTATCGCGAAGTGGAAGAACAGGGCTATAAAGTGAGCTTTGAAAGC
GCAAGCAAAAAGAGGTTGATAAGCTGGTTGAAGAGGGCAAACTGTATATGTTCCAGATTTACAACAAAGATTTTA
GCGACAAAAGCCATGGCACCCCGAATCTGCATACCATGTACTTTAAACTGCTGTTCGACGAAAATAACCATGGTCA
GATTCGTCTGAGCGGTGGTGCCGAACTGTTTATGCGTCGTGCAAGTCTGAAAAAAGAAGAACTGGTTGTTCATCCG
GCAAATAGCCCGATTGCAAACAAAAATCCGGACAATCCGAAAAAAACCACGACACTGAGCTATGATGTGTATAAAG
ACAAACGTTTTAGCGAGGATCAGTATCTGCTGCATATCCCGATTGCCATCAATAAATGCCCGAAAAACATCTTTAA
GATCAACACCGAAGTTCGCGTGCTGCTGAAACATGATGATAATCCGTATGTGATTGGCATTGATCGTGGTGAACGT
AACCTGCTGTATATTGTTGTTGTTGATGGTAAAGGCAACATCGTGGAACAGTATAGTCTGAACGAAATTATCAACA
ACTTTAACGGCATCCGCATCAAAACCGACTATCATAGCCTGCTGGACAAGAAAGAAAAAGAACGTTTTGAAGCACG
TCAGAACTGGACCAGTATTGAAAACATCAAAGAACTGAAAGCCGGTTATATTAGCCAGGTGGTTCATAAAATCTGT
GAGCTGGTAGAAAAATACGATGCAGTTATTGCACTGGAAGATCTGAATAGCGGTTTCAAAAATAGCCGTGTGAAAG
TCGAAAAACAGGTGTATCAGAAATTCGAGAAAATGCTGATCGACAAACTGAACTACATGGTCGACAAAAAAAGCAA
TCCGTGTGCAACCGGTGGTGCACTGAAAGGTTATCAGATTACCAACAAATTTGAAAGCTTTAAAAGCATGAGCACC
CAGAACGGCTTTATCTTCTATATTCCGGCATGGCTGACCAGCAAATTGATCCGAGCACCGGTTTTGTGAACCTGC
TGAAAACAAAATATACCTCCATTGCCGACAGCAAGAAGTTTATTAGCAGCTTTGATCGCATTATGTATGTTCCGGA
AGAGGACCTGTTTGAATTCGCACTGGATTACAAAAATTTCAGCCGTACCGATGCCGACTACATCAAAAAATGGAAA
CTGTACAGCTATGGTAACCGCATTCGCATTTTTCGCAACCCGAAGAAAAACAATGTGTTCGATTGGGAAGAAGTTT
GTCTGACCAGCGCATATAAAGAACTTTTCAACAAATACGGCATCAACTATCAGCAGGGTGATATTCGTCACTGCT
GTGTGAACAGAGCGATAAAGCGTTTTATAGCAGTTTTATGGCACTGATGAGCCTGATGCTGCAGATGCGTAATAGC
```

-continued

ATTACCGGTCGCACCGATGTGGATTTTCTGATTAGTCCGGTGAAAAATTCCGATGGCATCTTTTATGATAGCCGCA
ATTACGAAGCACAAGAAAATGCAATTCTGCCGAAAAACGCAGATGCAAATGGTGCATATAACATTGCACGTAAAGT
TCTGTGGGCAATTGGCCAGTTTAAGAAAGCAGAAGATGAGAAGCTGGACAAAGTGAAAATTGCGATCAGCAATAAA
GAGTGGCTGGAATACGCACAGACCAGCGTTAAACAT

SEQ ID NO: 15
Mutant D559P/E795L LbCas12a DNA sequence
ATGAGCAAACTGGAAAAGTTCACCAACTGTTATAGCCTGAGCAAAACCCTGCGTTTTAAAGCAATTCCGGTTGGTA
AAACCCAAGAGAACATTGATAATAAACGCCTGCTGGTCGAAGATGAAAAACGCGCTGAAGATTATAAAGGCGTGAA
AAAACTGCTGGATCGCTATTATCTGAGCTTCATTAACGATGTGCTGCACAGCATTAAACTGAAGAACCTGAACAAC
TATATCAGCCTGTTTCGTAAAAAAACCCGCACCGAAAAAGAAAACAAAGAGCTGGAAAACCTGGAAATCAATCTGC
GTAAAGAAATCGCCAAAGCGTTTAAAGGTAACGAGGGTTATAAAAGCCTGTTCAAGAAAGACATCATCGAAACCAT
TCTGCCGGAATTTCTGGATGATAAAGATGAAATTGCCCTGGTGAATAGCTTTAATGGCTTTACCACCGCATTTACC
GGCTTTTTTGATAATCGCGAAAACATGTTCAGCGAAGAAGCAAAAAGCACCAGCATTGCATTTCGCTGCATTAATG
AAAATCTGACCCGCTACATTAGCAACATGGATATCTTTGAAAAAGTGGACGCGATCTTCGATAAACACGAAGTGCA
AGAGATCAAAGAGAAATCCTGAACAGCGATTATGACGTCGAAGATTTTTTTGAAGGCGAGTTCTTTAACTTCGTT
CTGACCCAAGAAGGTATCGACGTTTATAACGCAATTATTGGTGGTTTTGTTACCGAAAGCGGTGAGAAAATCAAAG
GCCTGAATGAATATATCAACCTGTATAACCAGAAAACCAAACAGAAACTGCCGAAATTCAAACCGCTGTATAAACA
GGTTCTGAGCGATCGTGAAAGCCTGAGCTTTTATGGTGAAGGTTATACCAGTGATGAAGAGGTTCTGGAAGTTTTT
CGTAACACCCTGAATAAAAACAGCGAGATCTTTAGCAGCATCAAAAAGCTTGAGAAACTGTTCAAAAACTTTGATG
AGTATAGCAGCGCAGGCATCTTTGTTAAAAATGGTCCGGCAATTAGCACCATCAGCAAAGATATTTTTGGCGAATG
GAATGTGATCCGCGATAAATGGAATGCCGAATATGATGATATCCACCTGAAAAAAAAGGCCGTGGTGACCGAGAAA
TATGAAGATGATCGTCGTAAAAGCTTCAAGAAAATTGGTAGCTTTAGCCTGGAACAGCTGCAAGAATATGCAGATG
CAGATCTGAGCGTTGTGGAAAAACTGAAAGAAATCATCATTCAGAAGGTGGACGAGATCTATAAAGTTTATGGTAG
CAGCGAAAAACTGTTCGATGCAGATTTTGTTCTGGAAAAAAGCCTGAAAAAGAATGATGCCGTTGTGGCCATTATG
AAAGATCTGCTGGATAGCGTTAAGAGCTTCGAGAATTACATCAAAGCCTTTTTTGGTGAGGGCAAAGAAACCAATC
GTGATGAAAGTTTCTATGGCGATTTTGTGCTGGCCTATGATATTCTGCTGAAAGTGGACCATATTTATGATGCCAT
TCGCAATTATGTTACCCAGAAACCGTATAGCAAAGACAAGTTCAAACTGTACTTTCAGAACCCGCAGTTTATGGGT
GGTTGGGATAAAGATAAAGAAACCGATTATCGTGCCACCATCCTGCGTTATGGTAGTAAATACTATCTGGCCATCA
TGCCGAAAAAATACGCAAAATGCCTGCAGAAAATCGACAAAGATGATGTGAATGGCAACTATGAAAAAATCAACTA
CAAACTGCTGCCTGGTCCGAATAAAATGCTGCCGAAAGTGTTCTTTAGCAAGAAATGGATGGCCTATTATAACCCG
AGCGAGGATATCAAAGATCTACAAAATGGCACCTTTAAAAAGGGCGACATGTTCAATCTGAACGATTGCCACA
AACTGATCGATTTCTTCAAAGATTCAATTTCGCGTTATCCGAAATGGTCCAATGCCTATGATTTTAACTTTAGCGA
AACCGAAAAATACAAAGACATTGCCGGTTTTTATCGCGAAGTGGAAGAACAGGGCTATAAAAGTGAGCTTTGAAAGC
GCAAGCAAAAAAGAGGTTGATAAGCTGGTTGAAGAGGGCAAACTGTATATGTTCCAGATTTACAACAAAGATTTTA
GCGACAAAAGCCATGGCACCCGAATCTGCATACCATGTACTTTAAACTGCTGTTCGACGAAAATAACCATGGTCA
GATTCGTCTGAGCGGTGGTGCCGAACTGTTTATGCGTCGTGCAAGTCTGAAAAAAGAAGAACTGGTTGTTCATCCG
GCAAATAGCCCGATTGCAAACAAAAATCCGGACAATCCGAAAAAAACCACGACACTGAGCTATGATGTGTATAAAG
ACAAACGTTTTAGCGAGGATCAGTATCTGCTGCATATCCCGATTGCCATCAATAAATGCCCGAAAAACATCTTTAA
GATCAACACCGAAGTTCGCGTGCTGCTGAAACATGATGATAATCCGTATGTGATTGGCATTGATCGTGGTGAACGT
AACCTGCTGTATATTGTTGTTGTTGATGGTAAAGGCAACATCGTGGAACAGTATAGTCTGAACGAAATTATCAACA
ACTTTAACGGCATCCGCATCAAAACCGACTATCATAGCCTGCTCGACAAGAAAGAAAAAGAACGTTTTGAAGCACG
TCAGAACTGGACCAGTATTGAAAACATCAAAGAACTGAAAGCCGGTTATATTAGCCAGGTGGTTCATAAAATCTGT
GAGCTGGTAGAAAAATACGATGCAGTTATTGCACTGGAAGATCTGAATAGCGGTTTCAAAAATAGCCGTGTGAAAG
TCGAAAAACAGGTGTATCAGAAATTCGAGAAAATGCTGATCGACAAACTGAACTACATGGTCGACAAAAAAGCAA
TCCGTGTGCAACCGGTGGTGCACTGAAAGGTTATCAGATTACCAACAAATTTGAAAGCTTTAAAGCATGAGCACC
CAGAACGGCTTTATCTTCTATATTCCGGCATGGCTGACCAGCAAAATTGATCCGAGCACCGGTTTTGTGAACCTGC
TGAAAACAAAATATACCTCCATTGCCGACAGCAAGAAGTTTATTAGCAGCTTTGATCGCATTATGTATGTTCCGGA
AGAGGACCTGTTTGAATTCGCACTGGATTACAAAAATTTCAGCCGTACCGATGCCGACTACATCAAAAAATGGAAA
CTGTACAGCTATGGTAACCGCATTCGCATTTTTCGCAACCCGAAGAAAAACAATGTGTTCGATTGGGAAGAAGTTT
GTCTGACCAGCGCATATAAAGAACTTTTCAACAAATACGGCATCACTCAACTATCAGCAGGTGATATTCGTGCACTGCT
GTGTGAACAGAGCGATAAAGCGTTTTATAGCAGTTTTATGGCACTGATGAGCCTGATGCTGCAGATGCGTAATAGC
ATTACCGGTCGCACCGATGTGGATTTTCTGATTAGTCCGGTGAAAAATTCCGATGGCATCTTTTATGATAGCCGCA
ATTACGAAGCACAAGAAAATGCAATTCTGCCGAAAAACGCAGATGCAAATGGTGCATATAACATTGCACGTAAAGT
TCTGTGGGCAATTGGCCAGTTTAAGAAAGCAGAAGATGAGAAGCTGGACAAAGTGAAAATTGCGATCAGCAATAAA
GAGTGGCTGGAATACGCACAGACCAGCGTTAAACAT SEQ ID NO: 16
Mutant N527R/D559P/E795L LbCas12a DNA sequence
ATGAGCAAACTGGAAAAGTTCACCAACTGTTATAGCCTGAGCAAAACCCTGCGTTTTAAAGCAATTCCGGTTGGTA
AAACCCAAGAGAACATTGATAATAAACGCCTGCTGGTCGAAGATGAAAAACGCGCTGAAGATTATAAAGGCGTGAA
AAAACTGCTGGATCGCTATTATCTGAGCTTCATTAACGATGTGCTGCACAGCATTAAACTGAAGAACCTGAACAAC
TATATCAGCCTGTTTCGTAAAAAAACCCGCACCGAAAAAGAAAACAAAGAGCTGGAAAACCTGGAAATCAATCTGC
GTAAAGAAATCGCCAAAGCGTTTAAAGGTAACGAGGGTTATAAAAGCCTGTTCAAGAAAGACATCATCGAAACCAT
TCTGCCGGAATTTCTGGATGATAAAGATGAAATTGCCCTGGTGAATAGCTTTAATGGCTTTACCACCGCATTTACC
GGCTTTTTTGATAATCGCGAAAACATGTTCAGCGAAGAAGCAAAAAGCACCAGCATTGCATTTCGCTGCATTAATG
AAAATCTGACCCGCTACATTAGCAACATGGATATCTTTGAAAAAGTGGACGCGATCTTCGATAAACACGAAGTGCA
AGAGATCAAAGAGAAATCCTGAACAGCGATTATGACGTCGAAGATTTTTTTGAAGGCGAGTTCTTTAACTTCGTT
CTGACCCAAGAAGGTATCGACGTTTATAACGCAATTATTGGTGGTTTTGTTACCGAAAGCGGTGAGAAAATCAAAG
GCCTGAATGAATATATCAACCTGTATAACCAGAAAACCAAACAGAAACTGCCGAAATTCAAACCGCTGTATAAACA
GGTTCTGAGCGATCGTGAAAGCCTGAGCTTTTATGGTGAAGGTTATACCAGTGATGAAGAGGTTCTGGAAGTTTTT
CGTAACACCCTGAATAAAAACAGCGAGATCTTTAGCAGCATCAAAAAGCTTGAGAAACTGTTCAAAAACTTTGATG
AGTATAGCAGCGCAGGCATCTTTGTTAAAAATGGTCCGGCAATTAGCACCATCAGCAAAGATATTTTTGGCGAATG
GAATGTGATCCGCGATAAATGGAATGCCGAATATGATGATATCCACCTGAAAAAAAAGGCCGTGGTGACCGAGAAA
TATGAAGATGATCGTCGTAAAAGCTTCAAGAAAATTGGTAGCTTTAGCCTGGAACAGCTGCAAGAATATGCAGATG
CAGATCTGAGCGTTGTGGAAAAACTGAAAGAAATCATCATTCAGAAGGTGGACGAGATCTATAAAGTTTATGGTAG
CAGCGAAAAACTGTTCGATGCAGATTTTGTTCTGGAAAAAAGCCTGAAAAAGAATGATGCCGTTGTGGCCATTATG
AAAGATCTGCTGGATAGCGTTAAGAGCTTCGAGAATTACATCAAAGCCTTTTTTGGTGAGGGCAAAGAAACCAATC
GTGATGAAAGTTTCTATGGCGATTTTGTGCTGGCCTATGATATTCTGCTGAAAGTGGACCATATTTATGATGCCAT TCGCAATTATGTTACCCAGAAACCGTATAGCAAAGACAAGTTCAAACTGTACTTTCAGCGTCCGCAGTTTATGGGT
GGTTGGGATAAAGATAAAGAAACCGATTATCGTGCCACCATCCTGCGTTATGGTAGTAAATACTATCTGGCCATCA
TGCCGAAAAAATACGCAAAATGCCTGCAGAAAATCGACAAAGATGATGTGAATGGCAACTATGAAAAATCAACTA
CAAACTGCTGCCTGGTCCGAATAAAATGCTGCCGAAAGTGTTCTTTAGCAAGAAATGGATGGCCTATTATAACCCG
AGCGAGGATATTCAAAAGATCTACAAAAATGGCACCTTTAAAAAGGGCGACATGTTCAATCTGAACGATTGCCACA
AACTGATCGATTTCTTCAAAGATTCAATTTCGCGTTATCCGAAATGGTCCAATGCCTATGATTTTAACTTTAGCGA
AACCGAAAAATACAAAGACATTGCCGGTTTTTATCGCGAAGTGGAAGAACAGGGCTATAAAGTGAGCTTTGAAAGC
GCAAGCAAAAAGAGGTTGATAAGCTGGTTGAAGAGGGCAAACTGTATATGTTCCAGATTTACAACAAAGATTTTA
GCGACAAAAGCCATGGCACCCCGAATCTGCATACCATGTACTTTAAACTGCTGTTCGACGAAAATAACCATGGTCA
GATTCGTCTGAGCGGTGGTGCCGAACTGTTTATGCGTCGTGCAAGTCTGAAAAAGAAGAACTGGTTGTTCATCCG
GCAAATAGCCCGATTGCAAACAAAAATCCGGACAATCCGAAAAAAACCACGACACTGAGCTATGATGTGTATAAAG
ACAAACGTTTTAGCGAGGATCAGTATCTGCTGCATATCCCGATTGCCATCAATAAATGCCCGAAAAACATCTTTAA
GATCAACACCGAAGTTGCGTGCTGCTGAAACATGATGATAATCCGTATGTGATTGGCATTGATCGTGGTGAACGT
AACCTGCTGTATATTGTTGTTGTTGATGGTAAAGGCAACATCGTGGAACAGTATAGTCTGAACGAAATTATCAACA
ACTTTAACGGCATCCGCATCAAACCGACTATCATAGCCTGCTGGACAAGAAAGAAAAGAACGTTTTGAAGCACG
TCAGAACTGGACCAGTATTGAAAACATCAAAGAACTGAAAGCCGGTTATATTAGCCAGGTGGTTCATAAAATCTGT
GAGCTGGTAGAAAAATACGATGCAGTTATTGCACTGGAAGATCTGAATGCGGTTTCAAAAATAGCCGTGTGAAAG
TCGAAAAACAGGTGTATCAGAAATTCGAGAAAATGCTGATCGACAAACTGAACTACATGGTCGACAAAAAAGCAA
TCCGTGTGCAACCGGTGGTGCACTGAAAGGTTATCAGATTACCAACAAATTTGAAAGCTTTAAAAGCATGAGCACC
CAGAACGGCTTTATCTTCTATATTCCGGCATGGCTGACCAGCAAAATTGATCCGAGCACCGGTTTTGTGAACCTGC
TGAAAACAAAATATACCTCCATTGCCGACAGCAAGAAGTTTATTAGCAGCTTTGATCGCATTATGTATGTTCCGGA
AGAGGACCTGTTTGAATTCGCACTGGATTACAAAAATTTCAGCCGTACCGAACGCCGACTACATCAAAAAATGGAAA
CTGTACAGCTATGGTAACCGCATTCGCATTTTTCGCAACCCGAAGAAAAACAATGTGTTCGATTGGGAAGAAGTTT
GTCTGACCAGCGCATATAAGAACTTTTCAACAAATACGGCATCAACTATCAGCAGGGTGATATTCGTCACTGCT
GTGTGAACAGAGCGATAAAGCGTTTTATAGCAGTTTTATGGCACTGATGAGCCTGATGCTGCAGATGCGTAATAGC
ATTACCGGTCGCACCGATGTGGATTTTCTGATTAGTCCGGTGAAAAATTCCGATGCATCTTTTATGATAGCCGCA
ATTACGAAGCACAAGAAATGCAATTCTGCCGAAAAACGCAGATGCAAATGGTGCATATAACATTGCACGTAAAGT
TCTGTGGGCAATTGGCCAGTTTAAGAAAGCAGAAGATGAGAAGCTGGACAAAGTGAAAATTGCGATCAGCAATAAA
GAGTGGCTGGAATACGCACAGACCAGCGTTAAACAT SEQ ID NO: 17
WT AsCas12a DNA sequence
ATGACCCAGTTTGAAGGTTTCACCAATCTGTATCAGGTTAGCAAAACCCTGCGTTTTGAACTGATTCCGCAGGGTA
AAACCCTGAAACATATTCAAGAACAGGGCTTCATCGAAGAGGATAAAGCACGTAACGATCACTACAAAGAACTGAA
ACCGATTATCGACCGCATCTATAAAACCTATGCAGATCAGTGTCTGCAGCTGGTTCAGCTGGATTGGGAAAATCTG
AGCGCAGCAATTGATAGTTATCGCAAAGAAAAACCGAAGAAACCCGTAATGCACTGATTGAAGAACAGGCAACCT
ATCGTAATGCCATCCATGATTATTTCATTGGTCGTACCGATAATCTGACCGATGCAATTAACAAACGTCACGCCGA
AATCTATAAAGGCCTGTTTAAAGCCGAACTGTTTAATGGCAAAGTTCTGAAACAGCTGGGCACCGTTACCACCACC
GAACATGAAAATGCACTGCGCTAGCTTTGATAAATTCACCACCTATTTCAGCGGCTTTTATGAGAATCGCAAA
ACGTGTTTAGCGCAGAAGATATTAGCACCGCAATTCCGCATCGTATTGTGCAGGATAATTTCCCGAAATTCAAGA
GAACTGCCACATTTTTACCCGTCTGATTACCGCAGTTCCGAGCCTGCGTGAACATTTTGAAAACGTTAAAAAAGCC
ATCGGCATCTTTGTTAGCACCAGCATTGAAGAAGTTTTTAGCTTCCCGTTTTACAATCAGCTGCTGACCCAGACCC
AGATTGATCTGTATAACCAACTGCTGGGTGGTATTAGCCGTGAAGCAGGCACCGAAAAAATCAAAGGTCTGAATGA
AGTGCTGAATCTGGCCATTCAGAAAAATGATGAAACCGCACATATTATTGCAAGCCTGCCGCATCGTTTTATTCCG
CTGTTCAAACAATTCTGAGCGATCGTAATACCCTGAGCTTTATTCTGGAAGAATTCAAATCCGATGAAGAGGTGA
TTCAGAGCTTTTGCAAATACAAAACGCTGCTGCGCAATGAAAATGTTCTGGAAACTGCCGAAGCACTGTTTAACGA
ACTGAATAGCATTGATCTGACCCACATCTTTATCAGCCACAAAAAACTGGAAACCATTTCAAGCGCACTGTGTGAT
CATTGGGATACCCTGCGTAATGCCCTGTATGAACGTCGTATTAGCGAACTGACCGGTAAAATTACCAAAAGCGCGA
AAGAAAAAGTTCAGCGCAGTCTGAAACATGAGGATATTAATCTGCAAGAGATTATTAGCGCAGCCGGTAAAGAACT
GTCAGAAGCATTTAAACAGAAAACCAGCGAAATTCTGTCACATGCACATGCAGCACTGGATCAGCCGCTGCCGACC
ACCCTGAAAAAACAAGAAGAAAAAGAAATCCTGAAAAGCCAGCTGGATAGCCTGCTGGGTCTGTATCATCTGCTGG
ACTGGTTTGCAGTTGATGAAAGCAATGAAGTTGATCCGGAATTTAGCGCACGTCTGACCGGCATTAAACTGGAAAT
GGAACCGAGCCTGAGCTTTTATAACAAAGCCCGTAATTATGCCACCAAAAAACCGTATAGCGTCGAAAAATTCAA
CTGAACTTTCAGATGCCGACCCTGGCAAGCGGTTGGGATGTTAATAAAGAAAAAAACAACGGTGCCATCCTGTTCG
TGAAAAATGGCCTGTATTATCTGGGTATTATGCCGAAACAAAAACGTCTTATAAAGCGCTGAGCTTTGAACCGAC
GGAAAAAAACCAGTGAAGGTTTTGATAAAATGTACTACGACTATTTTCCGGATGCAGCCAAAATGATTCCGAAATGT
AGCACCCAGCTGAAAGCAGTTACCGCACATTTTCAGACCCATACCACCCCGATTCTGCTGAGCAATAACTTTATTG
AACCGCTGGAAATCACCAAAGAGATCTACGATCTGAATAACCCGGAAAAAGAGCCGAAAAAATTCCAGACCGCATA
TGCAAAAAAAACCGGTGATCAGAAAGGTTATCGTGAAGCGCTGTGTAAATGGATTGATTTCACCCGTGATTTTCTG
AGCAAATACACCAAAACCACCCAGTATCGATCTGAGCAGCCTGCGTCCGAGCAGCCAGTATAAAGATCTGGGCGAAT
ATTATGCAGAACTGAATCCGCTGCTGTATCATATTAGCTTTCAGCGTATTGCCGAGAAAGAAATCATGGACGCAGT
TGAAACCGGTAAACTGTACCTGTTCCAGATCTACAATAAAGATTTTGCCAAAGGCCATCATGGCAAACCGAATCTG
CATACCCTGTATTGGACCGGTCTGTTTAGCCCTGAAAATCTGGCAAAAACCTCGATTAAACTGAATGGTCAGGCCG
AACTGTTTTATCGTCCGAAAAGCCGTATGAAACGTATGGCACATCGTCTGGGTGAAAAAATGCTGAACAAAAAACT
GAAAGACCAGAAAACCCCGATCCCGGATACACTGTATCAAGAACTGTATGATTATGTGAACCATCGTCTGAGCCAT
GATCTGAGTGATGAAGCACGTGCCCTGCTGCCGAATGTTATTACCAAAGAAGTTAGCCACGAGATCATTAAGGATC
GTCGTTTTACCAGCGACAAATTCTTTTTTCATGTGCCGATTACCCTGAATTATCAGGCAGCAAATAGCCCGAGCAA
ATTTAACCAGCGTGTTAATGCATATCTGAAAGAACATCCAGAAACCCGGTTATTGGTATTGATCGTGGTGAACGT
AACCTGATTTATATCACCGTTATTGATAGCACCGGCAAAATCCTGGAACAGCGTAGCCTGAATACCATTCAGCAGT
TTGATTACCAGAAAAAACTGGATAATCGCGAGAAAGAACGTGTTGCAGCACGTCAGGCATGGTCAGTTGTTGGTAC
AATTAAAGACCTGAAACAGGGTTATCTGAGCCAGGTTATTCATGAAATTGTGGATCTGATGATTCACTATCAGGCC
GTTGTTGTGCTGGAAAACCTGAATTTTGGCTTTAAAAGCAAACGTACCGGCATTGCAGAAAAAGCAGTTTATCAGC
AGTTCGAGAAAATGCTGATTGACAAACTGAATTGCCTGGTGCTGAAAGATTATCCGGCTGAAAAAGTTGGTGGTGT
TCTGAATCCGTATCAGCTGACCGATCAGTTTACCAGCTTTGCAAAATGGGCACCCAGAGCGGATTTCTGTTTTAT
GTTCCGGCACCGTATACGAGCAAATTGATCCGCTGACCGGTTTTGTTGATCCGTTTGTTTGGAAAACCATCAAAA
ACCATGAAAGCCGCAAACATTTTCTGGAAGGTTTCGATTTTCTGCATTACGACGTTAAACGGGTGATTTCATCCT
GCACTTTAAAATGAATCGCAATCTGAGTTTTCAGCGTGGCCTGCCTGGTTTTATGCCTGCATGGGATATTGTGTTT
GAGAAAAACGAAACACAGTTCGATGCAAAAGGCACCCCGTTTATTGCAGGTAAACGTATTGTTCCGGTGATTGAAA
ATCATCGTTTCACCGGTCGTTATCGCGATCTGTATCCGGCAAATGAACTGATCGCACTGCTGGAAGAGAAAGGTAT SEQ ID NO: 18
WT AsCas12a amino acid sequence
MTQFEGFTNLYQVSKTLRFELIPQGKTLKHIQEQGFIEEDKARNDHYKELKPIIDRIYKTYADQCLQLVQLDWENL
SAAIDSYRKEKTEETRNALIEEQATYRNAIHDYFIGRTDNLTDAINKRHAEIYKGLFKAELFNGKVLKQLGTVTTT
EHENALLRSFDKFTTYFSGFYENRKNVFSAEDISTAIPHRIVQDNPKFKENCHIFTRLITAVPSLREHFENVKKA
IGIFVSTSIEEVFSFPFYNQLLTQTQIDLYNQLLGGISREAGTEKIKGLNEVLNLAIQKNDETAHIIASLPHRFIP
LFKQILSDRNTLSFILEEFKSDEEVIQSFCKYKTLLRNENVLETAEALFNELNSIDLTHIFISHKKLETISSALCD
HWDTLRNALYERRISELTGKITKSAKEKVQRSLKHEDINLQEIISAAGKELSEAFKQKTSEILSHAHAALDQPLPT
TLKKQEEKEILKSQLDSLLGLYHLLDWFAVDESNEVDPEFSARLTGIKLEMEPSLSFYNKARNYATKKPYSVEKFK
LNFQMPTLASGWDVNKEKNNGAILFVKNGLYYLGIMPKQKGRYKALSFEPTEKTSEGFDKMYYDYFPDAAKMIPKC
STQLKAVTAHFQTHTTPILLSNNFIEPLEITKEIYDLNNPEKEPKKFQTAYAKKTGDQKGYREALCKWIDFTRDFL
SKYTKTTSIDLSSLRPSSQYKDLGEYYAELNPLLYHISFQRIAEKEIMDAVETGKLYLFQIYNKDFAKGHHGKPNL
HTLYWTGLFSPENLAKTSIKLNGQAELFYRPKSRMKRMAHRLGEKMLNKKLKDQKTPIPDTLYQELYDYVNHRLSH
DLSDEARALLPNVITKEVSHEIIKDRRFTSDKFFFHVPITLNYQAANSPSKFNQRVNAYLKEHPETPIIGIDRGER
NLIYITVIDSTGKILEQRSLNTIQQFDYQKKLDNREKERVAARQAWSVVGTIKDLKQGYLSQVIHEIVDLMIHYQA
VVVLENLNFGFKSKRTGIAEKAVYQQFEKMLIDKLNCLVLKDYPAEKVGKVLNPYQLTDQFTSFAKMGTQSGFLFY
VPAPYTSKIDPLTGFVDPFVWKTIKNHESRKHFLEGFDFLHYDVKTGDFILHFKMNRNLSFQRGLPGFMPAWDIVF
EKNETQFDAKGTPFIAGKRIVPVIENHRFTGRYRDLYPANELIALLEEKGIVFRDGSNILPKLLENDDSHAIDTMV
ALIRSVLQMRNSNAATGEDYINSPVRDLNGVCFDSRFQNPEWPMDADANGAYHIALKGQLLLNHLKESKDLKLQNG
ISNQDWLAYIQELRN SEQ ID NO: 19
Mutant M537R/F870L AsCas12a DNA sequence
ATGACCCAGTTTGAAGGTTTCACCAATCTGTATCAGGTTAGCAAAACCCTGCGTTTTGAACTGATTCCGCAGGGTA
AAACCCTGAAACATATTCAAGAACAGGGCTTCATCGAAGAGGATAAAGCACGTAACGATCACTACAAAGAACTGAA
ACCGATTATCGACCGCATCTATAAAACCTATGCAGATCAGTGTCTGCAGCTGGTTCAGCTGGATTGGGAAAATCTG
AGCGCAGCAATTGATAGTTATCGCAAAGAAAAAACCGAAGAAACCCGTAATGCACTGATTGAAGAACAGGCAACCT
ATCGTAATGCCATCCATGATTATTTCATTGGTCGTACCGATAATCTGACCGATGCAATTAACAAACGTCACGCCGA
AATCTATAAAGGCCTGTTTAAAGCCGAACTGTTTAATGGCAAAGTTCTGAAACAGCTGGGCACCGTTACCACCACC
GAACATGAAAATGCACTGCTGCGTAGCTTTGATAAATTCACCACCTATTTCAGCGGCTTTTATGAGAATCGCAAAA
ACGTGTTTAGCGCAGAAGATATTAGCACCGCAATTCCGCATCGTATTGTGCAGGATAATTTCCCGAAATTCAAAGA
GAACTGCCACATTTTTACCCGTCTGATTACCGCAGTTCCGAGCCTGCGCGAACATTTTGAAAACGTTAAAAAAGCC
ATCGGCATCTTTGTTAGCACCAGCATTGAAGAAGTTTTTAGCTTCCCGTTTTACAATCAGCTGCTGACCCAGACCC
AGATTGATCTGTATAACCAACTGCTGGGTGGTATTAGCCGTGAAGCAGGCACCGAAAAAATCAAAGGTCTGAATGA
AGTGCTGAATCTGGCCATTCAGAAAAATGATGAAACCGCACATATTATTGCAAGCCTGCCGCATCGTTTTATTCCG
CTGTTCAAACAAATTCTGAGCGATCGTAATACCCTGAGCTTTATTCTGGAAGAATTCAAATCCGATGAAGAGGTGA
TTCAGAGCTTTTGCAAATACAAAACGCTGCTGCGCAATGAAAATGTTCTGGAAACTGCCGAAGCACTGTTTAACGA
ACTGAATAGCATTGATCTGACCCACATCTTTATCAGCCACAAAAAACTGGAAACATTTCAAGCGCACTGTGTGAT
CATTGGGATACCCTGCGTAATGCCCTGTATGAACGTCGTATTAGCGAACTGACCGGTAAAATTACCAAAAGCGCGA
AAGAAAAAGTTCAGCGCAGTCTGAAACATGAGGATATTAATCTGCAAGAGATTATTAGCGCAGCCGGTAAAGAACT
GTCAGAAGCATTTAAACAGAAAACCAGCGAAATTCTGTCACATGCACATGCAGCACTGGATCAGCCGCTGCCGACC
ACCCTGAAAAAACAAGAAGAAAAAGAAATCCTGAAAAGCCAGCTGGATAGCCTGCTGGGTCTGTATCATCTGCTGG
ACTGGTTTGCAGTTGATGAAAGCAATGAAGTTGATCCGGAATTTAGCGCACGTCTGACCGGCATTAAACTGGAAAT
GGAACCGAGCCTGAGCTTTTATAACAAAGCCCGTAATTATGCCACCAAAAAACCGTATAGCGTCGAAAAATTCAAA
CTGAACTTTCAGCGTCCGACCCTGGCAAGCGGTTGGGATGTTAATAAAGAAAAAAACAACGGTGCCATCCTGTTCG
TGAAAAATGGCCTGTATTATCTGGGTATTATGCCGAAACAGAAAGGTCGTTATAAAGCGCTGAGCTTTGAACCGAC
GGAAAAAACCAGTGAAGGTTTTGATAAAATGTACTACGACTATTTTCCGGATGCAGCCAAAATGATTCCGAAATGT
AGCACCCAGCTGAAAGCAGTTACCGCACATTTTCAGACCCATACCACCCCGATTCTGCTGAGCAATAACTTTATTG
AACCGCTGGAAATCACCAAAGAGATCTACGATCTGAATAACCCGGAAAAAGAGCCGAAAAAATTCCAGACCGCATA
TGCAAAAAAAACCGGTGATCAGAAAGGTTATCGTGAAGCGCTGTGTAAATGGATTGATTTTACCCGTGATTTTCTG
AGCAAATACACCAAAACCACCAGTATCGATCTGAGCAGCCTGCGTCCGAGCAGCCAGTATAAAGATCTGGGCGAAT
ATTATGCAGAACTGAATCCGCTGCTGTATCATATTAGCTTTCAGCGTATTGCCGAGAAAGAAATCATGGACGCAGT
TGAAACCGGTAAACTGTACCTGTTCCAGATCTACAATAAAGATTTTGCCAAAGGCCATCATGGCAAACCGAATCTG
CATACCCTGTATTGGACCGGTCTGTTTAGCCCTGAAAATCTGGCAAAAACCTCGATTAAACTGAATGGTCAGGCGG
AACTGTTTTATCGTCCGAAAAGCCGTATGAAACGTATGGCACATCGTCTGGGTGAAAAAATGCTGAACAAAAAACT
GAAAGACCAGAAAACCCCGATCCCGGATACACTGTATCAAGAACTGTATGATTATGTGAACCATCGTCTGAGCCAT
GATCTGAGTGATGAAGCACGTGCCCTGCTGCCGAATGTTATTACCAAAGAAGTTAGCCACGAGATCATTAAAGATC
GTCGTTTTACCAGCGACAAATTCCTGTTTCATGTGCCGATTACCCTGAATTATCAGGCAGCAAATAGCCCGAGCAA
ATTTAACCAGCGTGTTAATGCATATCTGAAAGAACATCCAGAAACGCCGATTATTGGTATTGATCGTGGTGAACGT
AACCTGATTTATATCACCGTTATTGATAGCACCGGCAAAATCCTGGAACAGCGTAGCCTGAATACCATTCAGCAGT
TTGATTACCAGAAAAAACTGGATAATCGCGAGAAGAACGTGTTGCAGCACGTCAGGCATGGTCAGTTGTTGGTAC
AATTAAAGACCTGAAACAGGGTTATCTGAGCCAGGTTATTCATGAAATTGTGGATCTGATGATTCACTATCAGGCC
GTTGTTGTGCTGGAAAACCTGAATTTTGGCTTTAAAAGCAAAGTACCCGGCATTGCAGAAAAAGCAGTTTATCAGC
AGTTCGAGAAAATGCTGATTGACAAACTGAATTGCCTGGTGCTGAAAGATTATCCGGCTGAAAAAGTTGGTGGTGT
TCTGAATCCGTATCAGCTGACCGATCAGTTTACCAGCTTTGCAAAAATGGGCACCCAGAGCGGATTTCTGTTTTAT
GTTCCGGCACCGTATACGAGCAAAATTGATCCGCTGACCGGTTTTGTTGATCCGTTTGTTTGGAAAACCATCAAAA
ACCATGAAAGCCGCAAACATTTTCTGGAAGGTTTCGATTTTCTGCATTACGACGTTAAAACGGGTGATTTCATCCT
GCACTTTAAAATGAATCGCAATCTGAGTTTTCAGCGTGGCCTGCCTGGTTTTATGCCTGCATGGGATATTGTGTTT
GAGAAAAACGAAACAGTTCGATGCAAAAGGCACCCCGTTTATTGCAGGTAAACGTATTGTTCCGGTGATTGAAA
ATCATCGTTTCACCGGTCGTTATCGCGATCTGTATCCGGCAAATGAACTGATCGCACTGCTGGAAGAGAAAGGTAT
TGTTTTTCGTGATGGCTCAAACATTCTGCCGAAACTGCTGGAAAATGATGATAGCCATGCAATTGATACCATGGTT
GCACTGATTCGTAGCGTTCTGCAGATGCGTAATAGCAATGCAGCAACCGGTGAAGATTACATTAATAGTCCGGTTC
GTGATCTGAATGGTGTTTGTTTTGATAGCCGTTTTCAGAATCCGGAATGGCCGATGGATGCAGATGCAAATGGTGC

```
ATATCATATTGCACTGAAAGGACAGCTGCTGCTGAACCACCTGAAAGAAAGCAAAGATCTGAAACTGCAAAACGGC
ATTAGCAATCAGGATTGGCTGGCATATATCCAAGAACTGCGTAAC

SEQ ID NO: 20
Mutant M537R/F870L AsCas12a amino acid sequence
MTQFEGETNLYQVSKTLRFELIPQGKTLKHIQEQGFIEEDKARNDHYKELKPIIDRIYKTYADQCLQLVQLDWENL
SAAIDSYRKEKTEETRNALIEEQATYRNAIHDYFIGRTDNLTDAINKRHAEIYKGLFKAELFNGKVLKQLGTVTTT
EHENALLRSFDKFTTYFSGFYENRKNVFSAEDISTAIPHRIVQDNFPKFKENCHIFTRLITAVPSLREHFENVKKA
IGIFVSTSIEEVFSFPPYNQLLTQTQIDLYNQLLGGISREAGTEKIKGLNEVLNLAIQKNDETAHIIASLPHRFIP
LFKQILSDRNTLSFILEEFKSDEEVIQSFCKYKTLLRNENVLETAEALFNELNSIDLTHIFISHKKLETISSALCD
HWDTLRNALYERRISELTGKITKSAKEKVQRSLKHEDINLQEIISAAGKELSEAFKQKTSEILSHAHAALDQPLPT
TLKKQEEKEILKSQLDSLLGLYHLLDWFAVDESNEVDPEFSARLTGIKLEMEPSLSFYNKARNYATKKPYSVEKFK
LNFQRPTLASGWDVNKEKNNGAILFVKNGLYYLGIMPKQKGRYKALSFEPTEKTSEGFDKMYYDYFPDAAKMIPKC
STQLKAVTAHFQTHTTPILLSNNFIEPLEITKEIYDLNNPEKEPKKFQTAYAKKTGDQKGYREALCKWIDFTRDFL
SKYTKTTSIDLSSLRPSSQYKDLGEYYAELNPLLYHISFQRIAEKEIMDAVETGKLYLFQIYNKDFAKGHHGKPNL
HTLYWTGLFSPENLAKTSIKLNGQAELFYRPKSRMKRMAHRLGEKMLNKKLKDQKTPIPDTLYQELYDYVNHRLSH
DLSDEARALLPNVITKEVSHEIIKDRRFTSDKFLFHVPITLNYQAANSPSKFNQRVNAYLKEHPETPIIGIDRGER
NLIYITVIDSTGKILEQRSLNTIQQFDYQKKLDNREKERVAARQAWSVVGTIKDLKQGYLSQVIHEIVDLMIHYQA
VVVLENLNFGFKSKRTGIAEKAVYQQFEKMLIDKLNCLVLKDYPAEKVGGVLNPYQLTDQFTSFAKMGTQSGFLFY
VPAPYTSKIDPLTGFVDPFVWKTIKNHESRKHFLEGFDFLHYDVKTGDFILHFKMNRNLSFQRGLPGFMPAWDIVE
EKNETQFDAKGTPFIAGKRIVPVIENHRFTGRYRDLYPANELIALLEEKGIVFRDGSNILPKLLENDDSHAIDTMV
ALIRSVLQMRNSNAATGEDYINSPVRDLNGVCFDSRFQNPEWPMDADANGAYHIALKGQLLLNHLKESKDLKLONG
ISNQDWLAYIQELRN
```

EXAMPLE 2

Overexpression and Purification of LbCas12a Mutants in *E. coli* Cells

This example demonstrates the over expression and purification of seven Cas12a mutants, N527R, D559P, E795L, N527R/D559P, D559P/E795L, N527R/E795L and N527R/D559P/E795L. The LbCas12a mutants were introduced by site-directed mutagenesis, using standard PCR conditions and primers (Table 1). After transformation into *E. coli* BL21(DE3) cells, a colony with the appropriate strain was used to inoculate TB media with kanamycin (0.05 mg/mL) and grown at 37° C. until an OD of approximately 0.9 was reached, then the flask was cooled to 18° C. for 30 minutes. The addition of 1 M IPTG (500 μL) was used to induce protein expression, followed by growth at 18° C. for 19 hours. Cells were harvested and the cell pellet was re-suspended and lysed on an Avestin Emulsiflex C3 pre-chilled to 4° C. at 15-20 kpsi with three passes. The lysate was centrifuged at 16,000×g for 20 minutes at 4° C. to remove cell debris The cleared lysate was put over a HisTrap HP column. The procedure consisted of equilibrating the resin with His-Bind buffer (20 mM NaPO₄ pH 6.8, 0.5 M NaCl, 10 mM imidazole, 5% glycerol), followed by sample loading. The sample was washed with His-Bind buffer, followed by an additional standard wash and a 10% "B" wash consisting of 10% His-Elution buffer (10 mM NaPO₄ pH 6.8, 250 mM NaCl, 150 mM imidazole, 5% glycerol). Finally, the sample was eluted using His-Elution buffer. The LbCas12a mutants were then put over a HiTrap Heparin HP column. The procedure consisted of equilibrating the resin with the Heparin-Bind buffer (20 mM NaPO4 pH 6.8, 250 mM NaCl, 10% glycerol), followed by sample loading. The sample was then washed with Heparin-Bind buffer, followed by a 5% "B" wash consisting of 5% Heparin Elution buffer (10 mM NaPO₄ pH 6.8, 1 M NaCl, 10% glycerol). Finally, the purified protein was eluted using Heparin Elution buffer (10 mM NaPO4, pH 6.8, 1 M NaCl, 10% glycerol). Finally, the purified protein was eluted using Heparin.

The purified LbCas12a mutants were concentrated to approximately 10 mg/mL and stored at −20° C. in storage buffer (25 mM Tris-HCl pH 7.4, 0.3 M NaCl).1 mM EDTA, 1 mM DTT, 50% glycerol).

TABLE 1

Sequences of primers use for site-directed mutagenesis with the amino acid codon underlined. All primers ordered as DNA oligos from Integrated DNA Technologies.

| Primer Name | Primer Sequence (5'-3') | SEQ ID NO. |
|---|---|---|
| LbCas12a N527R Fwd | GCAAAGACAAGTTCAAACTGTACTTTCAGCGTCCGCAGTTTATGGGTGGTTGG | 21 |
| LbCas12a N527R Rev | CCAACCACCCATAAACTGCGGACGCTGAAAGTACAGTTTGAACTTGTCTTTGC | 22 |
| LbCas12a D559P Fwd | TATGGTAGTAAATACTATCTGGCCATCATGCCGAAAAAATACGCAAAATGCCTGCAGA | 23 |
| LbCas12a D559P Rev | TCTGCAGGCATTTTGCGTATTTTTTCGGCATGATGGCCAGATAGTATTTACTACCATA | 24 |

TABLE 1-continued

Sequences of primers use for site-directed mutagenesis with the amino acid codon underlined. All primers ordered as DNA oligos from Integrated DNA Technologies.

| Primer Name | Primer Sequence (5'-3') | SEQ ID NO. |
|---|---|---|
| LbCas12a E795L Fwd | ACAAACGTTTTAGCGAGGATCAGTATCTGCTGCATATCCCGATTGCCATCA | 25 |
| LbCas12a E795L Rev | TGATGGCAATCGGGATATGCAGCAGATACTGATCCTCGCTAAAACGTTTGT | 26 |

EXAMPLE 3

Novel LbCas12a Substitution Mutants Enhance the Cleavage Activity in a Human Cell Line Based Activity Assay when Delivered into Human Cells Via Ribonucleoprotein Complex.

The following example demonstrates the ability of LbCas12a mutants to improve genome editing efficiency when delivered as an RNP complex. The example demonstrates the ability of LbCas12a mutants to show comparable genome editing efficiency when delivered at a high dose and increased genome editing efficiency when delivered at a low dose by ribonucleoprotein (RNP) complex into human cells with electroporation transfection.

The RNP complex was formed by incubating purified LbCas12a and sgRNA (Table 2, entries 3 and 9) at a ratio of 1:1.2 in PBS buffer for 10 minutes at room temperature. The RNP complexes (5 µM final dose) were transfected into HEK293 immortalized human cells using a Lonza 4D-Nucleofector™ and Amaxa® 96-well Shuttle Device with Alt-R® Cpf1 Electroporation Enhancer (3 µM, Integrated DNA Technologies). The experiments were performed in biological triplicate and after 48 hours at 37° C., adherent cells were lysed with QuickExtract™ DNA extraction solution (50 µL).

TABLE 2

Sequences of Cas12 (Cpf1) sgRNA used in genome editing of HEK293 cells. All sRNA ordered as RNA oligos from Integrated DNA Technologies with the AltR® end modifications on both the 5' and 3' ends.

| sgRNA | sgRNA Sequence (5'-3') | SEQ ID NO. |
|---|---|---|
| LbCpf1 HRPT 38094-S-23 | UAAUUUCUACUAAGUGUAGAUAUAGUCUUUCCUUGGGUCUGUUA | 27 |
| LbCpf1 HRPT 38104-S-23 | UAAUUUCUACUAAGUGUAGAUCUUGGGUGUGUUAAAAGUGACCA | 28 |
| LbCpf1 HRPT 38115-AS-23 | UAAUUUCUACUAAGUGUAGAUACACACCCAAGGAAAGACUAUGA | 29 |
| LbCpf1 HRPT 38146-AS-23 | UAAUUUCUACUAAGUGUAGAUAUCCGUGCUGAGUGUACCAUGCA | 30 |
| LbCpf1 HRPT 38164-AS-23 | UAAUUUCUACUAAGUGUAGAUUAAACACUGUUUCAUUUCAUCCG | 31 |
| LbCpf1 HRPT 38164-S-23 | UAAUUUCUACUAAGUGUAGAUGAAACGUCAGUCUUCUCUUUUGU | 32 |
| LbCpf1 HRPT 38186-S-23 | UAAUUUCUACUAAGUGUAGAUUAAUGCCCUGUAGUCUCUCUGUA | 33 |
| LbCpf1 HRPT 38228-S-23 | UAAUUUCUACUAAGUGUAGAUUAAUUAACAGCUUGCUGGUGAAA | 34 |
| LbCpf1 HRPT 38330-AS-23 | UAAUUUCUACUAAGUGUAGAUGGUUAAAGAUGGUUAAAUGAUUG | 35 |
| LbCpf1 HRPT 38343-S-23 | UAAUUUCUACUAAGUGUAGAUUGUGAAAUGGCUUAUAAUUGCUU | 36 |
| LbCpf1 HRPT 38455-S-23 | UAAUUUCUACUAAGUGUAGAUGUUGUUGGAUUUGAAAUUCCAGA | 37 |
| LbCpf1 HRPT 38486-S-23 | UAAUUUCUACUAAGUGUAGAUUUGUAGGAUAUGCCCUUGACUAU | 38 |
| AsCpf1 HRPT 38094-S | UAAUUUCUACUCUUGUAGAUAUAGUCUUUCCUUGGGUGUGU | 39 |

TABLE 2-continued

Sequences of Cas12 (Cpf1) sgRNA used in genome editing of HEK293 cells. All sRNA ordered as RNA oligos from Integrated DNA Technologies with the AltR ® end modifications on both the 5' and 3' ends.

| sgRNA | sgRNA Sequence (5'-3') | SEQ ID NO. |
|---|---|---|
| AsCpf1 HRPT 38104-S | UAAUUUCUACUCUUGUAGAUCUUGGGUGUGUUAAAAGUGAC | 40 |
| AsCpf1 HRPT 38115-AS | UAAUUUCUACUCUUGUAGAUACACACCCAAGGAAAGACUAU | 41 |
| AsCpf1 HRPT 38146-AS | UAAUUUCUACUCUUGUAGAUAUCCGUGCUGAGUGUACCAUG | 42 |
| AsCpf1 HRPT 38164-AS | UAAUUUCUACUCUUGUAGAUUAAACACUGUUUCAUUUCAUC | 43 |
| AsCpf1 HRPT 38164-S | UAAUUUCUACUCUUGUAGAUGAAACGUCAGUCUUCUCUUUU | 44 |
| AsCpf1 HRPT 38186-S | UAAUUUCUACUCUUGUAGAUUAAUGCCCUGUAGUCUCUCUG | 45 |
| AsCpf1 HRPT 38228-S | UAAUUUCUACUCUUGUAGAUUAAUUAACAGCUUGCUGGUGA | 46 |
| AsCpf1 HRPT 38330-AS | UAAUUUCUACUCUUGUAGAUGGUUAAAGAUGGUUAAAUGAU | 47 |
| AsCpf1 HRPT 38343-S | UAAUUUCUACUCUUGUAGAUUGUGAAAUGGCUUAUAAUUGC | 48 |
| AsCpf1 HRPT 38455-S | UAAUUUCUACUCUUGUAGAUGUUGUUGGAUUUGAAAUUCCA | 49 |
| AsCpf1 HRPT 38486-S | UAAUUUCUACUCUUGUAGAUUUGUAGGAUAUGCCCUUGACU | 50 |

Crude lysates were incubated at 65° C. for 15 minutes, followed by heat inactivation at 98° C. for 3 minutes. Crude genomic DNA was diluted 5-fold in TE buffer and used as PCR template. PCR (primers listed in Table 3) was used to amplify 1.2 kbp fragments of the HPRT loci using Q5® DNA Polymerase (New England Biolabs) and the following parameters: 98° C. for 30 sec, followed by 98° C. for 10 sec, 65° C. for 15 sec and 72° C. for 1 min which was repeated 24 times, followed by a final extension at 72° C. for 2 min. Heteroduplexes were formed by the addition of NEBuffer 2 and initially heating to 95° C. for 10 min with a slow cool down to room temperature. The heteroduplexes were then cleaved by 2 U of T7 Endonuclease I (New England Biolabs) for 1 hour at 37° C. The cleavage products were analyzed by capillary electrophoresis (Fragment Analyzer, Advanced Analytical).

TABLE 3

Sequences of primers used for amplification of edited genomic HEK293 DNA prior to analysis by T7EI. All primers ordered as DNA oligos from Integrated DNA Technologies.

| Primer Name | Primer Sequence (5'-3') | SEQ ID NO. |
|---|---|---|
| HRPT low GC | Fwdaagaagttgtgataaaaggtgatgct | 51 |
| HRPT low GC | Revacacatccatgggacttctgcctc | 52 |

The endonuclease activity of wild type and mutant LbCas12a in HEK293 human cells are described in FIG. 2 and Table 4. RNP delivery of LbCas12 mutants D559P, E795L and D559P/E795L resulted in similar activity as wild type LbCas12a and AsCas12a-M537R/F870L (~80% cleavage). As this initial screen was to determine activity at the highest dose (5 µM), a dose response with lower concentrations (2, 1 and 0.05 µM) of RNP was preformed to determine if these mutants can instill enhanced activity.

TABLE 4a

Endonuclease activity of LbCas12 mutants as compared to wild type LbCas12 and AsCas12a-M537R/F870L after 48 hours in HEK293 human cells at HRPT-38115. Values calculated as percent cleavage

| Cas12a | Replicate 1 | Replicate 2 | Replicate 3 | Average | Std Dev |
|---|---|---|---|---|---|
| LbCas12a-wild type | 78.9 | 80.7 | 81.5 | 80.35 | 1.07 |
| LbCas12a-N527R | 35.5 | 34.9 | 34.5 | 34.96 | 0.43 |
| LbCas12a-D559P | 78.2 | 76.6 | 79 | 77.96 | 0.99 |
| LbCas12a-E795L | 77.5 | 79.6 | 77.5 | 78.16 | 0.99 |
| LbCas12a-N527R/D559P | 9.3 | 9.3 | 9.5 | 9.39 | 0.06 |
| LbCas12a-N527R/E795L | 41 | 39.1 | 38.9 | 39.33 | 1.22 |
| LbCas12a-D559P/E795L | 80.3 | 77.8 | 79.7 | 79.28 | 1.09 |
| LbCas12a-N527R/D559P/E795L | 59.4 | 61 | 60.5 | 60.32 | 0.69 |
| AsCas12a-M537R/F870L | 70.8 | — | 76.6 | 73.7 | 2.89 |

TABLE 4b

Endonuclease activity of LbCas12 mutants as compared to wild type LbCas12 and AsCas12a-M537R/F870L after 48 hours in HEK293 human cells at HRPT-38330. Values calculated as percent cleavage

| Cas12a | Replicate 1 | Replicate 2 | Replicate 3 | Average | Std Dev |
|---|---|---|---|---|---|
| LbCas12a-wild type | 78.1 | 78.6 | 78.7 | 78.5 | 0.2 |
| LbCas12a-N527R | 10.1 | 9.7 | 9.0 | 9.6 | 0.5 |
| LbCas12a-D559P | 58.0 | 58.0 | 59.2 | 58.4 | 0.5 |
| LbCas12a-E795L | 78.9 | 79.6 | 79.9 | 79.5 | 0.4 |
| LbCas12a-N527R/D559P | 0.0 | 0.0 | 0.0 | 0.0 | 0.0 |
| LbCas12a-N527R/E795L | 20.4 | 22.0 | 21.1 | 21.2 | 0.7 |
| LbCas12a-D559P/E795L | 76.7 | 75.6 | 75.0 | 75.8 | 0.7 |
| LbCas12a-N527R/D559P/E795L | 28.2 | 29.4 | 28.8 | 28.8 | 0.5 |
| AsCas12a-M537R/F870L | 86.2 | 82.9 | 84.0 | 84.4 | 1.4 |

Figure 3:
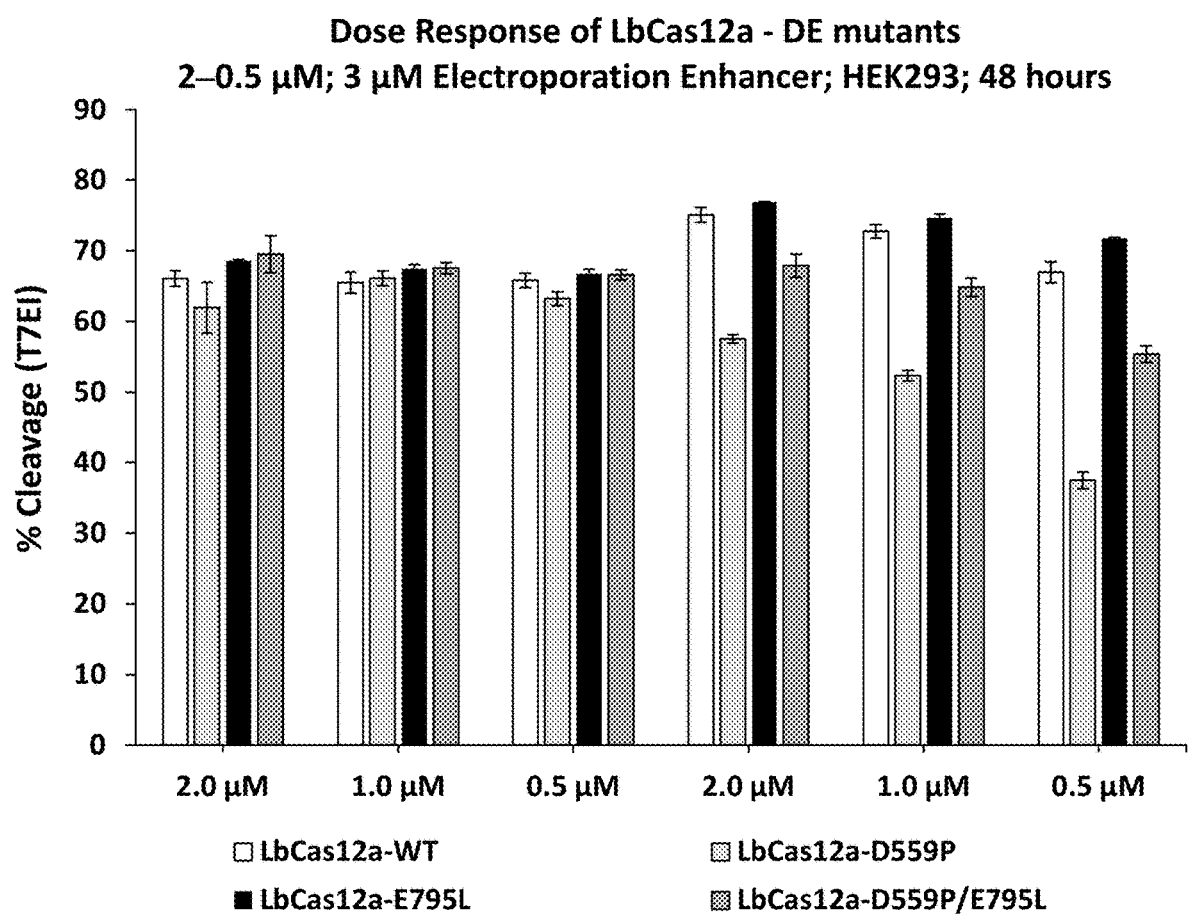
FIG. 3 shows the editing efficiency of LbCas12a mutants as compared to wild-type LbCas12a after 48 hours in HEK293 human cells with IDT Alt-R® Electroporation Enhancer.
Figure 4:
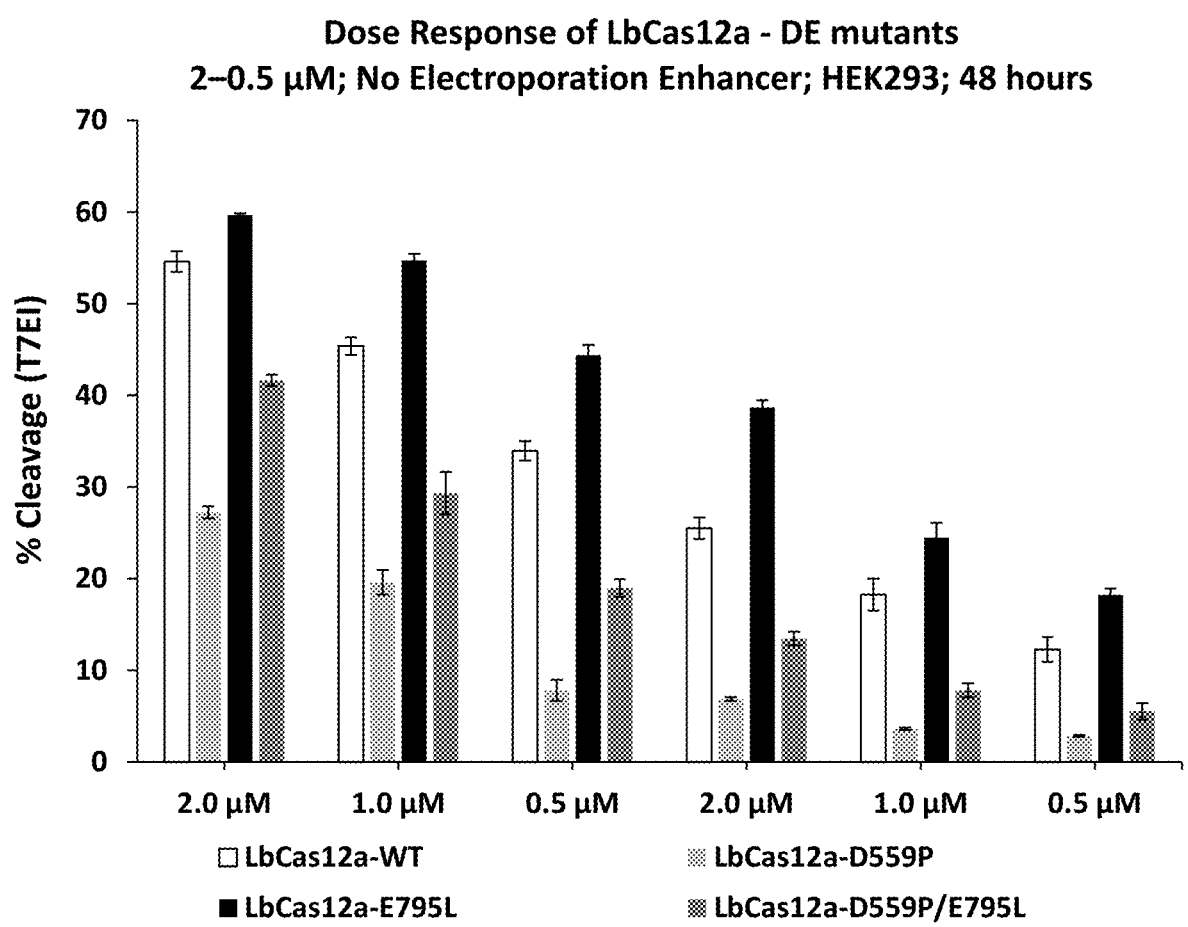
FIG. 4 shows the editing efficiency of LbCas2a mutants as compared to wild-type LbCas12a after 48 hours in HEK293 human cells without IDT Alt-R® Electroporation Enhancer.

The dose response was achieved as described above, reducing the amount of RNP by 2-fold increments (with and without Alt-R® Electroporation Enhancer) and beginning with a 2 µM dose. The results are shown in FIGS. 3-4 and Tables 5-6. RNP delivery of LbCas12a requires the addition of Alt-R® Cpf1 Electroporation Enhancer for maximum cutting efficiency. At these doses, LbCas12a mutants displayed either similar or a slight increase in activity as compared to wild type; therefore, new sites and even lower doses needed to be investigated to show differences in activity.

TABLE 5a

Endonuclease activity of LbCas12 mutants as compared to wild type LbCas12 after 48 hours in HEK293 human cells at HRPT-38115 with Alt-R® Electroporation Enhancer. Values calculated as percent cleavage

| Cas12a | Dose (µM) | Replicate 1 | Replicate 2 | Replicate 3 | Average | Std Dev |
|---|---|---|---|---|---|---|
| LbCas12a-wild type | 2.0 | 67.6 | 65.1 | 65.5 | 66.06 | 1.11 |
| | 1.0 | 67.4 | 65.3 | 63.7 | 65.49 | 1.49 |
| | 0.5 | 66.9 | 34.5 | 66.0 | 65.81 | 1.01 |
| LbCas12a-D559P | 2.0 | 66.9 | 58.6 | 60.4 | 61.95 | 3.59 |
| | 1.0 | 64.7 | 67.1 | 66.6 | 66.10 | 1.04 |
| | 0.5 | 61.8 | 63.9 | 63.9 | 63.22 | 0.98 |
| LbCas12a-E795L | 2.0 | 68.4 | 68.8 | 68.5 | 68.58 | 0.15 |
| | 1.0 | 66.7 | 68.1 | 67.5 | 67.45 | 0.59 |
| | 0.5 | 66.1 | 66.5 | 67.6 | 66.72 | 0.67 |
| LbCas12a-D559P/E795L | 2.0 | 73.1 | 66.9 | 68.5 | 69.49 | 2.61 |
| | 1.0 | 67.5 | 66.6 | 68.5 | 67.53 | 0.79 |
| | 0.5 | 67.5 | 66.3 | 65.9 | 66.58 | 0.68 |

TABLE 5b

Endonuclease activity of LbCas12 mutants as compared to wild type LbCas12 after 48 hours in HEK293 human cells at HRPT-38330 with Alt-R® Electroporation Enhancer. Values calculated as percent cleavage

| Cas12a | Dose (µM) | Replicate 1 | Replicate 2 | Replicate 3 | Average | Std Dev |
|---|---|---|---|---|---|---|
| LbCas12a-wild type | 2.0 | 76.5 | 74.5 | 74.2 | 75.06 | 1.06 |
| | 1.0 | 73.8 | 71.5 | 72.9 | 72.73 | 0.96 |
| | 0.5 | 65.0 | 68.6 | 67.2 | 66.95 | 1.49 |

TABLE 5b-continued

Endonuclease activity of LbCas12 mutants as compared to
wild type LbCas12 after 48 hours in HEK293 human cells at HRPT-38330
with Alt-R ® Electroporation Enhancer. Values calculated as percent cleavage

| Cas12a | Dose (µM) | Replicate 1 | Replicate 2 | Replicate 3 | Average | Std Dev |
|---|---|---|---|---|---|---|
| LbCas12a-D559P | 2.0 | 57.1 | 58.4 | 57.2 | 57.55 | 0.60 |
|  | 1.0 | 52.8 | 53.0 | 51.3 | 52.34 | 0.75 |
|  | 0.5 | 38.1 | 35.8 | 38.5 | 37.48 | 1.19 |
| LbCas12a-E795L | 2.0 | 76.9 | 76.7 | 76.9 | 76.84 | 0.10 |
|  | 1.0 | 74.7 | 75.3 | 73.9 | 74.63 | 0.55 |
|  | 0.5 | 72.0 | 71.7 | 71.5 | 71.72 | 0.18 |
| LbCas12a-D559P/E795L | 2.0 | 65.6 | 69.4 | 68.6 | 67.88 | 1.63 |
|  | 1.0 | 65.1 | 66.3 | 63.1 | 64.83 | 1.31 |
|  | 0.5 | 56.9 | 55.2 | 54.1 | 55.39 | 1.17 |

TABLE 6a

Endonuclease activity of LbCas12 mutants as compared
to wild type LbCas12 after 48 hours in HEK293 human
cells at HRPT-38115 without Alt-R ® Electroporation
Enhancer. Values calculated as percent cleavage

| Cas12a | Dose (µM) | Replicate 1 | Replicate 2 | Replicate 3 | Average | Std Dev |
|---|---|---|---|---|---|---|
| LbCas12a-wild type | 2.0 | 56.2 | 54.1 | 53.5 | 54.60 | 1.13 |
|  | 1.0 | 46.0 | 44.0 | 46.1 | 45.38 | 0.96 |
|  | 0.5 | 35.5 | 35.4 | 32.9 | 33.94 | 10.5 |
| LbCas12a-D559P | 2.0 | 26.5 | 27.2 | 28.1 | 27.24 | 0.66 |
|  | 1.0 | 21.5 | 18.6 | 18.7 | 19.61 | 1.34 |
|  | 0.5 | 6.3 | 9.2 | 7.9 | 7.81 | 1.16 |
| LbCas12a-E795L | 2.0 | 59.9 | 59.4 | 59.7 | 59.67 | 0.18 |
|  | 1.0 | 55.6 | 53.8 | 54.7 | 54.72 | 0.73 |
|  | 0.5 | 43.0 | 45.8 | 44.4 | 44.39 | 1.13 |
| LbCas12a-D559P/E795L | 2.0 | 41.6 | 42.4 | 40.9 | 41.64 | 0.63 |
|  | 1.0 | 32.3 | 29.1 | 26.6 | 29.33 | 2.32 |
|  | 0.5 | 20.3 | 18.7 | 18.0 | 18.99 | 0.97 |

TABLE 6b

Endonuclease activity of LbCas12 mutants as compared to wild
type LbCas12 after 48 hours in HEK293 human cells at HRPT-38330
without Alt-R ® Electroporation Enhancer. Values calculated as percent cleavage

| Cas12a | Dose (µM) | Replicate 1 | Replicate 2 | Replicate 3 | Average | Std Dev |
|---|---|---|---|---|---|---|
| LbCas12a-wild type | 2.0 | 24.9 | 24.4 | 27.1 | 25.49 | 1.18 |
|  | 1.0 | 18.4 | 20.3 | 16.0 | 18.26 | 1.75 |
|  | 0.5 | 14.2 | 11.0 | 11.6 | 12.27 | 1.36 |
| LbCas12a-D559P | 2.0 | 18.4 | 7.0 | 6.6 | 6.86 | 0.21 |
|  | 1.0 | 14.2 | 3.5 | 3.8 | 3.62 | 0.13 |
|  | 0.5 | 18.4 | 2.7 | 2.9 | 2.85 | 0.10 |
| LbCas12a-E795L | 2.0 | 38.1 | 38.1 | 39.8 | 38.66 | 0.82 |
|  | 1.0 | 26.8 | 23.5 | 23.2 | 24.48 | 1.63 |
|  | 0.5 | 19.2 | 18.0 | 17.4 | 18.21 | 0.72 |
| LbCas12a-D559P/E795L | 2.0 | 12.8 | 13.2 | 14.5 | 13.47 | 0.74 |
|  | 1.0 | 6.8 | 7.9 | 8.7 | 7.82 | 0.77 |
|  | 0.5 | 5.3 | 4.6 | 6.7 | 5.53 | 0.90 |

Figure 5:
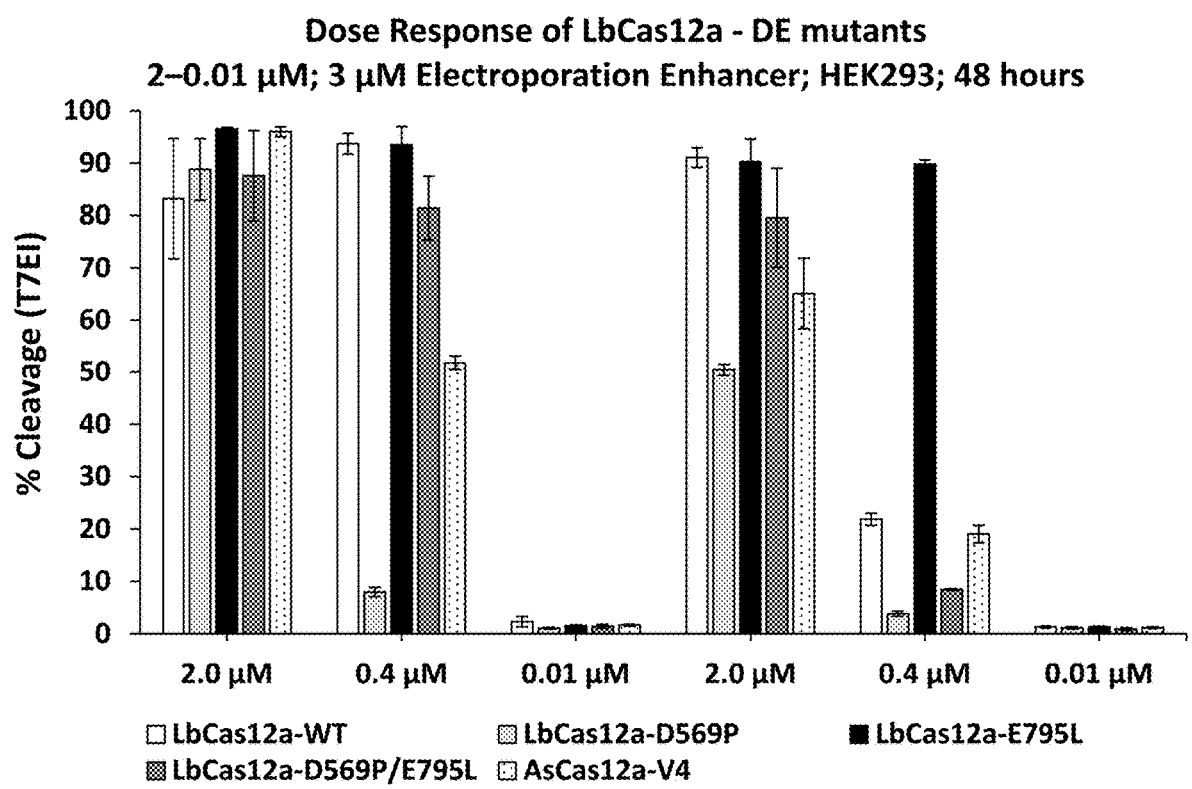
FIG. 5 shows the editing efficiency of LbCas12a mutants as compared to wild-type LBCas12a and AsCas12a-M537R/F870L mutant after 48 hours in HEK293 human cells with IDT Alt-R® Electroporation Enhancer.

The final dose response in this example was set up as described above, reducing the amount of RNP even further by 5-fold increments, starting with a 2 μM dose. The RNP was formed using sgRNA 2 and 8 for the LbCas12a RNP and 14 and 20 for the AsCas12a RNP (Table 1). The results are shown in FIG. 5 and Table 7. RNP delivery of LbCas12a-E795L showed increased activity (~90% cleavage) as compared to wild type LbCas12a (~22% cleavage) and AsCas12a-M537R/F870L (~19% cleavage) at the 38228 site of the HPRT loci at the low of 0.4 μM and retained the high cleavage activity (~90% cleavage) at the 38104 site as seen by the wild type LbCas12a. The single E795L mutant of the LbCas12a nuclease increased genome editing activity up to 4.5-fold at the lowest dose (0.4 μM).

TABLE 7a

Endonuclease activity of LbCas12 mutants as compared to wild type LbCas12 and AsCas12a-M537R/F870L after 48 hours in HEK293 human cells at HRPT-38104. Values calculated as percent cleavage.

| Cas12a | Dose (μM) | Replicate 1 | Replicate 2 | Replicate 3 | Average | Std Dev |
|---|---|---|---|---|---|---|
| LbCas12a-wild type | 2.0 | 76.0 | 99.4 | 74.2 | 83.22 | 11.50 |
| | 0.4 | 96.4 | 93.1 | 91.6 | 93.72 | 1.99 |
| | 0.01 | 2.5 | 3.7 | 1.9 | 2.68 | 0.74 |
| LbCas12a-D559P | 2.0 | 94.4 | 91.3 | 80.7 | 88.81 | 5.89 |
| | 0.4 | 9.0 | 8.1 | 6.8 | 7.96 | 0.88 |
| | 0.01 | 1.3 | 1.2 | 1.3 | 1.29 | 0.03 |
| LbCas12a-E795L | 2.0 | 96.5 | 96.1 | 96.9 | 96.51 | 0.32 |
| | 0.4 | 96.1 | 95.8 | 88.6 | 93.49 | 3.48 |
| | 0.01 | 1.7 | 2.1 | 1.7 | 1.81 | 0.18 |
| LbCas12a-D559P/E795L | 2.0 | 94.7 | 92.7 | 75.4 | 87.59 | 8.64 |
| | 0.4 | 87.5 | 75.3 | — | 81.39 | 6.11 |
| | 0.01 | 1.5 | 1.4 | 2.0 | 1.62 | 0.28 |
| AsCas12a-M537R/F870L | 2.0 | 100.0 | 96.6 | 96.7 | 97.78 | 1.57 |
| | 0.4 | 52.0 | 53.4 | 50.1 | 51.82 | 1.33 |
| | 0.01 | 2.1 | 1.8 | 1.9 | 1.92 | 0.11 |

TABLE 7b

Endonuclease activity of LbCas12 mutants as compared to wild type LbCas12 and AsCas12a-M537R/F870L after 48 hours in HEK293 human cells at HRPT-38228. Values calculated as percent cleavage

| Cas12a | Dose (μM) | Replicate 1 | Replicate 2 | Replicate 3 | Average | Std Dev |
|---|---|---|---|---|---|---|
| LbCas12a-wild type | 2.0 | 90.1 | 93.7 | 89.4 | 91.06 | 1.86 |
| | 0.4 | 20.7 | — | 23.0 | 21.85 | 1.16 |
| | 0.01 | 1.4 | 1.6 | 1.7 | 1.55 | 0.12 |
| LbCas12a-D559P | 2.0 | 49.3 | 51.5 | — | 50.42 | 1.09 |
| | 0.4 | 4.5 | 3.6 | 3.4 | 3.80 | 0.48 |
| | 0.01 | 1.4 | 1.5 | 1.3 | 1.40 | 0.07 |
| LbCas12a-E795L | 2.0 | 84.1 | 94.0 | 92.6 | 90.24 | 4.36 |
| | 0.4 | 90.6 | 89.0 | — | 89.79 | 0.79 |
| | 0.01 | 1.4 | 1.3 | 1.6 | 1.47 | 0.12 |
| LbCas12a-D559P/E795L | 2.0 | 83.3 | 66.5 | 88.8 | 79.54 | 9.48 |
| | 0.4 | 8.3 | 8.4 | 8.6 | 8.44 | 0.14 |
| | 0.01 | 1.6 | 1.1 | 1.3 | 1.37 | 0.20 |
| AsCas12a-M537R/F870L | 2.0 | 72.7 | 56.3 | 66.2 | 65.10 | 6.73 |
| | 0.4 | 19.8 | 20.5 | 16.7 | 19.02 | 1.66 |
| | 0.01 | 1.3 | 1.8 | 1.4 | 1.52 | 0.23 |

EXAMPLE 4

Single LbCas12a Substitution Mutant Enhances the Cleavage Activity in a Human Cell Line Based Activity Assay when Delivered into Human Cells Via Ribonucleoprotein Complex at Low Doses.

The following example demonstrates the ability of mutant E795L LbCas12a to show increased genome editing efficiency when delivered at low doses by RNP complex into human cells with electroporation transfection. That this invention increases genome editing efficiency when wild-type or mutant Cas12a is delivered into human cells as an RNP complex.

The RNP complex was formed by incubating purified Cas12a and sgRNA (Table 2, entries 1-12 for the LbCas12a RNP and entries 13-24 for the AsCas12a RNP) at a ratio of 1:1.2 in PBS buffer for 10 minutes at room temperature. The RNP complexes (1, 0.22, 0.05 and 0.01 µM final doses) were transfected into HEK293 immortalized human cells using a Lonza 4D-Nucleofector™ and Amaxa® 96-well Shuttle Device with Alt-R® Cpf1 Electroporation Enhancer (3 µM, Integrated DNA Technologies). The experiments were performed in biological duplicate and after 48 hours at 37° C., adherent cells were lysed with QuickExtract™ DNA extraction solution (50 µL).

Crude lysates were incubated at 65° C. for 15 minutes, followed by heat inactivation at 98° C. for 3 minutes. Crude genomic DNA was diluted 15-fold in TE buffer and used as PCR template. PCR (primers listed in Table 3) was used to amplify 1.2 kbp fragments of the HPRT loci using Q5@DNA Polymerase (New England Biolabs) and the following parameters: 98° C. for 30 sec, followed by 98° C. for 10 sec, 65° C. for 15 sec and 72° C. for 1 min which was repeated 24 times, followed by a final extension at 72° C. for 2 min. Heteroduplexes were formed by the addition of NEBuffer 2 and initially heating to 95° C. for 10 min with a slow cool down to room temperature. The heteroduplexes were then cleaved by 2 U of T7 Endonuclease I (New England Biolabs) for 1 hour at 37° C. The cleavage products were analyzed by capillary electrophoresis (Fragment Analyzer, Advanced Analytical).

Figure 6A:
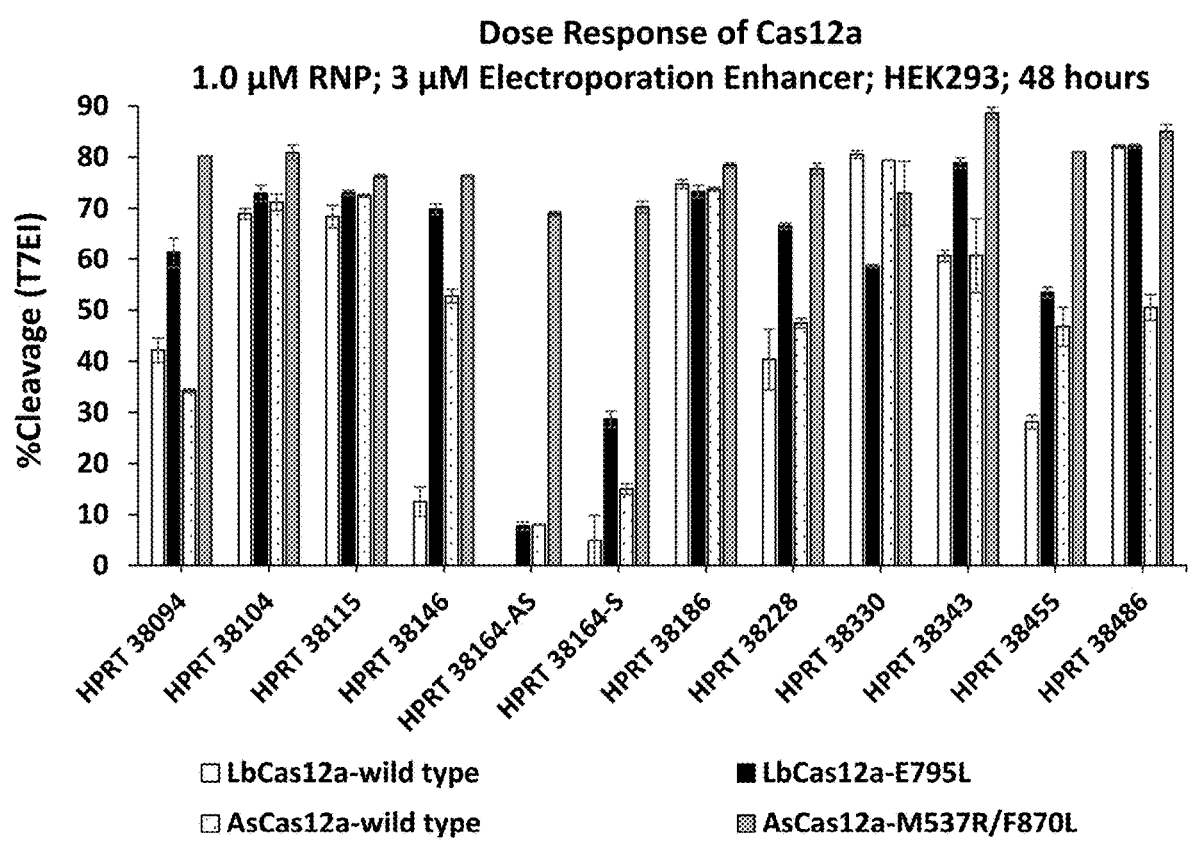
FIG. 6A shows the editing efficiency of LbCas12a wild type and E795L mutant LbCas12a as compared to AsCas12a wild type and AsCas12a-M537R/F870L mutant delivered as a 1.0 µM dose of RNP measured after 48 hours in HEK293 cells with IDT Alt-R® Electroporation Enhancer.
Figure 6B:
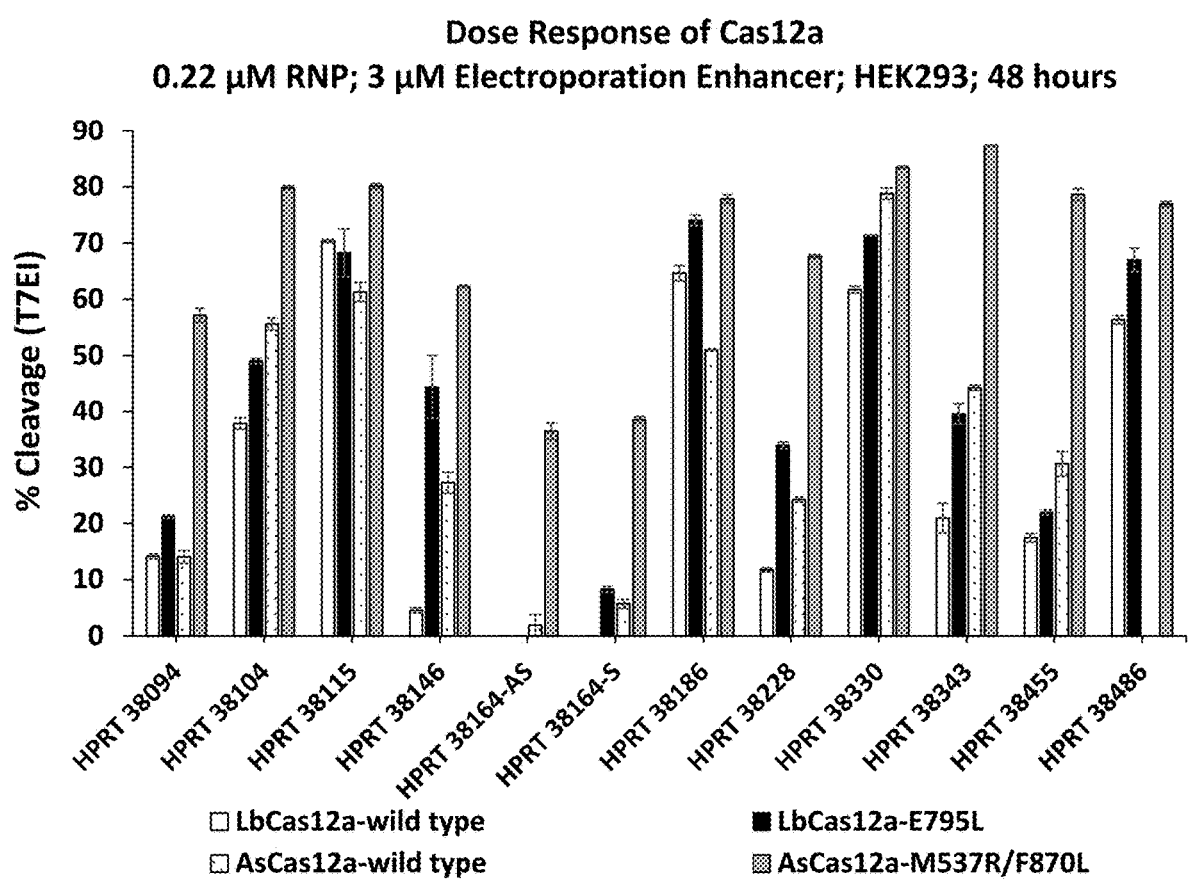
FIG. 6B shows the editing efficiency of LbCas12a wild type and E795L mutant LbCas12a as compared to AsCas12a wild type and AsCas12a-M537R/F870L mutant delivered as a 0.22 µM dose of RNP measured after 48 hours in HEK293 cells with IDT Alt-R® Electroporation Enhancer.
Figure 6C:
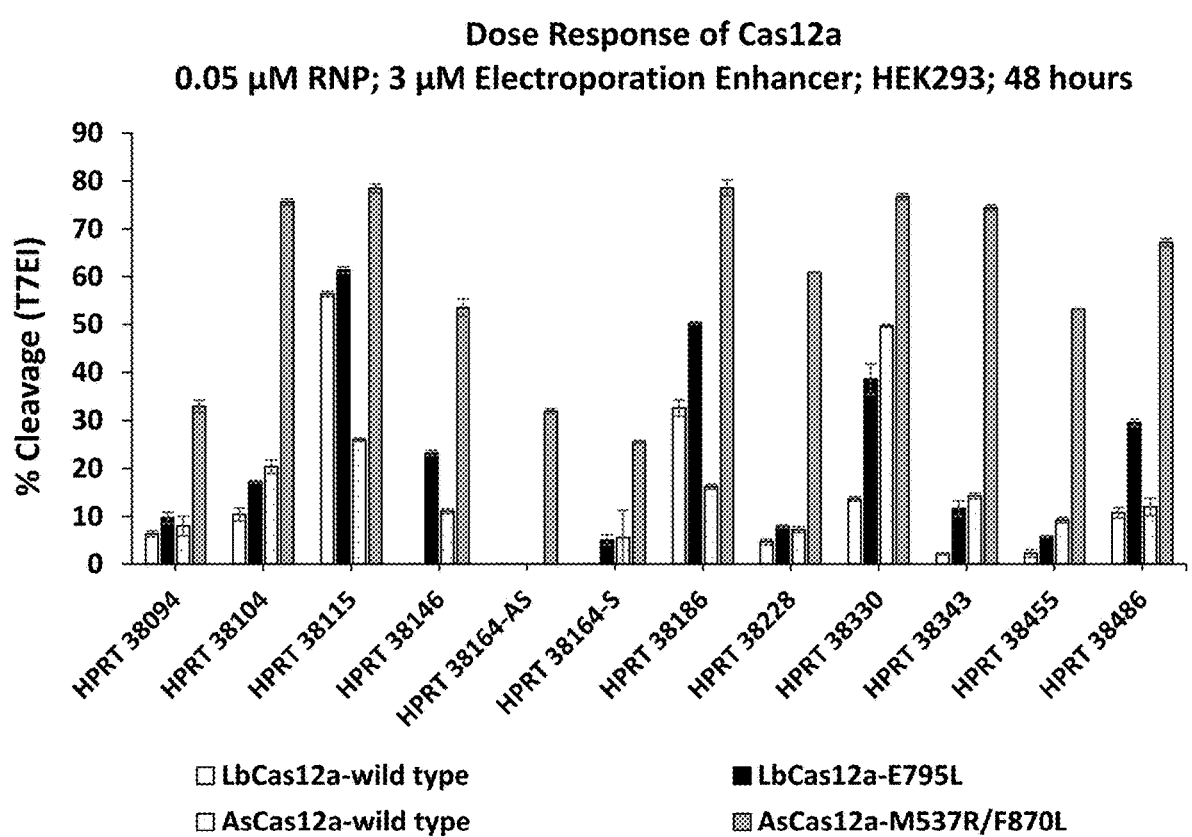
FIG. 6C shows the editing efficiency of LbCas12a wild type and E795L mutant LbCas12a as compared to AsCas12a wild type and AsCas12a-M537R/F870L mutant delivered as a 0.05 µM dose of RNP measured after 48 hours in HEK293 cells with IDT Alt-R® Electroporation Enhancer.
Figure 6D:
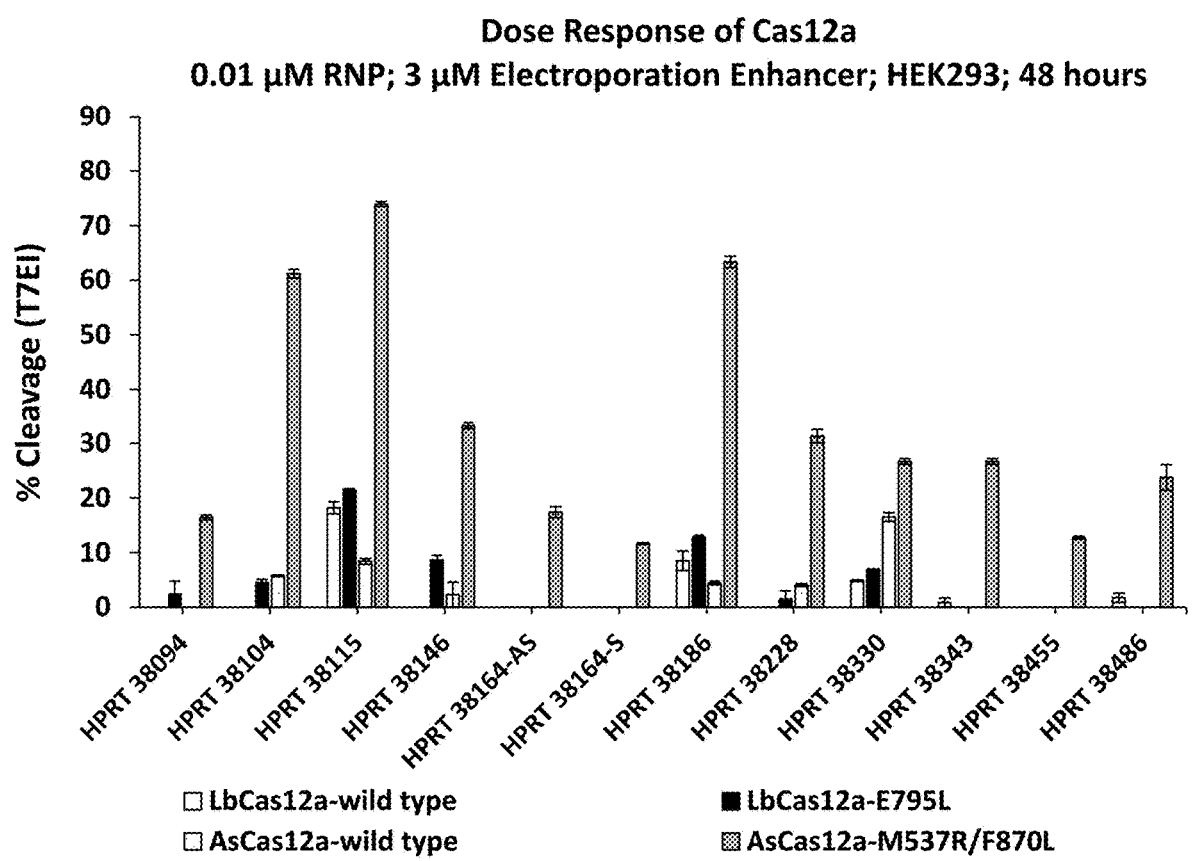
FIG. 6D shows the editing efficiency of LbCas12a wild type and E795L mutant LbCas12a as compared to AsCas12a wild type and AsCas12a-M537R/F870L mutant delivered as a 0.01 µM dose of RNP measured after 48 hours in HEK293 cells with IDT Alt-R® Electroporation Enhancer

The endonuclease activity of wild type and mutant LbCas12a as compared to wild type and mutant AsCas12a in HEK293 human cells are described in FIG. 6A, FIG. 6b, FIG. 6C, FIG. 6D and Table 8. Overall, RNP delivery of LbCas12a-E795L showed improved activity as compared to wild type Lb- and AsCas12a. The 0.05 µM dose shows the increased activity of the enzyme even at low doses (FIG. 6c). At this dose, LbCas12a-E795L exceeds wild type LbCas12a's activity up to 23-fold at the HPRT 38146 site (Table 8, entries 51 and 55) and wild type AsCas12a's activity up to 3-fold at the HPRT 38186 site (Table 8, entries 103 and 107). At the highest distinguishable dose (0.22 µM, FIG. 6b) for the LbCas12a variants, the E795L mutant exhibited increased activity over the wild type version up to 11-fold at the HPRT 38146 site (Table 8, entries 50 and 54) and almost 2-fold at the same site against the wild-type AsCas12a (Table 8, entries 54 and 58).

TABLE 8

Endonuclease activity of LbCas12a-E795L compared to wild type Lb- and AsCas12a and M AsCas12a-537R/F870L after 48 hours in HEK293 human cells at HRPT-38228. Values calculated as percent cleavage.

| Cas12a | Site | Dose (µM) | Replicate 1 | Replicate 2 | Average | Std Dev | Entry |
|---|---|---|---|---|---|---|---|
| LbCas12a-wild type | HPRT-38094-S | 1.00 | 39.8 | 44.5 | 42.2 | 2.36 | 1 |
| | | 0.22 | 13.7 | 14.6 | 14.2 | 0.45 | 2 |
| | | 0.05 | 5.8 | 7.0 | 6.4 | 0.60 | 3 |
| | | 0.01 | 0.0 | 0.0 | 0.0 | 0.00 | 4 |
| LbCas12a-E795L | HPRT-38094-S | 1.00 | 64.2 | 58.4 | 61.3 | 2.90 | 5 |
| | | 0.22 | 21.5 | 20.9 | 21.2 | 0.30 | 6 |
| | | 0.05 | 8.6 | 10.9 | 9.8 | 1.15 | 7 |
| | | 0.01 | 4.8 | 0.0 | 2.4 | 2.40 | 8 |
| AsCas12a-wild type | HPRT-38094-S | 1.00 | 34.6 | 33.9 | 34.3 | 0.35 | 9 |
| | | 0.22 | 12.9 | 15.2 | 14.1 | 1.15 | 10 |
| | | 0.05 | 10.1 | 6.0 | 8.1 | 2.05 | 11 |
| | | 0.01 | 0.0 | 0.0 | 0.0 | 0.00 | 12 |
| AsCas12a-M537R/F870L | HPRT-38094-S | 1.00 | 80.3 | 80.2 | 80.3 | 0.05 | 13 |
| | | 0.22 | 58.4 | 55.9 | 57.2 | 1.25 | 14 |
| | | 0.05 | 34.2 | 31.7 | 33.0 | 1.25 | 15 |
| | | 0.01 | 16.9 | 16.0 | 16.5 | 0.54 | 16 |
| LbCas12a-wild type | HPRT-38104-S | 1.00 | 67.9 | 70.0 | 69.0 | 1.05 | 17 |
| | | 0.22 | 36.8 | 38.8 | 37.8 | 1.00 | 18 |
| | | 0.05 | 11.8 | 9.1 | 10.5 | 1.35 | 19 |
| | | 0.01 | 0.0 | 0.0 | 0.0 | 0.00 | 20 |
| LbCas12a-E795L | HPRT-38104-S | 1.00 | 74.5 | 71.4 | 73.0 | 1.55 | 21 |
| | | 0.22 | 49.5 | 48.6 | 49.1 | 0.45 | 22 |
| | | 0.05 | 17.5 | 17.0 | 17.3 | 0.25 | 23 |
| | | 0.01 | 5.1 | 3.9 | 4.5 | 0.60 | 24 |
| AsCas12a-wild type | HPRT-38104-S | 1.00 | 72.8 | 69.6 | 71.2 | 1.60 | 25 |
| | | 0.22 | 54.5 | 56.7 | 55.6 | 1.10 | 26 |
| | | 0.05 | 21.8 | 19.0 | 20.4 | 1.40 | 27 |
| | | 0.01 | 5.6 | 5.9 | 5.8 | 0.15 | 28 |
| AsCas12a-M537R/F870L | HPRT-38104-S | 1.00 | 79.4 | 82.4 | 80.9 | 1.50 | 29 |
| | | 0.22 | 80.2 | 79.5 | 79.9 | 0.35 | 30 |
| | | 0.05 | 75.0 | 76.3 | 75.7 | 0.65 | 31 |
| | | 0.01 | 62.0 | 60.4 | 61.2 | 0.80 | 32 |
| LbCas12a-wild type | HPRT-38115-AS | 1.00 | 66.2 | 70.6 | 68.4 | 2.20 | 33 |
| | | 0.22 | 70.1 | 70.6 | 70.4 | 0.25 | 34 |
| | | 0.05 | 55.8 | 56.9 | 56.4 | 0.55 | 35 |
| | | 0.01 | 19.3 | 17.1 | 18.2 | 1.10 | 36 |
| LbCas12a-E795L | HPRT-38115-AS | 1.00 | 73.5 | 72.6 | 73.1 | 0.45 | 37 |
| | | 0.22 | 72.5 | 64.0 | 68.3 | 4.25 | 38 |
| | | 0.05 | 62.0 | 60.7 | 61.4 | 0.65 | 39 |
| | | 0.01 | 21.2 | 21.7 | 21.5 | 0.25 | 40 |
| AsCas12a-wild type | HPRT-38115-AS | 1.00 | 72.8 | 72.2 | 72.5 | 0.30 | 41 |
| | | 0.22 | 59.6 | 63.0 | 61.3 | 1.70 | 42 |
| | | 0.05 | 25.7 | 26.3 | 26.0 | 0.30 | 43 |
| | | 0.01 | 7.9 | 8.9 | 8.4 | 0.50 | 44 |
| Ascas12a-M537R/F870L | HPRT-38115-AS | 1.00 | 75.9 | 76.6 | 76.3 | 0.35 | 45 |
| | | 0.22 | 75.7 | 80.6 | 80.2 | 0.45 | 46 |
| | | 0.05 | 77.6 | 79.4 | 78.5 | 0.90 | 47 |
| | | 0.01 | 73.5 | 74.4 | 74.0 | 0.45 | 48 |
| LbCas12a-wild type | HPRT-38146-AS | 1.00 | 9.7 | 15.4 | 12.6 | 2.85 | 49 |
| | | 0.22 | 4.1 | 5.0 | 4.6 | 0.45 | 50 |
| | | 0.05 | 0.0 | 0.0 | 0.0 | 0.00 | 51 |
| | | 0.01 | 0.0 | 0.0 | 0.0 | 0.00 | 52 |
| LbCas12a-E795L | HPRT-38146-AS | 1.00 | 70.9 | 68.8 | 69.9 | 1.05 | 53 |
| | | 0.22 | 50.0 | 38.7 | 44.4 | 5.65 | 54 |
| | | 0.05 | 23.8 | 22.7 | 23.2 | 0.55 | 55 |
| | | 0.01 | 9.5 | 7.8 | 8.7 | 0.85 | 56 |
| AsCas12a-wild type | HPRT-38146-AS | 1.00 | 51.4 | 54.1 | 52.8 | 1.35 | 57 |
| | | 0.22 | 29.1 | 25.4 | 27.3 | 1.85 | 58 |
| | | 0.05 | 10.6 | 11.6 | 11.1 | 0.50 | 59 |
| | | 0.01 | 4.6 | 0.0 | 2.3 | 2.30 | 60 |
| AsCas12a-M537R/F870L | HPRT-38146-AS | 1.00 | 76.2 | 76.5 | 76.4 | 0.15 | 61 |
| | | 0.22 | 62.1 | 62.5 | 62.3 | 0.20 | 62 |
| | | 0.05 | 51.7 | 55.3 | 55.3 | 1.80 | 63 |
| | | 0.01 | 32.7 | 33.8 | 33.3 | 0.55 | 64 |
| LbCas12a-wild type | HPRT-38164-S | 1.00 | 0.0 | 0.0 | 0.0 | 0.0 | 65 |
| | | 0.22 | 0.0 | 0.0 | 0.0 | 0.0 | 66 |
| | | 0.05 | 0.0 | 0.0 | 0.0 | 0.0 | 67 |
| | | 0.01 | 0.0 | 0.0 | 0.0 | 0.0 | 68 |
| LbCas12a-E795L | HPRT-38164-S | 1.00 | 7.0 | 8.6 | 7.8 | 0.8 | 69 |
| | | 0.22 | 0.0 | 0.0 | 0.0 | 0.0 | 70 |
| | | 0.05 | 0.0 | 0.0 | 0.0 | 0.0 | 71 |
| | | 0.01 | 0.0 | 0.0 | 0.0 | 0.0 | 72 |

TABLE 8-continued

Endonuclease activity of LbCas12a-E795L compared
to wild type Lb- and AsCas12a and M AsCas12a-537R/F870L
after 48 hours in HEK293 human cells at HRPT-38228.
Values calculated as percent cleavage.

| Cas12a | Site | Dose (µM) | Replicate 1 | Replicate 2 | Average | Std Dev | Entry |
|---|---|---|---|---|---|---|---|
| AsCas12a-wild type | HPRT-38164-AS | 1.00 | 8.2 | 8.0 | 8.1 | 0.10 | 73 |
|  |  | 0.22 | 0.0 | 3.8 | 1.9 | 1.90 | 74 |
|  |  | 0.05 | 0.0 | 0.0 | 0.0 | 0.00 | 75 |
|  |  | 0.01 | 0.0 | 0.0 | 0.0 | 0.00 | 76 |
| AsCas12a-M537R/F870L | HPRT-38164-AS | 1.00 | 68.5 | 69.4 | 69.0 | 0.45 | 77 |
|  |  | 0.22 | 35.0 | 37.9 | 36.5 | 1.45 | 78 |
|  |  | 0.05 | 32.5 | 31.4 | 32.0 | 0.55 | 79 |
|  |  | 0.01 | 16.4 | 18.4 | 17.4 | 1 | 80 |
| LbCas12a-wild type | HPRT-38164-S | 1.00 | 0.0 | 9.9 | 5.0 | 4.95 | 81 |
|  |  | 0.22 | 0.0 | 0.0 | 0.0 | 0.0 | 82 |
|  |  | 0.05 | 0.0 | 0.0 | 0.0 | 0.0 | 83 |
|  |  | 0.01 | 0.0 | 0.0 | 0.0 | 0.0 | 84 |
| LbCas12a-E795L | HPRT-38164-S | 1.00 | 30.3 | 27.1 | 28.7 | 1.60 | 85 |
|  |  | 0.22 | 8.8 | 7.8 | 8.3 | 5.00 | 86 |
|  |  | 0.05 | 4.0 | 6.2 | 5.1 | 1.10 | 87 |
|  |  | 0.01 | 0.0 | 0.0 | 0.0 | 0.00 | 88 |
| AsCas12a-wild type | HPRT-38164-S | 1.00 | 16.1 | 14.0 | 15.1 | 1.05 | 89 |
|  |  | 0.22 | 65.0 | 4.9 | 5.7 | 0.80 | 90 |
|  |  | 0.05 | 0.0 | 11.3 | 5.7 | 5.65 | 91 |
|  |  | 0.01 | 0.0 | 0.0 | 0.0 | 0.0 | 92 |
| AsCas12a-M537R/F870L | HPRT-38164-S | 1.00 | 69.2 | 71.4 | 70.3 | 1.10 | 93 |
|  |  | 0.22 | 39.0 | 37.9 | 38.5 | 0.55 | 94 |
|  |  | 0.05 | 25.8 | 25.3 | 25.6 | 0.25 | 95 |
|  |  | 0.01 | 11.5 | 11.8 | 11.7 | 0.15 | 96 |
| LbCas12a-wild type | HPRT-38186-S | 1.00 | 73.9 | 75.6 | 74.8 | 0.85 | 97 |
|  |  | 0.22 | 66.0 | 63.3 | 64.7 | 1.35 | 98 |
|  |  | 0.05 | 30.9 | 34.3 | 32.6 | 1.70 | 99 |
|  |  | 0.01 | 6.7 | 10.3 | 8.5 | 1.80 | 100 |
| LbCas12a-E795L | HPRT-38186-S | 1.00 | 74.5 | 72.1 | 73.3 | 1.20 | 101 |
|  |  | 0.22 | 75.0 | 73.1 | 74.1 | 0.95 | 102 |
|  |  | 0.05 | 50.0 | 50.6 | 50.3 | 0.30 | 103 |
|  |  | 0.01 | 13.2 | 12.5 | 12.9 | 0.35 | 104 |
| AsCas12a-wild type | HPRT-38186-S | 1.00 | 73.4 | 74.1 | 73.8 | 0.35 | 105 |
|  |  | 0.22 | 51.2 | 50.8 | 51.0 | 0.50 | 106 |
|  |  | 0.05 | 16.7 | 15.7 | 16.2 | 0.50 | 107 |
|  |  | 0.01 | 4.1 | 4.8 | 4.5 | 0.35 | 108 |
| AsCas12a-M537R/F870L | HPRT-38186-S | 1.00 | 78.0 | 78.9 | 78.5 | 0.45 | 109 |
|  |  | 0.22 | 78.6 | 77.1 | 77.9 | 0.75 | 110 |
|  |  | 0.05 | 76.9 | 80.2 | 78.6 | 1.65 | 111 |
|  |  | 0.01 | 62.3 | 64.4 | 63.4 | 1.05 | 112 |
| LbCas12a-wild type | HPRT-38228-S | 1.00 | 34.4 | 40.4 | 40.4 | 5.95 | 113 |
|  |  | 0.22 | 11.4 | 12.1 | 11.8 | 0.35 | 114 |
|  |  | 0.05 | 5.3 | 4.0 | 4.7 | 0.65 | 115 |
|  |  | 0.01 | 0.0 | 0.0 | 0.0 | 0.00 | 116 |
| LbCas12a-E795L | HPRT-38228-S | 1.00 | 67.1 | 66.0 | 66.6 | 55.00 | 117 |
|  |  | 0.22 | 34.5 | 33.3 | 33.9 | 0.60 | 118 |
|  |  | 0.05 | 8.2 | 7.7 | 8.0 | 0.25 | 119 |
|  |  | 0.01 | 0.0 | 3.0 | 1.5 | 1.50 | 120 |
| AsCas12a-wild type | HPRT-38228-S | 1.00 | 46.5 | 48.4 | 47.5 | 0.95 | 121 |
|  |  | 0.22 | 23.8 | 24.7 | 24.3 | 0.45 | 122 |
|  |  | 0.05 | 7.9 | 6.7 | 7.3 | 0.60 | 123 |
|  |  | 0.01 | 4.3 | 3.8 | 4.1 | 0.25 | 124 |
| AsCas12a-M537R/F870L | HPRT-38228-S | 1.00 | 76.7 | 78.8 | 77.8 | 1.05 | 125 |
|  |  | 0.22 | 67.3 | 67.9 | 67.6 | 0.30 | 126 |
|  |  | 0.05 | 60.9 | 60.7 | 60.8 | 0.10 | 127 |
|  |  | 0.01 | 30.1 | 32.6 | 31.4 | 1.25 | 128 |
| LbCas12a-wild type | HPRT-38330-AS | 1.00 | 81.3 | 79.8 | 80.6 | 0.75 | 129 |
|  |  | 0.22 | 61.1 | 62.3 | 61.7 | 0.60 | 130 |
|  |  | 0.05 | 13.2 | 14.1 | 13.7 | 0.45 | 131 |
|  |  | 0.01 | 4.7 | 5.0 | 4.9 | 0.15 | 132 |
| LbCas12a-E795L | HPRT-38330-AS | 1.00 | 58.9 | 58.4 | 58.7 | 0.25 | 133 |
|  |  | 0.22 | 71.3 | 71.4 | 71.4 | 0.05 | 134 |
|  |  | 0.05 | 35.4 | 41.8 | 38.6 | 3.20 | 135 |
|  |  | 0.01 | 7.0 | 6.8 | 6.9 | 0.10 | 136 |
| AsCas12a-wild type | HPRT-38330-AS | 1.00 | — | 79.4 | 79.4 | 0.00 | 137 |
|  |  | 0.22 | 79.8 | 77.8 | 78.8 | 1.00 | 138 |
|  |  | 0.05 | 49.4 | 50.0 | 49.7 | 0.30 | 139 |
|  |  | 0.01 | 17.3 | 15.7 | 16.5 | 0.80 | 140 |
| AsCas12a-M537R/F870L | HPRT-38330-AS | 1.00 | 79.2 | 66.7 | 73.0 | 6.25 | 141 |
|  |  | 0.22 | 83.7 | 83.2 | 83.5 | 0.25 | 142 |
|  |  | 0.05 | 77.4 | 76.1 | 76.8 | 0.65 | 143 |
|  |  | 0.01 | 26.2 | 27.2 | 26.7 | 0.50 | 144 |

All references, including publications, patent applications, and patents, cited herein are hereby incorporated by reference to the same extent as if each reference were individually and specifically indicated to be incorporated by reference and were set forth in its entirety herein.

The use of the terms "a" and "an" and "the" and similar referents in the context of describing the invention (especially in the context of the following claims) are to be construed to cover both the singular and the plural, unless otherwise indicated herein or clearly contradicted by context. The terms "comprising," "having," "including," and "containing" are to be construed as open-ended terms (i.e., meaning "including, but no limited to") unless otherwise noted. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate the invention, and does not pose a limitation on the scope of the invention unless otherwise claimed. No language in the specification should be construed as indicating any non-claimed element as essential to the practice of the invention.

Preferred embodiments of this invention are described herein, including the best mode known to the inventors for carrying out the invention. Variations of those preferred embodiments may become apparent to those of ordinary skill in the art upon reading the foregoing description. The inventors expect skilled artisans to employ such variations as appropriate, and the inventors intend for the invention to be practiced otherwise than as specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

The term "wild-type LbCas12a" ("wild-type Lb enzyme" or "WT-LbCas12a") encompasses a protein having the identical amino acid sequence of the naturally-occurring Lachnospiraceae bacterium ND2006 Cas12a (e.g., SEQ ID NO: 2) and that has biochemical and biological activity when combined with a suitable crRNA to form and active CRISPR/Cas12a endonuclease system. The term "wild-type AsCas12a" ("wild-type as enzyme" or "WT-AsCas12a") encompasses a protein having the identical amino acid sequence of the naturally-occurring Acidaminococcus sp. BV3L6 Cas12a (e.g., SEQ ID NO: 18) and that has biochemical and biological activity when combined with a suitable crRNA to form and active CRISPR/Cas12a endonuclease system.

The term "mutant LbCas12a protein" encompasses protein forms having a different amino acid sequence form the wild-type *Lachnospiraceae bacterium* ND2006 Cas12a and that have biochemical and biological activity with combined with a suitable crRNA to form an active CRISPR-Cas12a endonuclease system. This includes orthologs and Cas12a variants having different amino acid sequences form the wild-type *Lachnospiraceae bacterium* ND2006 Cas12a.

The term "polypeptide" refers to any linear or branched peptide comprising more than one amino acid. Polypeptide includes protein or fragment thereof or fusion thereof, provided such protein, fragment or fusion retains a useful biochemical or biological activity.

Fusion proteins typically include extra amino acid information that is not native to the protein to which the extra amino acid information is covalently attached. Such extra amino acid information may include tags that enable purification or identification of the fusion protein. Such extra amino acid information may include peptides that enable the fusion proteins to be transported into cells and/or transported to specific locations within cells. Examples of tags for these purposes include the following: AviTag, which is a peptide allowing biotinylation by the enzyme BirA so the protein can be isolated by streptavidin (GLNDIFEAQKIEWHE) (SEQ ID NO: 53); Calmodulin-tag, which is a peptide bound by the protein calmodulin (KRRWKKNFIAVSAANRFK-KISSSGAL) (SEQ ID NO: 54); polyglutamate tag, which is a peptide binding efficiently to anion-exchange resin such as Mono-Q (EEEEEE) (SEQ ID NO: 55); E-tag, which is a peptide recognized by an antibody (GAPVPYPDPLEPR) (SEQ ID NO: 56); FLAG-tag, which is a peptide recognized by an antibody (DYKDDDDK) (SEQ ID NO: 57); HA-tag, which is a peptide from hemagglutinin recognized by an antibody (YPYDVPDYA) (SEQ ID NO: 58); His-tag, which is typically 5-10 histidines bound by a nickel or cobalt chelate (HHHHHH) (SEQ ID NO: 59); Myc-tag, which is a peptide derived from c-myc recognized by an antibody (EQKLISEEDL) (SEQ ID NO: 60); NE-tag, which is a novel 18-amino-acid synthetic peptide (TKENPRSNQEE-SYDDNES) (SEQ ID NO: 61) recognized by a monoclonal IgG1 antibody, which is useful in a wide spectrum of applications including Western blotting, ELISA, flow cytometry, immunocytochemistry, immunoprecipitation, and affinity purification of recombinant proteins; S-tag, which is a peptide derived from Ribonuclease A (KET-AAAKFERQHMDS) (SEQ ID NO: 62); SBP-tag, which is a peptide which binds to streptavidin; (MDEKTTGWRGGHVVEGLAGELEQLRAR-LEHHPQGQREP) (SEQ ID NO: 63); Softag 1, which is intended for mammalian expression (SLAELLNAGLGGS) (SEQ ID NO: 64); Softag 3, which is intended for prokaryotic expression (TQDPSRVG) (SEQ ID NO: 65); Strep-tag, which is a peptide which binds to streptavidin or the modified streptavidin called streptactin (Strep-tag II: WSHPQFEK) (SEQ ID NO: 66); TC tag, which is a tetracysteine tag that is recognized by FlAsH and ReAsH biarsenical compounds (CCPGCC) (SEQ ID NO: 67); V5 tag, which is a peptide recognized by an antibody (GKPIPN-PLLGLDST) (SEQ ID NO: 68); VSV-tag, a peptide recognized by an antibody (YTDIEMNRLGK) (SEQ ID NO: 69); Xpress tag (DLYDDDDK) (SEQ ID NO: 70); Isopeptag, which is a peptide which binds covalently to pilin-C protein (TDKDMTITFTNKKDAE) (SEQ ID NO: 71); SpyTag, which is a peptide which binds covalently to SpyCatcher protein (AHIVMVDAYKPTK) (SEQ ID NO: 72); SnoopTag, a peptide which binds covalently to Snoop-Catcher protein (KLGDIEFIKVNK) (SEQ ID NO: 73); BCCP (Biotin Carboxyl Carrier Protein), which is a protein domain biotinylated by BirA to enable recognition by streptavidin; Glutathione-S-transferase-tag, which is a protein that binds to immobilized glutathione; Green fluorescent protein-tag, which is a protein which is spontaneously fluorescent and can be bound by antibodies; HaloTag, which is a mutated bacterial haloalkane dehalogenase that covalently attaches to a reactive haloalkane substrate to allow attachment to a wide variety of substrates; Maltose binding protein-tag, a protein which binds to amylose agarose; Nustag; Thioredoxin-tag; and Fc-tag, derived from immunoglobulin Fc domain, which allows dimerization and solubilization and can be used for purification on Protein-A Sepharose. Nuclear localization signals (NLS), such as those obtained from SV40, allow for proteins to be transported to the nucleus immediately upon entering the cell. Given that the native Cas9 protein is bacterial in origin and therefore does not naturally comprise a NLS motif, addition of one or more NLS motifs to the recombinant Cas9 protein is expected to show improved genome editing activity when used in eukaryotic cells where the target genomic DNA substrate resides in the nucleus. One skilled in the art would appreciate these various fusion tag technologies, as well as how to make and use fusion proteins that include them.

REFERENCES

1. Zetsche, B., et al., Cpf1 Is a Single RNA-Guided Endonuclease of a Class 2 CRISPR-Cas System. *Cell*, 2015. 163: p. 759.
2. Hur, J. K., et al., Targeted mutagenesis in mice by electroporation of Cpf1 ribonucleoproteins. *Nature Biotechnology*, 2016. 34(8): p. 807.
3. Kim, Y., et al., Generation of knockdown mice by Cpf1-mediated gene targeting. *Nature Biotechnology*, 2016. 34(8): p. 808.
4. Kim, D., et al., Genome-wide analysis reveals specificities of Cpf1 endonucleases in human cells. *Nature Biotechnology*, 2016. 34(8): p. 863.
5. Kleinstiver, B. P., et al., Genome-wide specificities of CRISPR-Cas Cpf1 nucleases in human cells. *Nature Biotechnology*, 2016. 34(8): p. 869.
6. Kim, H. K., et al., In vivo high-throughput profiling of CRISPR-Cpf1 activity. *Nature Methods*, 2017. 14(2): p. 153.
7. Zetsche, B., et al., Multiplex gene editing by CRISPR-Cpf1 using a single rRNA array. *Nature Biotechnology*, 2017. 35(1): p. 31.
8. Kim, H., et al., CRISPR/Cpf1-mediated DNA-free plant genome editing. *Nature Communications*, 2017. 8(14406): p. 1.
9. Yamano, T., et al., Crystal Structure of Cpf1 in Complex with Guide RNA and Target RNA. *Cell*, 2016. 65: p. 949.
10. Yamano, T., et al., Structural Basis for the Canonical and Non-canonical PAM Recognition by CRISPR-Cpf1. *Molecular Cell*, 2017. 67: p. 633.
11. Gao, L., et al., Engineered Cpf1 variants with altered PAM specificities. *Nature Biotechnology*, 2017. 35(8): p. 789.
12. Robert, X. and Gouet, P., Deciphering key features in protein structures with the new ENDscript server. *Nucleic Acids Research*, 2014. 42(W1): p. W320.

What is claimed is:

1. An isolated mutant LbCas12a protein comprising a single amino acid substitution mutation introduced into the wild-type LbCas12a protein comprising E795L (SEQ ID NO: 5).

2. An isolated ribonucleoprotein complex, comprising:
(a) the mutant LbCas12a protein of claim 1; and
(b) a gRNA complex;
wherein the isolated ribonucleoprotein complex is active as a CRISPR/Cas12a endonuclease system, wherein the resultant CRISPR/Cas12a endonuclease system displays maintained on-target editing activity relative to a wild-type CRISPR/Cas12a endonuclease system.

3. A CRISPR/Cas12a endonuclease system comprising a mutant LbCas12a protein and a gRNA, wherein the CRISPR/Cas12a endonuclease system displays maintained on-target editing activity relative to a wild-type CRISPR/Cas12a endonuclease system, and wherein the mutant LbCas12a protein comprises a single amino acid substitution mutation introduced into the wild-type LbCas12a protein comprising E795L (SEQ ID NO: 5).

4. The CRISPR/Cas12a endonuclease system of claim 3, wherein the CRISPR/Cas12a endonuclease system is encoded by a DNA expression vector.

5. The CRISPR/Cas12a endonuclease system of claim 4, wherein the DNA expression vector comprises a plasmid-borne vector.

6. The CRISPR/Cas12a endonuclease system of claim 5, wherein the DNA expression vector is selected from a bacterial expression vector and a eukaryotic expression vector.

7. An isolated nucleic acid encoding a mutant LbCas12a protein, wherein the mutant LbCas12a protein is active in a CRISPR/Cas12a endonuclease system, wherein the CRISPR/Cas12a endonuclease system displays maintained on-target editing activity relative to a wild-type CRISPR/Cas12a endonuclease system, and wherein the mutant LbCas12a protein comprises a single amino acid substitution mutation introduced into the wild-type LbCas12a protein comprising E795L (SEQ ID NO: 5).

8. The isolated nucleic acid encoding a mutant LbCas12a protein of claim 7, wherein the isolated nucleic acid encoding the mutant LbCas12a protein is SEQ ID NO: 12.

* * * * *